(12) United States Patent
Lantto et al.

(10) Patent No.: US 7,879,329 B2
(45) Date of Patent: Feb. 1, 2011

(54) RECOMBINANT ANTIBODIES FOR TREATMENT OF RESPIRATORY SYNCYTIAL VIRUS INFECTIONS

(75) Inventors: Johan Lantto, Lund (SE); Henriette Schjønning Nielsen, Vaerloese (DK)

(73) Assignee: Symphogen A/S, Lyngby (DK)

( * ) Notice: Subject to any disclaimer, the term of this patent is extended or adjusted under 35 U.S.C. 154(b) by 0 days.

(21) Appl. No.: 12/073,538

(22) Filed: Mar. 6, 2008

(65) Prior Publication Data

US 2008/0226630 A1    Sep. 18, 2008

Related U.S. Application Data

(60) Provisional application No. 60/971,387, filed on Sep. 11, 2007.

(30) Foreign Application Priority Data

Sep. 7, 2007    (DK)    ................................ 2007 01291

(51) Int. Cl.
*A61K 39/42*    (2006.01)
*A61K 39/155*    (2006.01)

(52) U.S. Cl. ................................ 424/159.1; 424/211.1

(58) Field of Classification Search .................. None
See application file for complete search history.

(56) References Cited

U.S. PATENT DOCUMENTS

| | | | |
|---|---|---|---|
| 5,691,449 | A | 11/1997 | Paradiso et al. |
| 5,762,905 | A | 6/1998 | Burton et al. |
| 5,811,524 | A | 9/1998 | Brams et al. |
| 5,824,307 | A | 10/1998 | Johnson |
| 5,922,344 | A | 7/1999 | Hilty et al. |
| 6,077,511 | A | 6/2000 | Langedijk |
| 6,410,030 | B1 | 6/2002 | Binz et al. |
| 6,656,467 | B2 | 12/2003 | Young et al. |
| 6,699,478 | B1 | 3/2004 | Hancock et al. |
| 6,818,216 | B2 | 11/2004 | Young et al. |
| 7,070,786 | B2 | 7/2006 | Scallon |
| 2002/0098189 | A1 | 7/2002 | Young et al. |
| 2004/0009177 | A1 | 1/2004 | Tripp et al. |
| 2004/0096451 | A1 | 5/2004 | Young et al. |
| 2004/0224309 | A1 | 11/2004 | Cheng et al. |
| 2005/0019758 | A1 | 1/2005 | Deen et al. |
| 2005/0088491 | A1 | 4/2005 | Truninger et al. |
| 2005/0175986 | A1 | 8/2005 | Gross et al. |
| 2006/0018925 | A1 | 1/2006 | Tripp et al. |
| 2006/0099220 | A1 | 5/2006 | Tous et al. |
| 2006/0275766 | A1 | 12/2006 | Haurum et al. |
| 2007/0141048 | A1 | 6/2007 | Oleksiewicz et al. |
| 2008/0131882 | A1 | 6/2008 | Rasmussen et al. |

FOREIGN PATENT DOCUMENTS

| | | |
|---|---|---|
| EP | 1 516 929 A2 | 3/2005 |
| WO | WO 92/01473 A1 | 2/1992 |
| WO | WO 97/10846 A1 | 3/1997 |
| WO | WO 97/46581 A1 | 12/1997 |
| WO | WO 02/42326 A1 | 5/2002 |
| WO | WO 2004/061104 A2 | 7/2004 |
| WO | WO 2004/083373 A2 | 9/2004 |
| WO | WO 2004/092207 A2 | 10/2004 |
| WO | WO 2005/042774 A2 | 5/2005 |
| WO | WO 2006/007850 A1 | 1/2006 |
| WO | WO 2006/007853 A2 | 1/2006 |
| WO | WO 2006/023029 A2 | 3/2006 |
| WO | WO 2007/065433 A2 | 6/2007 |
| WO | WO 2007/101441 A1 * | 9/2007 |
| WO | WO 2008/095504 A1 | 8/2008 |

OTHER PUBLICATIONS

Rudikoff et al. PNAS USA, 1982, 79:1979.*
MacCallum et al. J. Mol. Biol., 1996, 262:732-745.*
De Pascalis et al. The Journal of Immunology, 2002, 169:3076-3084.*
Casset et al. BBRC, 2003, 307:198-205.*
Åkerlind-Stopner, B., et al., "Antibody Responses of Children to the C-Terminal Peptide of the SH Protein of Respiratory Syncytial Virus and the Immunological Characterization of This Protein," *J. Med. Virol.* 40:112-120, Wiley-Liss, Inc. (1993).
Anderson, L.J., et al., "Antigenic Characterization of Respiratory Syncytial Virus Strains with Monoclonal Antibodies," *J. Infect. Dis.* 151:626-633, The University of Chicago (1985).
Anderson, L.J., et al., "Identification of Epitopes on Respiratory Syncytial Virus Proteins by Competitive Binding Immunoassay," *J. Clin. Microbiol.* 23:475-480, American Society for Microbiology (1986).
Anderson, L.J., et al., "Neutralization of Respiratory Syncytial Virus by Individual and Mixtures of F and G Protein Monoclonal Antibodies," *J. Virol.* 62:4232-4238, American Society for Microbiology (1988).
Arbiza, J., et al., "Characterization of two antigenic sites recognized by neutralizing monoclonal antibodies directed against the fusion glycoprotein of human respiratory syncytial virus," *J. Gen. Virol.* 73:2225-2234, SGM (1992).
Barbas III, C.F., et al., "Human monoclonal Fab fragments derived from a combinatorial library bind to respiratory syncytial virus F glycoprotein and neutralize infectivity," *Proc. Natl. Acad. Sci. USA* 89:10164-10168, National Academy of Sciences (1992).

(Continued)

*Primary Examiner*—Stacy B Chen
(74) *Attorney, Agent, or Firm*—Sterne, Kessler, Goldstein & Fox P.L.L.C.

(57) ABSTRACT

Disclosed are novel polyclonal antibodies, which target respiratory syncytial virus (RSV), as well as novel high affinity antibody molecules reactive with RSV. The polyclonal antibodies may comprise antibody molecules which are reactive with both RSV protein F and RSV protein G, and preferably the polyclonal antibodies target a variety of epitopes on these proteins. The antibody molecules of the invention have shown superior efficacy in vitro and/or in vivo. Also disclosed are methods of producing the antibodies of the invention as well as methods of their use in treatment or prevention of RSV infection.

14 Claims, 6 Drawing Sheets

OTHER PUBLICATIONS

Beeler, J.A., and Van Wyke Coelingh, K., "Neutralization Epitopes of the F Glycoprotein of Respiratory Syncytial Virus: Effect of Mutation upon Fusion Function," *J. Virol.* 63:2941-2950, American Society for Microbiology (1989).

Brams, P., et al., "Antigen-Specific IgG Responses from Naive Human Splenocytes: In Vitro Priming Followed by Antigen Boost in the SCID Mouse," *J. Immunol.* 160:2051-2058, The American Association of Immunologies (1998).

Bregenholt, S., et al., "Recombinant Human Polyclonal Antibodies: A New Class of Therapeutic Antibodies Against Viral Infections," *Curr. Pharm. Des.* 12:2007-2015, Bentham Science Publishers Ltd. (2006).

Bukreyev, A., et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," *J. Virol.* 71:8973-8982, American Society for Microbiology (1997).

Chamat, S., et al., "Human Monoclonal Antibodies Isolated from Spontaneous Epstein-Barr Virus-Transformed Tumors of Hu-SPL-SCID Mice and Specific for Fusion Protein Display Broad Neutralizing Activity Toward Respiratory Syncytial Virus," *J. Infect. Dis.* 180:268-277, Infectious Diseases Society of America (1999).

Collins, P.L., et al., "Respiratory Syncytial Virus," in *Fields Virol.*, Fields, B.N., et al., eds., Lippincott-Raven Publishers, Philadelphia, PA, pp. 1313-1351 (1996).

Crowe, Jr., J.E., et al., "Recombinant human respiratory syncytial virus (RSV) monoclonal antibody Fab is effective therapeutically when introduced directly into the lungs of RSV-infected mice," *Proc. Natl. Acad. Sci. USA* 91:1386-1390, National Academy of Sciences (1994).

Crowe, Jr., J.E., et al., "Isolation of a Second Recombinant Human Respiratory Syncytial Virus Monoclonal Antibody Fragment (Fab RSVF2-5) that Exhibits Therapeutic Efficacy In Vivo," *J. Infect. Dis.* 177:1073-1076, The University of Chicago (1998).

Crowe, Jr., J.E., et al., "Monoclonal Antibody-Resistant Mutants Selected with a Respiratory Syncytial Virus-Neutralizing Human Antibody Fab Fragment (Fab 19) Define a Unique Epitope on the Fusion (F) Glycoprotein," *Virology* 252:373-375, Academic Press (1998).

De Bono, B., et al., "$V_H$ Gene Segments in the Mouse and Human Genomes," *J. Mol. Biol.* 342:131-143, Elsevier Ltd. (2004).

Delagrave, S., et al., "Effects of humanization by variable domain resurfacing on the antiviral activity of a single-chain antibody against respiratory syncytial virus," *Prot. Eng.* 12:357-362, Oxford University Press (1999).

García-Barreno, B., et al., "Marked Differences in the Antigenic Structure of Human Respiratory Syncytial Virus F and G Glycoproteins," *J. Virol.* 63:925-932, American Society for Microbiology (1989).

Guirakhoo, F., et al., "Cloning, expression and functional activities of a single chain antibody fragment directed to fusion protein of respiratory syncytial virus," *Immunotechnology* 2:219-228, Elsevier Science B.V. (1996).

Haurum, J.S., "Recombinant polyclonal antibodies: the next generation of antibody therapeutics?," *Drug Disc. Today* 11:655-660, Elsevier Ltd (Jul. 2006).

Heard, C., et al., "Two Neutralizing Human Anti-RSV Antibodies: Cloning, Expression, and Characterization," *Mol. Med.* 5:35-45, The Picower Institute Press (1999).

Johnson, S., et al., "Development of a Humanized Monoclonal Antibody (MEDI-493) with Potent In Vitro and In Vivo Activity against Respiratory Syncytial Virus," *J. Infect. Dis.* 176:1215-1224, The University of Chicago (1997).

Johnson, S., et al., "A Direct Comparison of the Activities of Two Humanized Respiratory Syncytial Virus Monoclonal Antibodies: MEDI-493 and RSHZ19," *J. Infect. Dis.* 180:35-40, Infectious Diseases Society of America (1999).

Logtenberg, T., "Antibody cocktails: next-generation biopharmaceuticals with improved potency," *Trends in Biotechnology* 25:390-394, Elsevier Ltd. (2007).

López, J.A., et al., "Antigenic Structure of Human Respiratory Syncytial Virus Fusion Glycoprotein," *J. Virol.* 72:6922-6928, American Society for Microbiology (1998).

Maggon, K., and Barik, S., "New drugs and treatment for respiratory syncytial virus," *Rev. Med. Virol.* 14:149-168, John Wiley & Sons, Ltd. (2004).

Martínez, I., et al., "Antigenic structure of the human respiratory syncytial virus G glycoprotein and relevance of hypermutation events for the generation of antigenic variants," *J. Gen. Virol.* 78:2419-2429, SGM (1997).

Martínez, I., and Melero, J.A., "Enhanced neutralization of human respiratory syncytial virus by mixtures of monoclonal antibodies to the attachment (G) glycoprotein," *J. Gen. Virol.* 79:2215-2220, SGM (1998).

McGill, A., et al., "Analysis of the binding of monoclonal and polyclonal antibodies to the glycoproteins of antigenic variants of human respiratory syncytial virus by surface plasmon resonance," *J. Immunol. Methods* 297:143-152, Elsevier B.V. (Feb. 2005).

MedImmune, Inc., "RespiGam, Respiratory Syncytial Virus Immune Globulin Intravenous (Human) RSV-IGIV," *Product Insert*, 2 pages, MedImmune, Inc. (2000).

Meijer, P.-J., et al., "Isolation of Human Antibody Repertoires with Preservation of the Natural Heavy and Light Chain Pairing," *J. Mol. Biol.* 358:764-772, Elsevier Ltd. (May 2006).

Mejías, A., et al., "Comparative Effects of Two Neutralizing Anti-Respiratory Syncytial Virus (RSV) Monoclonal Antibodies in the RSV Murine Model: Time versus Potency," *Antimicrob. Agents Chemother.* 49:4700-4707, American Society for Microbiology (Nov. 2005).

Morgan, L.A., et al., "Strain Variation of Respiratory Syncytial Vitus," *J. Gen. Virol.* 68:2781-2788, SGM (1987).

Ogra, P.L., "Respiratory syncytial virus: The virus, the disease and the immune response," *Paed. Resp. Rev.* 5(*Suppl. A*):S119-S126, Elsevier Science Ltd. (2004).

Prince, G.A., et al., "Mechanism of Antibody-Mediated Viral Clearance in Immunotherapy of Respiratory Syncytial Virus Infection of Cotton Rats," *J. Virol.* 64:3091-3092, American Society for Microbiology (1990).

Rixon, H.W.M., et al., "The small hydrophobic (SH) protein accumulates within lipid-raft structures of the Golgi complex during respiratory syncytial virus infection," *J. Gen. Virol.* 85:1153-1165, SGM (2004).

Polack, F.P., et al., "The cysteine-rich region of respiratory syncytial virus attachment protein inhibits innate immunity elicited by the virus and endotoxin," *Proc. Natl. Acad. Sci. USA* 102:8996-9001, National Academy of Sciences (Jun. 2005).
Poulsen, T.R., et al., "Kinetic, Affinity, and Diversity Limits of Human Polyclonal Antibody Responses against Tetanus Toxoid," *The Journal of Immunology 179*:3841-3850, The American Association of Immunologists, Inc. (2007).
Sastre, P., et al., "Comparison of Affinity Chromatography and Adsorption to Vaccinia Virus Recombinant Infected Cells for Depletion of Antibodies Directed Against Respiratory Syncytial Virus Glycoproteins Present in a Human Immunoglobulin Preparation," *J. Med. Virol. 76*:248-255, Wiley-Liss, Inc. (Jun. 2005).
Sharon, J., et al., "Recombinant Polyclonal Antibodies for Cancer Therapy," *Journal of Cellular Biochemistry 96*:305-313, Wiley-Liss, Inc. (Oct. 2005).
Sominina, A.A., et al., "Characteristics of monoclonal antibodies to RS virus in immunoenzyme and immunofluorescence techniques," *Vestn. Ross. Akad. Med. Nauk. 9*:49-54 (1995), abstract only.
Sullender, W., "Antigenic Analysis of Chimeric and Truncated G Proteins of Respiratory Syncytial Virus," *Virology 209*:70-79, Academic Press, Inc. (1995).
Sullender, W.M., "Respiratory Syncytial Virus Genetic and Antigenic Diversity," *Clin. Microbiol. Rev. 13*:1-15, American Society for Microbiology (2000).
Taylor, G., et al., "Monoclonal antibodies protect against respiratory syncytial virus infection in mice," *Immunology 52*:137-142, Blackwell Scientific Publications (1984).
Tempest, P.R., et al., "Reshaping a Human Monoclonal Antibody to Inhibit Human Respiratory Syncytial Virus Infection In Vivo," *Bio/Technology 9*:266-271, Nature Publishing Company (1991).

Tolstrup, A.B., et al., "Development of recombinant human polyclonal antibodies for the treatment of complex human diseases," *Expert Opin. Biol. Ther*. 6:905-912, Informa UK Ltd. (Sep. 2006).

Tripp, R.A., et al., "The G Glycoprotein of Respiratory Syncytial Virus Depresses Respiratory Rates through the CX3C Motif and Substance P," *J. Virol*. 77:6580-6584, American Society for Microbiology (2003).

Walsh, E.E., et al., "Protection from Respiratory Syncytial Virus Infection in Cotton Rats by Passive Transfer of Monoclonal Antibodies," *Infect. Immun*. 43:756-758, American Society for Microbiology (1984).

Walsh, E.E., et al., "Comparison of Antigenic Sites of Subtype-specific Respiratory Syncytial Virus Attachment Proteins," *J. Gen. Virol*. 70:2953-2961, SGM (1989).

Walsh, E.E., et al., "Monoclonal antibody neutralization escape mutants of respiratory syncytial virus with unique alterations in the attachment (G) protein," *J. Gen. Virol*. 79:479-487, SGM (1998).

Weltzin, R., et al., "Intranasal Monoclonal Immunoglobulin A against Respiratory Syncytial Virus Protects against Upper and Lower Respiratory Tract Infections in Mice," *Antimicrob. Agents Chemother*. 38:2785-2791, American Society for Microbiology (1994).

Weltzin, R., et al., "Intranasal Monoclonal IgA Antibody to Respiratory Syncytial Virus Protects Rhesus Monkeys against Upper and Lower Respiratory Tract Infection," *J. Infect. Dis*. 174:256-261, The University of Chicago (1996).

Wiberg, F.C., et al., "Production of Target-Specific Recombinant Human Polyclonal Antibodies in Mammalian Cells," *Biotechnol. Bioeng*. 94:396-405, Wiley Periodicals, Inc. (Jun. 2006).

Zhao, X., et al., "Variable Resistance to Palivizumab in Cotton Rats by Respiratory Syncytial Virus Mutants," *J. Infect. Dis*. *190*:1941-1946, Infectious Diseases Society of America (2004).

Zhao, X., and Sullender, W.M., "In Vivo Selection of Respiratory Syncytial Viruses Resistant to Palivizumab," *J. Virol*. 79:3962-3968, American Society for Microbiology (Apr. 2005).

International Search Report for International Application No. PCT/DK2007/000113, European Patent Office, Netherlands, mailed on Aug. 9, 2007.

Co-pending U.S. Appl. No. 11/632,937 inventors Rasmussen, S.K., et al., filed Jan. 19, 2007.

Co-pending U.S. Appl. No. 11/633,070, inventors Jensen, A., et al., filed Dec. 4, 2006.

Co-pending U.S. Appl. No. 11/792,927, inventors Lantto, J., et al., filed Mar. 6, 2007.

Co-pending U.S. Appl. No. 12/068,654, inventors Norgaard, J.V., et al., filed Feb. 8, 2008.

* cited by examiner

Fig. 2
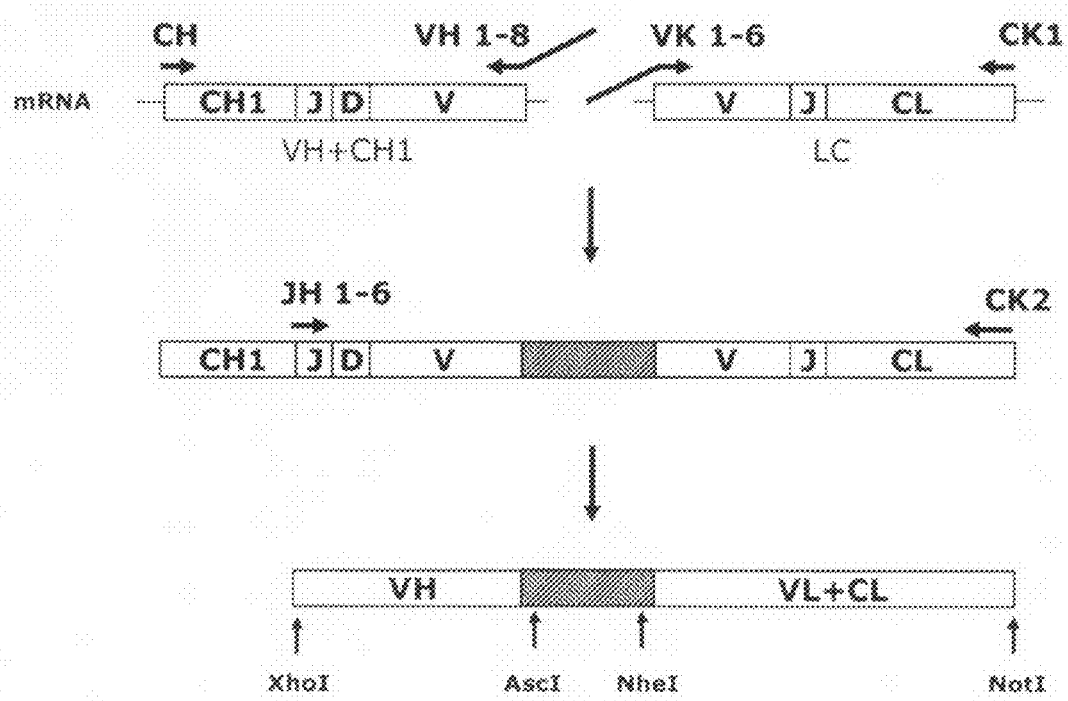
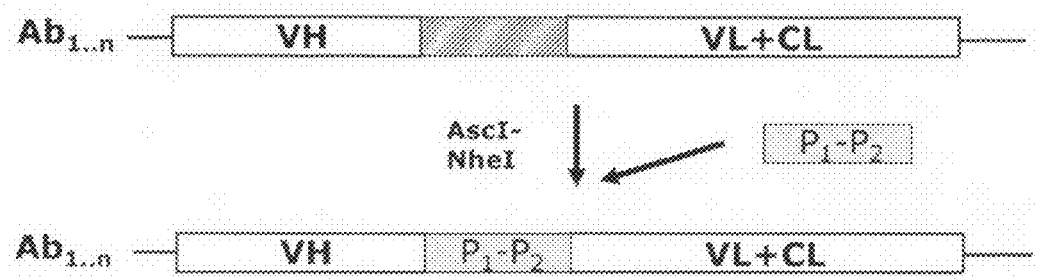

Fig. 5
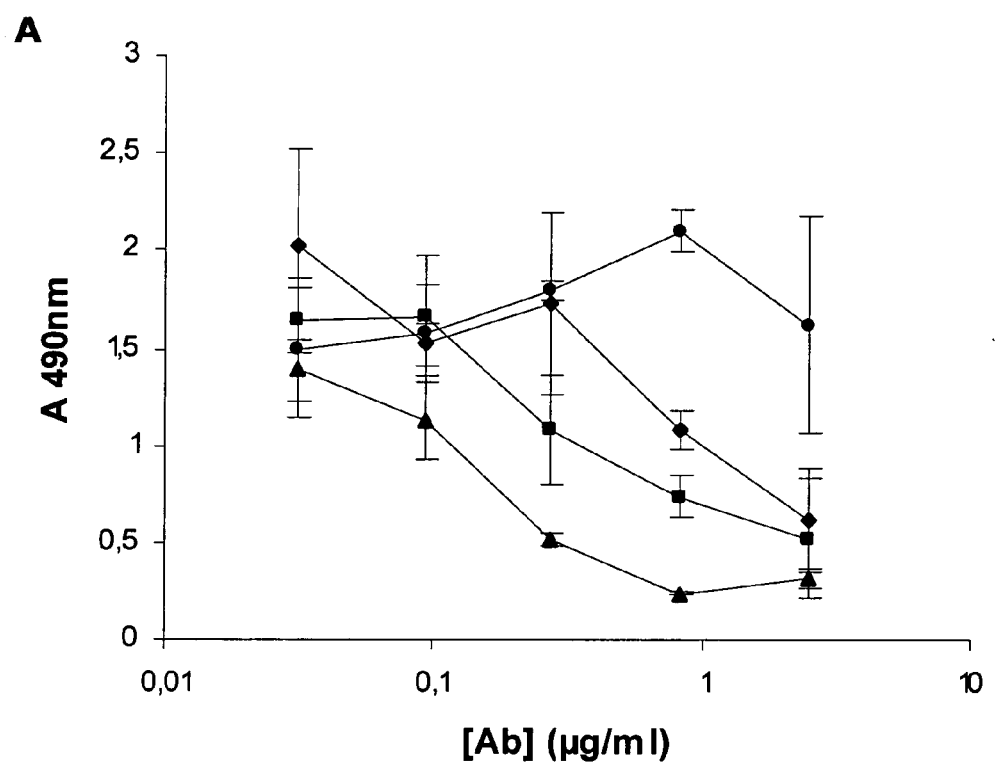
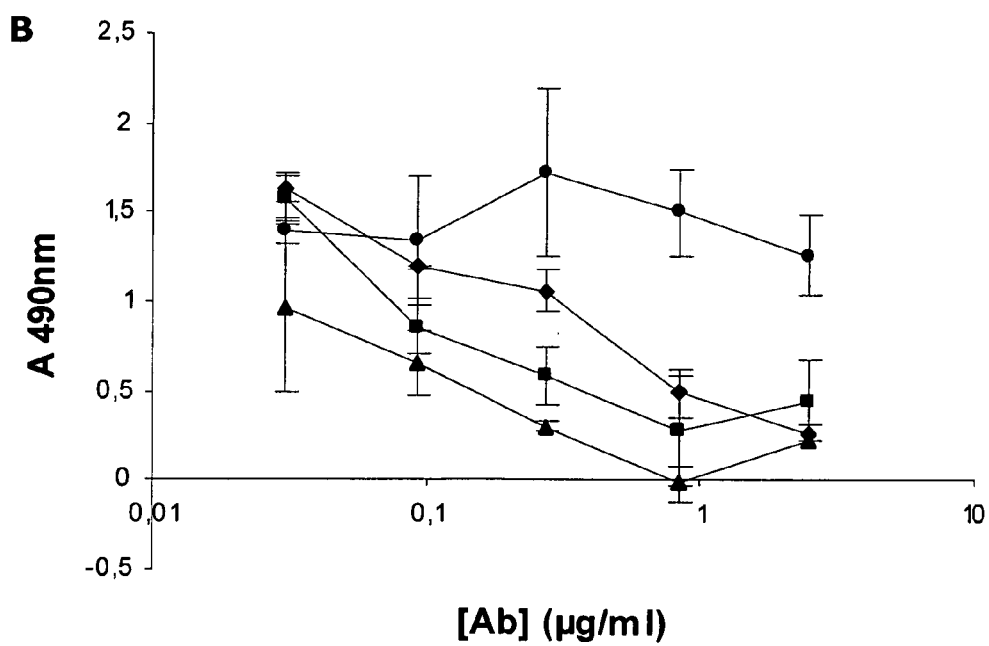

SEQUENCE LISTING

```
<160> NUMBER OF SEQ ID NOS: 717

<210> SEQ ID NO 1
<211> LENGTH: 122
<212> TYPE: PRT
<213> ORGANISM: homo sapiens

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Asn Gly Ala Ile Gly Asp Tyr
            20                  25                  30

Asp Trp Ser Trp Ile Arg Gln Ser Pro Gly Lys Gly Leu Glu Trp Ile
        35                  40                  45

Gly Asn Ile Asn Tyr Arg Gly Asn Thr Asn Tyr Asn Pro Ser Leu Lys
    50                  55                  60

Ser Arg Val Thr Met Ser Leu Arg Thr Ser Thr Met Gln Phe Ser Leu
65                  70                  75                  80

Lys Leu Ser Ser Ala Thr Ala Ala Asp Thr Ala Val Tyr Tyr Cys Ala
                85                  90                  95

Arg Asp Val Gly Tyr Gly Gly Gly Gln Tyr Phe Ala Met Asp Val Trp
            100                 105                 110

Ser Pro Gly Thr Thr Val Thr Val Ser Ser
        115                 120

<210> SEQ ID NO 2
<211> LENGTH: 129
<212> TYPE: PRT
<213> ORGANISM: homo sapiens

<400> SEQUENCE: 2
```

```
Gln Val Gln Leu Val Glu Ser Gly Gly Val Val Gln Pro Gly Gly
1               5                   10                  15

Ser Leu Arg Leu Ser Cys Thr Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Thr Gln Asp Tyr Val Asp Ser Val
50                      55                  60

Lys Gly Arg Phe Thr Ile Ser Arg Asp Asn Ser Lys Asn Met Val Tyr
65                  70                  75                  80

Val Gln Met Asn Ser Leu Arg Val Glu Asp Thr Ala Val Tyr Tyr Cys
                85                  90                  95

Ala Lys Asp Met Asp Tyr Tyr Gly Ser Arg Ser Tyr Ser Val Thr Tyr
            100                 105                 110

Tyr Tyr Gly Met Asp Val Trp Gly Gln Gly Thr Thr Val Thr Val Ser
        115                 120                 125

Ser

<210> SEQ ID NO 3
<211> LENGTH: 125
<212> TYPE: PRT
<213> ORGANISM: homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Tyr
                20                  25                  30

Tyr Met His Trp Val Arg Gln Ala Pro Gly Gln Gly Leu Glu Trp Met
            35                  40                  45

Gly Trp Ile Asn Thr Ser Ser Gly Gly Thr Asn Tyr Ala Gln Lys Phe
50                      55                  60

Gln Gly Arg Val Thr Met Thr Arg Asp Thr Ser Ile Ser Thr Ala His
65                  70                  75                  80

Met Glu Leu Arg Arg Leu Arg Ser Asp Asp Thr Ala Val Tyr Tyr Cys
                85                  90                  95

Ala Arg Glu Asp Gly Thr Met Gly Thr Asn Ser Trp Tyr Gly Trp Phe
            100                 105                 110

Asp Pro Trp Gly Gln Gly Thr Leu Val Thr Val Ser Ser
        115                 120                 125

<210> SEQ ID NO 4
<211> LENGTH: 127
<212> TYPE: PRT
<213> ORGANISM: homo sapiens

<400> SEQUENCE: 4

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Gly Asp Tyr
                20                  25                  30

Tyr Met Ser Trp Ile Arg Gln Ala Pro Gly Lys Gly Leu Glu Trp Val
            35                  40                  45

Ala Tyr Ile Asn Arg Gly Gly Thr Thr Ile Tyr Tyr Ala Asp Ser Val
50                      55                  60

Lys Gly Arg Phe Thr Ile Ser Arg Asp Asn Ala Lys Asn Ser Leu Phe
```

```
                65                  70                  75                  80
Leu Gln Met Asn Ser Leu Arg Ala Gly Asp Thr Ala Leu Tyr Tyr Cys
                    85                  90                  95

Ala Arg Gly Leu Ile Leu Ala Leu Pro Thr Ala Thr Val Glu Leu Gly
                100                 105                 110

Ala Phe Asp Ile Trp Gly Gln Gly Thr Met Val Thr Val Ser Ser
            115                 120                 125

<210> SEQ ID NO 5
<211> LENGTH: 126
<212> TYPE: PRT
<213> ORGANISM: homo sapiens

<400> SEQUENCE: 5

Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Ile Ser Ser Gly
                20                  25                  30

Asp Tyr Tyr Trp Ser Trp Ile Arg Gln Ser Pro Arg Lys Gly Leu Glu
            35                  40                  45

Trp Ile Gly Tyr Ile Phe His Ser Gly Thr Thr Tyr Tyr Asn Pro Ser
        50                  55                  60

Leu Lys Ser Arg Ala Val Ile Ser Leu Asp Thr Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Asp Val Asp Asp Phe Pro Val Trp Gly Met Asn Arg Tyr
                100                 105                 110

Leu Ala Leu Trp Gly Arg Gly Thr Leu Val Thr Val Ser Ser
            115                 120                 125

<210> SEQ ID NO 6
<211> LENGTH: 124
<212> TYPE: PRT
<213> ORGANISM: homo sapiens

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser His Phe
                20                  25                  30

Gly Met His Trp Val Arg Gln Val Pro Gly Lys Gly Leu Glu Trp Val
            35                  40                  45

Ala Ile Ile Ser Tyr Asp Gly Asn Asn Val His Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Asp Asp Thr Gly Val Tyr Tyr Cys
                85                  90                  95

Ala Lys Asp Asp Val Ala Thr Asp Leu Ala Ala Tyr Tyr Tyr Phe Asp
                100                 105                 110

Val Trp Gly Arg Gly Thr Leu Val Thr Val Ser Ser
            115                 120

<210> SEQ ID NO 7
<211> LENGTH: 123
<212> TYPE: PRT
```

<213> ORGANISM: homo sapiens

<400> SEQUENCE: 7

Gln Val Gln Leu Val Glu Ser Gly Gly Gly Val Val Gln Pro Gly Arg
1               5                   10                  15

Ser Leu Lys Leu Ser Cys Glu Ala Ser Gly Phe Asn Phe Asn Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Arg Asn Lys Tyr Phe Ala Asp Ser Val
    50                  55                  60

Lys Gly Arg Phe Ile Ile Ser Arg Asp Asp Ser Arg Asn Thr Val Phe
65                  70                  75                  80

Leu Gln Met Asn Ser Leu Arg Val Glu Asp Thr Ala Val Tyr Tyr Cys
                85                  90                  95

Ala Arg Gly Ser Val Gln Val Trp Leu His Leu Gly Leu Phe Asp Asn
            100                 105                 110

Trp Gly Gln Gly Thr Leu Val Thr Val Ser Ser
        115                 120

<210> SEQ ID NO 8
<211> LENGTH: 122
<212> TYPE: PRT
<213> ORGANISM: homo sapiens

<400> SEQUENCE: 8

Gln Val Gln Leu Val Glu Ser Gly Gly Ala Val Val Gln Pro Gly Arg
1               5                   10                  15

Ser Leu Arg Leu Ser Cys Glu Val Ser Gly Phe Ser Phe Ser Asp Tyr
            20                  25                  30

Gly Met Asn Trp Val Arg Gln Gly Pro Gly Lys Gly Leu Glu Trp Val
        35                  40                  45

Ala Val Ile Trp His Asp Gly Ser Asn Lys Asn Tyr Leu Asp Ser Val
    50                  55                  60

Lys Gly Arg Phe Thr Val Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Thr Pro Tyr Glu Phe Trp Ser Gly Tyr Tyr Phe Asp Phe Trp
            100                 105                 110

Gly Gln Gly Thr Leu Val Thr Val Ser Ser
        115                 120

<210> SEQ ID NO 9
<211> LENGTH: 116
<212> TYPE: PRT
<213> ORGANISM: homo sapiens

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Phe Asn Ser Tyr
            20                  25                  30

Ala Met His Trp Val Arg Gln Ala Pro Gly Lys Gly Leu Glu Trp Val
        35                  40                  45

Ala Val Ile Tyr Tyr Glu Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Lys Trp Leu Gly Met Asp Phe Trp Gly Gln Gly Thr Leu Val
            100                 105                 110

Thr Val Ser Ser
        115

<210> SEQ ID NO 10
<211> LENGTH: 120
<212> TYPE: PRT
<213> ORGANISM: homo sapiens

<400> SEQUENCE: 10

Glu Val Gln Leu Val Glu Ser Gly Gly Gly Leu Val Arg Pro Gly Gly
1               5                   10                  15

Ser Leu Arg Leu Ser Cys Ser Ala Ser Gly Phe Thr Phe Ser Asn Tyr
            20                  25                  30

Ala Met His Trp Val Arg Gln Ala Pro Gly Lys Arg Leu Glu Tyr Val
        35                  40                  45

Ser Ala Thr Ser Thr Asp Gly Gly Ser Thr Tyr Tyr Ala Asp Ser Leu
    50                  55                  60

Lys Gly Thr Phe Thr Ile Ser Arg Asp Asn Ser Lys Asn Thr Leu Tyr
65                  70                  75                  80

Leu Gln Met Ser Ser Leu Ser Thr Glu Asp Thr Ala Ile Tyr Tyr Cys
                85                  90                  95

Ala Arg Arg Phe Trp Gly Phe Gly Asn Phe Phe Asp Tyr Trp Gly Arg
            100                 105                 110

Gly Thr Leu Val Thr Val Ser Ser
            115                 120

<210> SEQ ID NO 11
<211> LENGTH: 122
<212> TYPE: PRT
<213> ORGANISM: homo sapiens

<400> SEQUENCE: 11

Gln Val Gln Leu Val Gln Ser Gly Ala Glu Val Lys Lys Ser Gly Ser
1               5                   10                  15

Ser Val Lys Val Ser Cys Arg Ala Ser Gly Gly Thr Phe Gly Asn Tyr
            20                  25                  30

Ala Ile Asn Trp Val Arg Gln Ala Pro Gly Gln Gly Leu Glu Trp Val
        35                  40                  45

Gly Arg Ile Ile Pro Val Phe Asp Thr Thr Asn Tyr Ala Gln Lys Phe
    50                  55                  60

Gln Gly Arg Val Thr Ile Thr Ala Asp Arg Ser Thr Asn Thr Ala Ile
65                  70                  75                  80

Met Gln Leu Ser Ser Leu Arg Pro Gln Asp Thr Ala Met Tyr Tyr Cys
                85                  90                  95

Leu Arg Gly Ser Thr Arg Gly Trp Asp Thr Asp Gly Phe Asp Ile Trp
            100                 105                 110

Gly Gln Gly Thr Met Val Thr Val Ser Ser
            115                 120

<210> SEQ ID NO 12

```
<211> LENGTH: 129
<212> TYPE: PRT
<213> ORGANISM: homo sapiens

<400> SEQUENCE: 12

Gln Val Gln Leu Val Gln Ser Gly Ala Val Val Glu Thr Pro Gly Ala
1               5                   10                  15

Ser Val Lys Val Ser Cys Lys Ala Ser Gly Tyr Ile Phe Gly Asn Tyr
            20                  25                  30

Tyr Ile His Trp Val Arg Gln Ala Pro Gly Gln Gly Leu Glu Trp Met
        35                  40                  45

Ala Val Ile Asn Pro Asn Gly Gly Ser Thr Thr Ser Ala Gln Lys Phe
    50                  55                  60

Gln Asp Arg Ile Thr Val Thr Arg Asp Thr Ser Thr Thr Thr Val Tyr
65                  70                  75                  80

Leu Glu Val Asp Asn Leu Arg Ser Gly Asp Thr Ala Thr Tyr Tyr Cys
                85                  90                  95

Ala Arg Gln Arg Ser Val Thr Gly Gly Phe Asp Ala Trp Leu Leu Ile
            100                 105                 110

Pro Asp Ala Ser Asn Thr Trp Gly Gln Gly Thr Met Val Thr Val Ser
        115                 120                 125

Ser

<210> SEQ ID NO 13
<211> LENGTH: 126
<212> TYPE: PRT
<213> ORGANISM: homo sapiens

<400> SEQUENCE: 13

Gln Val Gln Leu Val Gln Ser Gly Ala Glu Met Lys Lys Pro Gly Ser
1               5                   10                  15

Ser Val Lys Val Ser Cys Lys Ala Ser Gly Gly Ser Phe Ser Ser Tyr
            20                  25                  30

Ser Ile Ser Trp Val Arg Gln Ala Pro Gly Arg Gly Leu Glu Trp Val
        35                  40                  45

Gly Met Ile Leu Pro Ile Ser Gly Thr Thr Asn Tyr Ala Gln Thr Phe
    50                  55                  60

Gln Gly Arg Val Ile Ile Ser Ala Asp Thr Ser Thr Ser Thr Ala Tyr
65                  70                  75                  80

Met Glu Leu Thr Ser Leu Thr Ser Glu Asp Thr Ala Val Tyr Phe Cys
                85                  90                  95

Ala Arg Val Phe Arg Glu Phe Ser Thr Ser Leu Asp Pro Tyr Tyr
            100                 105                 110

Phe Asp Tyr Trp Gly Gln Gly Thr Leu Val Thr Val Ser Ser
        115                 120                 125

<210> SEQ ID NO 14
<211> LENGTH: 125
<212> TYPE: PRT
<213> ORGANISM: homo sapiens

<400> SEQUENCE: 14

Gln Val Gln Leu Val Glu Ser Gly Gly Val Val Gln Pro Gly Lys
1               5                   10                  15

Ser Val Arg Leu Ser Cys Val Gly Ser Gly Phe Arg Leu Met Asp Tyr
            20                  25                  30

Ala Met His Trp Val Arg Gln Ala Pro Gly Lys Gly Leu Asp Trp Val
```

```
                35                  40                  45
Ala Val Ile Ser Tyr Asp Gly Ala Asn Glu Tyr Tyr Ala Glu Ser Val
 50                  55                  60
Lys Gly Arg Phe Thr Val Ser Arg Asp Asn Ser Asp Asn Thr Leu Tyr
 65                  70                  75                  80
Leu Gln Met Lys Ser Leu Arg Ala Glu Asp Thr Ala Val Tyr Phe Cys
                 85                  90                  95
Ala Arg Ala Gly Arg Ser Ser Met Asn Glu Val Ile Met Tyr Phe
            100                 105                 110
Asp Asn Trp Gly Leu Gly Thr Leu Val Thr Val Ser Ser
            115                 120                 125

<210> SEQ ID NO 15
<211> LENGTH: 127
<212> TYPE: PRT
<213> ORGANISM: homo sapiens

<400> SEQUENCE: 15

Glu Val Gln Leu Leu Glu Ser Gly Gly Gly Leu Val Gln Pro Gly Gly
 1               5                  10                  15
Ser Leu Arg Leu Ser Cys Val Ala Ser Gly Phe Thr Phe Ser Thr Tyr
             20                  25                  30
Ala Met Thr Trp Val Arg Gln Ala Pro Gly Lys Gly Leu Glu Trp Val
             35                  40                  45
Ser Val Ile Arg Ala Ser Gly Asp Ser Glu Ile Tyr Ala Asp Ser Val
 50                  55                  60
Arg Gly Arg Phe Thr Ile Ser Arg Asp Asn Ser Lys Asn Thr Val Phe
 65                  70                  75                  80
Leu Gln Met Asp Ser Leu Arg Val Glu Asp Thr Ala Val Tyr Phe Cys
                 85                  90                  95
Ala Asn Ile Gly Gln Arg Arg Tyr Cys Ser Gly Asp His Cys Tyr Gly
            100                 105                 110
His Phe Asp Tyr Trp Gly Gln Gly Thr Leu Val Thr Val Ser Ser
            115                 120                 125

<210> SEQ ID NO 16
<211> LENGTH: 127
<212> TYPE: PRT
<213> ORGANISM: homo sapiens

<400> SEQUENCE: 16

Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Gly Phe Asn Thr His
             20                  25                  30
Gly Met His Trp Val Arg Gln Ala Pro Gly Lys Gly Leu Glu Trp Leu
             35                  40                  45
Ser Ile Ile Ser Leu Asp Gly Ile Lys Thr His Tyr Ala Asp Ser Val
 50                  55                  60
Lys Gly Arg Phe Thr Ile Ser Arg Asp Asn Ser Lys Asn Thr Val Phe
 65                  70                  75                  80
Leu Gln Leu Ser Gly Leu Arg Pro Glu Asp Thr Ala Val Tyr Tyr Cys
                 85                  90                  95
Ala Lys Asp His Ile Gly Gly Thr Asn Ala Tyr Phe Glu Trp Thr Val
            100                 105                 110
Pro Phe Asp Gly Trp Gly Gln Gly Thr Leu Val Thr Val Ser Ser
```

```
                115                 120                 125

<210> SEQ ID NO 17
<211> LENGTH: 126
<212> TYPE: PRT
<213> ORGANISM: homo sapiens

<400> SEQUENCE: 17

Gln Val Thr Leu Arg Glu Ser Gly Pro Ala Val Val Lys Pro Thr Glu
1               5                   10                  15

Thr Leu Thr Leu Thr Cys Ala Phe Ser Gly Phe Ser Leu Asn Ala Gly
            20                  25                  30

Arg Val Gly Val Ser Trp Ile Arg Gln Pro Pro Gly Gln Ala Pro Glu
        35                  40                  45

Trp Leu Ala Arg Ile Asp Trp Asp Asp Lys Ala Phe Arg Thr Ser
    50                  55                  60

Leu Lys Thr Arg Leu Ser Ile Ser Lys Asp Ser Ser Lys Asn Gln Val
65                  70                  75                  80

Val Leu Thr Leu Ser Asn Met Asp Pro Ala Asp Thr Ala Thr Tyr Tyr
                85                  90                  95

Cys Ala Arg Thr Gln Val Phe Ala Ser Gly Gly Tyr Tyr Leu Tyr Tyr
            100                 105                 110

Leu Asp His Trp Gly Gln Gly Thr Leu Val Thr Val Ser Ser
        115                 120                 125

<210> SEQ ID NO 18
<211> LENGTH: 129
<212> TYPE: PRT
<213> ORGANISM: homo sapiens

<400> SEQUENCE: 18

Gln Val Gln Leu Gln Glu Ser Gly Pro Gly Leu Val Lys Pro Ser Gln
1               5                   10                  15

Thr Leu Ser Leu Thr Cys Thr Val Ser Ser Gly Ala Ile Ser Gly Ala
            20                  25                  30

Asp Tyr Tyr Trp Ser Trp Ile Arg Gln Pro Pro Gly Lys Gly Leu Glu
        35                  40                  45

Trp Val Gly Phe Ile Tyr Asp Ser Gly Ser Thr Tyr Tyr Asn Pro Ser
    50                  55                  60

Leu Arg Ser Arg Val Thr Ile Ser Ile Asp Thr Ser Lys Lys Gln Phe
65                  70                  75                  80

Ser Leu Lys Leu Thr Ser Val Thr Ala Ala Asp Thr Ala Val Tyr Tyr
                85                  90                  95

Cys Ala Arg Asp Leu Gly Tyr Gly Gly Asn Ser Tyr Ser His Ser Tyr
            100                 105                 110

Tyr Tyr Gly Leu Asp Val Trp Gly Arg Gly Thr Thr Val Thr Val Ser
        115                 120                 125

Ser

<210> SEQ ID NO 19
<211> LENGTH: 119
<212> TYPE: PRT
<213> ORGANISM: homo sapiens

<400> SEQUENCE: 19

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Gly Asn Tyr
                20                  25                  30

Tyr Trp Gly Trp Ile Arg Gln Pro Pro Gly Lys Gly Leu Glu Trp Ile
            35                  40                  45

Gly His Ile Tyr Phe Gly Gly Asn Thr Asn Tyr Asn Pro Ser Leu Gln
    50                  55                  60

Ser Arg Val Thr Ile Ser Val Asp Thr Ser Arg Asn Gln Phe Ser Leu
65                  70                  75                  80

Lys Leu Asn Ser Val Thr Ala Ala Asp Thr Ala Val Tyr Tyr Cys Ala
                85                  90                  95

Arg Asp Ser Ser Asn Trp Pro Ala Gly Tyr Glu Asp Trp Gly Gln Gly
                100                 105                 110

Thr Leu Val Thr Val Ser Ser
            115
```

<210> SEQ ID NO 20
<211> LENGTH: 123
<212> TYPE: PRT
<213> ORGANISM: homo sapiens

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Asn
                20                  25                  30

Gly Leu Ser Trp Val Arg Gln Ala Pro Gly Gln Gly Phe Glu Trp Leu
            35                  40                  45

Gly Trp Ile Ser Ala Ser Ser Gly Asn Lys Lys Tyr Ala Pro Lys Phe
    50                  55                  60

Gln Gly Arg Val Thr Leu Thr Thr Asp Ile Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Gly Gly Thr Tyr Val Pro Tyr Ser Asp Ala Phe Asp Phe
                100                 105                 110

Trp Gly Gln Gly Thr Met Val Thr Val Ser Ser
            115                 120
```

<210> SEQ ID NO 21
<211> LENGTH: 118
<212> TYPE: PRT
<213> ORGANISM: homo sapiens

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Arg Val Ser Gly His Thr Phe Thr Ala Leu
                20                  25                  30

Ser Lys His Trp Met Arg Gln Gly Pro Gly Gly Gly Leu Glu Trp Met
                35                  40                  45

Gly Phe Phe Asp Pro Glu Asp Gly Asp Thr Gly Tyr Ala Gln Lys Phe
    50                  55                  60

Gln Gly Arg Val Thr Met Thr Glu Asp Thr Ala Thr Gly Thr Ala Tyr
65                  70                  75                  80

Met Glu Leu Ser Ser Leu Thr Ser Asp Asp Thr Ala Val Tyr Tyr Cys
                85                  90                  95
```

-continued

Ala Thr Val Ala Ala Ala Gly Asn Phe Asp Asn Trp Gly Gln Gly Thr
            100                 105                 110

Leu Val Thr Val Ser Ser
        115

<210> SEQ ID NO 22
<211> LENGTH: 126
<212> TYPE: PRT
<213> ORGANISM: homo sapiens

<400> SEQUENCE: 22

Gln Val Thr Leu Lys Glu Ser Gly Pro Ala Leu Val Lys Ala Thr Gln
1               5                   10                  15

Thr Leu Thr Leu Thr Cys Thr Phe Ser Gly Phe Ser Leu Ser Arg Asn
            20                  25                  30

Arg Met Ser Val Ser Trp Ile Arg Gln Pro Pro Gly Lys Ala Leu Glu
        35                  40                  45

Trp Leu Ala Arg Ile Asp Trp Asp Asp Lys Phe Tyr Asn Thr Ser
50                  55                  60

Leu Gln Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Gly Ile Tyr Asp Ser Ser Gly Tyr Tyr Leu Tyr Tyr
            100                 105                 110

Phe Asp Tyr Trp Gly Gly Thr Leu Val Thr Val Ser Ser
        115                 120                 125

<210> SEQ ID NO 23
<211> LENGTH: 130
<212> TYPE: PRT
<213> ORGANISM: homo sapiens

<400> SEQUENCE: 23

Gln Val Gln Leu Val Gln Ser Gly Ala Glu Val Lys Val Pro Gly Ala
1               5                   10                  15

Ser Val Lys Val Ser Cys Lys Ala Ser Gly Tyr Thr Phe Thr Thr Tyr
            20                  25                  30

Gly Val Ser Trp Val Arg Gln Ala Pro Gly Gln Gly Leu Glu Trp Met
        35                  40                  45

Gly Trp Ile Ser Ala Tyr Asn Gly Asn Thr Tyr Tyr Leu Gln Lys Leu
50                  55                  60

Gln Gly Arg Val Thr Met Thr Thr Asp Thr Ser Thr Ser Thr Ala Tyr
65                  70                  75                  80

Met Glu Leu Arg Gly Leu Arg Ser Asp Asp Thr Ala Met Tyr Tyr Cys
                85                  90                  95

Ala Arg Asp Arg Val Gly Gly Ser Ser Glu Val Leu Ser Arg Ala
            100                 105                 110

Lys Asn Tyr Gly Leu Asp Val Trp Gly Gln Gly Thr Thr Val Thr Val
        115                 120                 125

Ser Ser
    130

<210> SEQ ID NO 24
<211> LENGTH: 123
<212> TYPE: PRT
<213> ORGANISM: homo sapiens

```
<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Ala Asn Ile Phe Thr Tyr Ala
            20                  25                  30

Met His Trp Val Arg Gln Ala Pro Gly Gln Arg Leu Glu Trp Met Gly
        35                  40                  45

Trp Ile Asn Val Gly Asn Gly Gln Thr Lys Tyr Ser Gln Arg Phe Gln
    50                  55                  60

Gly Arg Val Thr Ile Thr Arg Asp Thr Ser Ala Thr Ala Tyr Met
65                  70                  75                  80

Glu Leu Ser Thr Leu Arg Ser Glu Asp Thr Ala Val Tyr Tyr Cys Ala
                85                  90                  95

Arg Arg Ala Ser Gln Tyr Gly Glu Val Tyr Gly Asn Tyr Phe Asp Tyr
            100                 105                 110

Trp Gly Gln Gly Thr Leu Val Thr Val Ser Ser
        115                 120

<210> SEQ ID NO 25
<211> LENGTH: 126
<212> TYPE: PRT
<213> ORGANISM: homo sapiens

<400> SEQUENCE: 25

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Ile Ser Tyr
            20                  25                  30

Gly Phe Ser Trp Val Arg Gln Ala Pro Gly Gln Gly Leu Glu Trp Met
        35                  40                  45

Gly Trp Ser Ser Val Tyr Asn Gly Asp Thr Asn Tyr Ala Gln Lys Phe
    50                  55                  60

His Gly Arg Val Asn Met Thr Thr Asp Thr Ser Thr Asn Thr Ala Tyr
65                  70                  75                  80

Met Glu Leu Arg Gly Leu Arg Ser Asp Asp Thr Ala Val Tyr Phe Cys
                85                  90                  95

Ala Arg Asp Arg Asn Val Val Leu Leu Pro Ala Ala Pro Phe Gly Gly
            100                 105                 110

Met Asp Val Trp Gly Gln Gly Thr Met Val Thr Val Ser Ser
        115                 120                 125

<210> SEQ ID NO 26
<211> LENGTH: 123
<212> TYPE: PRT
<213> ORGANISM: homo sapiens

<400> SEQUENCE: 26

Gln Val Gln Leu Val Glu Ser Gly Gly Gly Val Val Gln Pro Gly Thr
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Gly Lys Gly Leu Glu Trp Val
        35                  40                  45

Ala Val Ile Ser Tyr Asp Gly Asn Lys Lys Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Val Asn Ser Leu Arg Val Glu Asp Thr Ala Val Tyr Tyr Cys
                    85                  90                  95
Ala Ala Gln Thr Pro Tyr Phe Asn Glu Ser Ser Gly Leu Val Pro Asp
                    100                 105                 110
Trp Gly Gln Gly Thr Leu Val Thr Val Ser Ser
                    115                 120

<210> SEQ ID NO 27
<211> LENGTH: 126
<212> TYPE: PRT
<213> ORGANISM: homo sapiens

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Phe
                20                  25                  30

Gly Ile Ser Trp Val Arg Gln Ala Pro Gly Gln Gly Leu Glu Trp Met
                35                  40                  45

Gly Trp Ile Ser Ala Tyr Asn Gly Asn Thr Asp Tyr Ala Gln Arg Leu
            50                  55                  60

Gln Asp Arg Val Thr Met Thr Arg Asp Thr Ala Thr Ser Thr Ala Tyr
65                  70                  75                  80

Leu Glu Leu Arg Ser Leu Lys Ser Asp Asp Thr Ala Val Tyr Tyr Cys
                    85                  90                  95

Thr Arg Asp Glu Ser Met Leu Arg Gly Val Thr Glu Gly Phe Gly Pro
                    100                 105                 110

Ile Asp Tyr Trp Gly Gln Gly Thr Leu Val Thr Val Ser Ser
                    115                 120                 125

<210> SEQ ID NO 28
<211> LENGTH: 128
<212> TYPE: PRT
<213> ORGANISM: homo sapiens

<400> SEQUENCE: 28

Glu Val Gln Leu Val Gln Ser Gly Ala Glu Val Lys Lys Pro Gly Gln
1               5                   10                  15

Ser Leu Lys Ile Ser Cys Lys Thr Ser Gly Tyr Ile Phe Thr Asn Tyr
                20                  25                  30

Trp Ile Gly Trp Val Arg Gln Arg Pro Gly Lys Gly Leu Glu Trp Met
                35                  40                  45

Gly Val Ile Phe Pro Ala Asp Ser Asp Ala Arg Tyr Ser Pro Ser Phe
            50                  55                  60

Gln Gly Gln Val Thr Ile Ser Ala Asp Lys Ser Ile Gly Thr Ala Tyr
65                  70                  75                  80

Leu Gln Trp Ser Ser Leu Lys Ala Ser Asp Thr Ala Ile Tyr Tyr Cys
                    85                  90                  95

Ala Arg Pro Lys Tyr Tyr Phe Asp Ser Ser Gly Gln Phe Ser Glu Met
                    100                 105                 110

Tyr Tyr Phe Asp Phe Trp Gly Gln Gly Thr Leu Val Thr Val Ser Ser
                    115                 120                 125

<210> SEQ ID NO 29
<211> LENGTH: 119
<212> TYPE: PRT
```

<213> ORGANISM: homo sapiens

<400> SEQUENCE: 29

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Val Leu Thr Asn Tyr
            20                  25                  30

Ala Phe Ser Trp Val Arg Gln Ala Pro Gly Gln Gly Leu Glu Trp Leu
        35                  40                  45

Gly Trp Ile Ser Gly Ser Asn Gly Asn Thr Tyr Tyr Ala Glu Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Leu Leu Arg Ser Thr Tyr Phe Asp Tyr Trp Gly Gln Gly
            100                 105                 110

Thr Leu Val Thr Val Ser Ser
        115

<210> SEQ ID NO 30
<211> LENGTH: 126
<212> TYPE: PRT
<213> ORGANISM: homo sapiens

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Gly Phe Ser Trp Val Arg Gln Ala Pro Gly Arg Gly Leu Glu Trp Met
        35                  40                  45

Gly Trp Ile Ser Ala Tyr Asn Gly Asn Thr Tyr Tyr Ala Gln Asn Leu
    50                  55                  60

Gln Gly Arg Val Thr Met Thr Thr Asp Thr Ser Thr Thr Ala Tyr
65                  70                  75                  80

Met Val Leu Arg Ser Leu Arg Ser Asp Asp Thr Ala Met Tyr Tyr Cys
                85                  90                  95

Ala Arg Asp Gly Asn Thr Ala Gly Val Asp Met Trp Ser Arg Asp Gly
            100                 105                 110

Phe Asp Ile Trp Gly Gln Gly Thr Met Val Thr Val Ser Ser
        115                 120                 125

<210> SEQ ID NO 31
<211> LENGTH: 131
<212> TYPE: PRT
<213> ORGANISM: homo sapiens

<400> SEQUENCE: 31

Glu Val Gln Leu Leu Glu Ser Gly Gly Gly Leu Val Gln Pro Gly Gly
1               5                   10                  15

Pro Leu Arg Leu Ser Cys Val Ala Ser Gly Phe Ser Phe Ser Ser Tyr
            20                  25                  30

Ala Met Asn Trp Ile Arg Leu Ala Pro Gly Lys Gly Leu Glu Trp Val
        35                  40                  45

Ser Gly Ile Ser Gly Ser Gly Gly Ser Thr Tyr Tyr Gly Asp Ser Val
    50                  55                  60

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Pro Trp Ile Asp Ile Val Val Ala Ser Val Ile Ser Pro
            100                 105                 110

Tyr Tyr Tyr Asp Gly Met Asp Val Trp Gly Gln Gly Thr Thr Val Thr
            115                 120                 125

Val Ser Ser
    130

<210> SEQ ID NO 32
<211> LENGTH: 123
<212> TYPE: PRT
<213> ORGANISM: homo sapiens

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Ser Phe Asp Gly Tyr
            20                  25                  30

Thr Ile Ser Trp Leu Arg Gln Ala Pro Gly Gln Gly Leu Glu Trp Met
            35                  40                  45

Gly Arg Val Val Pro Thr Leu Gly Phe Pro Asn Tyr Ala Gln Lys Phe
        50                  55                  60

Gln Gly Arg Val Thr Val Thr Ala Asp Arg Ser Thr Asn Thr Ala Tyr
65                  70                  75                  80

Leu Glu Leu Ser Arg Leu Thr Ser Glu Asp Thr Ala Val Tyr Tyr Cys
                85                  90                  95

Ala Arg Met Asn Leu Gly Ser His Ser Gly Arg Pro Gly Phe Asp Met
            100                 105                 110

Trp Gly Gln Gly Thr Leu Val Thr Val Ser Ser
            115                 120

<210> SEQ ID NO 33
<211> LENGTH: 129
<212> TYPE: PRT
<213> ORGANISM: homo sapiens

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Val Ser Gly Ser Ser Phe Ser Lys Tyr
            20                  25                  30

Gly Ile His Trp Val Arg Gln Ala Pro Gly Lys Gly Leu Glu Trp Val
            35                  40                  45

Ala Val Ile Ser Tyr Asp Gly Ser Lys Lys Tyr Phe Thr Asp Ser Val
        50                  55                  60

Lys Gly Arg Phe Thr Ile Ala Arg Asp Asn Ser Gln Asn Thr Val Phe
65                  70                  75                  80

Leu Gln Met Asn Ser Leu Arg Ala Glu Asp Thr Ala Val Tyr Tyr Cys
                85                  90                  95

Ala Thr Gly Gly Gly Val Asn Val Thr Ser Trp Ser Asp Val Glu His
            100                 105                 110

Ser Ser Ser Leu Gly Tyr Trp Gly Leu Gly Thr Leu Val Thr Val Ser
            115                 120                 125

Ser

<210> SEQ ID NO 34
<211> LENGTH: 125
<212> TYPE: PRT
<213> ORGANISM: homo sapiens

<400> SEQUENCE: 34

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Glu Val Tyr Asp Ser Ser Gly Tyr Tyr Leu Tyr Tyr Phe
            100                 105                 110

Asp Ser Trp Gly Gln Gly Thr Leu Val Thr Val Ser Ser
        115                 120                 125

<210> SEQ ID NO 35
<211> LENGTH: 127
<212> TYPE: PRT
<213> ORGANISM: homo sapiens

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Ser Ile Ser Ala Ser Thr Val Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Asp Tyr Asp Phe Trp Ser Gly Tyr Pro Gly Gly Gln Tyr Trp
            100                 105                 110

Phe Phe Asp Leu Trp Gly Arg Gly Thr Leu Val Thr Val Ser Ser
        115                 120                 125

<210> SEQ ID NO 36
<211> LENGTH: 123
<212> TYPE: PRT
<213> ORGANISM: homo sapiens

<400> SEQUENCE: 36

Gln Val Gln Leu Gln Glu Ser Gly Pro Gly Leu Val Thr Pro Ser Glu
1               5                   10                  15

Thr Leu Ser Val Thr Cys Thr Val Ser Asn Tyr Ser Ile Asp Asn Ala

```
                  20                  25                  30
Tyr Tyr Trp Gly Trp Ile Arg Gln Pro Pro Gly Lys Gly Leu Glu Trp
            35                  40                  45
Ile Gly Ser Ile His His Ser Gly Ser Ala Tyr Tyr Asn Ser Ser Leu
 50                  55                  60
Lys Ser Arg Ala Thr Ile Ser Ile Asp Thr Ser Lys Asn Gln Phe Ser
 65                  70                  75                  80
Leu Asn Leu Arg Ser Val Thr Ala Ala Asp Thr Ala Val Tyr Tyr Cys
                85                  90                  95
Ala Arg Asp Thr Ile Leu Thr Phe Gly Glu Pro His Trp Phe Asp Pro
            100                 105                 110
Trp Gly Gln Gly Thr Leu Val Thr Val Ser Ser
            115                 120

<210> SEQ ID NO 37
<211> LENGTH: 124
<212> TYPE: PRT
<213> ORGANISM: homo sapiens

<400> SEQUENCE: 37

Gln Val Gln Leu Gln Glu Ser Gly Pro Gly Leu Val Lys Pro Ser Glu
 1               5                  10                  15
Thr Leu Ser Leu Thr Cys Thr Val Ser Gly Asp Ser Ile Ser Asn Tyr
                20                  25                  30
Tyr Trp Ser Trp Ile Arg Gln Pro Pro Gly Lys Gly Leu Glu Trp Ile
            35                  40                  45
Gly Glu Ile Ser Asn Thr Trp Ser Thr Asn Tyr Asn Pro Ser Leu Lys
 50                  55                  60
Ser Arg Val Thr Ile Ser Leu Asp Met Pro Lys Asn Gln Leu Ser Leu
 65                  70                  75                  80
Lys Leu Ser Ser Val Thr Ala Ala Asp Thr Ala Val Tyr Tyr Cys Ala
                85                  90                  95
Arg Gly Leu Phe Tyr Asp Ser Gly Gly Tyr Tyr Leu Phe Tyr Phe Gln
            100                 105                 110
His Trp Gly Gln Gly Thr Leu Val Thr Val Ser Ser
            115                 120

<210> SEQ ID NO 38
<211> LENGTH: 125
<212> TYPE: PRT
<213> ORGANISM: homo sapiens

<400> SEQUENCE: 38

Gln Val Gln Leu Val Glu Ser Gly Gly Gly Val Val Gln Pro Gly Arg
 1               5                  10                  15
Ser Leu Arg Val Ser Cys Ala Ala Ser Gly Phe Thr Phe Ser Asn Tyr
                20                  25                  30
Gly Met His Trp Val Arg Gln Ala Pro Gly Lys Gly Leu Glu Trp Val
            35                  40                  45
Ala Val Ile Trp Tyr Asp Asp Ser Asn Lys Gln Tyr Gly Asp Ser Val
 50                  55                  60
Lys Gly Arg Phe Thr Ile Ser Arg Asp Asn Ser Lys Ser Thr Leu Tyr
 65                  70                  75                  80
Leu Gln Met Asp Arg Leu Arg Val Glu Asp Thr Ala Val Tyr Tyr Cys
                85                  90                  95
Ala Arg Ala Ser Glu Tyr Ser Ile Ser Trp Arg His Arg Gly Val Leu
```

```
                  100                 105                 110

Asp Tyr Trp Gly Gln Gly Thr Leu Val Thr Val Ser Ser
        115                 120                 125

<210> SEQ ID NO 39
<211> LENGTH: 126
<212> TYPE: PRT
<213> ORGANISM: homo sapiens

<400> SEQUENCE: 39

Gln Ile Thr Leu Lys Glu Ser Gly Pro Thr Leu Val Arg Pro Thr Gln
1               5                   10                  15

Thr Leu Thr Leu Thr Cys Thr Phe Ser Gly Phe Ser Leu Ser Thr Ser
            20                  25                  30

Lys Leu Gly Val Gly Trp Ile Arg Gln Pro Pro Gly Lys Ala Leu Glu
        35                  40                  45

Trp Leu Ala Leu Val Asp Trp Asp Asp Arg Arg Tyr Arg Pro Ser
    50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Ala Tyr Tyr Ser Ser Gly Tyr Tyr Leu Gln Tyr
            100                 105                 110

Phe His His Trp Gly Pro Gly Thr Leu Val Thr Val Ser Ser
        115                 120                 125

<210> SEQ ID NO 40
<211> LENGTH: 125
<212> TYPE: PRT
<213> ORGANISM: homo sapiens

<400> SEQUENCE: 40

Glu Val Gln Leu Val Glu Ser Gly Gly Gly Val Val Gln Pro Gly Gly
1               5                   10                  15

Ser Leu Arg Leu Ser Cys Glu Val Ser Gly Phe Thr Phe Asn Ser Tyr
            20                  25                  30

Glu Met Thr Trp Val Arg Gln Ala Pro Gly Lys Gly Leu Glu Trp Val
        35                  40                  45

Ser His Ile Gly Asn Ser Gly Ser Met Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Ser Asp Tyr Tyr Asp Ser Ser Gly Tyr Tyr Leu Leu Tyr Leu
            100                 105                 110

Asp Ser Trp Gly His Gly Thr Leu Val Thr Val Ser Ser
        115                 120                 125

<210> SEQ ID NO 41
<211> LENGTH: 120
<212> TYPE: PRT
<213> ORGANISM: homo sapiens

<400> SEQUENCE: 41

Gln Val Gln Leu Val Gln Ser Gly Ala Glu Val Arg Lys Pro Gly Ala
1               5                   10                  15
```

Ser Val Lys Val Ser Cys Lys Ala Ser Gly His Thr Phe Ile Asn Phe
            20                  25                  30

Ala Met His Trp Val Arg Gln Ala Pro Gly Gln Gly Leu Glu Trp Met
         35                  40                  45

Gly Tyr Ile Asn Ala Val Asn Gly Asn Thr Gln Tyr Ser Gln Lys Phe
     50                  55                  60

Gln Gly Arg Val Thr Phe Thr Arg Asp Thr Ser Ala Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Asn Gly Gly Ser Ala Ile Ile Phe Tyr Tyr Trp Gly Gln
            100                 105                 110

Gly Thr Leu Val Thr Val Ser Ser
        115                 120

<210> SEQ ID NO 42
<211> LENGTH: 122
<212> TYPE: PRT
<213> ORGANISM: homo sapiens

<400> SEQUENCE: 42

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
         35                  40                  45

Ala Val Ile Ser Asn Asp Gly Ser Asn Lys Tyr Tyr Ala Asp Ser Val
     50                  55                  60

Lys Gly Arg Phe Thr Ile Ser Arg Asp Asn Ser Lys Lys Thr Met Tyr
65                  70                  75                  80

Leu Gln Met Asn Ser Leu Arg Ala Glu Asp Thr Ala Val Tyr Phe Cys
                85                  90                  95

Ala Lys Thr Thr Asp Gln Arg Leu Leu Val Asp Trp Phe Asp Pro Trp
            100                 105                 110

Gly Gln Gly Thr Leu Val Thr Val Ser Ser
        115                 120

<210> SEQ ID NO 43
<211> LENGTH: 130
<212> TYPE: PRT
<213> ORGANISM: homo sapiens

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Ala Ser Gly Gly Ser Ile Asn Ser Ser
            20                  25                  30

Asn Phe Tyr Trp Gly Trp Ile Arg Gln Pro Pro Gly Lys Gly Leu Glu
         35                  40                  45

Trp Ile Gly Ser Ile Phe Tyr Ser Gly Thr Thr Tyr Tyr Asn Pro Ser
     50                  55                  60

Leu Lys Ser Arg Val Thr Ile Ser Val Asp Thr Ser Lys Asn Gln Phe
65                  70                  75                  80

Ser Leu Lys Leu Ser Pro Val Thr Ala Ala Asp Thr Ala Val Tyr His
                85                  90                  95

Cys Ala Arg His Gly Phe Arg Tyr Cys Asn Asn Gly Val Cys Ser Ile
                100                 105                 110

Asn Leu Asp Ala Phe Asp Ile Trp Gly Gln Gly Thr Met Val Thr Val
        115                 120                 125

Ser Ser
    130

<210> SEQ ID NO 44
<211> LENGTH: 122
<212> TYPE: PRT
<213> ORGANISM: homo sapiens

<400> SEQUENCE: 44

Gln Val Gln Leu Val Glu Ser Gly Gly Val Val Gln Pro Gly Lys
1               5                   10                  15

Ser Leu Arg Leu Ser Cys Ala Ala Ser Gly Phe Arg Phe Ser Asp Tyr
            20                  25                  30

Gly Met His Trp Val Arg Gln Ala Pro Ser Lys Gly Leu Glu Trp Val
        35                  40                  45

Ala Val Ile Trp His Asp Gly Ser Asn Ile Arg Tyr Ala Asp Ser Val
    50                  55                  60

Arg Gly Arg Phe Ser Ile Ser Arg Asp Asn Ser Lys Asn Thr Leu Tyr
65                  70                  75                  80

Leu Gln Met Asn Ser Met Arg Ala Asp Thr Ala Phe Tyr Tyr Cys
                85                  90                  95

Ala Arg Val Pro Phe Gln Ile Trp Ser Gly Leu Tyr Phe Asp His Trp
            100                 105                 110

Gly Gln Gly Thr Leu Val Thr Val Ser Ser
        115                 120

<210> SEQ ID NO 45
<211> LENGTH: 366
<212> TYPE: DNA
<213> ORGANISM: homo sapiens

<400> SEQUENCE: 45
caggtgcagc tgcaggagtc gggcccagga ctggtgaagc cttcggagac cctgtccctc      60
acgtgcactg tgtctaatgg cgccatcggc gactacgact ggagctggat tcgtcagtcc     120
ccagggaagg gactggagtg gattgggaac ataaattaca gagggaacac caactacaac     180
ccctccctca agagtcgagt caccatgtcc ctacgcacgt ccacgatgca gttctccctg     240
aagctgagct ctgcgaccgc tgcggacacg gccgtctatt actgtgcgag agatgtaggc     300
tacggtggcg ggcagtattt cgcgatggac gtctggagcc agggaccacg gtcaccgtc      360 tcgagt                                                                366

<210> SEQ ID NO 46
<211> LENGTH: 387
<212> TYPE: DNA
<213> ORGANISM: homo sapiens

<400> SEQUENCE: 46
caggtgcagc tggtggagtc tgggggaggc gtggtccagc ctgggggtc cctgagactc       60 tcctgtacag cgtctggatt caccttcagt acctatggca tgcactgggt ccgccaggct     120
cccggcaagg ggctggaatg gtggcattt atacggtatg atggaagtac tcaagactat      180
gtagactccg tgaagggccg attcaccatc tccagagaca attccaagaa tatggtgtat     240

```
gtgcagatga acagcctgag agttgaggac acggctgtct attactgtgc gaaagacatg    300
gattactatg gttcgcggag ttattctgtc acctactact acggaatgga cgtctggggc    360
caagggacca cggtcaccgt ctcgagt                                        387

<210> SEQ ID NO 47
<211> LENGTH: 375
<212> TYPE: DNA
<213> ORGANISM: homo sapiens

<400> SEQUENCE: 47
caggtgcagc tggtgcagtc tggggctgag gtgaagaagc ctggggcctc agtgaaggtc    60
tcctgcaagg cttctggata caccttcagc ggctattata tgcactgggt gcgacaggcc    120
cctggacaag gcttgagtg gatgggatgg atcaacacta gcagtggtgg cacaaactat    180
gcgcagaagt ttcagggcag gtcaccatg accaggaca cgtccatcag cacagcccac    240
atggaactga ggaggctgag atctgacgac acggccgtgt attattgtgc gagagaggac    300
ggcaccatgg gtactaatag ttggtatggc tggttcgacc cctggggcca gggaaccctg    360
gtcaccgtct cgagt                                                     375

<210> SEQ ID NO 48
<211> LENGTH: 381
<212> TYPE: DNA
<213> ORGANISM: homo sapiens

<400> SEQUENCE: 48
caggtgcagc tggtggagtc tgggggaggc ttggtcaagc ctggggggtc cctgagactc    60
tcctgtgcgg cctctggatt ccccttcggt gactactaca tgagctggat ccgccaggct    120
ccagggaagg gactggagtg ggttgcatac attaatagag gtggcactac catatactac    180
gcagactctg tgaagggccg attcaccatc tccaggggaca cgccaagaa ctccctgttt    240 ctgcaaatga acagcctgag agccggggac acggccctct attactgtgc gagagggcta    300
attctagcac taccgactgc tacggttgag ttaggagctt ttgatatctg gggccaaggg    360
acaatggtca ccgtctcgag t                                              381

<210> SEQ ID NO 49
<211> LENGTH: 378
<212> TYPE: DNA
<213> ORGANISM: homo sapiens

<400> SEQUENCE: 49
caggtgcagc tgcaggagtc gggcccagga ctggtgaagc cttcacagac cctgtccctc    60
acctgcactg tctctggtgc ctccatcagc agtggtgatt attactggag ttggatccgt    120
cagtctccaa ggaagggcct ggagtggatt gggtacatct ccacagtgg gaccacgtac    180 tacaacccgt ccctcaagag tcgagctgtc atctcactgg acacgtccaa gaaccaattc    240
tccctgaggc tgacgtctgt gactgccgca gacacggccg tctattattg tgccagagat    300
gtcgacgatt ttccgtttg gggtatgaat cgatatcttg ccctctgggg ccggggaacc    360
ctggtcaccg tctcgagt                                                  378

<210> SEQ ID NO 50
<211> LENGTH: 372
<212> TYPE: DNA
<213> ORGANISM: homo sapiens
```

```
<400> SEQUENCE: 50
caggtgcagc tggtggagtc tgggggaggc gtggtccagc ctgggaggtc cctgagactc    60
tcctgtgcag cctctggatt cagcttcagt cactttggca tgcactgggt ccgccaggtt   120
ccaggcaagg ggctggagtg ggtggcaatt atatcatatg atgggaataa tgtacactat   180
gccgactccg taaagggccg attcaccatc tccagagaca attccaagaa cacgctgttt   240
ctgcaaatga acagcctgag agatgacgac acgggtgtgt attactgtgc aaggacgac    300 gtggcgacag atttggctgc ctactactac ttcgatgtct ggggccgtgg caccctggtc   360
accgtctcga gt                                                       372

<210> SEQ ID NO 51
<211> LENGTH: 369
<212> TYPE: DNA
<213> ORGANISM: homo sapiens

<400> SEQUENCE: 51
caggtgcagc tggtggagtc tgggggcggc gtggtccagc ctgggaggtc cctgaaactc    60
tcttgtgaag cctctggatt caacttcaat aattatggca tgcactgggt ccgccaggca   120
ccaggcaagg ggctggagtg ggtggcagtt atttcatatg acggaagaaa taagtatttt   180
gctgactccg tgaagggccg attcatcatc tccagagacg attccaggaa cacagtgttt   240
ctgcaaatga acagcctgcg agttgaagat acggccgtct attactgtgc gagaggcagc   300
gtacaagtct ggctacattt gggactttttt gacaactggg gccagggaac cctggtcacc   360
gtctcgagt                                                           369

<210> SEQ ID NO 52
<211> LENGTH: 366
<212> TYPE: DNA
<213> ORGANISM: homo sapiens

<400> SEQUENCE: 52
caggtgcagc tggtggagtc tgggggagcc gtggtccagc ctgggaggtc cctgagactc    60
tcctgtgaag tgtctggatt cagtttcagt gactatggca tgaactgggt ccgccagggt   120
ccaggcaagg ggctggagtg ggtggcagtt atatggcatg acggaagtaa taaaaattat   180
ctagactccg tgaagggccg attcaccgtc tccagagaca attccaagaa cacattgttt   240
ctgcaaatga acagcctgag agccgaagac acggctgtat attactgtgc gaggacgcct   300
tacgagtttt ggagtggcta ttactttgac ttctggggcc agggaaccct ggtcaccgtc   360
tcgagt                                                              366

<210> SEQ ID NO 53
<211> LENGTH: 348
<212> TYPE: DNA
<213> ORGANISM: homo sapiens

<400> SEQUENCE: 53
caggtgcagc tggtggagtc tgggggaggc gtggtccagc ctgggaggtc cctgagactc    60
tcctgtgcag cgtctggatt ccccttcaat agctatgcca tgcactgggt ccgccaggct   120
ccaggcaagg ggctggagtg ggtggcagtg atatattatg aagggagtaa tgaatattat   180
gcagactccg tgaagggccg attcaccatc tccagagaca attccaagaa cactctgtat   240
ttgcaaatgg atagcctgag agccgaggac acggctgtct attactgtgc gaggaagtgg   300
ctggggatgg acttctgggg ccagggaacc ctggtcaccg tctcgagt                348
```

<210> SEQ ID NO 54
<211> LENGTH: 360
<212> TYPE: DNA
<213> ORGANISM: homo sapiens

<400> SEQUENCE: 54

```
gaggtgcagc tggtggagtc tgggggaggc ttggtccggc ctgggggtc cctgagactc      60 tcctgttcag cctctggatt caccttcagt aactatgcta tgcactgggt ccgccaggct     120
ccagggaaga gactggaata tgtttcagct actagtactg atgggggag cacatactac     180 gcagactccc taaagggcac attcaccatc tccagagaca attccaagaa cacactgtat     240
cttcaaatga gcagtctcag tactgaggac acggctattt attactgcgc ccgccgattc     300
tggggatttg gaaacttttt tgactactgg ggccggggaa ccctggtcac cgtctcgagt     360
```

<210> SEQ ID NO 55
<211> LENGTH: 366
<212> TYPE: DNA
<213> ORGANISM: homo sapiens

<400> SEQUENCE: 55

```
caggtgcagc tggtgcagtc tggggctgag gtgaagaagt ccgggtcctc ggtgaaggtc      60
tcctgcaggg cttctggagg caccttcggc aattatgcta tcaactgggt gcgacaggcc     120
cctggacaag ggcttgagtg ggtgggaagg atcatccctg tctttgatac aacaaactac     180
gcacagaagt tccagggcag agtcacgatt accgcggaca gatccacaaa cacagccatc     240
atgcaactga gcagtctgcg acctcaggac acggccatgt attattgttt gagaggttcc     300
acccgtggct gggatactga tggttttgat atctggggcc aagggacaat ggtcaccgtc     360
tcgagt                                                                366
```

<210> SEQ ID NO 56
<211> LENGTH: 387
<212> TYPE: DNA
<213> ORGANISM: homo sapiens

<400> SEQUENCE: 56

```
caggttcagc tggtgcagtc tggggctgtc gtggagacgc ctggggcctc agtgaaggtc      60
tcctgcaagg catctggata catcttcggc aactactata tccactgggt gcggcaggcc     120
cctggacaag ggcttgagtg gatggcagtt atcaatccca atggtggtag cacaacttcc     180
gcacagaagt tccaagacag aatcaccgtg accagggaca cgtccacgac cactgtctat     240
ttggaggttg acaacctgag atctgaggac acggccacat attattgtgc gagacagaga     300
tctgtaacag ggggctttga cgcgtggctt ttaatcccag atgcttctaa tacctggggc     360 cagggacaa tggtcaccgt ctcgagt                                          387
```

<210> SEQ ID NO 57
<211> LENGTH: 378
<212> TYPE: DNA
<213> ORGANISM: homo sapiens

<400> SEQUENCE: 57

```
caggtgcagc tggtgcagtc tggggctgag atgaagaagc ctgggtcctc ggtgaaggtc      60
tcctgcaagg cttctggagg ctccttcagc agctattcta tcagctgggt gcgacaggcc     120
cctggacgag ggcttgagtg ggtgggaatg atcctgccta tctctggtac aacaaactac     180
```

| | |
|---|---|
| gcacagacat tcagggcag agtcatcatt agcgcggaca catccacgag cacagcctac | 240 |
| atggagctga ccagcctcac atctgaagac acggccgtgt atttctgtgc gagagtcttt | 300 |
| agagaattta gcacctcgac ccttgacccc tactactttg actactgggg ccagggaacc | 360 |
| ctggtcaccg tctcgagt | 378 |

<210> SEQ ID NO 58
<211> LENGTH: 375
<212> TYPE: DNA
<213> ORGANISM: homo sapiens

<400> SEQUENCE: 58

| | |
|---|---|
| caggtgcagc tggtggagtc tgggggaggc gtggtccagc ctgggaagtc cgtgagactc | 60 |
| tcctgtgtag gctctggctt caggctcatg gactatgcta tgcactgggt ccgccaggct | 120 |
| ccaggcaagg gactggattg ggtggcagtt atttcatatg atggagccaa tgaatactac | 180 |
| gcagagtccg tgaagggccg attcaccgtc tccagagaca attcagacaa cactctgtat | 240 |
| ctacaaatga gagcctgag agctgaggac acggctgtgt atttctgtgc gagagcgggc | 300 |
| cgttcctcta tgaatgaaga agttattatg tactttgaca actggggcct gggaaccctg | 360 |
| gtcaccgtct cgagt | 375 |

<210> SEQ ID NO 59
<211> LENGTH: 381
<212> TYPE: DNA
<213> ORGANISM: homo sapiens

<400> SEQUENCE: 59

| | |
|---|---|
| gaggtgcagc tgttggagtc tgggggaggc ttggtccagc ctgggggtc cctgagactc | 60 |
| tcctgtgtag cctccggatt cacctttagt acctacgcca tgacctgggt ccgccaggct | 120 |
| ccagggaagg ggctggagtg ggtctcagtc attcgtgcta gtggtgatag tgaaatctac | 180 |
| gcagactccg tgaggggccg gttcaccatc tccagagaca attccaagaa cacggtgttt | 240 |
| ctgcaaatgg acagcctgag agtcgaggac acggccgtat atttctgtgc gaatataggc | 300 |
| cagcgtcggt attgtagtgg tgatcactgc tacggacact ttgactactg gggccaggga | 360 |
| accctggtca ccgtctcgag t | 381 |

<210> SEQ ID NO 60
<211> LENGTH: 381
<212> TYPE: DNA
<213> ORGANISM: homo sapiens

<400> SEQUENCE: 60

| | |
|---|---|
| caggtgcagc tggtggagtc tgggggaggc gtggtccaac ctggggaggtc cctgagactc | 60 |
| tcctgtgcag cctctggatt cggcttcaac acccatggca tgcactgggt ccgccaggct | 120 |
| ccaggcaagg ggctggagtg gctgtcaatt atctcacttg atgggattaa gacccactat | 180 |
| gcagactccg tgaagggccg attcaccatc tccagagaca attccaagaa cacggtgttt | 240 |
| ctacaattga gtggcctgag acctgaagac acggctgtat attactgtgc gaaagatcat | 300 |
| attgggggga cgaacgcata ttttgaatgg acagtcccgt ttgacggctg gggccaggga | 360 |
| accctggtca ccgtctcgag t | 381 |

<210> SEQ ID NO 61
<211> LENGTH: 378
<212> TYPE: DNA
<213> ORGANISM: homo sapiens -continued

<400> SEQUENCE: 61

```
caggtcacct tgagggagtc tggtccagcg gtggtgaagc ccacagaaac gctcactctg      60
acctgcgcct tctctgggtt ctcactcaac gccggtagag tgggtgtgag ttggatccgt     120
cagcccccag ggcaggcccc ggaatggctt gcacgcattg attgggatga tgataaagcg     180
ttccgcacat ctctgaagac cagactcagc atctccaagg actcctccaa aaaccaggtg     240
gtccttacac tgagcaacat ggaccctgcg acacagcca catattactg tcccggaca      300
caggtcttcg caagtggagg ctactacttg tactaccttg accactgggg ccagggaacc     360
ctggtcaccg tctcgagt                                                   378
```

<210> SEQ ID NO 62
<211> LENGTH: 387
<212> TYPE: DNA
<213> ORGANISM: homo sapiens

<400> SEQUENCE: 62

```
caggtgcagc tgcaggagtc gggcccagga ctggtgaagc cttcacagac cctgtccctc      60
acctgcactg tctctagtgg cgccatcagt ggtgctgatt actactggag ttggatccgc     120
cagcccccag ggaagggcct ggagtgggtt gggttcatct atgacagtgg gagcacctac     180
tacaacccgt ccctcaggag tcgagtgacc atatcaatag acacgtccaa gaagcagttc     240
tccctgaagc tgacctctgt gactgccgca gacacggccg tgtattactg tgccagagat     300
ctaggctacg gtggtaactc ttactcccac tcctactact acggtttgga cgtctggggc     360
cgagggacca cggtcaccgt ctcgagt                                         387
```

<210> SEQ ID NO 63
<211> LENGTH: 357
<212> TYPE: DNA
<213> ORGANISM: homo sapiens

<400> SEQUENCE: 63

```
caggtgcagc tgcaggagtc gggcccagga ctggtgaagc cttcggagac cctgtccctc      60
acctgcactg tctctggtgg ctccatcgga aattactact ggggctggat ccggcagccc     120
ccagggaagg gacttgagtg gattgggcat atctacttcg gtggcaacac caactacaac     180
ccttccctcc agagtcgagt caccatttca gtcgacacgt ccaggaacca gttctccctg     240
aagttgaact ctgtgaccgc cgcggacacg gccgtgtatt actgtgcgag ggatagcagc     300
aactggcccg caggctatga ggactgggc cagggaaccc tggtcaccgt ctcgagt        357
```

<210> SEQ ID NO 64
<211> LENGTH: 369
<212> TYPE: DNA
<213> ORGANISM: homo sapiens

<400> SEQUENCE: 64

```
caggttcagc tggtgcagtc tggagctgag gtgaagaagc ctggggcctc agtgaaggtc      60
tcctgcaagg tttctggtta cacctttacc agtaatggtc tcagctgggt gcgacaggcc     120
cctggacaag gtttgagtg gctgggatgg atcagcgcta gtagtggaaa caaaaagtat     180
gccccgaaat tccagggaag agtcaccttg accacagaca tttccacgag cacagcctac     240
atggaactga ggagtctgag atctgacgat acggccgtat attactgtgc gaaagatggg     300
ggcacctacg tgccctattc tgatgccttt gatttctggg gccaggggac aatggtcacc     360
```

```
gtctcgagt                                                                369
```

<210> SEQ ID NO 65
<211> LENGTH: 354
<212> TYPE: DNA
<213> ORGANISM: homo sapiens

<400> SEQUENCE: 65

```
caggtccagc tggtacagtc tggggctgag gtgaagaagc ctggggcctc agtgaaggtc         60
tcctgcaggg tttccggaca cactttcact gcattatcca aacactggat gcgacagggt        120
cctggaggag ggcttgagtg gatgggattt tttgatcctg aagatggtga cacaggctac        180
gcacagaagt tccagggcag agtcaccatg accgaggaca cagccacagg cacagcctac        240
atggagctga gcagcctgac atctgacgac acggccgtat attattgtgc aacagtagcg        300
gcagctggaa actttgacaa ctggggccag ggaaccctgg tcaccgtctc gagt              354
```

<210> SEQ ID NO 66
<211> LENGTH: 378
<212> TYPE: DNA
<213> ORGANISM: homo sapiens

<400> SEQUENCE: 66

```
caggtcacct tgaaggagtc tggtcctgcg ctggtgaaag ccacacagac cctgacactg         60
acctgcacct tctctgggtt ttcactcagt aggaatagaa tgagtgtgag ctggatccgt        120
cagcccccag ggaaggccct ggagtggctt gcacgcattg attgggatga tgataaattc        180
tacaacacat ctctgcagac caggctcacc atctccaagg acacctccaa aaaccaggtg        240
gtccttacaa tgaccaacat ggaccctgtg gacacagcca cctattactg cgcacggact        300
gggatatatg atagtagtgg ttattacctc tactactttg actactgggg ccagggaacc        360
ctggtcaccg tctcgagt                                                      378
```

<210> SEQ ID NO 67
<211> LENGTH: 390
<212> TYPE: DNA
<213> ORGANISM: homo sapiens

<400> SEQUENCE: 67

```
caggtgcagc tggtgcagtc tggagctgag gtgaaggtgc ctggggcctc agtgaaggtc         60
tcctgcaagg cttctggtta caccttacc acttacggtg tcagctgggt gcggcaggcc        120
cctggacaag ggcttgagtg gatgggttgg atcagcgctt acaatggtaa cacatactat        180
ctacagaagc tccagggcag agtcaccatg accacagaca catccacgag cacagcctac        240
atggagctgc ggggcctgag gtctgacgac acggccatgt attactgtgc gagagatcgt        300
gttgggggca gctcgtccga ggttctatcg cgggccaaaa actacggttt ggacgtctgg        360
ggccaaggga ccacggtcac cgtctcgagt                                         390
```

<210> SEQ ID NO 68
<211> LENGTH: 369
<212> TYPE: DNA
<213> ORGANISM: homo sapiens

<400> SEQUENCE: 68

```
caggttcagc tggtgcagtc tggggctgag gtgaagaagc ctggggcctc agttaaggtt         60
tcctgcaagg cttctgcaaa catcttcact tatgcaatgc attgggtgcg ccaggccccc        120
ggacaaaggc ttgagtggat gggatggatc aacgttggca atggtcagac aaaatattca        180
```

```
cagaggttcc agggcagagt caccattacc agggacacgt ccgcgactac agcctacatg    240
gagctgagca ccctgagatc tgaggacacg gctgtgtatt actgtgcgag gcgtgcgagc    300
caatatgggg aggtctatgg caactacttt gactactggg gccagggaac cctggtcacc    360
gtctcgagt                                                            369
```

<210> SEQ ID NO 69
<211> LENGTH: 378
<212> TYPE: DNA
<213> ORGANISM: homo sapiens

<400> SEQUENCE: 69

```
caggtgcagc tggtgcagtc tggagctgag gtgaagaggc ctggggcctc agtgaaggtc    60
tcctgcaagg cttcaggtta cacctttatc agctatggtt tcagctgggt gcgacaggcc   120
cctggacaag gcttgagtg gatgggatgg agcagcgttt acaatggtga cacaaactat    180
gcacagaagt tccacggcag agtcaacatg acgactgaca tcgacgaa cacggcctac     240 atggaactca ggggcctgag atctgacgac acggccgtgt atttctgtgc gagggatcgc   300
aatgttgttc tacttccagc tgctcctttt ggaggtatgg acgtctgggg ccaagggaca   360
atggtcaccg tctcgagt                                                 378
```

<210> SEQ ID NO 70
<211> LENGTH: 369
<212> TYPE: DNA
<213> ORGANISM: homo sapiens

<400> SEQUENCE: 70

```
caggtgcagc tggtggagtc tgggggaggc gtggtccagc cggggacttc cctgagactc    60
tcctgtgcag cctctggatt caccttcagt acgtttggca tgcactgggt ccgccaggct   120
ccaggcaagg gctggagtg gtggcagtt atatcatatg atggaaataa gaaatactat     180
gcagactccg tgaagggccg attcaccatc tccagagaca attccaagaa cacgctgtat   240
ctgcaagtga acagcctgag agtcgaggac acggctgtgt attactgtgc ggcccaaact   300
ccatatttca tgagagcag tgggttagtg ccggactggg gccagggcac cctggtcacc    360
gtctcgagt                                                            369
```

<210> SEQ ID NO 71
<211> LENGTH: 378
<212> TYPE: DNA
<213> ORGANISM: homo sapiens

<400> SEQUENCE: 71

```
caggtgcagc tggtgcagtc tggagctgag gtgaagaagc ctggggcctc agtgaaggtc    60
tcctgcaagg cttctggtta cacctttatc agttttggca tcagctgggt gcgacaggcc   120
cctggacaag gacttgagtg gatgggatgg atcagcgctt acaatggtaa cacagactat   180
gcacagaggc tccaggacag agtcaccatg actagagaca cagccacgag cacagcctac   240
ttggagctga ggagcctgaa atctgacgac acggccgtgt actattgcac tagagacgag   300
tcgatgcttc ggggagttac tgaaggattc ggacccattg actactgggg ccagggaacc   360
ctggtcaccg tctcgagt                                                 378
```

<210> SEQ ID NO 72
<211> LENGTH: 384
<212> TYPE: DNA

<213> ORGANISM: homo sapiens

<400> SEQUENCE: 72

| | | | | | |
|---|---|---|---|---|---|
| gaagtgcagc | tggtgcagtc | tggagcagag | gtgaaaaagc | cggggcagtc | tctgaagatc | 60 |
| tcctgtaaga | cttctggata | catctttacc | aactactgga | tcggctgggt | gcgccagagg | 120 |
| cccgggaaag | gcctggagtg | gatgggggtc | atctttcctg | ctgactctga | tgccagatac | 180 |
| agcccgtcgt | tccaaggcca | ggtcaccatc | tcagccgaca | gtccatcgg | tactgcctac | 240 |
| ctgcagtgga | gtagcctgaa | ggcctcggac | accgccatat | attactgtgc | gagaccgaaa | 300 |
| tattactttg | atagtagtgg | gcaattctcc | gagatgtact | actttgactt | ctggggccag | 360 |
| ggaaccctgg | tcaccgtctc | gagt | | | | 384 |

<210> SEQ ID NO 73
<211> LENGTH: 357
<212> TYPE: DNA
<213> ORGANISM: homo sapiens

<400> SEQUENCE: 73

| | | | | | |
|---|---|---|---|---|---|
| caggttcagc | tggtgcagtc | tggacctgag | gtgaagaagc | ctggggcctc | agtgaaggtc | 60 |
| tcctgcaagg | cttctggtta | tgtgttgacc | aactatgcct | tcagctgggt | gcggcaggcc | 120 |
| cctggacaag | gcttgagtg | gctgggatgg | atcagcggct | ccaatggtaa | cacatactat | 180 |
| gcagagaagt | tccagggccg | agtcaccatg | accacagaca | catccacgag | cacagcctac | 240 |
| atggagctga | ggagtctgag | atctgacgac | acggccgttt | atttctgtgc | gagagatctt | 300 |
| ctgcggtcca | cttactttga | ctactggggc | cagggaaccc | tggtcaccgt | ctcgagt | 357 |

<210> SEQ ID NO 74
<211> LENGTH: 378
<212> TYPE: DNA
<213> ORGANISM: homo sapiens

<400> SEQUENCE: 74

| | | | | | |
|---|---|---|---|---|---|
| caggtgcagc | tggtgcagtc | tggagctgag | gtgaagaagc | ctggggcctc | agtgaaggtc | 60 |
| tcctgcaagg | cttctggtta | caccttttcc | aactacggtt | tcagctgggt | gcgacaggcc | 120 |
| cctggacgag | gcttgagtg | gatgggatgg | atcagcgctt | acaatggtaa | cacatactat | 180 |
| gcacagaacc | tccagggcag | agtcaccatg | accacagaca | catccacgac | cacagcctac | 240 |
| atggtactga | ggagcctgag | atctgacgac | acggccatgt | attactgtgc | gagagatgga | 300 |
| aatacagcag | gggttgatat | gtggtcgcgt | gatggttttg | atatctgggg | ccaggggaca | 360 |
| atggtcaccg | tctcgagt | | | | | 378 |

<210> SEQ ID NO 75
<211> LENGTH: 393
<212> TYPE: DNA
<213> ORGANISM: homo sapiens

<400> SEQUENCE: 75

| | | | | | |
|---|---|---|---|---|---|
| gaggtgcagc | tgttggagtc | tgggggaggc | ttggtacagc | ctgggggcc | cctgaggctc | 60 |
| tcctgtgtag | cctctggatt | cagctttagc | agctatgcca | tgaactggat | ccgcctggct | 120 |
| ccagggaagg | ggctggagtg | gtctcaggt | attagtggta | gcgtggtag | cacttactac | 180 |
| ggagactccg | tgaagggccg | gttcaccatc | tccagagaca | attccaagaa | cacgctgtat | 240 |
| ctgcaaatga | acagcctgag | agccgaggac | acggccgtat | attactgtgc | gaaagagccg | 300 |
| tggatcgata | tagtagtggc | atctgttata | tcccctact | actacgacgg | aatggacgtc | 360 |

```
tggggccaag ggaccacggt caccgtctcg agt                                393
```

<210> SEQ ID NO 76
<211> LENGTH: 369
<212> TYPE: DNA
<213> ORGANISM: homo sapiens

<400> SEQUENCE: 76

```
caggttcagc tggtgcagtc tggggctgag gtgaagaagc ctgggtcctc ggtgaaggtc    60
tcctgcaagg cctctggagg atccttcgac ggctacacta tcagctggct gcgacaggcc   120
cctggacagg gcttgagtg gatgggaagg tcgtcccta cacttggttt tccaaactac    180
gcacagaagt tccaaggcag agtcaccgtt accgcggaca gatccaccaa cacagcctac   240
ttggaattga gcagactgac atctgaagac acggccgtat attactgtgc gaggatgaat   300
ctcggatcgc atagcgggcg ccccgggttc gacatgtggg gccaaggaac cctggtcacc   360
gtctcgagt                                                           369
```

<210> SEQ ID NO 77
<211> LENGTH: 387
<212> TYPE: DNA
<213> ORGANISM: homo sapiens

<400> SEQUENCE: 77

```
caggtgcagc tggtggagtc tgggggaggc gtggtccagc ctggagggtc cttgagactc    60
tcctgtgcag tgtctggatc cagcttcagt aaatatggca tacactgggt ccgccaggct   120
ccaggcaagg ggctgagtg gtggcagtt atatcgtatg atggaagtaa aaagtatttc    180
acagactccg tgaagggccg attcaccatc gccagagaca attcccagaa cacggttttt   240
ctgcaaatga acagcctgag agccgaggac acggctgtct attactgtgc gacaggaggg   300
ggtgttaatg tcacctcgtg gtccgacgta gagcactcgt cgtccttagg ctactgggc    360
ctgggaaccc tggtcaccgt ctcgagt                                       387
```

<210> SEQ ID NO 78
<211> LENGTH: 375
<212> TYPE: DNA
<213> ORGANISM: homo sapiens

<400> SEQUENCE: 78

```
caggtgcagc tggtggagtc tgggggaggc gtggtccagc ctgggggtc cctgagactc     60
tcctgtgcag cgtctggatt caccttcagt agctatggca tgcactgggt ccgccaggct   120
ccaggcaagg ggctggagtg gtggcattt atatggaatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgt gaaagatgag   300
gtctatgata gtagtggtta ttacctgtac tactttgact cttggggcca gggaaccctg   360
gtcaccgtct cgagt                                                    375
```

<210> SEQ ID NO 79
<211> LENGTH: 381
<212> TYPE: DNA
<213> ORGANISM: homo sapiens

<400> SEQUENCE: 79

```
gaggtgcagc tgttggagtc tgggggaggc ttggtacagc ctggggggtc cctgagactc    60
```

-continued

| | |
|---|---|
| tcctgtgcag cctctggatt cacgtttagc tcctatacca tgagctgggt ccgccaggct | 120 |
| ccagggaagg ggctggagtg ggtctcaagt attagtgcta gtactgttct cacatactac | 180 |
| gcagactccg tgaagggccg cttcaccatc tccagagaca attccaagaa cacgctgtat | 240 |
| ctgcaaatga gtagcctgag agccgaggac acggccgtat attactgtgc gaaagattac | 300 |
| gattttggga gtggctatcc cgggggacag tactggttct tcgatctctg ggccgtggc | 360 |
| accctggtca ccgtctcgag t | 381 |

<210> SEQ ID NO 80
<211> LENGTH: 369
<212> TYPE: DNA
<213> ORGANISM: homo sapiens

<400> SEQUENCE: 80

| | |
|---|---|
| caggtgcagc tgcaggagtc gggcccagga ctggtgacgc cttcggagac cctgtccgtc | 60 |
| acttgcactg tctctaatta ttccatcgac aatgcttact actggggctg gatccggcag | 120 |
| cccccaggga agggtctgga gtggataggc agtatccatc atagtgggag cgcctactac | 180 |
| aattcgtccc tcaagagtcg agccaccata tctatagaca cgtccaagaa ccaattctcg | 240 |
| ttgaacctga ggtctgtgac cgccgcagac acggccgtat attactgtgc gcgcgatacc | 300 |
| atcctcacgt tcggggagcc ccactggttc gaccccggg gccagggaac cctggtcacc | 360 |
| gtctcgagt | 369 |

<210> SEQ ID NO 81
<211> LENGTH: 372
<212> TYPE: DNA
<213> ORGANISM: homo sapiens

<400> SEQUENCE: 81

| | |
|---|---|
| caggtgcagc tgcaggagtc gggcccagga ctggtgaagc cttcggagac cttgtccctc | 60 |
| acctgcactg tctcaggtga ctccatcagt aattactact ggagttggat ccggcagccc | 120 |
| ccagggaagg gactggagtg gattggagaa atatctaaca cttggagcac caattacaac | 180 |
| ccctccctca agagtcgagt caccatatct ctagacatgc caagaaccca gttgtccctg | 240 |
| aagctgagct ctgtgaccgc tgcggacacg gccgtatatt actgtgcgag agggcttttc | 300 |
| tatgacagtg gtggttacta cttgtttttac ttccaacact ggggccaggg caccctggtc | 360 |
| accgtctcga gt | 372 |

<210> SEQ ID NO 82
<211> LENGTH: 375
<212> TYPE: DNA
<213> ORGANISM: homo sapiens

<400> SEQUENCE: 82

| | |
|---|---|
| caggtgcagc tggtggagtc tgggggaggc gtggtccagc ctgggaggtc cctgagagtc | 60 |
| tcctgtgcag cgtctggatt caccttcagt aactatggca tgcactgggt ccgccaggct | 120 |
| ccaggcaagg ggctggagtg ggtggcagtt atatggtatg atgacagtaa taaacagtat | 180 |
| ggagactccg tgaagggccg attcaccatc tccagagaca attccaagag tacgctgtat | 240 |
| ctgcaaatgg acagactgag agtcgaggac acggctgtgt attattgtgc gagagcctcc | 300 |
| gagtatagta tcagctggcg acacaggggg gtccttgact actggggcca gggaaccctg | 360 |
| gtcaccgtct cgagt | 375 |

<210> SEQ ID NO 83
<211> LENGTH: 378
<212> TYPE: DNA
<213> ORGANISM: homo sapiens

<400> SEQUENCE: 83

| | | | | | |
|---|---|---|---|---|---|
| cagatcacct | tgaaggagtc | tggtcctacg | ctggtgagac | ccacacagac | cctcacactg | 60 |
| acctgcacct | tctctgggtt | ctcactcagc | actagtaaac | tgggtgtggg | ctggatccgt | 120 |
| cagcccccag | gaaaggccct | ggagtggctt | gcactcgttg | attgggatga | tgataggcgc | 180 |
| tacaggccat | ctttgaagag | caggctcacc | gtcaccaagg | acacctccaa | aaaccaggtg | 240 |
| gtccttacaa | tgaccaacat | ggaccctgtg | gacacagcca | catattactg | tgcacacagt | 300 |
| gcctactata | ctagtagtgg | ttattaccct | caatacttcc | atcactgggg | cccgggcacc | 360 |
| ctggtcaccg | tctcgagt | | | | | 378 |

<210> SEQ ID NO 84
<211> LENGTH: 375
<212> TYPE: DNA
<213> ORGANISM: homo sapiens

<400> SEQUENCE: 84

| | | | | | |
|---|---|---|---|---|---|
| gaggtgcagc | tggtggagtc | tgggggaggc | gtggtacagc | ctggaggctc | cctgagactc | 60 |
| tcctgtgaag | tctccggatt | caccttcaat | agttatgaaa | tgacctgggt | ccgccaggcc | 120 |
| ccagggaagg | ggctggagtg | ggtttcacac | attggtaata | gtggttctat | gatatactac | 180 |
| gctgactctg | tgaagggccg | attcaccatc | tccagagaca | acgccaagaa | ctcactatat | 240 |
| ctgcaaatga | acagcctgag | agtcgaggac | acggctgttt | attactgtgc | gaggtcagat | 300 |
| tactatgata | gtagtggtta | ttatctcctc | tacttagact | cctggggcca | tggaaccctg | 360 |
| gtcaccgtct | cgagt | | | | | 375 |

<210> SEQ ID NO 85
<211> LENGTH: 360
<212> TYPE: DNA
<213> ORGANISM: homo sapiens

<400> SEQUENCE: 85

| | | | | | |
|---|---|---|---|---|---|
| caggtgcagc | tggtgcagtc | tggggctgag | gtgaggaagc | ctggggcctc | agtgaaggtt | 60 |
| tcctgcaagg | cttctggaca | tactttcatt | aactttgcta | tgcattgggt | gcgccaggcc | 120 |
| cccggacagg | ggcttgagtg | gatgggatac | atcaacgctg | tcaatggtaa | cacacagtat | 180 |
| tcacagaagt | tccagggcag | agtcaccttt | acgagggaca | catccgcgaa | cacagcctac | 240 |
| atggagctga | gcagcctgag | atctgaagac | acggctgtgt | attactgtgc | gagaaacaat | 300 |
| gggggctctg | ctatcatttt | ttactactgg | ggccagggaa | ccctggtcac | cgtctcgagt | 360 |

<210> SEQ ID NO 86
<211> LENGTH: 366
<212> TYPE: DNA
<213> ORGANISM: homo sapiens

<400> SEQUENCE: 86

| | | | | | |
|---|---|---|---|---|---|
| caggtgcagc | tggtggagtc | tgggggaggc | gtggtccagc | ctgggaggtc | cctgagactc | 60 |
| tcctgtgcag | cctctggatt | cagcttcagt | agctatggca | tgcactgggt | ccgccaggct | 120 |
| ccaggcaagg | ggctggagtg | ggtggcagtt | atatcaaatg | atggaagtaa | taaatactat | 180 |
| gcagactccg | tgaagggccg | attcaccatc | tccagagaca | attccaagaa | aacgatgtat | 240 |

-continued

```
ctgcaaatga acagcctgag agctgaggac acggctgtgt atttctgtgc gaagacaaca      300
gaccagcggc tattagtgga ctggttcgac ccctggggcc agggaaccct ggtcaccgtc      360
tcgagt                                                                  366
```

<210> SEQ ID NO 87
<211> LENGTH: 390
<212> TYPE: DNA
<213> ORGANISM: homo sapiens

<400> SEQUENCE: 87

```
cagctgcagc tgcaggagtc gggcccagga ctggtgaagc catcggagac cctgtccctc       60
acctgcactg cctctggtgg ctccatcaac agtagtaatt tctactgggg ctggatccgc      120
cagcccccag ggaaggggct ggagtggatt gggagtatct tttatagtgg gaccacctac      180
tacaacccgt ccctcaagag tcgagtcacc atatccgtag acacgtccaa gaaccagttc      240
tccctgaagc tgagccctgt gaccgccgca gacacggctg tctatcactg tgcgagacat      300
ggcttccggt attgtaataa tggtgtatgc tctataaatc tcgatgcttt tgatatctgg      360
ggccaaggga caatggtcac cgtctcgagt                                        390
```

<210> SEQ ID NO 88
<211> LENGTH: 366
<212> TYPE: DNA
<213> ORGANISM: homo sapiens

<400> SEQUENCE: 88

```
caggtgcagc tggtggagtc tgggggaggc gtcgtccagc ctggaaagtc cctgagactc       60
tcctgtgcag cgtctggatt cagattcagt gactacggca tgcactgggt ccggcaggct      120
ccaagcaagg ggctggagtg ggtggcagtt atctggcatg acggaagtaa tataaggtat      180
gcagactccg tgaggggccg attttccatc tccagagaca attccaagaa cacgctgtat      240
ttgcaaatga acagcatgag agccgacgac acggcttttt attattgtgc gagagtcccg      300
ttccagattt ggagtggtct ttattttgac cactggggcc agggaaccct ggtcaccgtc      360
tcgagt                                                                  366
```

<210> SEQ ID NO 89
<211> LENGTH: 216
<212> TYPE: PRT
<213> ORGANISM: homo sapiens

<400> SEQUENCE: 89

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Ser His
            20                  25                  30

Leu Ala Trp Tyr Gln Gln Lys Pro Gly Gln Ala Pro Arg Leu Leu Ile
        35                  40                  45

Tyr Asn Thr Phe Asn Arg Val Thr Gly Ile Pro Ala Arg Phe Ser Gly
    50                  55                  60

Ser Gly Ser Gly Thr Asp Phe Thr Leu Thr Ile Ser Ser Leu Ala Thr
65                  70                  75                  80

Glu Asp Phe Gly Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110
```

-continued

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 90
<211> LENGTH: 215
<212> TYPE: PRT
<213> ORGANISM: homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Phe Thr Cys Arg Ala Ser Gln Arg Ile Ser Asn His
            20                  25                  30

Leu Asn Trp Tyr Gln Gln Lys Pro Gly Lys Ala Pro Lys Leu Leu Ile
        35                  40                  45

Phe Gly Ala Ser Thr Leu Gln Ser Gly Ala Pro Ser Arg Phe Ser Gly
    50                  55                  60

Ser Gly Ser Gly Thr Asp Phe Thr Leu Thr Ile Thr Asn Val Gln Pro
65                  70                  75                  80

Asp Asp Phe Ala Thr Tyr Tyr Cys Gln Gln Ser Tyr Arg Thr Pro Pro
                85                  90                  95

Ile Asn Phe Gly Gln Gly Thr Arg Leu Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 91
<211> LENGTH: 217
<212> TYPE: PRT
<213> ORGANISM: homo sapiens

<400> SEQUENCE: 91

-continued

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Leu
                85                  90                  95

Ser Thr Trp Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
        180                 185                 190

Lys Val Tyr Ala Cys Glu Val Thr His Gln Gly Leu Ser Ser Pro Val
    195                 200                 205

Thr Lys Ser Phe Asn Arg Gly Glu Cys
    210                 215

<210> SEQ ID NO 92
<211> LENGTH: 213
<212> TYPE: PRT
<213> ORGANISM: homo sapiens

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Gly Tyr
            20                  25                  30

Leu Asn Trp Tyr Gln Gln Lys Pro Gly Lys Ala Pro Lys Leu Leu Ile
        35                  40                  45

Tyr Ala Thr Ser Thr Leu Gln Ser Glu Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 93
<211> LENGTH: 215
<212> TYPE: PRT
<213> ORGANISM: homo sapiens

<400> SEQUENCE: 93

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile His Gly Ala Ser Thr Gly Ala Thr Gly Thr Pro Asp Arg Phe Ser
    50                  55                  60

Gly Ser Gly Ser Gly Thr Asp Phe Thr Leu Thr Ile Ser Thr Leu Glu
65                  70                  75                  80

Pro Glu Asp Phe Ala Val Tyr Tyr Cys Gln Gln Tyr Gly Arg Thr Pro
                85                  90                  95

Tyr Thr Phe Gly Gln Gly Thr Lys Leu Glu Asn Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 94
<211> LENGTH: 219
<212> TYPE: PRT
<213> ORGANISM: homo sapiens

<400> SEQUENCE: 94

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Leu Arg Ser
            20                  25                  30

Asp Gly Lys Thr Phe Leu Tyr Trp Tyr Leu Gln Lys Pro Gly Gln Ser
        35                  40                  45
```

```
Pro Gln Pro Leu Met Tyr Glu Val Ser Ser Arg Phe Ser Gly Val Pro
    50                  55                  60

Asp Arg Phe Ser Gly Ser Gly Ser Gly Ala Asp Phe Thr Leu Asn Ile
65              70                  75                      80

Ser Arg Val Glu Thr Glu Asp Val Gly Ile Tyr Tyr Cys Met Gln Gly
                85                  90                  95

Leu Lys Ile Arg Arg Thr Phe Gly Pro Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 95
<211> LENGTH: 215
<212> TYPE: PRT
<213> ORGANISM: homo sapiens

<400> SEQUENCE: 95

Asp Ile Gln Met Thr Gln Ser Pro Ser Thr Leu Ser Ala Ser Val Gly
1               5                   10                  15

Asp Arg Val Thr Phe Ser Cys Arg Ala Ser Gln Ser Val Ser Ser Trp
            20                  25                  30

Val Ala Trp Tyr Gln Gln Lys Pro Gly Lys Ala Pro Lys Leu Leu Ile
        35                  40                  45

Ser Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65              70                  75                      80

Glu Asp Phe Ala Thr Tyr Tyr Cys Gln Gln Tyr His Ser Tyr Ser Gly
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
```

-continued

```
               195                 200                 205

Ser Phe Asn Arg Gly Glu Cys
        210                 215

<210> SEQ ID NO 96
<211> LENGTH: 214
<212> TYPE: PRT
<213> ORGANISM: homo sapiens

<400> SEQUENCE: 96

Ala Ile Gln Leu Thr Gln Ser Pro Ser Ser Leu Ser Ala Ser Val Gly
1               5                   10                  15

Asp Arg Val Thr Leu Thr Cys Arg Ala Ser Gln Gly Ile Thr Asp Ser
            20                  25                  30

Leu Ala Trp Tyr Gln Gln Lys Pro Gly Lys Ala Pro Lys Val Leu Leu
        35                  40                  45

Tyr Ala Ala Ser Arg Leu Glu Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Ser Pro Ala
                85                  90                  95

Thr Phe Gly Pro Gly Thr Lys Val Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 97
<211> LENGTH: 219
<212> TYPE: PRT
<213> ORGANISM: homo sapiens

<400> SEQUENCE: 97

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Asn Gly Phe Asn Tyr Val Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

-continued

```
                85                  90                  95
Leu Glu Thr Pro Leu Thr Phe Gly Gly Gly Thr Lys Val Glu Ile Lys
                100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 98
<211> LENGTH: 215
<212> TYPE: PRT
<213> ORGANISM: homo sapiens

<400> SEQUENCE: 98

Glu Ile Val Leu Thr Gln Ser Pro Gly Thr Leu Ser Leu Ser Pro Gly
1               5                   10                  15
Gly Arg Ala Thr Leu Ser Cys Arg Ala Ser Gln Ser Val Ser Ser Gly
                20                  25                  30
Tyr Leu Ala Trp Tyr Gln Gln Lys Pro Gly Gln Ala Pro Arg Leu Leu
            35                  40                  45
Ile Tyr Gly Ala Ser Gly Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Phe Gly Ser Pro
                85                  90                  95
Tyr Thr Phe Gly Gln Gly Thr Lys Leu Glu Leu Lys Arg Thr Val Ala
                100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 99
<211> LENGTH: 214
```

```
<212> TYPE: PRT
<213> ORGANISM: homo sapiens

<400> SEQUENCE: 99

Asn Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Val Trp Phe Gln Gln Lys Pro Gly Lys Val Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ile Ser Pro Tyr
                85                  90                  95

Thr Phe Gly Gln Gly Thr Lys Leu Glu Thr Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 100
<211> LENGTH: 220
<212> TYPE: PRT
<213> ORGANISM: homo sapiens

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Arg Ser Ser Glu Thr Val Leu Tyr Thr
            20                  25                  30

Ser Lys Asn Gln Ser Tyr Leu Ala Trp Tyr Gln Gln Lys Ala Arg Gln
        35                  40                  45

Pro Pro Lys Leu Leu Leu Tyr Trp Ala Ser Thr Arg Glu Ser Gly Val
50                  55                  60

Pro Ala Arg Phe Ser Gly Ser Gly Ser Gly Thr Asp Phe Thr Leu Ala
65                  70                  75                  80

Ile Ser Ser Leu Gln Ala Glu Asp Val Ala Val Tyr Tyr Cys Gln Gln
                85                  90                  95

Phe Phe Arg Ser Pro Phe Thr Phe Gly Pro Gly Thr Arg Leu Glu Ile
            100                 105                 110

Lys Arg Thr Val Ala Ala Pro Ser Val Phe Ile Phe Pro Pro Ser Asp
        115                 120                 125
```

```
Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 101
<211> LENGTH: 215
<212> TYPE: PRT
<213> ORGANISM: homo sapiens

<400> SEQUENCE: 101

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Ser Ser
                20                  25                  30

Tyr Ile Ala Trp Tyr Gln Gln Lys Pro Gly Gln Ala Pro Arg Leu Val
            35                  40                  45

Ile Tyr Ala Ala Ser Arg Arg Ala Thr Gly Val Pro Asp Arg Phe Ser
        50                  55                  60

Gly Ser Gly Ser Ala Thr Asp Phe Thr Leu Thr Ile Ser Arg Leu Glu
65                  70                  75                  80

Pro Glu Asp Leu Ala Val Tyr Tyr Cys Gln His Tyr Gly Asn Ser Leu
                85                  90                  95

Phe Thr Phe Gly Pro Gly Thr Lys Val Asp Val Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
            210                 215

<210> SEQ ID NO 102
<211> LENGTH: 215
<212> TYPE: PRT
<213> ORGANISM: homo sapiens

<400> SEQUENCE: 102

Asp Ile Gln Met Thr Gln Ser Pro Ser Thr Leu Ser Ala Ser Val Gly
1               5                   10                  15
```

Asp Arg Val Thr Ile Thr Cys Arg Ala Ser Gln Ser Ile Gly Ser Arg
                20                  25                  30

Leu Ala Trp Tyr Gln Gln Pro Gly Lys Ala Pro Lys Phe Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Leu Ala Thr Tyr Tyr Cys Gln Gln Tyr Asn Arg Asp Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 103
<211> LENGTH: 219
<212> TYPE: PRT
<213> ORGANISM: homo sapiens

<400> SEQUENCE: 103

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asp Gly Arg Tyr Tyr Val Asp Trp Tyr Leu Gln Lys Pro Gly Gln Ser
            35                  40                  45

Pro His Leu Leu Ile Tyr Leu Ala Ser Asn Arg Ala Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Thr Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 104
<211> LENGTH: 213
<212> TYPE: PRT
<213> ORGANISM: homo sapiens

<400> SEQUENCE: 104

```
Glu Ile Val Met Thr Gln Ser Pro Ala Thr Leu Ser Ala Ser Pro Gly
1               5                   10                  15

Glu Arg Ala Thr Leu Ser Cys Trp Ala Ser Gln Thr Ile Gly Gly Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln Gln Tyr Lys Asn Trp Tyr Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 105
<211> LENGTH: 215
<212> TYPE: PRT
<213> ORGANISM: homo sapiens

<400> SEQUENCE: 105

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ala Ser Tyr
            20                  25                  30

Val Asn Trp Tyr Gln Gln Lys Pro Gly Arg Ala Pro Ser Leu Leu Ile
        35                  40                  45

Tyr Ala Ala Ser Asn Leu Gln Ser Gly Val Pro Arg Phe Ser Gly
50                  55                  60
```

```
Ser Gly Ser Gly Thr Asp Phe Thr Leu Thr Ile Ser Gly Leu Gln Pro
 65                  70                  75                  80

Asp Asp Phe Ala Thr Tyr Tyr Cys Gln Gln Ser Tyr Ser Tyr Arg Ala
                 85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 106
<211> LENGTH: 216
<212> TYPE: PRT
<213> ORGANISM: homo sapiens

<400> SEQUENCE: 106

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Leu Ala Trp Tyr Gln Gln Thr Pro Gly Gln Ala Pro Arg Leu Leu Ile
        35                  40                  45

Tyr Asp Ala Ser Tyr Arg Val Thr Gly Ile Pro Ala Arg Phe Ser Gly
    50                  55                  60

Ser Gly Ser Gly Ile Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Gly Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
```

```
                210              215

<210> SEQ ID NO 107
<211> LENGTH: 214
<212> TYPE: PRT
<213> ORGANISM: homo sapiens

<400> SEQUENCE: 107

Ala Ile Gln Leu Thr Gln Ser Pro Ser Ser Leu Ser Ala Ser Val Gly
1               5                   10                  15

Asp Thr Val Thr Val Thr Cys Arg Pro Ser Gln Asp Ile Ser Ser Ala
            20                  25                  30

Leu Ala Trp Tyr Gln Gln Lys Pro Gly Lys Pro Lys Leu Leu Ile
        35                  40                  45

Tyr Gly Ala Ser Thr Leu Asp Tyr Gly Val Pro Leu Arg Phe Ser Gly
    50                  55                  60

Thr Ala Ser Gly Thr His Phe Thr Leu Thr Ile Ser Ser Leu Gln Pro
65                  70                  75                  80

Glu Asp Phe Ala Thr Tyr Tyr Cys Gln Gln Phe Asn Thr Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 108
<211> LENGTH: 220
<212> TYPE: PRT
<213> ORGANISM: homo sapiens

<400> SEQUENCE: 108

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Ser Asn Asn Lys Asn Tyr Leu Ala Trp Tyr Gln Gln Lys Pro Gly Gln
        35                  40                  45

Pro Pro Lys Leu Leu Ile His Leu Ala Ser Thr Arg Glu Tyr Gly Val
    50                  55                  60

Pro Asp Arg Phe Ser Gly Ser Gly Ser Gly Thr Asp Phe Ala Leu Ile
65                  70                  75                  80

Ile Ser Ser Leu Gln Ala Glu Asp Val Ala Val Tyr Tyr Cys Gln Gln
                85                  90                  95

Tyr Tyr Gln Thr Pro Leu Thr Phe Gly Gln Gly Thr Lys Val Glu Ile
```

-continued

```
                100                 105                 110
Lys Arg Thr Val Ala Ala Pro Ser Val Phe Ile Phe Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 109
<211> LENGTH: 214
<212> TYPE: PRT
<213> ORGANISM: homo sapiens

<400> SEQUENCE: 109

Asp Ile Gln Met Thr Gln Ser Pro Ser Ser Leu Ala Ala Ser Val Gly
1               5                   10                  15

Asp Arg Val Thr Ile Thr Cys Arg Ala Ser Gln Phe Ile Ser Ser Tyr
            20                  25                  30

Leu His Trp Tyr Gln Gln Arg Pro Gly Lys Ala Pro Lys Leu Leu Met
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Asn Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 110
<211> LENGTH: 214
<212> TYPE: PRT
<213> ORGANISM: homo sapiens
```

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ser Tyr Ser Thr Arg Phe
                85                  90                  95

Thr Phe Gly Pro Gly Thr Lys Val Asp Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 111
<211> LENGTH: 214
<212> TYPE: PRT
<213> ORGANISM: homo sapiens

<400> SEQUENCE: 111

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Thr Ser Glu
            20                  25                  30

Leu Ala Trp Tyr Gln Gln Lys Pro Gly Lys Ala Pro Asn Phe Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 112
<211> LENGTH: 214
<212> TYPE: PRT
<213> ORGANISM: homo sapiens

<400> SEQUENCE: 112

Asp Ile Gln Met Thr Gln Ser Pro Ser Thr Leu Ser Ala Ser Val Gly
1               5                   10                  15

Asp Arg Leu Thr Ile Thr Cys Arg Ala Ser Gln Asn Ile Tyr Asn Trp
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Leu Ser Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 113
<211> LENGTH: 214
<212> TYPE: PRT
<213> ORGANISM: homo sapiens

<400> SEQUENCE: 113

Asp Ile Gln Leu Thr Gln Ser Pro Ser Phe Leu Ser Ala Ser Leu Glu
1               5                   10                  15

Asp Arg Val Thr Ile Thr Cys Arg Ala Ser Gln Gly Ile Ser Ser Tyr
            20                  25                  30
```

```
Leu Ala Trp Tyr Gln Gln Lys Pro Gly Lys Ala Pro Lys Leu Leu Leu
             35                  40                  45

Asp Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Arg
                 85                  90                  95

Thr Phe Gly Gln Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 114
<211> LENGTH: 214
<212> TYPE: PRT
<213> ORGANISM: homo sapiens

<400> SEQUENCE: 114

Asp Ile Gln Met Thr Gln Ser Pro Ser Ser Leu Ser Ala Ser Val Gly
 1               5                  10                  15

Asp Arg Val Ser Ile Thr Cys Arg Ala Ser Gln Gly Ile Ser Asn Tyr
                 20                  25                  30

Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Gln
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205
Phe Asn Arg Gly Glu Cys
    210

<210> SEQ ID NO 115
<211> LENGTH: 220
<212> TYPE: PRT
<213> ORGANISM: homo sapiens

<400> SEQUENCE: 115

Asp Ile Val Met Thr Gln Ser Pro Asp Ser Leu Ala Val Ser Leu Gly
1               5                   10                  15
Glu Arg Ala Thr Ile Asn Cys Arg Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Val Tyr Trp Ala Ser Thr Arg Ala Ser Gly Val
    50                  55                  60
Pro Asp Arg Phe Ser Gly Ser Gly Ser Gly Thr Asp Phe Thr Leu Thr
65                  70                  75                  80
Leu Ser Ser Leu Gln Ala Glu Asp Val Ala Val Tyr Tyr Cys Gln Gln
                85                  90                  95
Phe His Ser Thr Pro Arg Thr Phe Gly Gln Gly Thr Lys Val Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220

<210> SEQ ID NO 116
<211> LENGTH: 215
<212> TYPE: PRT
<213> ORGANISM: homo sapiens

<400> SEQUENCE: 116

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Ala Gly Met Pro Asp Arg Phe Ser
    50                  55                  60
Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Asn Ser Pro
                85                  90                  95

Leu Thr Phe Gly Gly Gly Thr Glu Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 117
<211> LENGTH: 214
<212> TYPE: PRT
<213> ORGANISM: homo sapiens

<400> SEQUENCE: 117

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ala Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ala Asp Thr Phe Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 118
<211> LENGTH: 220
<212> TYPE: PRT
<213> ORGANISM: homo sapiens

<400> SEQUENCE: 118

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asn Asp Gly Asn Thr Tyr Leu Asp Trp Tyr Leu Gln Lys Pro Gly Gln
        35                  40                  45

Ser Pro Gln Leu Leu Ile Tyr Thr Phe Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 119
<211> LENGTH: 219
<212> TYPE: PRT
<213> ORGANISM: homo sapiens

<400> SEQUENCE: 119

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Glu Tyr Asn Tyr Leu Asp Trp Tyr Leu Gln Lys Pro Gly Gln Ser
        35                  40                  45

Pro Gln Leu Leu Ile Tyr Trp Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu

```
              115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 120
<211> LENGTH: 214
<212> TYPE: PRT
<213> ORGANISM: homo sapiens

<400> SEQUENCE: 120

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Phe Asp Ala Thr Lys Leu Glu Thr Gly Val Pro Thr Arg Phe Ile Gly
    50                  55                  60

Ser Gly Ser Gly Thr Asp Phe Thr Val Thr Ile Thr Ser Leu Gln Pro
65                  70                  75                  80

Glu Asp Val Ala Thr Tyr Tyr Cys Gln His Phe Ala Asn Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 214
<212> TYPE: PRT
<213> ORGANISM: homo sapiens

<400> SEQUENCE: 121

Asp Ile Gln Met Thr Gln Ser Pro Ser Ser Leu Ser Ala Ser Val Gly
```

```
                        1               5                   10                  15
Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Val Pro Lys Leu Leu Val
            35                  40                  45

Phe Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Ser Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 122
<211> LENGTH: 215
<212> TYPE: PRT
<213> ORGANISM: homo sapiens

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ala Ser Tyr
                20                  25                  30

Leu Asn Trp Tyr Gln Gln Lys Pro Gly Arg Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Phe Thr Phe Gly Pro Gly Thr Lys Val Asn Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 123
<211> LENGTH: 213
<212> TYPE: PRT
<213> ORGANISM: homo sapiens

<400> SEQUENCE: 123

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 124
<211> LENGTH: 215
<212> TYPE: PRT
<213> ORGANISM: homo sapiens

<400> SEQUENCE: 124

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Lys Asn Asn
            20                  25                  30

Leu Ala Trp Tyr Gln Val Lys Pro Gly Gln Ala Pro Arg Leu Leu Thr
        35                  40                  45
```

```
Ser Gly Ala Ser Ala Arg Ala Thr Gly Ile Pro Gly Arg Phe Ser Gly
    50                  55                  60

Ser Gly Ser Gly Thr Asp Phe Thr Leu Thr Ile Ser Ser Leu Gln Ser
65                  70                  75                  80

Glu Asp Ile Ala Val Tyr Tyr Cys Gln Glu Tyr Asn Asn Trp Pro Leu
                85                  90                  95

Leu Thr Phe Gly Gly Gly Thr Lys Val Glu Ile Gln Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 125
<211> LENGTH: 215
<212> TYPE: PRT
<213> ORGANISM: homo sapiens

<400> SEQUENCE: 125

Asp Ile Gln Met Thr Gln Ser Pro Ser Leu Ser Ala Ser Val Gly
1               5                   10                  15

Asp Arg Val Thr Ile Thr Cys Arg Ala Ser Gln Arg Ile Ala Ser Tyr
            20                  25                  30

Leu Asn Trp Tyr Gln Gln Lys Pro Gly Arg Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Tyr Ala Thr Tyr Tyr Cys Gln Gln Ser Tyr Ser Thr Pro Ile
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215

<210> SEQ ID NO 126
<211> LENGTH: 214
<212> TYPE: PRT
<213> ORGANISM: homo sapiens

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Phe Asp Ala Ser Asn Leu Glu Ser Glu Val Pro Ser Arg Phe Ser Gly
    50                  55                  60

Arg Gly Ser Gly Thr Asp Phe Thr Phe Ser Ile Ser Ser Leu Gln Pro
65                  70                  75                  80

Glu Asp Ile Ala Thr Tyr Phe Cys Gln Gln Tyr Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 127
<211> LENGTH: 214
<212> TYPE: PRT
<213> ORGANISM: homo sapiens

<400> SEQUENCE: 127

Asp Ile Gln Met Thr Gln Ser Pro Ser Ser Leu Ala Ala Ser Val Gly
1               5                   10                  15

Asp Arg Val Thr Ile Thr Cys Arg Ala Ser Gln Thr Ile Ala Ser Tyr
            20                  25                  30

Val Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Phe Cys Gln Gln Ser Tyr Ser Phe Pro Tyr
                85                  90                  95
```

```
Thr Phe Gly Gln Gly Thr Lys Leu Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 128
<211> LENGTH: 215
<212> TYPE: PRT
<213> ORGANISM: homo sapiens

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ala Ser Tyr
            20                  25                  30

Val Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Val Pro Arg
                85                  90                  95

Leu Thr Phe Gly Gly Gly Thr Lys Val Asp Ile Thr Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 129
<211> LENGTH: 213
<212> TYPE: PRT
```

<213> ORGANISM: homo sapiens

<400> SEQUENCE: 129

```
Asp Ile Gln Met Thr Gln Ser Pro Ser Ser Leu Ser Ala Ser Val Gly
1               5                   10                  15
Asp Arg Val Thr Ile Thr Cys Arg Ser Ser Gln Thr Ile Ser Val Phe
            20                  25                  30
Leu Asn Trp Tyr Gln Gln Lys Pro Gly Lys Ala Pro Lys Leu Leu Ile
        35                  40                  45
Tyr Ala Ala Ser Ser Leu His Ser Ala Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Ser Ala Thr Tyr Tyr Cys Gln Glu Ser Phe Ser Ser Ser Thr
                85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 130
<211> LENGTH: 215
<212> TYPE: PRT
<213> ORGANISM: homo sapiens

<400> SEQUENCE: 130

```
Glu Ile Val Met Thr Gln Ser Pro Ala Thr Leu Ser Val Ser Pro Gly
1               5                   10                  15
Glu Thr Ala Thr Leu Ser Cys Arg Ala Ser Gln Ser Val Ser Ser Asn
            20                  25                  30
Leu Ala Trp Tyr Gln His Lys Pro Gly Gln Ala Pro Arg Leu Leu Ile
        35                  40                  45
His Ser Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Met Trp Pro Pro
                85                  90                  95
Trp Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
```

```
            130                 135                 140
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
    210                 215

<210> SEQ ID NO 131
<211> LENGTH: 219
<212> TYPE: PRT
<213> ORGANISM: homo sapiens

<400> SEQUENCE: 131

Asp Ile Val Met Thr Gln Ser Pro Leu Ser Leu Pro Val Thr Pro Gly
1               5                   10                  15

Ala Pro Ala Ser Ile Ser Cys Arg Ser Ser Gln Ser Leu Leu Arg Thr
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Ile Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Gln Thr Ser Ile Thr Phe Gly Gln Gly Thr Arg Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215

<210> SEQ ID NO 132
<211> LENGTH: 214
<212> TYPE: PRT
<213> ORGANISM: homo sapiens

<400> SEQUENCE: 132

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Asn Asn
```

```
            20                  25                  30
Leu Ala Trp Tyr Gln Gln Arg Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asp Lys Trp Pro Glu
                 85                  90                  95

Thr Phe Gly Gln Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 133
<211> LENGTH: 648
<212> TYPE: DNA
<213> ORGANISM: homo sapiens

<400> SEQUENCE: 133
gaaattgtgt tgacacagtc tccagccacc ctgtccttgt ctccaggaga aagagccacc      60
ctctcctgca gggccagtca gagtgttaac agccacttag cctggtacca acagaaacct    120
ggccaggctc ccaggctcct catctataat acattcaata gggtcactgg catcccagcc    180
aggttcagtg gcagtgggtc tgggacagac ttcactctca ccatcagcag ccttgcgact    240
gaagattttg cgtttatta ctgtcagcag cgtagcaact ggcctcccgc cctcactttc     300
ggcggaggga ccaaagtgga gatcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                 648

<210> SEQ ID NO 134
<211> LENGTH: 645
<212> TYPE: DNA
<213> ORGANISM: homo sapiens

<400> SEQUENCE: 134
gacatccaga tgacccagtc tccatcctcc ctgtctgcat ctgtgggaga cagagtcacc      60
ttcacttgcc gggccagtca gaggattagc aaccatttaa attggtatca acaaaagcca    120
```

```
gggaaagccc ctaaactcct gatctttggt gcatccactc ttcaaagtgg ggccccatca        180
aggttcagtg gcagtggatc tgggacagat ttcactctca ccatcactaa tgtacaacct        240
gacgattttg caacttacta ctgtcaacag agttacagaa ctcccccgat caacttcggc        300
caagggacac gcctggacat taagcgaact gtggctgcac catctgtctt catcttcccg        360
ccatctgatg agcagttgaa atctggaact gcctctgttg tgtgcctgct gaataacttc        420
tatcccagag aggccaaagt acagtggaag gtggataacg ccctccaatc gggtaactcc        480
caggagagtg tcacagagca ggacagcaag acagcacct acagcctcag cagcaccctg         540
acgctgagca aagcagacta cgagaaacac aaagtctacg cctgcgaagt cacccatcag        600
ggcctgagct cgcccgtcac aaagagcttc aacaggggag agtgt                       645
```

<210> SEQ ID NO 135
<211> LENGTH: 651
<212> TYPE: DNA
<213> ORGANISM: homo sapiens

<400> SEQUENCE: 135

```
gaaattgtgt tgacgcagtc tccaggcacc ctgtctttgt ctccagggga aagagccacc         60
ctctcctgca gggccagtca gagtgttagc agcagctact tagcctggta tcagcagaaa        120
cctggccagg ctcccaggct cctcatctat ggtgcatcca gcaggccac tggcatccca         180 gacaggttca gtggcagtgg gtctgggaca gacttcactc tcaccatcag cagactggag        240
cctgaagatt ttgcagtgta ttactgtcag cagtatgata gctcactttc tacgtggacg        300
ttcggccaag gaccaaggt ggaaatcaaa cgaactgtgg ctgcaccatc tgtcttcatc         360
ttcccgccat ctgatgagca gttgaaatct ggaactgcct ctgttgtgtg cctgctgaat        420
aacttctatc ccagagaggc caaagtacag tggaaggtgg ataacgcccct ccaatcgggt       480 aactcccagg agagtgtcac agagcaggac agcaaggaca gcacctacag cctcagcagc        540
accctgacgc tgagcaaagc agactacgag aaacacaaag tctacgcctg cgaagtcacc        600
catcagggcc tgagctcgcc cgtcacaaag agcttcaaca ggggagagtg t                651
```

<210> SEQ ID NO 136
<211> LENGTH: 639
<212> TYPE: DNA
<213> ORGANISM: homo sapiens

<400> SEQUENCE: 136

```
gacatccaga tgacccagtc tccatcctcc ctgtctgcat ctgtaggaga cagagtcacc         60
atcacttgcc gggcaagtca gagcattacc ggctatttaa attggtatca gcagaaacca        120
gggaaagccc ctaaactcct gatctatgct acatccactt tgcaaagtga ggtcccatca        180
aggttcagtg gcagtggatc tgggacagat ttcactctca ccatcagcag tcttcaacct        240
gaagattttg caacttacta ctgtcaacag agttataata ccctcacttt cggcggaggg        300
accaaggtgg agatcaaacg aactgtggct gcaccatctg tcttcatctt cccgccatct        360
gatgagcagt tgaaatctgg aactgcctct gttgtgtgcc tgctgaataa cttctatccc        420
agagaggcca agtacagtg gaaggtggat aacgccctcc aatcgggtaa ctcccaggag         480
agtgtcacag agcaggacag caaggacagc acctacagcc tcagcagcac cctgacgctg        540
agcaaagcag actacgagaa acacaaagtc tacgcctgcg aagtcaccca tcagggcctg        600
agctcgcccg tcacaaagag cttcaacagg ggagagtgt                              639
```

<210> SEQ ID NO 137
<211> LENGTH: 645
<212> TYPE: DNA
<213> ORGANISM: homo sapiens

<400> SEQUENCE: 137

| | | | | | |
|---|---|---|---|---|---|
| gaaattgtgt | tgacgcagtc | tccaggcacc | ctgtctttgt | ctccagggga | aagagccacc | 60 |
| ctctcctgca | gggccagtca | gagtgttagc | agcagctact | tagcctggta | tcagcagaaa | 120 |
| cctggccagg | ctcccaggct | cctcatacat | ggcgcatcca | ccggggccac | tggcacccca | 180 |
| gacaggttca | gtggcagtgg | gtctgggaca | gacttcactc | tcaccatcag | tacactggag | 240 |
| cctgaagatt | ttgcagtgta | ttactgtcag | caatatggta | ggacaccgta | cacttttggc | 300 |
| caggggacca | agctggagaa | caaacgaact | gtggctgcac | catctgtctt | catcttcccg | 360 |
| ccatctgatg | agcagttgaa | atctggaact | gcctctgttg | tgtgcctgct | gaataacttc | 420 |
| tatcccagag | aggccaaagt | acagtggaag | gtggataacg | ccctccaatc | gggtaactcc | 480 |
| caggagagtg | tcacagagca | ggacagcaag | gacagcacct | acagcctcag | cagcaccctg | 540 |
| acgctgagca | aagcagacta | cgagaaacac | aaagtctacg | cctgcgaagt | cacccatcag | 600 |
| ggcctgagct | cgcccgtcac | aaagagcttc | aacaggggag | agtgt | | 645 |

<210> SEQ ID NO 138
<211> LENGTH: 657
<212> TYPE: DNA
<213> ORGANISM: homo sapiens

<400> SEQUENCE: 138

| | | | | | |
|---|---|---|---|---|---|
| gatattgtga | tgacccagac | tccactctct | ctgtccgtca | cccctggaca | gccggcctcc | 60 |
| atctcctgca | ggtctagtca | gagcctcctg | cgaagtgatg | gaaagacgtt | tttgtattgg | 120 |
| tatctgcaga | agccaggcca | gtctccccaa | cccctaatgt | atgaggtgtc | cagccggttc | 180 |
| tctggagtgc | cagataggtt | cagtggcagc | gggtcagggg | cagatttcac | actgaacatc | 240 |
| agccgggtgg | agactgagga | tgttgggatc | tattactgca | tgcaaggttt | gaaaattcgt | 300 |
| cggacgtttg | gccagggac | caaggtcgaa | atcaagcgaa | ctgtggctgc | accatctgtc | 360 |
| ttcatcttcc | cgccatctga | tgagcagttg | aaatctggaa | ctgcctctgt | tgtgtgcctg | 420 |
| ctgaataact | tctatcccag | agaggccaaa | gtacagtgga | aggtggataa | cgccctccaa | 480 |
| tcgggtaact | cccaggagag | tgtcacagag | caggacagca | aggacagcac | ctacagcctc | 540 |
| agcagcaccc | tgacgctgag | caaagcagac | tacgagaaac | acaaagtcta | cgcctgcgaa | 600 |
| gtcacccatc | agggcctgag | ctcgcccgtc | acaaagagct | tcaacagggg | agagtgt | 657 |

<210> SEQ ID NO 139
<211> LENGTH: 645
<212> TYPE: DNA
<213> ORGANISM: homo sapiens

<400> SEQUENCE: 139

| | | | | | |
|---|---|---|---|---|---|
| gacatccaga | tgacccagtc | tccttccacc | ctgtctgcat | ctgtaggaga | cagagtcacc | 60 |
| ttctcttgcc | gggccagtca | gagtgttagt | agttgggtgg | cctggtatca | gcagaaacca | 120 |
| ggaaaagccc | ctaagctcct | gatctctgag | gcctccaatt | tggaaagtgg | ggtcccatcc | 180 |
| cggttcagcg | gcagtggatc | cgggacagaa | ttcactctca | ccatcagcag | cctgcagcct | 240 |
| gaagattttg | caacttatta | ctgccaacag | tatcatagtt | actctgggta | cacttttggc | 300 |
| caggggacca | agttggaaat | caagcgaact | gtggctgcac | catctgtctt | catcttcccg | 360 |

```
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag acagcacct acagcctcag cagcaccctg     540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 140
<211> LENGTH: 642
<212> TYPE: DNA
<213> ORGANISM: homo sapiens

<400> SEQUENCE: 140

```
gccatccagt tgacccagtc tccatcgtcc ctgtctgcat ctgtaggcga cagagtcacc     60
ctcacttgcc gggcgagtca gggcattacc gattctttag cctggtatca gcagaaacca   120
gggaaagccc ctaaggtcct gctctatgct gcttccagat tggaaagtgg ggtcccatcc   180
aggttcagtg gccgtggatc tgggacggat ttcactctca ccatcagcag cctgcagcct   240
gaagactttg caacttatta ctgtcaacag tattctaagt cccctgcgac gttcggccca   300
gggaccaagg tggaaatcag acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctacg cctcagcag cacccctgacg   540 ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 141
<211> LENGTH: 657
<212> TYPE: DNA
<213> ORGANISM: homo sapiens

<400> SEQUENCE: 141

```
gatattgtga tgacccagtc tccactctcc ctgcccgtca cccctggaga gccggcctcc     60
atctcctgca ggtctagtca gagcctccta aatagtaatg gattcaacta tgtggattgg   120
tacctgcaga agccagggca gtctccacaa ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct agaaactccg   300
ctcactttcg gcggagggac caaggtggag atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

<210> SEQ ID NO 142
<211> LENGTH: 645
<212> TYPE: DNA
<213> ORGANISM: homo sapiens

<400> SEQUENCE: 142

```
gaaattgtgt tgacgcagtc tccaggcacc ctgtctttgt ctccagggg aagagccacc      60 ctctcctgca gggccagtca gagtgttagc agcggctact tagcctggta ccagcagaaa     120
cctggccagg ctcccaggct cctcatctat ggtgcatccg gcagggccac tggcatccca     180
gacaggttca gtggcagtgg gtctgggaca gacttcactc tcaccatcag cagactggag     240
cctgaagatt ttgcagtgta ttactgtcag cagtattttg gctcaccgta cacttttggc     300
caggggacca agctggagct caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag acagcacct acagcctcag cagcaccctg      540
acgctgagca aagcagacta cgagaaacac aaagtctacg cctgcgaagt cacccatcag     600
ggcctgagct cgcccgtcac aaagagcttc aacaggggag agtgt                     645

<210> SEQ ID NO 143
<211> LENGTH: 642
<212> TYPE: DNA
<213> ORGANISM: homo sapiens

<400> SEQUENCE: 143
aacatccaga tgacccagtc tccatctgcc atgtctgcat ctgtaggaga cagagtcacc      60
atcacttgtc gggcgagtca gggcattagt aattatttag tctggtttca gcagaaacca    120
gggaaagtcc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatattt ccccttacac ttttggccag    300
gggaccaagc tggagaccaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 144
<211> LENGTH: 660
<212> TYPE: DNA
<213> ORGANISM: homo sapiens

<400> SEQUENCE: 144
gacatcgtga tgacccagtc tccagactcc ctggctgtgt ctctgggcga gagggccacc     60
atcaactgca ggtccagtga gactgtttta tacacctcta aaaatcagag ctacttagct    120
tggtaccagc agaaagcacg acagcctcct aaactactcc tttactgggc atctacccgg    180
gaatccgggg tccctgcccg attcagtggc agcggatctg ggacagattt cactctcgcc    240
atcagcagcc tgcaggctga agatgtggca gtttattact gtcagcaatt ttttaggagt    300 ccttttcactt tcggccccgg gaccagactg gagattaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
```

```
gaagtcaccc atcagggcct gagctcgccc gtcacaaaga gcttcaacag gggagagtgt    660

<210> SEQ ID NO 145
<211> LENGTH: 645
<212> TYPE: DNA
<213> ORGANISM: homo sapiens

<400> SEQUENCE: 145
gaaattgtgt tgacgcagtc tccaggcacc ctgtctttgt ctccagggga aagagttacc     60
ctctcttgca gggccagtca gagtgttagc agcagttaca tagcctggta ccagcagaag    120
cctggccagg ctcccaggct cgtcatctat gctgcatccc gcagggccac tggcgtccca    180
gacaggttca gtggcagtgg gtctgcgaca gacttcactc tcaccatcag tagactggag    240
cctgaagatc ttgcagtgta ttactgtcag cactatggta actcactatt cactttcggc    300
cctgggacca aggtggatgt caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac  aaagtctacg cctgcgaagt cacccatcag    600
ggcctgagct cgcccgtcac aaagagcttc aacaggggag agtgt                    645

<210> SEQ ID NO 146
<211> LENGTH: 645
<212> TYPE: DNA
<213> ORGANISM: homo sapiens

<400> SEQUENCE: 146
gacatccaga tgacccagtc tcctccacc ctgtctgcat ctgtcggaga cagagtcacc      60
atcacttgcc gggccagtca gagtattggt agcggttgg cctggtatca gcagcaacca    120
gggaaagccc ctaaattcct gatctatgat gcctccagtt tggaaagtgg ggtcccatca    180
aggttcagcg gcagtggatc agggacagaa ttcactctca ccatcagcag cctgcagccg    240
gaggatcttg caacttatta ctgccaacag tacaatagag attctccgtg gacgttcggc    300
caagggacca aggtggaaat caagcgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac  aaagtctacg cctgcgaagt cacccatcag    600
ggcctgagct cgcccgtcac aaagagcttc aacaggggag agtgt                    645

<210> SEQ ID NO 147
<211> LENGTH: 657
<212> TYPE: DNA
<213> ORGANISM: homo sapiens

<400> SEQUENCE: 147
gatattgtga tgacccagtc tccactctcc ctgcccgtca cccaggaga gccggcctcc      60 atctcctgca ggtctagtca gagcctcctg catagtgatg gacgctacta tgtggattgg    120
tacctgcaga agccagggca gtctccacac ctcctgatct atttggcttc taatcgggcc    180 tccgggtcc ctgacaggtt cactggcagt ggatcaggca cagatttac actgaaaatc    240
```

```
agcagagtgg aggctgagga tgttggcgtt tattactgca tgcaaggtct acacactcct    300
tggacgttcg gccaggggac caaggtggac atcaagcgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657
```

<210> SEQ ID NO 148
<211> LENGTH: 639
<212> TYPE: DNA
<213> ORGANISM: homo sapiens

<400> SEQUENCE: 148

```
gaaattgtaa tgacacagtc tccagccacc ctgtctgcgt ccccagggga aagagccacc     60
ctctcctgtt gggccagtca gactattgga ggcaacttag cctggtacca gcagaaacct    120
ggccaggctc ccaggctcct catctatggt gcatccacca gggccactgg tgtcccagcc    180
aggttcagtg gcagtgggtc tgggacagag ttcactctcg ccatcagcag cctgcagtct    240
gaagattttg cagtttatta ctgtcagcag tataaaaact ggtacacttt tggccagggg    300
accaagctgg agctcaaacg aactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                           639
```

<210> SEQ ID NO 149
<211> LENGTH: 645
<212> TYPE: DNA
<213> ORGANISM: homo sapiens

<400> SEQUENCE: 149

```
gacatccaga tgacccagtc tccatcctcc ctgtctgcat ctgtaggaga cagagtcacc     60
atcacttgcc gggcaagtca gaccattgcc agttacgtaa attggtacca acaaaaacca    120
gggagagccc ctagtctcct gatctatgct gcatctaact tgcagagtgg ggtcccacca    180
aggttcagtg gcagtggatc tgggacagac ttcactctca ccatcagcgg tctgcaacct    240
gacgattttg caacttatta ctgtcaacag agttacagtt atcgagcgct cacttttcggc    300 ggagggacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 150
<211> LENGTH: 648
<212> TYPE: DNA
<213> ORGANISM: homo sapiens

<400> SEQUENCE: 150

| gaaattgtgt tgacacagtc tccagccacc ctgtcgttgt ccccagggga aagagccacc | 60 |
| ctctcctgca gggccagtca gagtgttagc agctccttag cctggtacca acagacacct | 120 |
| ggccaggctc ccaggcttct catctatgat gcgtcctaca gggtcactgg catcccagcc | 180 |
| aggttcagtg gcagtgggtc tgggatagac ttcactctca ccatcagcag cctagagcct | 240 |
| gaagattttg cagtttacta ttgtcagcag cgtagcaact ggcctccggg gctcactttc | 300 |
| ggcgggggga ccaaggtgga gatcaaacga actgtggctg caccatctgt cttcatcttc | 360 |
| ccgccatctg atgagcagtt gaaatctgga actgcctctg ttgtgtgcct gctgaataac | 420 |
| ttctatccca gagaggccaa agtacagtgg aaggtggata acgccctcca atcgggtaac | 480 |
| tcccaggaga gtgtcacaga gcaggacagc aaggacagca cctacagcct cagcagcacc | 540 |
| ctgacgctga gcaaagcaga ctacgagaaa cacaaagtct acgcctgcga agtcacccat | 600 |
| cagggcctga gctcgcccgt cacaaagagc ttcaacaggg gagagtgt | 648 |

<210> SEQ ID NO 151
<211> LENGTH: 642
<212> TYPE: DNA
<213> ORGANISM: homo sapiens

<400> SEQUENCE: 151

| gccatccagt tgacccagtc tccatcctcc ctgtctgcat ctgttggaga cacagtcacc | 60 |
| gtcacttgcc ggccaagtca ggacattagc agtgctttag cctggtatca gcagaaacca | 120 |
| gggaaacctc ctaagctcct gatctatggt gcctccactt tggattatgg ggtcccatta | 180 |
| aggttcagcg gcactgcatc tgggacacat ttcactctca ccatcagcag cctgcaacct | 240 |
| gaagattttg caacttatta ctgtcaacag tttaatactt acccattcac tttcggccct | 300 |
| gggaccaaag tggatatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaacacaaa gtctacgcct gcgaagtcac ccatcagggc | 600 |
| ctgagctcgc ccgtcacaaa gagcttcaac aggggagagt gt | 642 |

<210> SEQ ID NO 152
<211> LENGTH: 660
<212> TYPE: DNA
<213> ORGANISM: homo sapiens

<400> SEQUENCE: 152

| gacatcgtga tgacccagtc tccagactcc ctggctgtgt ctctgggcga gagggccacc | 60 |
| atcaactgca agtccagcca gagtgtttta tacaactcca acaataagaa ctacttagcc | 120 |
| tggtatcagc agaaaccagg acagcctcct aagctcctca ttcacttggc atctacccgg | 180 |
| gaatacgggg tccctgaccg attcagtggc agcgggtctg ggacagattt cgctctcatc | 240 |
| atcagcagcc tgcaggctga agatgtggca gtttattact gtcaacaata ttatcaaact | 300 |
| cctctaactt ttggccaggg gaccaaggtg gagatcaaac gaactgtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |

```
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
```

<210> SEQ ID NO 153
<211> LENGTH: 642
<212> TYPE: DNA
<213> ORGANISM: homo sapiens
<400> SEQUENCE: 153

```
gacatccaga tgacccagtc tccatcctcc ctggctgcat ctgtaggaga cagagtcacc       60
atcacttgcc gggcaagtca gttcattagc agctatttac attggtatca gcaaagacca      120
ggcaaggccc ctaaactcct gatgtatgct gcctccactt tgcaaagtgg ggtcccatca      180
aggttcagtg gcagtggatc tgggacagat ttcactctca ccatcagcag tctgcaacct      240
gaagattttg caacttacta ctgtcaacag agttacacta acccatacac ttttggccag      300
gggaccaagc tggagatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642
```

<210> SEQ ID NO 154
<211> LENGTH: 642
<212> TYPE: DNA
<213> ORGANISM: homo sapiens
<400> SEQUENCE: 154

```
gacatccaga tgacccagtc tccatcctcc ctatctgcat ctgtaggaga cagagtcacc       60
atcacttgcc gggcaagtca gagcattgcc agctatttaa attggtatca gcagaaacca      120
gggaaagccc ccaaactcct gatctatgct gcatccagtt tgcatagtgg ggtcccatca      180
agattcagtg gcagtggatc tgggacagat ttcactctca ccatcagcag tctgcaacct      240
gaagattttg caacttacta ctgtcaacac agttacagta ctcgattcac tttcggccct      300
gggaccaaag tggatgtcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642
```

<210> SEQ ID NO 155
<211> LENGTH: 642
<212> TYPE: DNA
<213> ORGANISM: homo sapiens
<400> SEQUENCE: 155

```
gacatccaga tgacccagtc tccttcgacc ctgtctgcat ctgtaggaga cagagtcacc       60
atcacttgcc gggccagtca gagtgttact agtgagttgg cctggtatca gcagaaacca      120
gggaaagccc ctaacttcct gatctataag gcgtctagtt tagaaagtgg ggtcccatca      180
```

```
aggttcagcg gcagtggatc tgggacagaa ttcactctca ccatcagcag cctgcagcct    240
gatgattttg caacttatta ctgccaacag tataatagtt ttccgtacac ttttggccag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga aaacacaaa gtctacgcct gcgaagtcac ccatcagggc    600
ctgagctcgc ccgtcacaaa gagcttcaac aggggagagt gt    642
```

```
<210> SEQ ID NO 156
<211> LENGTH: 642
<212> TYPE: DNA
<213> ORGANISM: homo sapiens

<400> SEQUENCE: 156
```

```
gacatccaga tgacccagtc tccttccacc ctgtctgcat ctgtaggcga cagactcacc    60
atcacttgcc gggccagtca gaatatttat aactggttgg cctggtatca gcagaaacca    120
gggaaagccc ctaaactcct gatctatgac gcctccactt tggaaagtgg ggtcccatca    180
aggttcagcg gcagtggatc tgggacagag ttcactctca ccatcagcag cctgcagcct    240
gatgattttg cgacttatta ctgccaacaa tataatagtt tgtctccgac gttcggccaa    300
gggaccaagg tggaaatcaa gcgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga aaacacaaa gtctacgcct gcgaagtcac ccatcagggc    600
ctgagctcgc ccgtcacaaa gagcttcaac aggggagagt gt    642
```

```
<210> SEQ ID NO 157
<211> LENGTH: 642
<212> TYPE: DNA
<213> ORGANISM: homo sapiens

<400> SEQUENCE: 157
```

```
gacatccagt tgacccagtc tccatccttc ctgtctgcat ctttagaaga cagagtcact    60
atcacttgcc gggccagtca gggcattagc agttatttag cctggtatca gcaaaaacca    120
gggaaagccc ctaagctcct gctcgatgct gcatccactt tgcaaagtgg ggtcccatca    180
aggttcagcg gcagtggatc tgggacagag ttcactctca caatcagcag cctgcagcct    240
gaagattttg caacttatta ctgtcaacag cttaatagtt accctcggac gttcggccaa    300
gggaccaagg tggacatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga aaacacaaa gtctacgcct gcgaagtcac ccatcagggc    600
ctgagctcgc ccgtcacaaa gagcttcaac aggggagagt gt    642
```

```
<210> SEQ ID NO 158
```

<211> LENGTH: 642
<212> TYPE: DNA
<213> ORGANISM: homo sapiens

<400> SEQUENCE: 158

```
gacatccaga tgacccagtc tccatcctcc ctgtctgcat ctgtaggaga cagagtcagc      60
atcacttgcc gggcgagtca gggcattagc aattatttag cctggtatca gcagaaacca     120
gggaaggttc ctaagctcct gatctatgct gcatccactt tgcaatcagg ggtcccatct     180
cggttcagtg gcagtggatc tgggacagat ttcactctca ccatcagcag cctgcagcct     240
gaggatgttg caacttatta ctgtcaaaag tataacagtg cccctcaaac gttcggccaa     300
gggaccaagg tggaaatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 159
<211> LENGTH: 660
<212> TYPE: DNA
<213> ORGANISM: homo sapiens

<400> SEQUENCE: 159

```
gacatcgtga tgacccagtc tccagactcc ctggctgtgt ctctgggcga gagggccacc      60
atcaactgca ggtccagcca gagtgtttta tacagctcca acaataagaa ctacttagct     120
tggtaccagc agaaaccagg acagcctcct aagctgctcg tttactgggc atcaacccgg     180
gcatccgggg tccctgaccg attcagtggc agcgggtctg ggacagattt cactctcacc     240
ctcagcagcc tgcaggctga agatgtggca gtttattact gtcagcagtt tcatagtact     300
cctcggacgt tcggccaagg gaccaaggtg gagatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaagt ctacgcctgc     600
gaagtcaccc atcagggcct gagctcgccc gtcacaaaga gcttcaacag gggagagtgt     660
```

<210> SEQ ID NO 160
<211> LENGTH: 645
<212> TYPE: DNA
<213> ORGANISM: homo sapiens

<400> SEQUENCE: 160

```
gaaattgtgt tgacgcagtc tccaggcacc ctgtctttgt ctccagggga aagagccacc      60
ctctcctgca gggccagtca gagtgttagc agcaactact tagcctggta ccagcagaaa     120
cctggccagg ctcccaggct cctcatctat ggtgcatcca gcagggccgc tggcatgcca     180
gacaggttca gtggcagtgg gtctgggaca gacttcactc tcaccatcag cagactggag     240
cctgaagatt ttgcagtgta ttactgtcag cagtatggta actcaccgct cactttcggc     300
ggagggaccc gagtggagat caaacgaact gtggctgcac catctgtctt catcttcccg     360
ccatctgatg agcagttgaa atctggaact gcctctgttg tgtgcctgct gaataacttc     420
```

```
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgt                    645

<210> SEQ ID NO 161
<211> LENGTH: 642
<212> TYPE: DNA
<213> ORGANISM: homo sapiens

<400> SEQUENCE: 161
gacatccaga tgacccagtc tccatcttct gtgtctgcat ctgtaggaga cagagtcacc     60
atcacttgtc gggcgagtca ggctattagt aactggttag cctggtatca gcagaaacca    120
ggaaaagccc ctaagctcct gatctatgct gcatccagtt tgcaaagtgg ggtcccatca    180
agattcagcg gcagtggatc tgggacagat ttcactctca ctatcagcgg cctgcagcct    240
gaggattttg caacttacta ttgtcaacag gctgacactt tccctttcac tttcggccct    300
gggaccaaag tggatatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                        642

<210> SEQ ID NO 162
<211> LENGTH: 660
<212> TYPE: DNA
<213> ORGANISM: homo sapiens

<400> SEQUENCE: 162
gatattgtga tgacccagac tccactctcc ctgcccgtca cccctggaga gccggcctcc     60
atctcctgca ggtctagtca gagcctcttg gatagtaatg atggaaacac ctatttggac    120
tggtacctgc agaagccagg gcagtctcca cagctcctga tttatacatt ttcctatcgg    180
gcctctggag tcccagacag gttcagtggc agtgggtctg gcactgattt cacactgaaa    240
atcagcaggg tggaggccga ggatgttgga gtttattact gcatgcaacg tatcgagttt    300
ccgtacactt ttggccaggg gaccaagctg gagatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660

<210> SEQ ID NO 163
<211> LENGTH: 657
<212> TYPE: DNA
<213> ORGANISM: homo sapiens

<400> SEQUENCE: 163
gatattgtga tgacccagtc tccactctcc ctgcccgtca cccctggaga gccggcctcc     60
```

```
atctcctgca ggtctagtca gagcctcctg catagaaatg agtacaacta tttggattgg      120
tacttgcaga agccagggca gtctccacag ctcctgatct attggggttc taatcgggcc      180 tccgggtcc ctgacaggtt cagtggcagt ggatcaggca cagattttac actgaaaatc      240
agcagagtgg aggctgagga tgttggggtt tattactgca tgcaaactct acaaactcct      300
cggacgttcg gccaagggac caaggtggaa atcaaacgaa ctgtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct caacagggg agagtgt       657
```

<210> SEQ ID NO 164
<211> LENGTH: 642
<212> TYPE: DNA
<213> ORGANISM: homo sapiens

<400> SEQUENCE: 164

```
gacatccaga tgacccagtc tccatcctcc gtgtctgcat ctgtgggaga cagagtcacc       60
atcacttgcc aggcgagtca agacattagc aactatttaa attggtatca gcagaaacca      120
gggaaagccc ctaagctcct gatcttcgat gcaaccaaat tggagacagg gtcccaaca       180 aggttcattg gaagtggatc tgggacagat tttactgtca ccatcaccag cctgcagcct      240
gaagatgttg caacatatta ctgtcaacac tttgctaatc tcccatacac ttttggccag      300
gggaccaagc tggagatcaa gcgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag cccctgacg      540 ctgagcaaag cagactacga aaacacaaa gtctacgcct gcgaagtcac ccatcagggc      600
ctgagctcgc ccgtcacaaa gagcttcaac aggggagagt gt                        642
```

<210> SEQ ID NO 165
<211> LENGTH: 642
<212> TYPE: DNA
<213> ORGANISM: homo sapiens

<400> SEQUENCE: 165

```
gacatccaga tgacccagtc tccatcttcc ctgtctgcat ctgtaggaga cagagtcacc       60
atcacttgcc gggcgagtca gggcattagg aattatttag cctggtatca gcagaaacca      120
gggaaagttc ctaagctcct ggtctttgct gcatccactt tgcaatcagg gtcccatct       180 cggttcagtg gcagtggatc tgggacagat ttcactctca ccatcagcag cctgcagcct      240
gaggatgttg caacttatta ctgtcaaagg tataacagtg ccccgctcac tttcggcgga      300
gggacgaagg tggagatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag cccctgacg      540 ctgagcaaag cagactacga aaacacaaa gtctacgcct gcgaagtcac ccatcagggc      600
ctgagctcgc ccgtcacaaa gagcttcaac aggggagagt gt                        642
```

```
<210> SEQ ID NO 166
<211> LENGTH: 645
<212> TYPE: DNA
<213> ORGANISM: homo sapiens

<400> SEQUENCE: 166
gacatccaga tgacccagtc tccatcctcc ctgtctgcat ctgtaggaga cagagtcacc     60
atcacttgcc gggcaagtca gatcattgcc agctatttaa attggtatca gcagaaacca    120
ggcagagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccccatatt cactttcggc    300
cctgggacca aggtgaatat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645

<210> SEQ ID NO 167
<211> LENGTH: 639
<212> TYPE: DNA
<213> ORGANISM: homo sapiens

<400> SEQUENCE: 167
gaaattgtgt tgacacagtc tccagccacc ctgtctttgt ctccagggga aagagccacc     60
ctctcctgca ggaccagtca gagtgttagc agctacttag cctggtacca acagaaacct    120
ggccaggctc ccaggctcct catctatgat gcttccaata gggccactgg catcccagcc    180
aggttcagtg gcagtgggtc tgggacagac ttcactctca ccatcagcag cctagagcct    240
gaagattttg cagtttatta ctgtcagcag cgtagtgact ggctcacttt cggcggaggg    300
accaaggtgg agatcaaacg aactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                           639

<210> SEQ ID NO 168
<211> LENGTH: 645
<212> TYPE: DNA
<213> ORGANISM: homo sapiens

<400> SEQUENCE: 168
gaaattgtaa tgacacagtc tccagccacc ctgtctgtgt ctccagggga aagagccacc     60
ctctcctgca gggccagtca gagtattaaa acaacttggg cctggtacca ggtgaaacct    120
ggccaggctc ccaggctcct cacctctggt gcatccgcca gggccactgg aattccaggc    180
aggttcagtg gcagtgggtc tgggactgac ttcactctca ccatcagcag cctccagtct    240
gaagatattg cagtttatta ctgtcaggag tataataatt ggcccctgct cactttcggc    300
```

```
ggagggacca aggtggagat ccaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgt                   645

<210> SEQ ID NO 169
<211> LENGTH: 645
<212> TYPE: DNA
<213> ORGANISM: homo sapiens

<400> SEQUENCE: 169
gacatccaga tgacccagtc tcctccctcc ctgtctgcat ctgtgggaga cagagtcacc     60
atcacttgcc gggcaagtca gaggattgcc agctatttaa attggtatca gcagaaacca    120
gggagagccc ctaagctcct gatctttgct gcatccagtt tacaaagtgg ggtcccatca    180
aggttcagtg gcagtggatc tgggacagac ttcactctca ccatcagtag tctgcaacct    240
gaagattatg cgacttacta ctgtcaacag agttacagta ctcccatcta cacttttggc    300
caggggacca agctggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgt                   645

<210> SEQ ID NO 170
<211> LENGTH: 642
<212> TYPE: DNA
<213> ORGANISM: homo sapiens

<400> SEQUENCE: 170
gacatccaga tgacccagtc tccatcctcc ctgtctgcat ctgtaggaga cagagtcacc     60
atcacttgcc aggcgagtca gggcattagc aactatttaa attggtatca acagaaacca    120
gggaaagccc ctaagctcct gatcttcgat gcatccaatt tggaatcaga ggtcccatca    180
aggttcagtg gacgtggatc tgggacagat tttactttct ccatcagcag cctgcagcct    240
gaagatattg caacatattt ctgtcaacag tatgataatt tcccgtacac ttttggccag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg   540 ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 171
<211> LENGTH: 642
<212> TYPE: DNA
<213> ORGANISM: homo sapiens

<400> SEQUENCE: 171
```

```
gacatccaga tgacccagtc tccatcctcc ctggctgcat ctgtaggaga cagagtcacc      60
atcacctgcc gggcaagtca gacgattgcc agttatgtaa attggtatca acagaaacca     120
gggaaagccc ctaatctcct gatctatgct gcatccagtt tgcaaagtgg ggtcccatca     180
aggttcagtg gcagtggatc tgggacagat ttcactctca ccatcagcag tctgcaacct     240
gaagattttg catcttactt ctgtcaacag agttacagtt tcccgtacac ttttggccag     300
gggaccaagc tggatatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 172
<211> LENGTH: 645
<212> TYPE: DNA
<213> ORGANISM: homo sapiens

<400> SEQUENCE: 172
gacatccaga tgacccagtc tccatcctcc ctgtctgcat ctgtaggaga cagagtcacc      60
atcacttgcc gggcaagtca gaccattgcc agctatgtaa attggtatca gcagaaacca     120
gggaaagccc ctaagctcct gatctatgct gcatccaatt tgcaaagtgg ggtcccttca     180
aggttcagtg gcagtggatc tgggacagat ttcactctca ccatcagcag tctgcaacct     240
gaagattttg caacttacta ctgtcaacag agttacagtt ccctcggct cactttcggc      300 ggagggacca aggtggacat cacacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacagggag agtgt                      645

<210> SEQ ID NO 173
<211> LENGTH: 639
<212> TYPE: DNA
<213> ORGANISM: homo sapiens

<400> SEQUENCE: 173
gacatccaga tgacccagtc tccatcctcc ctgtctgcat ctgtaggaga cagagtcacc      60
atcacttgcc ggtcaagtca gaccattagc gtctttttaa attggtatca gcagaaacca     120
gggaaagccc ctaagctcct gatctatgcc gcatccagtt gcacagtgc ggtcccatca      180 aggttcagtg gcagtggatc tgggacagat ttcactctca ccatcagcag tctgcaacct     240
gaagattctg caacttacta ctgtcaagag agtttcagta gctcaacttt cggcggaggg     300
accaaggtgg agatcaaacg aactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg    540
```

| | | | |
|---|---|---|---|
| agcaaagcag | actacgagaa | acacaaagtc tacgcctgcg aagtcaccca tcagggcctg | 600 |
| agctcgcccg | tcacaaagag | cttcaacagg ggagagtgt | 639 |

<210> SEQ ID NO 174
<211> LENGTH: 645
<212> TYPE: DNA
<213> ORGANISM: homo sapiens

<400> SEQUENCE: 174

| | | | | | |
|---|---|---|---|---|---|
| gaaattgtaa | tgacacagtc | tccagccacc | ctgtctgtgt | ctccagggga aacagccacc | 60 |
| ctctcctgca | gggccagtca | gagtgttagc | agcaacttag | cctggtacca acataaacct | 120 |
| ggccaggctc | ccaggctcct | catccatagt | gcatccacca | gggccactgg gatcccagcc | 180 |
| aggttcagtg | gcagtgggtc | tgggacagag | ttcactctca | ccataagcag cctgcagtct | 240 |
| gaagattttg | cagtttatta | ctgtcagcag | tataatatgt | ggcctccctg acgttcggc | 300 |
| caagggacca | aggtggaaat | caaacgaact | gtggctgcac | catctgtctt catcttcccg | 360 |
| ccatctgatg | agcagttgaa | atctggaact | gcctctgttg | tgtgcctgct gaataacttc | 420 |
| tatcccagag | aggccaaagt | acagtggaag | gtggataacg | ccctccaatc gggtaactcc | 480 |
| caggagagtg | tcacagagca | ggacagcaag | gacagcacct | acagcctcag cagcaccctg | 540 |
| acgctgagca | aagcagacta | cgagaaacac | aaagtctacg | cctgcgaagt cacccatcag | 600 |
| ggcctgagct | cgcccgtcac | aaagagcttc | aacaggggag | agtgt | 645 |

<210> SEQ ID NO 175
<211> LENGTH: 657
<212> TYPE: DNA
<213> ORGANISM: homo sapiens

<400> SEQUENCE: 175

| | | | | | |
|---|---|---|---|---|---|
| gatattgtga | tgacccagtc | tccactctcc | ctgcccgtca | cccctggagc gccggcctcc | 60 |
| atctcctgca | ggtctagtca | gagcctcctg | cgtactaatg | gatacaacta tttggattgg | 120 |
| tacctgcaga | agccagggca | gtctccacag | ctcctgatct | atttgggttc tattcgggcc | 180 |
| tccggggtcc | ctgacaggtt | cagtggcagt | ggctcaggca | cagattttac actgaaaatc | 240 |
| agcagagtgg | aggctgagga | tgttggggtt | tattactgca | tgcaatctct acaaacttcg | 300 |
| atcaccttcg | gccaagggac | acgactggag | attaaacgaa | ctgtggctgc accatctgtc | 360 |
| ttcatcttcc | cgccatctga | tgagcagttg | aaatctggaa | ctgcctctgt tgtgtgcctg | 420 |
| ctgaataact | tctatcccag | agaggccaaa | gtacagtgga | aggtggataa cgccctccaa | 480 |
| tcgggtaact | cccaggagag | tgtcacagag | caggacagca | aggacagcac ctacagcctc | 540 |
| agcagcaccc | tgacgctgag | caaagcagac | tacgagaaac | acaaagtcta cgcctgcgaa | 600 |
| gtcacccatc | agggcctgag | ctcgcccgtc | acaaagagct | tcaacagggg agagtgt | 657 |

<210> SEQ ID NO 176
<211> LENGTH: 642
<212> TYPE: DNA
<213> ORGANISM: homo sapiens

<400> SEQUENCE: 176

| | | | | | |
|---|---|---|---|---|---|
| gaaattgtaa | tgacacagtc | tccagccacc | ctgtctgtgt | ctccggggga aagagccacc | 60 |
| ctctcctgca | gggctagtca | gagtgttggc | aacaacttag | cctggtacca gcagagacct | 120 |
| ggccaggctc | ccagactcct | catctatggt | gcgtccacca | gggccactgg tatcccagcc | 180 |
| aggttcagtg | gcagtgggtc | tgggacagag | ttcactctca | ccatcagcag cctgcagtct | 240 |

```
gaggattttg cagtttatta ctgtcagcag tatgataagt ggcctgagac gttcggccag      300
gggaccaagg tggacatcaa gcgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642
```

<210> SEQ ID NO 177
<211> LENGTH: 1602
<212> TYPE: DNA
<213> ORGANISM: Homo sapiens
<220> FEATURE:
<221> NAME/KEY: CDS
<222> LOCATION: (1)..(298)
<220> FEATURE:
<221> NAME/KEY: CDS
<222> LOCATION: (690)..(734)
<220> FEATURE:
<221> NAME/KEY: CDS
<222> LOCATION: (853)..(1182)
<220> FEATURE:
<221> NAME/KEY: CDS
<222> LOCATION: (1280)..(1599)

<400> SEQUENCE: 177

```
agt gcc tcc acc aag ggc cca tcg gtc ttc ccc ctg gca ccc tcc tcc       48
Ser Ala Ser Thr Lys Gly Pro Ser Val Phe Pro Leu Ala Pro Ser Ser
1               5                   10                  15 aag agc acc tct ggg ggc aca gcg gcc ctg ggc tgc ctg gtc aag gac       96
Lys Ser Thr Ser Gly Gly Thr Ala Ala Leu Gly Cys Leu Val Lys Asp
            20                  25                  30 tac ttc ccc gaa ccg gtg acg gtg tcg tgg aac tca ggc gcc ctg acc      144
Tyr Phe Pro Glu Pro Val Thr Val Ser Trp Asn Ser Gly Ala Leu Thr
        35                  40                  45 agc ggc gtg cac acc ttc ccg gct gtc cta cag tcc tca gga ctc tac      192
Ser Gly Val His Thr Phe Pro Ala Val Leu Gln Ser Ser Gly Leu Tyr
    50                  55                  60 tcc ctc agc agc gtg gtg acc gtg ccc tcc agc agc ttg ggc acc cag      240
Ser Leu Ser Ser Val Val Thr Val Pro Ser Ser Ser Leu Gly Thr Gln
65                  70                  75                  80 acc tac atc tgc aac gtg aat cac aag ccc agc aac acc aag gtg gac      288
Thr Tyr Ile Cys Asn Val Asn His Lys Pro Ser Asn Thr Lys Val Asp
                85                  90                  95 aag aga gtt g gtgagaggcc agcacaggga ggggagggtgt ctgctggaag            338
Lys Arg Val ccaggctcag cgctcctgcc tggacgcatc ccggctatgc agtcccagtc cagggcagca     398
aggcaggccc cgtctgcctc ttcacccgga ggcctctgcc cgcccactc atgctcaggg      458 agagggtctt ctggcttttt ccccaggctc tgggcaggca caggctaggt gcccctaacc     518
caggccctgc acacaaaggg gcaggtgctg ggctcagacc tgccaagagc catatccggg     578
aggaccctgc ccctgaccta agcccacccc aaaggccaaa ctctccactc cctcagctcg     638
gacaccttct ctcctcccag attccagtaa ctcccaatct tctctctgcag   ag  ccc     694
                                                              Glu Pro
                                                              100 aaa tct tgt gac aaa act cac aca tgc cca ccg tgc cca g gtaagccagc      744
Lys Ser Cys Asp Lys Thr His Thr Cys Pro Pro Cys Pro
        105                 110
```

```
ccaggcctcg ccctccagct caaggcggga caggtgccct agagtagcct gcatccaggg            804
acaggcccca gccgggtgct gacacgtcca cctccatctc ttcctcag ca  cct gaa            860
                                                        Ala Pro Glu
                                                            115 ctc ctg ggg gga ccg tca gtc ttc ctc ttc ccc cca aaa ccc aag gac             908
Leu Leu Gly Gly Pro Ser Val Phe Leu Phe Pro Pro Lys Pro Lys Asp
        120                 125                 130 acc ctc atg atc tcc cgg acc cct gag gtc aca tgc gtg gtg gtg gac             956
Thr Leu Met Ile Ser Arg Thr Pro Glu Val Thr Cys Val Val Val Asp
135                 140                 145 gtg agc cac gaa gac cct gag gtc aag ttc aac tgg tac gtg gac ggc            1004
Val Ser His Glu Asp Pro Glu Val Lys Phe Asn Trp Tyr Val Asp Gly
150                 155                 160                 165 gtg gag gtg cat aat gcc aag aca aag ccg cgg gag gag cag tac aac            1052
Val Glu Val His Asn Ala Lys Thr Lys Pro Arg Glu Glu Gln Tyr Asn
            170                 175                 180 agc acg tac cgt gtg gtc agc gtc ctc acc gtc ctg cac cag gac tgg            1100
Ser Thr Tyr Arg Val Val Ser Val Leu Thr Val Leu His Gln Asp Trp
        185                 190                 195 ctg aat ggc aag gag tac aag tgc aag gtc tcc aac aaa gcc ctc cca            1148
Leu Asn Gly Lys Glu Tyr Lys Cys Lys Val Ser Asn Lys Ala Leu Pro
    200                 205                 210 gcc ccc atc gag aaa acc atc tcc aaa gcc aaa g gtgggacccg                    1192
Ala Pro Ile Glu Lys Thr Ile Ser Lys Ala Lys
215                 220 tggggtgcga gggccacatg gacagaggcc ggctcggccc accctctgcc ctgagagtga          1252
ccgctgtacc aacctctgtc cctacag gg  cag ccc cga gaa cca cag gtg tac          1305
                                Gly Gln Pro Arg Glu Pro Gln Val Tyr
                                                225                 230 acc ctg ccc cca tcc cgg gag gag atg acc aag aac cag gtc agc ctg            1353
Thr Leu Pro Pro Ser Arg Glu Glu Met Thr Lys Asn Gln Val Ser Leu
        235                 240                 245 acc tgc ctg gtc aaa ggc ttc tat ccc agc gac atc gcc gtg gag tgg            1401
Thr Cys Leu Val Lys Gly Phe Tyr Pro Ser Asp Ile Ala Val Glu Trp
250                 255                 260                 265 gag agc aat ggg cag ccg gag aac aac tac aag acc acg cct ccc gtg            1449
Glu Ser Asn Gly Gln Pro Glu Asn Asn Tyr Lys Thr Thr Pro Pro Val
            270                 275                 280 ctg gac tcc gac ggc tcc ttc ttc ctc tat agc aag ctc acc gtg gac            1497
Leu Asp Ser Asp Gly Ser Phe Phe Leu Tyr Ser Lys Leu Thr Val Asp
        285                 290                 295 aag agc agg tgg cag cag ggg aac gtc ttc tca tgc tcc gtg atg cat            1545
Lys Ser Arg Trp Gln Gln Gly Asn Val Phe Ser Cys Ser Val Met His
    300                 305                 310 gag gct ctg cac aac cac tac acg cag aag agc ctc tcc ctg tcc ccg            1593
Glu Ala Leu His Asn His Tyr Thr Gln Lys Ser Leu Ser Leu Ser Pro
315                 320                 325 ggt aaa tga                                                                 1602
Gly Lys
330

<210> SEQ ID NO 178
<211> LENGTH: 331
<212> TYPE: PRT
<213> ORGANISM: Homo sapiens

<400> SEQUENCE: 178

Ser Ala Ser Thr Lys Gly Pro Ser Val Phe Pro Leu Ala Pro Ser Ser
1               5                   10                  15
```

```
Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
            85                  90                  95

Lys Arg Val Glu Pro Lys Ser Cys Asp Lys Thr His Thr Cys Pro Pro
        100                 105                 110

Cys Pro Ala Pro Glu Leu Leu Gly Gly Pro Ser Val Phe Leu Phe Pro
    115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
            165                 170                 175

Glu Glu Gln Tyr Asn Ser Thr Tyr Arg Val Val Ser Val Leu Thr Val
        180                 185                 190

Leu His Gln Asp Trp Leu Asn Gly Lys Glu Tyr Lys Cys Lys Val Ser
    195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
            245                 250                 255

Tyr Pro Ser Asp Ile Ala Val Glu Trp Glu Ser Asn Gly Gln Pro Glu
        260                 265                 270

Asn Asn Tyr Lys Thr Thr Pro Pro Val Leu Asp Ser Asp Gly Ser Phe
    275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330

<210> SEQ ID NO 179
<211> LENGTH: 20
<212> TYPE: DNA
<213> ORGANISM: artificial sequence
<220> FEATURE:
<223> OTHER INFORMATION: Synthetic DNA primer
<220> FEATURE:
<221> NAME/KEY: misc_feature
<222> LOCATION: (4)..(4)
<223> OTHER INFORMATION: n is G or C

<400> SEQUENCE: 179
gacngatggg cccttggtgg                                              20

<210> SEQ ID NO 180
```

```
<211> LENGTH: 20
<212> TYPE: DNA
<213> ORGANISM: artificial sequence
<220> FEATURE:
<223> OTHER INFORMATION: Synthetic DNA primer

<400> SEQUENCE: 180
gagtggctcc tgggggaaga                                              20

<210> SEQ ID NO 181
<211> LENGTH: 36
<212> TYPE: DNA
<213> ORGANISM: artificial sequence
<220> FEATURE:
<223> OTHER INFORMATION: Synthetic DNA primer
<220> FEATURE:
<221> NAME/KEY: misc_feature
<222> LOCATION: (21)..(21)
<223> OTHER INFORMATION: n is a or g
<220> FEATURE:
<221> NAME/KEY: misc_feature
<222> LOCATION: (35)..(35)
<223> OTHER INFORMATION: n is a or g

<400> SEQUENCE: 181
tattcccatg gcgcgcccag ntgcagctgg tgcant                            36

<210> SEQ ID NO 182
<211> LENGTH: 36
<212> TYPE: DNA
<213> ORGANISM: artificial sequence
<220> FEATURE:
<223> OTHER INFORMATION: Synthetic DNA primer
<220> FEATURE:
<221> NAME/KEY: misc_feature
<222> LOCATION: (18)..(18)
<223> OTHER INFORMATION: n is g or c
<220> FEATURE:
<221> NAME/KEY: misc_feature
<222> LOCATION: (32)..(32)
<223> OTHER INFORMATION: n is a or g

<400> SEQUENCE: 182
tattcccatg gcgcgccnag gtccagctgg tncagt                            36

<210> SEQ ID NO 183
<211> LENGTH: 36
<212> TYPE: DNA
<213> ORGANISM: artificial sequence
<220> FEATURE:
<223> OTHER INFORMATION: Synthetic DNA primer
<220> FEATURE:
<221> NAME/KEY: misc_feature
<222> LOCATION: (21)..(21)
<223> OTHER INFORMATION: n is a or g

<400> SEQUENCE: 183
tattcccatg gcgcgcccag ntcaccttga aggagt                            36

<210> SEQ ID NO 184
<211> LENGTH: 35
<212> TYPE: DNA
<213> ORGANISM: artificial sequence
<220> FEATURE:
<223> OTHER INFORMATION: Synthetic DNA primer
<220> FEATURE:
<221> NAME/KEY: misc_feature
<222> LOCATION: (18)..(18)
<223> OTHER INFORMATION: n is g or c

<400> SEQUENCE: 184
```

```
tattcccatg gcgcgccnag gtgcagctgg tggag                              35

<210> SEQ ID NO 185
<211> LENGTH: 36
<212> TYPE: DNA
<213> ORGANISM: artificial sequence
<220> FEATURE:
<223> OTHER INFORMATION: Synthetic DNA primer

<400> SEQUENCE: 185
tattcccatg gcgcgcccag gtgcagctac agcagt                             36

<210> SEQ ID NO 186
<211> LENGTH: 36
<212> TYPE: DNA
<213> ORGANISM: artificial sequence
<220> FEATURE:
<223> OTHER INFORMATION: Synthetic DNA primer
<220> FEATURE:
<221> NAME/KEY: misc_feature
<222> LOCATION: (21)..(21)
<223> OTHER INFORMATION: n is g or c

<400> SEQUENCE: 186
tattcccatg gcgcgcccag ntgcagctgc aggagt                             36

<210> SEQ ID NO 187
<211> LENGTH: 36
<212> TYPE: DNA
<213> ORGANISM: artificial sequence
<220> FEATURE:
<223> OTHER INFORMATION: Synthetic DNA primer
<220> FEATURE:
<221> NAME/KEY: misc_feature
<222> LOCATION: (20)..(20)
<223> OTHER INFORMATION: n is a or g

<400> SEQUENCE: 187
tattcccatg gcgcgccgan gtgcagctgg tgcagt                             36

<210> SEQ ID NO 188
<211> LENGTH: 37
<212> TYPE: DNA
<213> ORGANISM: artificial sequence
<220> FEATURE:
<223> OTHER INFORMATION: Synthetic DNA primer

<400> SEQUENCE: 188
tattcccatg gcgcgcccag gtacagctgc agcagtc                            37

<210> SEQ ID NO 189
<211> LENGTH: 38
<212> TYPE: DNA
<213> ORGANISM: artificial sequence
<220> FEATURE:
<223> OTHER INFORMATION: Synthetic DNA primer

<400> SEQUENCE: 189
atatatatgc ggccgcttat taacactctc ccctgttg                           38

<210> SEQ ID NO 190
<211> LENGTH: 45
<212> TYPE: DNA
<213> ORGANISM: artificial sequence
<220> FEATURE:
<223> OTHER INFORMATION: Synthetic DNA primer
<220> FEATURE:
```

```
<221> NAME/KEY: misc_feature
<222> LOCATION: (34)..(34)
<223> OTHER INFORMATION: n is a or t

<400> SEQUENCE: 190
ggcgcgccat gggaatagct agccgacatc cagntgaccc agtct          45

<210> SEQ ID NO 191
<211> LENGTH: 45
<212> TYPE: DNA
<213> ORGANISM: artificial sequence
<220> FEATURE:
<223> OTHER INFORMATION: Synthetic DNA primer

<400> SEQUENCE: 191
ggcgcgccat gggaatagct agccgatgtt gtgatgactc agtct          45

<210> SEQ ID NO 192
<211> LENGTH: 45
<212> TYPE: DNA
<213> ORGANISM: artificial sequence
<220> FEATURE:
<223> OTHER INFORMATION: Synthetic DNA primer
<220> FEATURE:
<221> NAME/KEY: misc_feature
<222> LOCATION: (34)..(34)
<223> OTHER INFORMATION: n is a or t
<220> FEATURE:
<221> NAME/KEY: misc_feature
<222> LOCATION: (39)..(39)
<223> OTHER INFORMATION: n is a or g

<400> SEQUENCE: 192
ggcgcgccat gggaatagct agccgaaatt gtgntgacnc agtct          45

<210> SEQ ID NO 193
<211> LENGTH: 45
<212> TYPE: DNA
<213> ORGANISM: artificial sequence
<220> FEATURE:
<223> OTHER INFORMATION: Synthetic DNA primer

<400> SEQUENCE: 193
ggcgcgccat gggaatagct agccgatatt gtgatgaccc acact          45

<210> SEQ ID NO 194
<211> LENGTH: 43
<212> TYPE: DNA
<213> ORGANISM: artificial sequence
<220> FEATURE:
<223> OTHER INFORMATION: Synthetic DNA primer

<400> SEQUENCE: 194
ggcgcgccat gggaatagct agccgaaacg acactcacgc agt            43

<210> SEQ ID NO 195
<211> LENGTH: 45
<212> TYPE: DNA
<213> ORGANISM: artificial sequence
<220> FEATURE:
<223> OTHER INFORMATION: Synthetic DNA primer

<400> SEQUENCE: 195
ggcgcgccat gggaatagct agccgaaatt gtgctgactc agtct          45

<210> SEQ ID NO 196
<211> LENGTH: 51
```

<212> TYPE: DNA
<213> ORGANISM: artificial sequence
<220> FEATURE:
<223> OTHER INFORMATION: Synthetic DNA primer

<400> SEQUENCE: 196
accgcctcca ccggcggccg cttattaaca ctctcccctg ttgaagctct t        51

<210> SEQ ID NO 197
<211> LENGTH: 30
<212> TYPE: DNA
<213> ORGANISM: artificial sequence
<220> FEATURE:
<223> OTHER INFORMATION: Synthetic DNA primer

<400> SEQUENCE: 197
ggaggcgctc gagacggtga ccagggtgcc                                 30

<210> SEQ ID NO 198
<211> LENGTH: 30
<212> TYPE: DNA
<213> ORGANISM: artificial sequence
<220> FEATURE:
<223> OTHER INFORMATION: Synthetic DNA primer

<400> SEQUENCE: 198
ggaggcgctc gagacggtga ccattgtccc                                 30

<210> SEQ ID NO 199
<211> LENGTH: 30
<212> TYPE: DNA
<213> ORGANISM: artificial sequence
<220> FEATURE:
<223> OTHER INFORMATION: Synthetic DNA primer

<400> SEQUENCE: 199
ggaggcgctc gagacggtga ccagggttcc                                 30

<210> SEQ ID NO 200
<211> LENGTH: 30
<212> TYPE: DNA
<213> ORGANISM: artificial sequence
<220> FEATURE:
<223> OTHER INFORMATION: Synthetic DNA primer

<400> SEQUENCE: 200
ggaggcgctc gagacggtga ccgtggtccc                                 30

<210> SEQ ID NO 201
<211> LENGTH: 5
<212> TYPE: PRT
<213> ORGANISM: Homo sapiens

<400> SEQUENCE: 201

Asp Tyr Asp Trp Ser
1               5

<210> SEQ ID NO 202
<211> LENGTH: 5
<212> TYPE: PRT
<213> ORGANISM: Homo sapiens

<400> SEQUENCE: 202

Thr Tyr Gly Met His
1               5

```
<210> SEQ ID NO 203
<211> LENGTH: 5
<212> TYPE: PRT
<213> ORGANISM: Homo sapiens

<400> SEQUENCE: 203

Thr Tyr Ala Leu Thr
1               5

<210> SEQ ID NO 204
<211> LENGTH: 5
<212> TYPE: PRT
<213> ORGANISM: Homo sapiens

<400> SEQUENCE: 204

Gly Tyr Tyr Met His
1               5

<210> SEQ ID NO 205
<211> LENGTH: 5
<212> TYPE: PRT
<213> ORGANISM: Homo sapiens

<400> SEQUENCE: 205

Asp Tyr Tyr Met Ser
1               5

<210> SEQ ID NO 206
<211> LENGTH: 5
<212> TYPE: PRT
<213> ORGANISM: Homo sapiens

<400> SEQUENCE: 206

Asn Tyr Gly Leu Asn
1               5

<210> SEQ ID NO 207
<211> LENGTH: 7
<212> TYPE: PRT
<213> ORGANISM: Homo sapiens

<400> SEQUENCE: 207

Ser Gly Asp Tyr Tyr Trp Ser
1               5

<210> SEQ ID NO 208
<211> LENGTH: 5
<212> TYPE: PRT
<213> ORGANISM: Homo sapiens

<400> SEQUENCE: 208

His Phe Gly Met His
1               5

<210> SEQ ID NO 209
<211> LENGTH: 5
<212> TYPE: PRT
<213> ORGANISM: Homo sapiens

<400> SEQUENCE: 209

Arg Phe Gly Ile Ser
1               5

<210> SEQ ID NO 210
```

```
<211> LENGTH: 5
<212> TYPE: PRT
<213> ORGANISM: Homo sapiens

<400> SEQUENCE: 210

Ser Tyr Val Met Asn
1               5

<210> SEQ ID NO 211
<211> LENGTH: 5
<212> TYPE: PRT
<213> ORGANISM: Homo sapiens

<400> SEQUENCE: 211

Asn Tyr Gly Met His
1               5

<210> SEQ ID NO 212
<211> LENGTH: 5
<212> TYPE: PRT
<213> ORGANISM: Homo sapiens

<400> SEQUENCE: 212

Asp Tyr Gly Met Asn
1               5

<210> SEQ ID NO 213
<211> LENGTH: 5
<212> TYPE: PRT
<213> ORGANISM: Homo sapiens

<400> SEQUENCE: 213

Ser Tyr Ala Met His
1               5

<210> SEQ ID NO 214
<211> LENGTH: 5
<212> TYPE: PRT
<213> ORGANISM: Homo sapiens

<400> SEQUENCE: 214

Ser Tyr Glu Met Asn
1               5

<210> SEQ ID NO 215
<211> LENGTH: 7
<212> TYPE: PRT
<213> ORGANISM: Homo sapiens

<400> SEQUENCE: 215

Ser Gly Asp Tyr Phe Trp Ser
1               5

<210> SEQ ID NO 216
<211> LENGTH: 5
<212> TYPE: PRT
<213> ORGANISM: Homo sapiens

<400> SEQUENCE: 216

Asn Tyr Ala Met His
1               5

<210> SEQ ID NO 217
<211> LENGTH: 5
<212> TYPE: PRT
```

<213> ORGANISM: Homo sapiens

<400> SEQUENCE: 217

Gly Asp Phe Trp Ser
1               5

<210> SEQ ID NO 218
<211> LENGTH: 5
<212> TYPE: PRT
<213> ORGANISM: Homo sapiens

<400> SEQUENCE: 218

Ser Tyr Trp Ile Gly
1               5

<210> SEQ ID NO 219
<211> LENGTH: 7
<212> TYPE: PRT
<213> ORGANISM: Homo sapiens

<400> SEQUENCE: 219

Thr Thr Arg Met Ser Val Ser
1               5

<210> SEQ ID NO 220
<211> LENGTH: 7
<212> TYPE: PRT
<213> ORGANISM: Homo sapiens

<400> SEQUENCE: 220

Phe Val Ser Thr Trp Ile Gly
1               5

<210> SEQ ID NO 221
<211> LENGTH: 5
<212> TYPE: PRT
<213> ORGANISM: Homo sapiens

<400> SEQUENCE: 221

Asn Tyr Ala Ile Asn
1               5

<210> SEQ ID NO 222
<211> LENGTH: 5
<212> TYPE: PRT
<213> ORGANISM: Homo sapiens

<400> SEQUENCE: 222

Asn Tyr Tyr Ile His
1               5

<210> SEQ ID NO 223
<211> LENGTH: 5
<212> TYPE: PRT
<213> ORGANISM: Homo sapiens

<400> SEQUENCE: 223

Ser Tyr Ser Ile Ser
1               5

<210> SEQ ID NO 224
<211> LENGTH: 5
<212> TYPE: PRT
<213> ORGANISM: Homo sapiens

```
<400> SEQUENCE: 224

Ser Tyr Trp Ile Gly
1               5

<210> SEQ ID NO 225
<211> LENGTH: 5
<212> TYPE: PRT
<213> ORGANISM: Homo sapiens

<400> SEQUENCE: 225

Asp Tyr Ala Met His
1               5

<210> SEQ ID NO 226
<211> LENGTH: 5
<212> TYPE: PRT
<213> ORGANISM: Homo sapiens

<400> SEQUENCE: 226

Thr Tyr Ala Met Thr
1               5

<210> SEQ ID NO 227
<211> LENGTH: 5
<212> TYPE: PRT
<213> ORGANISM: Homo sapiens

<400> SEQUENCE: 227

Thr His Gly Met His
1               5

<210> SEQ ID NO 228
<211> LENGTH: 7
<212> TYPE: PRT
<213> ORGANISM: Homo sapiens

<400> SEQUENCE: 228

Ala Gly Arg Val Gly Val Ser
1               5

<210> SEQ ID NO 229
<211> LENGTH: 7
<212> TYPE: PRT
<213> ORGANISM: Homo sapiens

<400> SEQUENCE: 229

Gly Ala Asp Tyr Tyr Trp Ser
1               5

<210> SEQ ID NO 230
<211> LENGTH: 5
<212> TYPE: PRT
<213> ORGANISM: Homo sapiens

<400> SEQUENCE: 230

Asn Ser Trp Ile Gly
1               5

<210> SEQ ID NO 231
<211> LENGTH: 6
<212> TYPE: PRT
<213> ORGANISM: Homo sapiens

<400> SEQUENCE: 231
```

```
Ser Gly His Phe Trp Gly
1               5

<210> SEQ ID NO 232
<211> LENGTH: 5
<212> TYPE: PRT
<213> ORGANISM: Homo sapiens

<400> SEQUENCE: 232

Asn Tyr Tyr Trp Gly
1               5

<210> SEQ ID NO 233
<211> LENGTH: 5
<212> TYPE: PRT
<213> ORGANISM: Homo sapiens

<400> SEQUENCE: 233

Ser Asn Gly Leu Ser
1               5

<210> SEQ ID NO 234
<211> LENGTH: 5
<212> TYPE: PRT
<213> ORGANISM: Homo sapiens

<400> SEQUENCE: 234

Ala Leu Ser Lys His
1               5

<210> SEQ ID NO 235
<211> LENGTH: 5
<212> TYPE: PRT
<213> ORGANISM: Homo sapiens

<400> SEQUENCE: 235

Thr Asn Gly Leu His
1               5

<210> SEQ ID NO 236
<211> LENGTH: 7
<212> TYPE: PRT
<213> ORGANISM: Homo sapiens

<400> SEQUENCE: 236

Arg Asn Arg Met Ser Val Ser
1               5

<210> SEQ ID NO 237
<211> LENGTH: 5
<212> TYPE: PRT
<213> ORGANISM: Homo sapiens

<400> SEQUENCE: 237

Thr Tyr Gly Val Ser
1               5

<210> SEQ ID NO 238
<211> LENGTH: 4
<212> TYPE: PRT
<213> ORGANISM: Homo sapiens

<400> SEQUENCE: 238

Tyr Ala Met His
1
```

<210> SEQ ID NO 239
<211> LENGTH: 5
<212> TYPE: PRT
<213> ORGANISM: Homo sapiens

<400> SEQUENCE: 239

Tyr Ile Gly Met His
1               5

<210> SEQ ID NO 240
<211> LENGTH: 5
<212> TYPE: PRT
<213> ORGANISM: Homo sapiens

<400> SEQUENCE: 240

Thr Tyr Gly Leu Asn
1               5

<210> SEQ ID NO 241
<211> LENGTH: 5
<212> TYPE: PRT
<213> ORGANISM: Homo sapiens

<400> SEQUENCE: 241

Ser Tyr Gly Phe Ser
1               5

<210> SEQ ID NO 242
<211> LENGTH: 6
<212> TYPE: PRT
<213> ORGANISM: Homo sapiens

<400> SEQUENCE: 242

Ser Gly His Tyr Trp Gly
1               5

<210> SEQ ID NO 243
<211> LENGTH: 5
<212> TYPE: PRT
<213> ORGANISM: Homo sapiens

<400> SEQUENCE: 243

Thr Phe Gly Met His
1               5

<210> SEQ ID NO 244
<211> LENGTH: 5
<212> TYPE: PRT
<213> ORGANISM: Homo sapiens

<400> SEQUENCE: 244

Ser Tyr Gly Leu His
1               5

<210> SEQ ID NO 245
<211> LENGTH: 5
<212> TYPE: PRT
<213> ORGANISM: Homo sapiens

<400> SEQUENCE: 245

Ser Phe Gly Ile Ser
1               5

```
<210> SEQ ID NO 246
<211> LENGTH: 5
<212> TYPE: PRT
<213> ORGANISM: Homo sapiens

<400> SEQUENCE: 246

Arg Tyr Gly Ile Ser
1               5

<210> SEQ ID NO 247
<211> LENGTH: 5
<212> TYPE: PRT
<213> ORGANISM: Homo sapiens

<400> SEQUENCE: 247

Asn Ser Gly Val Ser
1               5

<210> SEQ ID NO 248
<211> LENGTH: 5
<212> TYPE: PRT
<213> ORGANISM: Homo sapiens

<400> SEQUENCE: 248

Ser Tyr Gly Ile Ser
1               5

<210> SEQ ID NO 249
<211> LENGTH: 7
<212> TYPE: PRT
<213> ORGANISM: Homo sapiens

<400> SEQUENCE: 249

Ser Gly Gly Tyr Ser Trp Ser
1               5

<210> SEQ ID NO 250
<211> LENGTH: 7
<212> TYPE: PRT
<213> ORGANISM: Homo sapiens

<400> SEQUENCE: 250

Ser Asp Lys Asn Tyr Trp Ser
1               5

<210> SEQ ID NO 251
<211> LENGTH: 5
<212> TYPE: PRT
<213> ORGANISM: Homo sapiens

<400> SEQUENCE: 251

Gly Ser Thr Met His
1               5

<210> SEQ ID NO 252
<211> LENGTH: 5
<212> TYPE: PRT
<213> ORGANISM: Homo sapiens

<400> SEQUENCE: 252

Thr Tyr Thr Leu His
1               5

<210> SEQ ID NO 253
<211> LENGTH: 5
```

```
<212> TYPE: PRT
<213> ORGANISM: Homo sapiens

<400> SEQUENCE: 253

Ser Leu Gly Phe Ser
1               5

<210> SEQ ID NO 254
<211> LENGTH: 5
<212> TYPE: PRT
<213> ORGANISM: Homo sapiens

<400> SEQUENCE: 254

Gly Tyr Thr Ile His
1               5

<210> SEQ ID NO 255
<211> LENGTH: 5
<212> TYPE: PRT
<213> ORGANISM: Homo sapiens

<400> SEQUENCE: 255

Asn Tyr Trp Ile Gly
1               5

<210> SEQ ID NO 256
<211> LENGTH: 5
<212> TYPE: PRT
<213> ORGANISM: Homo sapiens

<400> SEQUENCE: 256

Asn Tyr Ala Phe Ser
1               5

<210> SEQ ID NO 257
<211> LENGTH: 5
<212> TYPE: PRT
<213> ORGANISM: Homo sapiens

<400> SEQUENCE: 257

Asn Tyr Gly Phe Ser
1               5

<210> SEQ ID NO 258
<211> LENGTH: 5
<212> TYPE: PRT
<213> ORGANISM: Homo sapiens

<400> SEQUENCE: 258

Ser Tyr Ala Met Asn
1               5

<210> SEQ ID NO 259
<211> LENGTH: 5
<212> TYPE: PRT
<213> ORGANISM: Homo sapiens

<400> SEQUENCE: 259

Gly Tyr Thr Ile Ser
1               5

<210> SEQ ID NO 260
<211> LENGTH: 5
<212> TYPE: PRT
<213> ORGANISM: Homo sapiens
```

<400> SEQUENCE: 260

Lys Tyr Gly Ile His
1               5

<210> SEQ ID NO 261
<211> LENGTH: 5
<212> TYPE: PRT
<213> ORGANISM: Homo sapiens

<400> SEQUENCE: 261

Ser Tyr Gly Met His
1               5

<210> SEQ ID NO 262
<211> LENGTH: 5
<212> TYPE: PRT
<213> ORGANISM: Homo sapiens

<400> SEQUENCE: 262

Ser Tyr Thr Met Ser
1               5

<210> SEQ ID NO 263
<211> LENGTH: 5
<212> TYPE: PRT
<213> ORGANISM: Homo sapiens

<400> SEQUENCE: 263

Thr Tyr Gly Ile Ser
1               5

<210> SEQ ID NO 264
<211> LENGTH: 5
<212> TYPE: PRT
<213> ORGANISM: Homo sapiens

<400> SEQUENCE: 264

Arg Tyr Thr Ile His
1               5

<210> SEQ ID NO 265
<211> LENGTH: 6
<212> TYPE: PRT
<213> ORGANISM: Homo sapiens

<400> SEQUENCE: 265

Asn Ala Tyr Tyr Trp Gly
1               5

<210> SEQ ID NO 266
<211> LENGTH: 5
<212> TYPE: PRT
<213> ORGANISM: Homo sapiens

<400> SEQUENCE: 266

Tyr Tyr Ala Met His
1               5

<210> SEQ ID NO 267
<211> LENGTH: 5
<212> TYPE: PRT
<213> ORGANISM: Homo sapiens

<400> SEQUENCE: 267

```
Asn Tyr Tyr Trp Ser
1               5

<210> SEQ ID NO 268
<211> LENGTH: 5
<212> TYPE: PRT
<213> ORGANISM: Homo sapiens

<400> SEQUENCE: 268

Asn Tyr Gly Met His
1               5

<210> SEQ ID NO 269
<211> LENGTH: 5
<212> TYPE: PRT
<213> ORGANISM: Homo sapiens

<400> SEQUENCE: 269

His Tyr Gly Met His
1               5

<210> SEQ ID NO 270
<211> LENGTH: 5
<212> TYPE: PRT
<213> ORGANISM: Homo sapiens

<400> SEQUENCE: 270

Ala Tyr Ala Met Ser
1               5

<210> SEQ ID NO 271
<211> LENGTH: 7
<212> TYPE: PRT
<213> ORGANISM: Homo sapiens

<400> SEQUENCE: 271

Thr Ser Lys Leu Gly Val Gly
1               5

<210> SEQ ID NO 272
<211> LENGTH: 5
<212> TYPE: PRT
<213> ORGANISM: Homo sapiens

<400> SEQUENCE: 272

Ser Tyr Glu Met Thr
1               5

<210> SEQ ID NO 273
<211> LENGTH: 5
<212> TYPE: PRT
<213> ORGANISM: Homo sapiens

<400> SEQUENCE: 273

Asn Phe Ala Met His
1               5

<210> SEQ ID NO 274
<211> LENGTH: 6
<212> TYPE: PRT
<213> ORGANISM: Homo sapiens

<400> SEQUENCE: 274

Ser Asn Tyr Tyr Trp Gly
```

-continued

```
1               5

<210> SEQ ID NO 275
<211> LENGTH: 5
<212> TYPE: PRT
<213> ORGANISM: Homo sapiens

<400> SEQUENCE: 275

Ser Tyr Gly Met His
1               5

<210> SEQ ID NO 276
<211> LENGTH: 7
<212> TYPE: PRT
<213> ORGANISM: Homo sapiens

<400> SEQUENCE: 276

Thr Ser Arg Met Ser Val Ser
1               5

<210> SEQ ID NO 277
<211> LENGTH: 7
<212> TYPE: PRT
<213> ORGANISM: Homo sapiens

<400> SEQUENCE: 277

Ser Ser Asn Phe Tyr Trp Gly
1               5

<210> SEQ ID NO 278
<211> LENGTH: 5
<212> TYPE: PRT
<213> ORGANISM: Homo sapiens

<400> SEQUENCE: 278

Thr Tyr Gly Ile Ser
1               5

<210> SEQ ID NO 279
<211> LENGTH: 5
<212> TYPE: PRT
<213> ORGANISM: Homo sapiens

<400> SEQUENCE: 279

Lys Phe Tyr Ile His
1               5

<210> SEQ ID NO 280
<211> LENGTH: 5
<212> TYPE: PRT
<213> ORGANISM: Homo sapiens

<400> SEQUENCE: 280

Ser Tyr Thr Met His
1               5

<210> SEQ ID NO 281
<211> LENGTH: 5
<212> TYPE: PRT
<213> ORGANISM: Homo sapiens

<400> SEQUENCE: 281

Asn Ala Trp Met Ser
1               5
```

<210> SEQ ID NO 282
<211> LENGTH: 5
<212> TYPE: PRT
<213> ORGANISM: Homo sapiens

<400> SEQUENCE: 282

Ile Tyr Gly Met His
1               5

<210> SEQ ID NO 283
<211> LENGTH: 5
<212> TYPE: PRT
<213> ORGANISM: Homo sapiens

<400> SEQUENCE: 283

Asp Tyr Gly Met His
1               5

<210> SEQ ID NO 284
<211> LENGTH: 6
<212> TYPE: PRT
<213> ORGANISM: Homo sapiens

<400> SEQUENCE: 284

Ser Glu Tyr Tyr Trp Gly
1               5

<210> SEQ ID NO 285
<211> LENGTH: 5
<212> TYPE: PRT
<213> ORGANISM: Homo sapiens

<400> SEQUENCE: 285

Asp Tyr Cys Met His
1               5

<210> SEQ ID NO 286
<211> LENGTH: 16
<212> TYPE: PRT
<213> ORGANISM: Homo sapiens

<400> SEQUENCE: 286

Asn Ile Asn Tyr Arg Gly Asn Thr Asn Tyr Asn Pro Ser Leu Lys Ser
1               5                   10                  15

<210> SEQ ID NO 287
<211> LENGTH: 17
<212> TYPE: PRT
<213> ORGANISM: Homo sapiens

<400> SEQUENCE: 287

Phe Ile Arg Tyr Asp Gly Ser Thr Gln Asp Tyr Val Asp Ser Val Lys
1               5                   10                  15

Gly

<210> SEQ ID NO 288
<211> LENGTH: 17
<212> TYPE: PRT
<213> ORGANISM: Homo sapiens

<400> SEQUENCE: 288

Arg Ile Thr Pro Met Phe Asp Ile Thr Asn Tyr Ala Gln Lys Phe Gln
1               5                   10                  15

Gly

<210> SEQ ID NO 289
<211> LENGTH: 17
<212> TYPE: PRT
<213> ORGANISM: Homo sapiens

<400> SEQUENCE: 289

Trp Ile Asn Thr Ser Ser Gly Gly Thr Asn Tyr Ala Gln Lys Phe Gln
1               5                   10                  15

Gly

<210> SEQ ID NO 290
<211> LENGTH: 17
<212> TYPE: PRT
<213> ORGANISM: Homo sapiens

<400> SEQUENCE: 290

Tyr Ile Asn Arg Gly Gly Thr Thr Ile Tyr Tyr Ala Asp Ser Val Lys
1               5                   10                  15

Gly

<210> SEQ ID NO 291
<211> LENGTH: 17
<212> TYPE: PRT
<213> ORGANISM: Homo sapiens

<400> SEQUENCE: 291

Trp Ile Asn Ala Tyr Asn Asp Asn Thr Tyr Tyr Ser Pro Ser Leu Gln
1               5                   10                  15

Gly

<210> SEQ ID NO 292
<211> LENGTH: 16
<212> TYPE: PRT
<213> ORGANISM: Homo sapiens

<400> SEQUENCE: 292

Tyr Ile Phe His Ser Gly Thr Thr Tyr Tyr Asn Pro Ser Leu Lys Ser
1               5                   10                  15

<210> SEQ ID NO 293
<211> LENGTH: 17
<212> TYPE: PRT
<213> ORGANISM: Homo sapiens

<400> SEQUENCE: 293

Ile Ile Ser Tyr Asp Gly Asn Asn Val His Tyr Ala Asp Ser Val Lys
1               5                   10                  15

Gly

<210> SEQ ID NO 294
<211> LENGTH: 17
<212> TYPE: PRT
<213> ORGANISM: Homo sapiens

<400> SEQUENCE: 294

Trp Ile Ser Ala Asp Asn Gly Asn Thr Tyr Tyr Ala Gln Asn Phe Gln
1               5                   10                  15

Asp

<210> SEQ ID NO 295
<211> LENGTH: 17
<212> TYPE: PRT
<213> ORGANISM: Homo sapiens

<400> SEQUENCE: 295

Trp Ile Asn Thr Asn Thr Gly Asp Pro Ala Tyr Ala Gln Asp Phe Thr
1               5                   10                  15
Gly

<210> SEQ ID NO 296
<211> LENGTH: 17
<212> TYPE: PRT
<213> ORGANISM: Homo sapiens

<400> SEQUENCE: 296

Val Ile Ser Tyr Asp Gly Arg Asn Lys Tyr Phe Ala Asp Ser Val Lys
1               5                   10                  15
Gly

<210> SEQ ID NO 297
<211> LENGTH: 17
<212> TYPE: PRT
<213> ORGANISM: Homo sapiens

<400> SEQUENCE: 297

Val Ile Trp His Asp Gly Ser Asn Lys Asn Tyr Leu Asp Ser Val Lys
1               5                   10                  15
Gly

<210> SEQ ID NO 298
<211> LENGTH: 17
<212> TYPE: PRT
<213> ORGANISM: Homo sapiens

<400> SEQUENCE: 298

Val Ile Tyr Tyr Glu Gly Ser Asn Glu Tyr Tyr Ala Asp Ser Val Lys
1               5                   10                  15
Gly

<210> SEQ ID NO 299
<211> LENGTH: 17
<212> TYPE: PRT
<213> ORGANISM: Homo sapiens

<400> SEQUENCE: 299

Tyr Ile Gly Thr Gly Gly Ser Asp Ile Tyr Tyr Gly Asp Ser Val Lys
1               5                   10                  15
Gly

<210> SEQ ID NO 300
<211> LENGTH: 16
<212> TYPE: PRT
<213> ORGANISM: Homo sapiens

<400> SEQUENCE: 300

Tyr Ile Tyr Ser Ser Gly Ser Thr Phe Tyr Asn Ala Ser Leu Lys Ser
1               5                   10                  15

<210> SEQ ID NO 301
<211> LENGTH: 17
<212> TYPE: PRT

```
<213> ORGANISM: Homo sapiens

<400> SEQUENCE: 301

Ala Thr Ser Thr Asp Gly Gly Ser Thr Tyr Tyr Ala Asp Ser Leu Lys
1               5                   10                  15

Gly

<210> SEQ ID NO 302
<211> LENGTH: 16
<212> TYPE: PRT
<213> ORGANISM: Homo sapiens

<400> SEQUENCE: 302

Tyr Ile Tyr Tyr Arg Gly Ser Thr Tyr Tyr Asn Pro Ser Leu Lys Ser
1               5                   10                  15

<210> SEQ ID NO 303
<211> LENGTH: 17
<212> TYPE: PRT
<213> ORGANISM: Homo sapiens

<400> SEQUENCE: 303

Ile Val Tyr Pro Gly Asp Ser Asp Thr Thr Tyr Ser Pro Ser Phe Gln
1               5                   10                  15

Gly

<210> SEQ ID NO 304
<211> LENGTH: 16
<212> TYPE: PRT
<213> ORGANISM: Homo sapiens

<400> SEQUENCE: 304

Arg Ile Asp Trp Asp Asp Asp Lys Tyr Tyr Ser Thr Ser Leu Lys Thr
1               5                   10                  15

<210> SEQ ID NO 305
<211> LENGTH: 17
<212> TYPE: PRT
<213> ORGANISM: Homo sapiens

<400> SEQUENCE: 305

Ile Ile Asn Pro Ala Asp Ser Asp Thr Arg Tyr Ser Pro Ser Phe Gln
1               5                   10                  15

Gly

<210> SEQ ID NO 306
<211> LENGTH: 17
<212> TYPE: PRT
<213> ORGANISM: Homo sapiens

<400> SEQUENCE: 306

Arg Ile Ile Pro Val Phe Asp Thr Thr Asn Tyr Ala Gln Lys Phe Gln
1               5                   10                  15

Gly

<210> SEQ ID NO 307
<211> LENGTH: 17
<212> TYPE: PRT
<213> ORGANISM: Homo sapiens

<400> SEQUENCE: 307

Val Ile Asn Pro Asn Gly Gly Ser Thr Thr Ser Ala Gln Lys Phe Gln
```

-continued

```
                1               5                  10                  15
Asp

<210> SEQ ID NO 308
<211> LENGTH: 17
<212> TYPE: PRT
<213> ORGANISM: Homo sapiens

<400> SEQUENCE: 308

Met Ile Leu Pro Ile Ser Gly Thr Thr Asn Tyr Ala Gln Thr Phe Gln
1               5                   10                  15

Gly

<210> SEQ ID NO 309
<211> LENGTH: 17
<212> TYPE: PRT
<213> ORGANISM: Homo sapiens

<400> SEQUENCE: 309

Ile Ile Tyr Pro Gly Asp Ser Asp Thr Arg Asn Ser Pro Ser Phe Gln
1               5                   10                  15

Gly

<210> SEQ ID NO 310
<211> LENGTH: 17
<212> TYPE: PRT
<213> ORGANISM: Homo sapiens

<400> SEQUENCE: 310

Val Ile Ser Tyr Asp Gly Ala Asn Glu Tyr Tyr Ala Glu Ser Val Lys
1               5                   10                  15

Gly

<210> SEQ ID NO 311
<211> LENGTH: 17
<212> TYPE: PRT
<213> ORGANISM: Homo sapiens

<400> SEQUENCE: 311

Val Ile Arg Ala Ser Gly Asp Ser Glu Ile Tyr Ala Asp Ser Val Arg
1               5                   10                  15

Gly

<210> SEQ ID NO 312
<211> LENGTH: 17
<212> TYPE: PRT
<213> ORGANISM: Homo sapiens

<400> SEQUENCE: 312

Ile Ile Ser Leu Asp Gly Ile Lys Thr His Tyr Ala Asp Ser Val Lys
1               5                   10                  15

Gly

<210> SEQ ID NO 313
<211> LENGTH: 16
<212> TYPE: PRT
<213> ORGANISM: Homo sapiens

<400> SEQUENCE: 313

Arg Ile Asp Trp Asp Asp Asp Lys Ala Phe Arg Thr Ser Leu Lys Thr
1               5                   10                  15
```

<210> SEQ ID NO 314
<211> LENGTH: 16
<212> TYPE: PRT
<213> ORGANISM: Homo sapiens

<400> SEQUENCE: 314

Phe Ile Tyr Asp Ser Gly Ser Thr Tyr Tyr Asn Pro Ser Leu Arg Ser
1               5                   10                  15

<210> SEQ ID NO 315
<211> LENGTH: 17
<212> TYPE: PRT
<213> ORGANISM: Homo sapiens

<400> SEQUENCE: 315

Ile Ile Tyr Pro Gly Asp Ser Thr Thr Thr Tyr Thr Pro Ser Phe Gln
1               5                   10                  15
Gly

<210> SEQ ID NO 316
<211> LENGTH: 16
<212> TYPE: PRT
<213> ORGANISM: Homo sapiens

<400> SEQUENCE: 316

Ser Ile Phe His Ser Gly Thr Thr Phe His Asn Pro Ser Leu Lys Ser
1               5                   10                  15

<210> SEQ ID NO 317
<211> LENGTH: 16
<212> TYPE: PRT
<213> ORGANISM: Homo sapiens

<400> SEQUENCE: 317

His Ile Tyr Phe Gly Gly Asn Thr Asn Tyr Asn Pro Ser Leu Gln Ser
1               5                   10                  15

<210> SEQ ID NO 318
<211> LENGTH: 17
<212> TYPE: PRT
<213> ORGANISM: Homo sapiens

<400> SEQUENCE: 318

Trp Ile Ser Ala Ser Ser Gly Asn Lys Lys Tyr Ala Pro Lys Phe Gln
1               5                   10                  15
Gly

<210> SEQ ID NO 319
<211> LENGTH: 17
<212> TYPE: PRT
<213> ORGANISM: Homo sapiens

<400> SEQUENCE: 319

Phe Phe Asp Pro Glu Asp Gly Asp Thr Gly Tyr Ala Gln Lys Phe Gln
1               5                   10                  15
Gly

<210> SEQ ID NO 320
<211> LENGTH: 17
<212> TYPE: PRT
<213> ORGANISM: Homo sapiens -continued

<400> SEQUENCE: 320

Leu Ile Asn Ala Gly Asn Gly Asp Thr Arg Phe Ser Gln Lys Phe Gln
1               5                   10                  15

Gly

<210> SEQ ID NO 321
<211> LENGTH: 16
<212> TYPE: PRT
<213> ORGANISM: Homo sapiens

<400> SEQUENCE: 321

Arg Ile Asp Trp Asp Asp Asp Lys Phe Tyr Asn Thr Ser Leu Gln Thr
1               5                   10                  15

<210> SEQ ID NO 322
<211> LENGTH: 17
<212> TYPE: PRT
<213> ORGANISM: Homo sapiens

<400> SEQUENCE: 322

Trp Ile Ser Ala Tyr Asn Gly Asn Thr Tyr Tyr Leu Gln Lys Leu Gln
1               5                   10                  15

Gly

<210> SEQ ID NO 323
<211> LENGTH: 17
<212> TYPE: PRT
<213> ORGANISM: Homo sapiens

<400> SEQUENCE: 323

Trp Ile Asn Val Gly Asn Gly Gln Thr Lys Tyr Ser Gln Arg Phe Gln
1               5                   10                  15

Gly

<210> SEQ ID NO 324
<211> LENGTH: 17
<212> TYPE: PRT
<213> ORGANISM: Homo sapiens

<400> SEQUENCE: 324

Ala Ile Ser Tyr Asp Gly Ser Asn Lys Gln Tyr Ala Asp Ser Val Lys
1               5                   10                  15

Gly

<210> SEQ ID NO 325
<211> LENGTH: 17
<212> TYPE: PRT
<213> ORGANISM: Homo sapiens

<400> SEQUENCE: 325

Trp Val Ser Ala His Asn Gly Asn Thr Tyr Tyr Ala Glu Lys Phe His
1               5                   10                  15

Asp

<210> SEQ ID NO 326
<211> LENGTH: 17
<212> TYPE: PRT
<213> ORGANISM: Homo sapiens

<400> SEQUENCE: 326

Trp Ser Ser Val Tyr Asn Gly Asp Thr Asn Tyr Ala Gln Lys Phe His

-continued

```
                1               5                  10                  15

Gly

<210> SEQ ID NO 327
<211> LENGTH: 16
<212> TYPE: PRT
<213> ORGANISM: Homo sapiens

<400> SEQUENCE: 327

Ser Ile Tyr Asp Ser Gly Asn Thr Tyr Tyr Thr Pro Ser Leu Lys Ser
1               5                  10                  15

<210> SEQ ID NO 328
<211> LENGTH: 17
<212> TYPE: PRT
<213> ORGANISM: Homo sapiens

<400> SEQUENCE: 328

Val Ile Ser Tyr Asp Gly Asn Lys Lys Tyr Tyr Ala Asp Ser Val Lys
1               5                  10                  15

Gly

<210> SEQ ID NO 329
<211> LENGTH: 17
<212> TYPE: PRT
<213> ORGANISM: Homo sapiens

<400> SEQUENCE: 329

Glu Ile Ser Tyr Asp Gly Gly Ser Lys Phe Tyr Thr Asp Ser Val Lys
1               5                  10                  15

Gly

<210> SEQ ID NO 330
<211> LENGTH: 17
<212> TYPE: PRT
<213> ORGANISM: Homo sapiens

<400> SEQUENCE: 330

Trp Ile Ser Ala Tyr Asn Gly Asn Thr Asp Tyr Ala Gln Arg Leu Gln
1               5                  10                  15

Asp

<210> SEQ ID NO 331
<211> LENGTH: 17
<212> TYPE: PRT
<213> ORGANISM: Homo sapiens

<400> SEQUENCE: 331

Trp Ile Ser Ala Tyr Asn Gly Asn Thr Tyr Tyr Ala Gln Asn Leu Gln
1               5                  10                  15

Gly

<210> SEQ ID NO 332
<211> LENGTH: 17
<212> TYPE: PRT
<213> ORGANISM: Homo sapiens

<400> SEQUENCE: 332

Trp Ile Ser Ala Tyr Asn Gly Asn Thr Tyr Tyr Arg Gln Ser Leu Gln
1               5                  10                  15

Asp
```

<210> SEQ ID NO 333
<211> LENGTH: 17
<212> TYPE: PRT
<213> ORGANISM: Homo sapiens

<400> SEQUENCE: 333

Trp Ile Gly Thr Asp Asn Gly Asn Thr Tyr Tyr Ala Gln Lys Phe Gln
1               5                   10                  15
Gly

<210> SEQ ID NO 334
<211> LENGTH: 16
<212> TYPE: PRT
<213> ORGANISM: Homo sapiens

<400> SEQUENCE: 334

Tyr Ile Tyr His Ser Gly Ser Thr Tyr Tyr Asn Pro Ser Leu Lys Ser
1               5                   10                  15

<210> SEQ ID NO 335
<211> LENGTH: 16
<212> TYPE: PRT
<213> ORGANISM: Homo sapiens

<400> SEQUENCE: 335

Arg Leu Tyr Pro Ser Gly Asn Thr Asp Tyr His Pro Ser Leu Lys Ser
1               5                   10                  15

<210> SEQ ID NO 336
<211> LENGTH: 19
<212> TYPE: PRT
<213> ORGANISM: Homo sapiens

<400> SEQUENCE: 336

Arg Ile Arg Ser Lys Ala Asn Ser Tyr Ala Thr Glu Tyr Ala Ala Ser
1               5                   10                  15
Val Lys Gly

<210> SEQ ID NO 337
<211> LENGTH: 17
<212> TYPE: PRT
<213> ORGANISM: Homo sapiens

<400> SEQUENCE: 337

Leu Ile Asn Ala Ala Asn Gly His Thr Lys Tyr Ser Gln Arg Phe Gln
1               5                   10                  15
Gly

<210> SEQ ID NO 338
<211> LENGTH: 17
<212> TYPE: PRT
<213> ORGANISM: Homo sapiens

<400> SEQUENCE: 338

Trp Thr Ser Ala His Asn Gly Asn Thr Tyr Tyr Ala Glu Glu Phe Gln
1               5                   10                  15
Asp

<210> SEQ ID NO 339
<211> LENGTH: 17
<212> TYPE: PRT

-continued

<213> ORGANISM: Homo sapiens

<400> SEQUENCE: 339

Arg Leu Val Pro Ser Leu Asn Ile Pro Asn Tyr Ala Gln Lys Phe Gln
1               5                   10                  15

Gly

<210> SEQ ID NO 340
<211> LENGTH: 17
<212> TYPE: PRT
<213> ORGANISM: Homo sapiens

<400> SEQUENCE: 340

Val Ile Phe Pro Ala Asp Ser Asp Ala Arg Tyr Ser Pro Ser Phe Gln
1               5                   10                  15

Gly

<210> SEQ ID NO 341
<211> LENGTH: 17
<212> TYPE: PRT
<213> ORGANISM: Homo sapiens

<400> SEQUENCE: 341

Trp Ile Ser Gly Ser Asn Gly Asn Thr Tyr Tyr Ala Glu Lys Phe Gln
1               5                   10                  15

Gly

<210> SEQ ID NO 342
<211> LENGTH: 17
<212> TYPE: PRT
<213> ORGANISM: Homo sapiens

<400> SEQUENCE: 342

Trp Ile Ser Ala Tyr Asn Gly Asn Thr Tyr Tyr Ala Gln Asn Leu Gln
1               5                   10                  15

Gly

<210> SEQ ID NO 343
<211> LENGTH: 17
<212> TYPE: PRT
<213> ORGANISM: Homo sapiens

<400> SEQUENCE: 343

Gly Ile Ser Gly Ser Gly Gly Ser Thr Tyr Tyr Gly Asp Ser Val Lys
1               5                   10                  15

Gly

<210> SEQ ID NO 344
<211> LENGTH: 17
<212> TYPE: PRT
<213> ORGANISM: Homo sapiens

<400> SEQUENCE: 344

Arg Val Val Pro Thr Leu Gly Phe Pro Asn Tyr Ala Gln Lys Phe Gln
1               5                   10                  15

Gly

<210> SEQ ID NO 345
<211> LENGTH: 17
<212> TYPE: PRT
<213> ORGANISM: Homo sapiens

<400> SEQUENCE: 345

Val Ile Ser Tyr Asp Gly Ser Lys Lys Tyr Phe Thr Asp Ser Val Lys
1               5                   10                  15

Gly

<210> SEQ ID NO 346
<211> LENGTH: 17
<212> TYPE: PRT
<213> ORGANISM: Homo sapiens

<400> SEQUENCE: 346

Phe Ile Trp Asn Asp Gly Ser Asn Lys Tyr Tyr Ala Asp Ser Val Lys
1               5                   10                  15

Gly

<210> SEQ ID NO 347
<211> LENGTH: 17
<212> TYPE: PRT
<213> ORGANISM: Homo sapiens

<400> SEQUENCE: 347

Ser Ile Ser Ala Ser Thr Val Leu Thr Tyr Tyr Ala Asp Ser Val Lys
1               5                   10                  15

Gly

<210> SEQ ID NO 348
<211> LENGTH: 17
<212> TYPE: PRT
<213> ORGANISM: Homo sapiens

<400> SEQUENCE: 348

Trp Ile Ser Ala Asp Asn Gly Asn Thr Tyr Tyr Ala Gln Lys Phe Gln
1               5                   10                  15

Gly

<210> SEQ ID NO 349
<211> LENGTH: 17
<212> TYPE: PRT
<213> ORGANISM: Homo sapiens

<400> SEQUENCE: 349

Arg Val Val Pro Ser Leu Gly Ile Pro Asn Tyr Ala Pro Lys Phe Gln
1               5                   10                  15

Gly

<210> SEQ ID NO 350
<211> LENGTH: 16
<212> TYPE: PRT
<213> ORGANISM: Homo sapiens

<400> SEQUENCE: 350

Ser Ile His His Ser Gly Ser Ala Tyr Tyr Asn Ser Ser Leu Lys Ser
1               5                   10                  15

<210> SEQ ID NO 351
<211> LENGTH: 17
<212> TYPE: PRT
<213> ORGANISM: Homo sapiens

<400> SEQUENCE: 351

```
Val Ile Ser Tyr Gly Glu Thr Asn Lys Leu Tyr Ala Asp Ser Val Lys
1               5                   10                  15

Gly

<210> SEQ ID NO 352
<211> LENGTH: 16
<212> TYPE: PRT
<213> ORGANISM: Homo sapiens

<400> SEQUENCE: 352

Glu Ile Ser Asn Thr Trp Ser Thr Asn Tyr Asn Pro Ser Leu Lys Ser
1               5                   10                  15

<210> SEQ ID NO 353
<211> LENGTH: 17
<212> TYPE: PRT
<213> ORGANISM: Homo sapiens

<400> SEQUENCE: 353

Val Ile Trp Tyr Asp Asp Ser Asn Lys Gln Tyr Gly Asp Ser Val Lys
1               5                   10                  15

Gly

<210> SEQ ID NO 354
<211> LENGTH: 17
<212> TYPE: PRT
<213> ORGANISM: Homo sapiens

<400> SEQUENCE: 354

Val Ile Ser His Asp Gly Asn Ile Lys Tyr Ser Ala Asp Ser Val Lys
1               5                   10                  15

Gly

<210> SEQ ID NO 355
<211> LENGTH: 17
<212> TYPE: PRT
<213> ORGANISM: Homo sapiens

<400> SEQUENCE: 355

Ala Ile Ser Gly Gly Gly Gly Thr Thr Tyr Tyr Ala Asp Ser Val Lys
1               5                   10                  15

Gly

<210> SEQ ID NO 356
<211> LENGTH: 16
<212> TYPE: PRT
<213> ORGANISM: Homo sapiens

<400> SEQUENCE: 356

Leu Val Asp Trp Asp Asp Asp Arg Arg Tyr Arg Pro Ser Leu Lys Ser
1               5                   10                  15

<210> SEQ ID NO 357
<211> LENGTH: 17
<212> TYPE: PRT
<213> ORGANISM: Homo sapiens

<400> SEQUENCE: 357

His Ile Gly Asn Ser Gly Ser Met Ile Tyr Tyr Ala Asp Ser Val Lys
1               5                   10                  15

Gly
```

```
<210> SEQ ID NO 358
<211> LENGTH: 17
<212> TYPE: PRT
<213> ORGANISM: Homo sapiens

<400> SEQUENCE: 358

Tyr Ile Asn Ala Val Asn Gly Asn Thr Gln Tyr Ser Gln Lys Phe Gln
1               5                   10                  15

Gly

<210> SEQ ID NO 359
<211> LENGTH: 16
<212> TYPE: PRT
<213> ORGANISM: Homo sapiens

<400> SEQUENCE: 359

Ser Met His His Ser Gly Ser Ser Tyr Tyr Lys Pro Ser Leu Lys Ser
1               5                   10                  15

<210> SEQ ID NO 360
<211> LENGTH: 17
<212> TYPE: PRT
<213> ORGANISM: Homo sapiens

<400> SEQUENCE: 360

Val Ile Ser Asn Asp Gly Ser Asn Lys Tyr Tyr Ala Asp Ser Val Lys
1               5                   10                  15

Gly

<210> SEQ ID NO 361
<211> LENGTH: 16
<212> TYPE: PRT
<213> ORGANISM: Homo sapiens

<400> SEQUENCE: 361

Arg Ile Asp Trp Asp Asp Asp Lys Tyr Tyr Ser Thr Ser Leu Lys Thr
1               5                   10                  15

<210> SEQ ID NO 362
<211> LENGTH: 16
<212> TYPE: PRT
<213> ORGANISM: Homo sapiens

<400> SEQUENCE: 362

Ser Ile Phe Tyr Ser Gly Thr Thr Tyr Tyr Asn Pro Ser Leu Lys Ser
1               5                   10                  15

<210> SEQ ID NO 363
<211> LENGTH: 17
<212> TYPE: PRT
<213> ORGANISM: Homo sapiens

<400> SEQUENCE: 363

Trp Ile Ser Ala Tyr Asn Gly Asn Thr Phe Tyr Ala Gln Arg Leu Gln
1               5                   10                  15

Gly

<210> SEQ ID NO 364
<211> LENGTH: 17
<212> TYPE: PRT
<213> ORGANISM: Homo sapiens

<400> SEQUENCE: 364
```

```
Ile Ile Asn Pro Ser Gly Gly Ser Thr Thr Tyr Ala Gln Thr Phe Gln
1               5                   10                  15

Asp

<210> SEQ ID NO 365
<211> LENGTH: 17
<212> TYPE: PRT
<213> ORGANISM: Homo sapiens

<400> SEQUENCE: 365

Val Val Ser Tyr Asp Gly Asn His Asn Asp Tyr Ala Asp Ser Val Lys
1               5                   10                  15

Gly

<210> SEQ ID NO 366
<211> LENGTH: 19
<212> TYPE: PRT
<213> ORGANISM: Homo sapiens

<400> SEQUENCE: 366

Leu Ile Lys Ser His Phe Glu Gly Gly Ala Thr Asp Tyr Ala Ala Pro
1               5                   10                  15

Val Lys Gly

<210> SEQ ID NO 367
<211> LENGTH: 17
<212> TYPE: PRT
<213> ORGANISM: Homo sapiens

<400> SEQUENCE: 367

Val Ile Ser Tyr Asp Gly Ala Lys Lys Phe Tyr Ala Asn Ser Val Lys
1               5                   10                  15

Gly

<210> SEQ ID NO 368
<211> LENGTH: 17
<212> TYPE: PRT
<213> ORGANISM: Homo sapiens

<400> SEQUENCE: 368

Val Ile Trp His Asp Gly Ser Asn Ile Arg Tyr Ala Asp Ser Val Arg
1               5                   10                  15

Gly

<210> SEQ ID NO 369
<211> LENGTH: 16
<212> TYPE: PRT
<213> ORGANISM: Homo sapiens

<400> SEQUENCE: 369

Ser Val His His Ser Gly Ser Thr Tyr Tyr Asn Pro Ser Leu Lys Ser
1               5                   10                  15

<210> SEQ ID NO 370
<211> LENGTH: 17
<212> TYPE: PRT
<213> ORGANISM: Homo sapiens

<400> SEQUENCE: 370

Ile Leu Asn Pro Asp Gly Gly Thr Thr Phe Tyr Ala Glu Lys Phe Gln
1               5                   10                  15
```

Asp

<210> SEQ ID NO 371
<211> LENGTH: 18
<212> TYPE: PRT
<213> ORGANISM: Homo sapiens

<400> SEQUENCE: 371

Cys Ala Arg Asp Val Gly Tyr Gly Gly Gly Gln Tyr Phe Ala Met Asp
1               5                   10                  15

Val Trp

<210> SEQ ID NO 372
<211> LENGTH: 24
<212> TYPE: PRT
<213> ORGANISM: Homo sapiens

<400> SEQUENCE: 372

Cys Ala Lys Asp Met Asp Tyr Tyr Gly Ser Arg Ser Tyr Ser Val Thr
1               5                   10                  15

Tyr Tyr Tyr Gly Met Asp Val Trp
            20

<210> SEQ ID NO 373
<211> LENGTH: 24
<212> TYPE: PRT
<213> ORGANISM: Homo sapiens

<400> SEQUENCE: 373

Cys Ala Arg Arg Gly Ala Val Ala Leu Val Pro Ala Ala Glu Asp Pro
1               5                   10                  15

Tyr Tyr Tyr Gly Met Asp Val Trp
            20

<210> SEQ ID NO 374
<211> LENGTH: 20
<212> TYPE: PRT
<213> ORGANISM: Homo sapiens

<400> SEQUENCE: 374

Cys Ala Arg Glu Asp Gly Thr Met Gly Thr Asn Ser Trp Tyr Gly Trp
1               5                   10                  15

Phe Asp Pro Trp
            20

<210> SEQ ID NO 375
<211> LENGTH: 22
<212> TYPE: PRT
<213> ORGANISM: Homo sapiens

<400> SEQUENCE: 375

Cys Ala Arg Gly Leu Ile Leu Ala Leu Pro Thr Ala Thr Val Glu Leu
1               5                   10                  15

Gly Ala Phe Asp Ile Trp
            20

<210> SEQ ID NO 376
<211> LENGTH: 26
<212> TYPE: PRT
<213> ORGANISM: Homo sapiens

<400> SEQUENCE: 376

-continued

Cys Ala Arg Ser Tyr Arg Ser Gln Thr Asp Ile Leu Thr Gly Arg Tyr
1               5                   10                  15

Lys Gly Pro Gly Asp Val Phe Asp Asn Trp
            20                  25

<210> SEQ ID NO 377
<211> LENGTH: 20
<212> TYPE: PRT
<213> ORGANISM: Homo sapiens

<400> SEQUENCE: 377

Cys Ala Arg Asp Val Asp Phe Pro Val Trp Gly Met Asn Arg Tyr
1               5                   10                  15

Leu Ala Leu Trp
            20

<210> SEQ ID NO 378
<211> LENGTH: 19
<212> TYPE: PRT
<213> ORGANISM: Homo sapiens

<400> SEQUENCE: 378

Cys Ala Lys Asp Asp Val Ala Thr Asp Leu Ala Ala Tyr Tyr Tyr Phe
1               5                   10                  15

Asp Val Trp

<210> SEQ ID NO 379
<211> LENGTH: 20
<212> TYPE: PRT
<213> ORGANISM: Homo sapiens

<400> SEQUENCE: 379

Cys Val Arg Gly Gly Val Val Thr Asn Arg Val Tyr Tyr Tyr Gly
1               5                   10                  15

Met Asp Val Trp
            20

<210> SEQ ID NO 380
<211> LENGTH: 13
<212> TYPE: PRT
<213> ORGANISM: Homo sapiens

<400> SEQUENCE: 380

Cys Ala Trp Phe Gly Glu Phe Gly Leu Phe Asp Tyr Trp
1               5                   10

<210> SEQ ID NO 381
<211> LENGTH: 18
<212> TYPE: PRT
<213> ORGANISM: Homo sapiens

<400> SEQUENCE: 381

Cys Ala Arg Gly Ser Val Gln Val Trp Leu His Leu Gly Leu Phe Asp
1               5                   10                  15

Asn Trp

<210> SEQ ID NO 382
<211> LENGTH: 17
<212> TYPE: PRT
<213> ORGANISM: Homo sapiens

<400> SEQUENCE: 382

```
Cys Ala Arg Thr Pro Tyr Glu Phe Trp Ser Gly Tyr Tyr Phe Asp Phe
1               5                   10                  15

Trp

<210> SEQ ID NO 383
<211> LENGTH: 11
<212> TYPE: PRT
<213> ORGANISM: Homo sapiens

<400> SEQUENCE: 383

Cys Ala Arg Lys Trp Leu Gly Met Asp Phe Trp
1               5                   10

<210> SEQ ID NO 384
<211> LENGTH: 13
<212> TYPE: PRT
<213> ORGANISM: Homo sapiens

<400> SEQUENCE: 384

Cys Ala Arg Ala Arg Pro Gly Tyr Lys Val Asp Phe Trp
1               5                   10

<210> SEQ ID NO 385
<211> LENGTH: 17
<212> TYPE: PRT
<213> ORGANISM: Homo sapiens

<400> SEQUENCE: 385

Cys Ala Arg Gly Gly Thr Leu Tyr Thr Thr Gly Gly Glu Met His Ile
1               5                   10                  15

Trp

<210> SEQ ID NO 386
<211> LENGTH: 15
<212> TYPE: PRT
<213> ORGANISM: Homo sapiens

<400> SEQUENCE: 386

Cys Ala Arg Arg Phe Trp Gly Phe Gly Asn Phe Phe Asp Tyr Trp
1               5                   10                  15

<210> SEQ ID NO 387
<211> LENGTH: 20
<212> TYPE: PRT
<213> ORGANISM: Homo sapiens

<400> SEQUENCE: 387

Cys Ala Arg Glu Gly His His Ser Gly Ser Gly Asp Tyr Tyr Ser Phe
1               5                   10                  15

Phe Asp Tyr Trp
            20

<210> SEQ ID NO 388
<211> LENGTH: 22
<212> TYPE: PRT
<213> ORGANISM: Homo sapiens

<400> SEQUENCE: 388

Cys Val Arg Arg Gly Gly Phe Cys Thr Ala Thr Gly Cys Tyr Ala Gly
1               5                   10                  15

His Trp Phe Asp Pro Trp
            20
```

<210> SEQ ID NO 389
<211> LENGTH: 20
<212> TYPE: PRT
<213> ORGANISM: Homo sapiens

<400> SEQUENCE: 389

Cys Ala Arg Ile Val Phe His Thr Ser Gly Gly Tyr Tyr Asn Pro Tyr
1               5                   10                  15

Met Asp Val Trp
            20

<210> SEQ ID NO 390
<211> LENGTH: 15
<212> TYPE: PRT
<213> ORGANISM: Homo sapiens

<400> SEQUENCE: 390

Cys Ala Arg Arg Ala Tyr Asp Ser Gly Trp His Phe Glu His Trp
1               5                   10                  15

<210> SEQ ID NO 391
<211> LENGTH: 17
<212> TYPE: PRT
<213> ORGANISM: Homo sapiens

<400> SEQUENCE: 391

Cys Leu Arg Gly Ser Thr Arg Gly Trp Asp Thr Asp Gly Phe Asp Ile
1               5                   10                  15

Trp

<210> SEQ ID NO 392
<211> LENGTH: 24
<212> TYPE: PRT
<213> ORGANISM: Homo sapiens

<400> SEQUENCE: 392

Cys Ala Arg Gln Arg Ser Val Thr Gly Gly Phe Asp Ala Trp Leu Leu
1               5                   10                  15

Ile Pro Asp Ala Ser Asn Thr Trp
            20

<210> SEQ ID NO 393
<211> LENGTH: 21
<212> TYPE: PRT
<213> ORGANISM: Homo sapiens

<400> SEQUENCE: 393

Cys Ala Arg Val Phe Arg Glu Phe Ser Thr Ser Thr Leu Asp Pro Tyr
1               5                   10                  15

Tyr Phe Asp Tyr Trp
            20

<210> SEQ ID NO 394
<211> LENGTH: 22
<212> TYPE: PRT
<213> ORGANISM: Homo sapiens

<400> SEQUENCE: 394

Cys Val Arg Gln Gly Gly Tyr Tyr Asp Arg Asn Gly Tyr His Glu Lys
1               5                   10                  15

Tyr Ala Phe Asp Ile Trp

-continued

```
                20

<210> SEQ ID NO 395
<211> LENGTH: 20
<212> TYPE: PRT
<213> ORGANISM: Homo sapiens

<400> SEQUENCE: 395

Cys Ala Arg Ala Gly Arg Ser Ser Met Asn Glu Glu Val Ile Met Tyr
1               5                   10                  15

Phe Asp Asn Trp
            20

<210> SEQ ID NO 396
<211> LENGTH: 22
<212> TYPE: PRT
<213> ORGANISM: Homo sapiens

<400> SEQUENCE: 396

Cys Ala Asn Ile Gly Gln Arg Arg Tyr Cys Ser Gly Asp His Cys Tyr
1               5                   10                  15

Gly His Phe Asp Tyr Trp
            20

<210> SEQ ID NO 397
<211> LENGTH: 22
<212> TYPE: PRT
<213> ORGANISM: Homo sapiens

<400> SEQUENCE: 397

Cys Ala Lys Asp His Ile Gly Gly Thr Asn Ala Tyr Phe Glu Trp Thr
1               5                   10                  15

Val Pro Phe Asp Gly Trp
            20

<210> SEQ ID NO 398
<211> LENGTH: 20
<212> TYPE: PRT
<213> ORGANISM: Homo sapiens

<400> SEQUENCE: 398

Cys Ala Arg Thr Gln Val Phe Ala Ser Gly Gly Tyr Tyr Leu Tyr Tyr
1               5                   10                  15

Leu Asp His Trp
            20

<210> SEQ ID NO 399
<211> LENGTH: 23
<212> TYPE: PRT
<213> ORGANISM: Homo sapiens

<400> SEQUENCE: 399

Cys Ala Arg Asp Leu Gly Tyr Gly Gly Asn Ser Tyr Ser His Ser Tyr
1               5                   10                  15

Tyr Tyr Gly Leu Asp Val Trp
            20

<210> SEQ ID NO 400
<211> LENGTH: 11
<212> TYPE: PRT
<213> ORGANISM: Homo sapiens

<400> SEQUENCE: 400
```

Cys Ala Arg Gln Gly Arg Gly Phe Gly Leu Trp
1               5                   10

<210> SEQ ID NO 401
<211> LENGTH: 12
<212> TYPE: PRT
<213> ORGANISM: Homo sapiens

<400> SEQUENCE: 401

Cys Ala Arg Val His Gly Gly Gly Phe Asp His Trp
1               5                   10

<210> SEQ ID NO 402
<211> LENGTH: 15
<212> TYPE: PRT
<213> ORGANISM: Homo sapiens

<400> SEQUENCE: 402

Cys Ala Arg Asp Ser Ser Asn Trp Pro Ala Gly Tyr Glu Asp Trp
1               5                   10                  15

<210> SEQ ID NO 403
<211> LENGTH: 18
<212> TYPE: PRT
<213> ORGANISM: Homo sapiens

<400> SEQUENCE: 403

Cys Ala Lys Asp Gly Gly Thr Tyr Val Pro Tyr Ser Asp Ala Phe Asp
1               5                   10                  15

Phe Trp

<210> SEQ ID NO 404
<211> LENGTH: 13
<212> TYPE: PRT
<213> ORGANISM: Homo sapiens

<400> SEQUENCE: 404

Cys Ala Thr Val Ala Ala Ala Gly Asn Phe Asp Asn Trp
1               5                   10

<210> SEQ ID NO 405
<211> LENGTH: 16
<212> TYPE: PRT
<213> ORGANISM: Homo sapiens

<400> SEQUENCE: 405

Cys Ala Arg Ile Ala Ile Thr Met Val Arg Asn Pro Phe Asp Ile Trp
1               5                   10                  15

<210> SEQ ID NO 406
<211> LENGTH: 20
<212> TYPE: PRT
<213> ORGANISM: Homo sapiens

<400> SEQUENCE: 406

Cys Ala Arg Thr Gly Ile Tyr Asp Ser Ser Gly Tyr Tyr Leu Tyr Tyr
1               5                   10                  15

Phe Asp Tyr Trp
            20

<210> SEQ ID NO 407
<211> LENGTH: 25
<212> TYPE: PRT

-continued

<213> ORGANISM: Homo sapiens

<400> SEQUENCE: 407

Cys Ala Arg Asp Arg Val Gly Gly Ser Ser Ser Glu Val Leu Ser Arg
1               5                   10                  15

Ala Lys Asn Tyr Gly Leu Asp Val Trp
            20                  25

<210> SEQ ID NO 408
<211> LENGTH: 19
<212> TYPE: PRT
<213> ORGANISM: Homo sapiens

<400> SEQUENCE: 408

Cys Ala Arg Arg Ala Ser Gln Tyr Gly Glu Val Tyr Gly Asn Tyr Phe
1               5                   10                  15

Asp Tyr Trp

<210> SEQ ID NO 409
<211> LENGTH: 21
<212> TYPE: PRT
<213> ORGANISM: Homo sapiens

<400> SEQUENCE: 409

Cys Ala Lys Asp Asp Phe Gly Asn Ser Asn Gly Val Phe Phe Met Ser
1               5                   10                  15

Arg Val Ala Phe Trp
            20

<210> SEQ ID NO 410
<211> LENGTH: 21
<212> TYPE: PRT
<213> ORGANISM: Homo sapiens

<400> SEQUENCE: 410

Cys Val Arg Gly Phe Asn Glu Gln Gln Leu Val Pro Gly Leu Ser Phe
1               5                   10                  15

Trp Phe Asp Tyr Trp
            20

<210> SEQ ID NO 411
<211> LENGTH: 21
<212> TYPE: PRT
<213> ORGANISM: Homo sapiens

<400> SEQUENCE: 411

Cys Ala Arg Asp Arg Asn Val Val Leu Leu Pro Ala Ala Pro Phe Gly
1               5                   10                  15

Gly Met Asp Val Trp
            20

<210> SEQ ID NO 412
<211> LENGTH: 13
<212> TYPE: PRT
<213> ORGANISM: Homo sapiens

<400> SEQUENCE: 412

Cys Ala Arg Gly Ser Pro Gly Asp Ala Phe Asp Ile Trp
1               5                   10

<210> SEQ ID NO 413
<211> LENGTH: 18

```
<212> TYPE: PRT
<213> ORGANISM: Homo sapiens

<400> SEQUENCE: 413

Cys Ala Ala Gln Thr Pro Tyr Phe Asn Glu Ser Ser Gly Leu Val Pro
1               5                   10                  15

Asp Trp

<210> SEQ ID NO 414
<211> LENGTH: 18
<212> TYPE: PRT
<213> ORGANISM: Homo sapiens

<400> SEQUENCE: 414

Cys Ala Arg Asp Leu Gly Asp Gly Tyr Thr Ala Trp Gly Trp Phe Asp
1               5                   10                  15

Pro Trp

<210> SEQ ID NO 415
<211> LENGTH: 21
<212> TYPE: PRT
<213> ORGANISM: Homo sapiens

<400> SEQUENCE: 415

Cys Thr Arg Asp Glu Ser Met Leu Arg Gly Val Thr Glu Gly Phe Gly
1               5                   10                  15

Pro Ile Asp Tyr Trp
            20

<210> SEQ ID NO 416
<211> LENGTH: 18
<212> TYPE: PRT
<213> ORGANISM: Homo sapiens

<400> SEQUENCE: 416

Cys Val Ile Ser Phe Asp Ser Thr Ile Ala Ala Ala Glu Tyr Phe Asp
1               5                   10                  15

Tyr Trp

<210> SEQ ID NO 417
<211> LENGTH: 22
<212> TYPE: PRT
<213> ORGANISM: Homo sapiens

<400> SEQUENCE: 417

Cys Ala Arg Glu Gly His Tyr Ser Gly Ser Ser Tyr Gln Arg Asp
1               5                   10                  15

Asp Ala Phe Asp Ile Trp
            20

<210> SEQ ID NO 418
<211> LENGTH: 23
<212> TYPE: PRT
<213> ORGANISM: Homo sapiens

<400> SEQUENCE: 418

Cys Ala Arg Gly Gly Thr Ile Glu Ala Thr Pro Glu Arg Glu Tyr Tyr
1               5                   10                  15

Tyr Tyr Gly Met Asp Val Trp
            20
```

```
<210> SEQ ID NO 419
<211> LENGTH: 13
<212> TYPE: PRT
<213> ORGANISM: Homo sapiens

<400> SEQUENCE: 419

Cys Ala Ser Arg Ser Phe Tyr Gly Asp Tyr Val Tyr Trp
1               5                   10

<210> SEQ ID NO 420
<211> LENGTH: 13
<212> TYPE: PRT
<213> ORGANISM: Homo sapiens

<400> SEQUENCE: 420

Cys Ala Lys Glu Gly Ser Gly Trp Tyr Phe Glu Ser Trp
1               5                   10

<210> SEQ ID NO 421
<211> LENGTH: 18
<212> TYPE: PRT
<213> ORGANISM: Homo sapiens

<400> SEQUENCE: 421

Cys Thr Arg His Val Gly Glu Met Ser Thr Ile Trp Trp Tyr Phe Asp
1               5                   10                  15

Leu Trp

<210> SEQ ID NO 422
<211> LENGTH: 19
<212> TYPE: PRT
<213> ORGANISM: Homo sapiens

<400> SEQUENCE: 422

Cys Ala Lys Ser Gly Ser His Tyr Gly Glu Val Tyr Gly Ala Tyr Phe
1               5                   10                  15

Asp Tyr Trp

<210> SEQ ID NO 423
<211> LENGTH: 20
<212> TYPE: PRT
<213> ORGANISM: Homo sapiens

<400> SEQUENCE: 423

Cys Ala Arg Asp Arg Gly Pro Gly Tyr Ser Asp Ser Ser Phe Tyr Val
1               5                   10                  15

Phe Asp Tyr Trp
            20

<210> SEQ ID NO 424
<211> LENGTH: 18
<212> TYPE: PRT
<213> ORGANISM: Homo sapiens

<400> SEQUENCE: 424

Cys Thr Arg Ala Pro Arg Gly Ser Thr Ala Ser His Leu Leu Phe Asp
1               5                   10                  15

Tyr Trp

<210> SEQ ID NO 425
<211> LENGTH: 23
<212> TYPE: PRT
<213> ORGANISM: Homo sapiens
```

-continued

<400> SEQUENCE: 425

Cys Ala Arg Pro Lys Tyr Tyr Phe Asp Ser Ser Gly Gln Phe Ser Glu
1               5                   10                  15

Met Tyr Tyr Phe Asp Phe Trp
            20

<210> SEQ ID NO 426
<211> LENGTH: 14
<212> TYPE: PRT
<213> ORGANISM: Homo sapiens

<400> SEQUENCE: 426

Cys Ala Arg Asp Leu Leu Arg Ser Thr Tyr Phe Asp Tyr Trp
1               5                   10

<210> SEQ ID NO 427
<211> LENGTH: 21
<212> TYPE: PRT
<213> ORGANISM: Homo sapiens

<400> SEQUENCE: 427

Cys Ala Arg Asp Gly Asn Thr Ala Gly Val Asp Met Trp Ser Arg Asp
1               5                   10                  15

Gly Phe Asp Ile Trp
            20

<210> SEQ ID NO 428
<211> LENGTH: 26
<212> TYPE: PRT
<213> ORGANISM: Homo sapiens

<400> SEQUENCE: 428

Cys Ala Lys Glu Pro Trp Ile Asp Ile Val Ala Ser Val Ile Ser
1               5                   10                  15

Pro Tyr Tyr Tyr Asp Gly Met Asp Val Trp
            20                  25

<210> SEQ ID NO 429
<211> LENGTH: 18
<212> TYPE: PRT
<213> ORGANISM: Homo sapiens

<400> SEQUENCE: 429

Cys Ala Arg Met Asn Leu Gly Ser His Ser Gly Arg Pro Gly Phe Asp
1               5                   10                  15

Met Trp

<210> SEQ ID NO 430
<211> LENGTH: 24
<212> TYPE: PRT
<213> ORGANISM: Homo sapiens

<400> SEQUENCE: 430

Cys Ala Thr Gly Gly Gly Val Asn Val Thr Ser Trp Ser Asp Val Glu
1               5                   10                  15

His Ser Ser Ser Leu Gly Tyr Trp
            20

<210> SEQ ID NO 431
<211> LENGTH: 20
<212> TYPE: PRT

-continued

<213> ORGANISM: Homo sapiens

<400> SEQUENCE: 431

Cys Val Lys Asp Glu Val Tyr Asp Ser Gly Tyr Tyr Leu Tyr Tyr
1               5                   10                  15

Phe Asp Ser Trp
            20

<210> SEQ ID NO 432
<211> LENGTH: 22
<212> TYPE: PRT
<213> ORGANISM: Homo sapiens

<400> SEQUENCE: 432

Cys Ala Lys Asp Tyr Asp Phe Trp Ser Gly Tyr Pro Gly Gly Gln Tyr
1               5                   10                  15

Trp Phe Phe Asp Leu Trp
            20

<210> SEQ ID NO 433
<211> LENGTH: 21
<212> TYPE: PRT
<213> ORGANISM: Homo sapiens

<400> SEQUENCE: 433

Cys Val Arg Gly Gly Thr Tyr Ser Ser Asp Val Glu Tyr Tyr Tyr
1               5                   10                  15

Gly Met Asp Val Trp
            20

<210> SEQ ID NO 434
<211> LENGTH: 18
<212> TYPE: PRT
<213> ORGANISM: Homo sapiens

<400> SEQUENCE: 434

Cys Ala Arg Leu Thr Leu Gly Ser Tyr Thr Gly Arg Pro Gly Phe Asp
1               5                   10                  15

Ser Trp

<210> SEQ ID NO 435
<211> LENGTH: 18
<212> TYPE: PRT
<213> ORGANISM: Homo sapiens

<400> SEQUENCE: 435

Cys Ala Arg Asp Thr Ile Leu Thr Phe Gly Glu Pro His Trp Phe Asp
1               5                   10                  15

Pro Trp

<210> SEQ ID NO 436
<211> LENGTH: 19
<212> TYPE: PRT
<213> ORGANISM: Homo sapiens

<400> SEQUENCE: 436

Cys Ala Arg Asp Leu Arg Tyr Leu Thr Tyr Tyr Ser Gly Ser Gly Asp
1               5                   10                  15

Asp Ser Trp

<210> SEQ ID NO 437

```
<211> LENGTH: 20
<212> TYPE: PRT
<213> ORGANISM: Homo sapiens

<400> SEQUENCE: 437

Cys Ala Arg Gly Leu Phe Tyr Asp Ser Gly Tyr Tyr Leu Phe Tyr
1               5                   10                  15

Phe Gln His Trp
            20

<210> SEQ ID NO 438
<211> LENGTH: 20
<212> TYPE: PRT
<213> ORGANISM: Homo sapiens

<400> SEQUENCE: 438

Cys Ala Arg Ala Ser Glu Tyr Ser Ile Ser Trp Arg His Arg Gly Val
1               5                   10                  15

Leu Asp Tyr Trp
            20

<210> SEQ ID NO 439
<211> LENGTH: 19
<212> TYPE: PRT
<213> ORGANISM: Homo sapiens

<400> SEQUENCE: 439

Cys His Gly Glu Gly Tyr Ser Thr Ser Trp Leu Gly Thr Ala Ala Leu
1               5                   10                  15

Asp Tyr Trp

<210> SEQ ID NO 440
<211> LENGTH: 18
<212> TYPE: PRT
<213> ORGANISM: Homo sapiens

<400> SEQUENCE: 440

Cys Ala Lys Thr Arg Gly Tyr Ser Tyr Thr Trp Gly Asp Ala Phe Asp
1               5                   10                  15

Leu Trp

<210> SEQ ID NO 441
<211> LENGTH: 20
<212> TYPE: PRT
<213> ORGANISM: Homo sapiens

<400> SEQUENCE: 441

Cys Ala His Ser Ala Tyr Tyr Thr Ser Ser Gly Tyr Tyr Leu Gln Tyr
1               5                   10                  15

Phe His His Trp
            20

<210> SEQ ID NO 442
<211> LENGTH: 20
<212> TYPE: PRT
<213> ORGANISM: Homo sapiens

<400> SEQUENCE: 442

Cys Ala Arg Ser Asp Tyr Tyr Asp Ser Gly Tyr Tyr Leu Leu Tyr
1               5                   10                  15

Leu Asp Ser Trp
            20
```

<210> SEQ ID NO 443
<211> LENGTH: 15
<212> TYPE: PRT
<213> ORGANISM: Homo sapiens

<400> SEQUENCE: 443

Cys Ala Arg Asn Asn Gly Gly Ser Ala Ile Ile Phe Tyr Tyr Trp
1               5                   10                  15

<210> SEQ ID NO 444
<211> LENGTH: 20
<212> TYPE: PRT
<213> ORGANISM: Homo sapiens

<400> SEQUENCE: 444

Cys Ala Arg Asp Leu Val Val Val Thr Asp Ile Ser Ile Lys Asn Tyr
1               5                   10                  15

Phe Asp Pro Trp
            20

<210> SEQ ID NO 445
<211> LENGTH: 17
<212> TYPE: PRT
<213> ORGANISM: Homo sapiens

<400> SEQUENCE: 445

Cys Ala Lys Thr Thr Asp Gln Arg Leu Leu Val Asp Trp Phe Asp Pro
1               5                   10                  15

Trp

<210> SEQ ID NO 446
<211> LENGTH: 20
<212> TYPE: PRT
<213> ORGANISM: Homo sapiens

<400> SEQUENCE: 446

Cys Ala Arg Thr Leu Val Tyr Ala Pro Asp Ser Tyr Tyr Leu Tyr Tyr
1               5                   10                  15

Phe Asp Tyr Trp
            20

<210> SEQ ID NO 447
<211> LENGTH: 24
<212> TYPE: PRT
<213> ORGANISM: Homo sapiens

<400> SEQUENCE: 447

Cys Ala Arg His Gly Phe Arg Tyr Cys Asn Asn Gly Val Cys Ser Ile
1               5                   10                  15

Asn Leu Asp Ala Phe Asp Ile Trp
            20

<210> SEQ ID NO 448
<211> LENGTH: 21
<212> TYPE: PRT
<213> ORGANISM: Homo sapiens

<400> SEQUENCE: 448

Cys Ala Arg Asp Leu Arg Met Leu Pro Gly Gly Leu Pro Thr Arg Arg
1               5                   10                  15

Gly Met Asp Val Trp

<210> SEQ ID NO 449
<211> LENGTH: 25
<212> TYPE: PRT
<213> ORGANISM: Homo sapiens

<400> SEQUENCE: 449

Cys Ala Arg Gly Ile Arg Glu Gly Gly Val Ser Val Glu Asp Trp Met
1               5                   10                  15

Leu Val Tyr Ser Trp Phe Asp Pro Trp
            20                  25

<210> SEQ ID NO 450
<211> LENGTH: 13
<212> TYPE: PRT
<213> ORGANISM: Homo sapiens

<400> SEQUENCE: 450

Cys Val Arg Ala Pro Gly Ser Met Gly Leu Asp Val Trp
1               5                   10

<210> SEQ ID NO 451
<211> LENGTH: 13
<212> TYPE: PRT
<213> ORGANISM: Homo sapiens

<400> SEQUENCE: 451

Cys Ala Pro Leu Gly Gly Pro Thr Pro Phe Asp Tyr Trp
1               5                   10

<210> SEQ ID NO 452
<211> LENGTH: 15
<212> TYPE: PRT
<213> ORGANISM: Homo sapiens

<400> SEQUENCE: 452

Cys Ala Thr Ala Ser Thr Tyr Phe Tyr Asp Ser Arg Asp Tyr Trp
1               5                   10                  15

<210> SEQ ID NO 453
<211> LENGTH: 17
<212> TYPE: PRT
<213> ORGANISM: Homo sapiens

<400> SEQUENCE: 453

Cys Ala Arg Val Pro Phe Gln Ile Trp Ser Gly Leu Tyr Phe Asp His
1               5                   10                  15

Trp

<210> SEQ ID NO 454
<211> LENGTH: 18
<212> TYPE: PRT
<213> ORGANISM: Homo sapiens

<400> SEQUENCE: 454

Cys Ala Arg Asp Arg Val Ala Leu Gly Val His Tyr Trp Tyr Phe Asp
1               5                   10                  15

Ile Trp

<210> SEQ ID NO 455
<211> LENGTH: 23
<212> TYPE: PRT

-continued

<213> ORGANISM: Homo sapiens

<400> SEQUENCE: 455

Cys Ala Ile Leu Ile Ala Arg Ala Tyr Cys Gly Leu Ala Asp Gly Gln
1               5                   10                  15

Glu Gly Asp Phe Asp Thr Trp
            20

<210> SEQ ID NO 456
<211> LENGTH: 11
<212> TYPE: PRT
<213> ORGANISM: Homo sapiens

<400> SEQUENCE: 456

Arg Ala Ser Gln Ser Val Asn Ser His Leu Ala
1               5                   10

<210> SEQ ID NO 457
<211> LENGTH: 11
<212> TYPE: PRT
<213> ORGANISM: Homo sapiens

<400> SEQUENCE: 457

Arg Ala Ser Gln Arg Ile Ser Asn His Leu Asn
1               5                   10

<210> SEQ ID NO 458
<211> LENGTH: 16
<212> TYPE: PRT
<213> ORGANISM: Homo sapiens

<400> SEQUENCE: 458

Arg Ser Ser Gln Ser Leu Leu His Ser Asn Gly Asn Asn Tyr Leu Asp
1               5                   10                  15

<210> SEQ ID NO 459
<211> LENGTH: 12
<212> TYPE: PRT
<213> ORGANISM: Homo sapiens

<400> SEQUENCE: 459

Arg Ala Ser Gln Ser Val Ser Ser Ser Tyr Leu Ala
1               5                   10

<210> SEQ ID NO 460
<211> LENGTH: 11
<212> TYPE: PRT
<213> ORGANISM: Homo sapiens

<400> SEQUENCE: 460

Arg Ala Ser Gln Ser Ile Thr Gly Tyr Leu Asn
1               5                   10

<210> SEQ ID NO 461
<211> LENGTH: 11
<212> TYPE: PRT
<213> ORGANISM: Homo sapiens

<400> SEQUENCE: 461

Arg Ala Ser Glu Gly Ile Ser Ser Trp Leu Ala
1               5                   10

<210> SEQ ID NO 462
<211> LENGTH: 12

```
<212> TYPE: PRT
<213> ORGANISM: Homo sapiens

<400> SEQUENCE: 462

Arg Ala Ser Gln Ser Val Ser Ser Tyr Leu Ala
1               5                   10

<210> SEQ ID NO 463
<211> LENGTH: 16
<212> TYPE: PRT
<213> ORGANISM: Homo sapiens

<400> SEQUENCE: 463

Arg Ser Ser Gln Ser Leu Leu Arg Ser Asp Gly Lys Thr Phe Leu Tyr
1               5                   10                  15

<210> SEQ ID NO 464
<211> LENGTH: 11
<212> TYPE: PRT
<213> ORGANISM: Homo sapiens

<400> SEQUENCE: 464

Arg Ala Ser Gln Gly Ile Ser Ser Tyr Leu Ala
1               5                   10

<210> SEQ ID NO 465
<211> LENGTH: 11
<212> TYPE: PRT
<213> ORGANISM: Homo sapiens

<400> SEQUENCE: 465

Arg Ala Ser Gln Asp Ile Asn Asn Tyr Leu Ala
1               5                   10

<210> SEQ ID NO 466
<211> LENGTH: 11
<212> TYPE: PRT
<213> ORGANISM: Homo sapiens

<400> SEQUENCE: 466

Arg Ala Ser Gln Ser Val Ser Ser Trp Val Ala
1               5                   10

<210> SEQ ID NO 467
<211> LENGTH: 11
<212> TYPE: PRT
<213> ORGANISM: Homo sapiens

<400> SEQUENCE: 467

Arg Ala Ser Gln Gly Ile Thr Asp Ser Leu Ala
1               5                   10

<210> SEQ ID NO 468
<211> LENGTH: 16
<212> TYPE: PRT
<213> ORGANISM: Homo sapiens

<400> SEQUENCE: 468

Arg Ser Ser Gln Ser Leu Leu Asn Ser Asn Gly Phe Asn Tyr Val Asp
1               5                   10                  15

<210> SEQ ID NO 469
<211> LENGTH: 11
<212> TYPE: PRT
<213> ORGANISM: Homo sapiens
```

```
<400> SEQUENCE: 469

Arg Ala Ser Gln Gly Ile Ser Ser Tyr Leu Ala
1               5                   10

<210> SEQ ID NO 470
<211> LENGTH: 12
<212> TYPE: PRT
<213> ORGANISM: Homo sapiens

<400> SEQUENCE: 470

Arg Ala Ser Gln Thr Val Ser Ser Ser Tyr Leu Val
1               5                   10

<210> SEQ ID NO 471
<211> LENGTH: 12
<212> TYPE: PRT
<213> ORGANISM: Homo sapiens

<400> SEQUENCE: 471

Arg Ala Ser Gln Ser Val Ser Ser Gly Tyr Leu Ala
1               5                   10

<210> SEQ ID NO 472
<211> LENGTH: 11
<212> TYPE: PRT
<213> ORGANISM: Homo sapiens

<400> SEQUENCE: 472

Arg Ala Ser Gln Gly Ile Asn Thr Tyr Leu Asn
1               5                   10

<210> SEQ ID NO 473
<211> LENGTH: 12
<212> TYPE: PRT
<213> ORGANISM: Homo sapiens

<400> SEQUENCE: 473

Arg Ala Ser Gln Ser Ile Ser Ser Gly Tyr Leu Ala
1               5                   10

<210> SEQ ID NO 474
<211> LENGTH: 11
<212> TYPE: PRT
<213> ORGANISM: Homo sapiens

<400> SEQUENCE: 474

Arg Ala Ser Gln Thr Ile Ala Ser Tyr Leu Ser
1               5                   10

<210> SEQ ID NO 475
<211> LENGTH: 11
<212> TYPE: PRT
<213> ORGANISM: Homo sapiens

<400> SEQUENCE: 475

Arg Ala Ser Gln Ser Val Gly Ser Lys Leu Ala
1               5                   10

<210> SEQ ID NO 476
<211> LENGTH: 11
<212> TYPE: PRT
<213> ORGANISM: Homo sapiens

<400> SEQUENCE: 476
```

```
Arg Ala Ser Gln Gly Ile Ser Asn Tyr Leu Val
1               5                   10
```

<210> SEQ ID NO 477
<211> LENGTH: 17
<212> TYPE: PRT
<213> ORGANISM: Homo sapiens

<400> SEQUENCE: 477

```
Arg Ser Ser Glu Thr Val Leu Tyr Thr Ser Lys Asn Gln Ser Tyr Leu
1               5                   10                  15

Ala
```

<210> SEQ ID NO 478
<211> LENGTH: 12
<212> TYPE: PRT
<213> ORGANISM: Homo sapiens

<400> SEQUENCE: 478

```
Arg Ala Ser Gln Ser Val Ser Ser Ser Tyr Ile Ala
1               5                   10
```

<210> SEQ ID NO 479
<211> LENGTH: 11
<212> TYPE: PRT
<213> ORGANISM: Homo sapiens

<400> SEQUENCE: 479

```
Arg Ala Ser Gln Ser Ile Ser Ser Trp Leu Ala
1               5                   10
```

<210> SEQ ID NO 480
<211> LENGTH: 11
<212> TYPE: PRT
<213> ORGANISM: Homo sapiens

<400> SEQUENCE: 480

```
Arg Ala Ser Gln Ser Ile Gly Ser Arg Leu Ala
1               5                   10
```

<210> SEQ ID NO 481
<211> LENGTH: 16
<212> TYPE: PRT
<213> ORGANISM: Homo sapiens

<400> SEQUENCE: 481

```
Arg Ser Ser Gln Ser Leu Leu His Ser Asp Gly Arg Tyr Tyr Val Asp
1               5                   10                  15
```

<210> SEQ ID NO 482
<211> LENGTH: 11
<212> TYPE: PRT
<213> ORGANISM: Homo sapiens

<400> SEQUENCE: 482

```
Trp Ala Ser Gln Thr Ile Gly Gly Asn Leu Ala
1               5                   10
```

<210> SEQ ID NO 483
<211> LENGTH: 11
<212> TYPE: PRT
<213> ORGANISM: Homo sapiens

<400> SEQUENCE: 483

Arg Ala Ser Gln Thr Ile Ala Ser Tyr Val Asn
1               5                   10

<210> SEQ ID NO 484
<211> LENGTH: 11
<212> TYPE: PRT
<213> ORGANISM: Homo sapiens

<400> SEQUENCE: 484

Arg Ala Ser Gln Ser Val Ser Ser Ser Leu Ala
1               5                   10

<210> SEQ ID NO 485
<211> LENGTH: 11
<212> TYPE: PRT
<213> ORGANISM: Homo sapiens

<400> SEQUENCE: 485

Gln Ala Ser Gln Asp Ile Thr Tyr Tyr Leu Ser
1               5                   10

<210> SEQ ID NO 486
<211> LENGTH: 11
<212> TYPE: PRT
<213> ORGANISM: Homo sapiens

<400> SEQUENCE: 486

Gln Ala Ser Gln Asp Ile Gly Asp Ser Leu Asn
1               5                   10

<210> SEQ ID NO 487
<211> LENGTH: 11
<212> TYPE: PRT
<213> ORGANISM: Homo sapiens

<400> SEQUENCE: 487

Arg Pro Ser Gln Asp Ile Ser Ser Ala Leu Ala
1               5                   10

<210> SEQ ID NO 488
<211> LENGTH: 17
<212> TYPE: PRT
<213> ORGANISM: Homo sapiens

<400> SEQUENCE: 488

Lys Ser Ser Gln Ser Val Leu Tyr Asn Ser Asn Asn Lys Asn Tyr Leu
1               5                   10                  15

Ala

<210> SEQ ID NO 489
<211> LENGTH: 11
<212> TYPE: PRT
<213> ORGANISM: Homo sapiens

<400> SEQUENCE: 489

Arg Ala Ser Gln Phe Ile Ser Ser Tyr Leu His
1               5                   10

<210> SEQ ID NO 490
<211> LENGTH: 11
<212> TYPE: PRT
<213> ORGANISM: Homo sapiens

<400> SEQUENCE: 490

```
Arg Ala Ser Gln Ser Ile Gly Ser Trp Leu Ala
1               5                   10
```

<210> SEQ ID NO 491
<211> LENGTH: 11
<212> TYPE: PRT
<213> ORGANISM: Homo sapiens

<400> SEQUENCE: 491

```
Arg Ala Ser Gln Ser Ile Ala Ser Tyr Leu Asn
1               5                   10
```

<210> SEQ ID NO 492
<211> LENGTH: 11
<212> TYPE: PRT
<213> ORGANISM: Homo sapiens

<400> SEQUENCE: 492

```
Arg Ala Ser Gln Ser Val Thr Ser Glu Leu Ala
1               5                   10
```

<210> SEQ ID NO 493
<211> LENGTH: 11
<212> TYPE: PRT
<213> ORGANISM: Homo sapiens

<400> SEQUENCE: 493

```
Arg Ala Ser Gln Asn Ile Tyr Asn Trp Leu Ala
1               5                   10
```

<210> SEQ ID NO 494
<211> LENGTH: 11
<212> TYPE: PRT
<213> ORGANISM: Homo sapiens

<400> SEQUENCE: 494

```
Arg Ala Asn Gln Asp Ile Asp Asn Tyr Leu Ala
1               5                   10
```

<210> SEQ ID NO 495
<211> LENGTH: 11
<212> TYPE: PRT
<213> ORGANISM: Homo sapiens

<400> SEQUENCE: 495

```
Arg Ala Ser Gln Gly Ile Ser Lys Arg Leu Ala
1               5                   10
```

<210> SEQ ID NO 496
<211> LENGTH: 11
<212> TYPE: PRT
<213> ORGANISM: Homo sapiens

<400> SEQUENCE: 496

```
Arg Ala Ser Gln Gly Ile Ser Ser Tyr Leu Ala
1               5                   10
```

<210> SEQ ID NO 497
<211> LENGTH: 11
<212> TYPE: PRT
<213> ORGANISM: Homo sapiens

<400> SEQUENCE: 497

```
Arg Ala Ser Gln Gly Ile Gly Thr Trp Leu Ala
```

```
                   1               5                   10

<210> SEQ ID NO 498
<211> LENGTH: 11
<212> TYPE: PRT
<213> ORGANISM: Homo sapiens

<400> SEQUENCE: 498

Arg Ala Ser Gln Gly Ile Ser Asn Tyr Leu Ala
1               5                   10

<210> SEQ ID NO 499
<211> LENGTH: 12
<212> TYPE: PRT
<213> ORGANISM: Homo sapiens

<400> SEQUENCE: 499

Arg Ala Ser Gln Ser Val Gly Gly Arg Ser Leu Ala
1               5                   10

<210> SEQ ID NO 500
<211> LENGTH: 17
<212> TYPE: PRT
<213> ORGANISM: Homo sapiens

<400> SEQUENCE: 500

Arg Ser Ser Gln Ser Val Leu Tyr Ser Asn Asn Lys Asn Tyr Leu
1               5                   10                  15

Ala

<210> SEQ ID NO 501
<211> LENGTH: 11
<212> TYPE: PRT
<213> ORGANISM: Homo sapiens

<400> SEQUENCE: 501

Arg Ala Ser Gln Thr Ile Ser Asn Ser Leu Ala
1               5                   10

<210> SEQ ID NO 502
<211> LENGTH: 11
<212> TYPE: PRT
<213> ORGANISM: Homo sapiens

<400> SEQUENCE: 502

Arg Ala Ser Gln Gly Ile Ser Asn Tyr Leu Ala
1               5                   10

<210> SEQ ID NO 503
<211> LENGTH: 11
<212> TYPE: PRT
<213> ORGANISM: Homo sapiens

<400> SEQUENCE: 503

Arg Ala Ser Gln Gly Ile Ser Ser Tyr Leu Ala
1               5                   10

<210> SEQ ID NO 504
<211> LENGTH: 12
<212> TYPE: PRT
<213> ORGANISM: Homo sapiens

<400> SEQUENCE: 504

Arg Ala Ser Gln Ser Val Ser Ser Ser Tyr Leu Ala
```

-continued

```
1               5                   10
```

<210> SEQ ID NO 505
<211> LENGTH: 11
<212> TYPE: PRT
<213> ORGANISM: Homo sapiens

<400> SEQUENCE: 505

```
Arg Ala Ser Gln Gly Ile Ser Ala Trp Leu Ala
1               5                   10
```

<210> SEQ ID NO 506
<211> LENGTH: 11
<212> TYPE: PRT
<213> ORGANISM: Homo sapiens

<400> SEQUENCE: 506

```
Arg Ala Ser Gln Ser Ile Ser Ser Tyr Leu Asn
1               5                   10
```

<210> SEQ ID NO 507
<211> LENGTH: 11
<212> TYPE: PRT
<213> ORGANISM: Homo sapiens

<400> SEQUENCE: 507

```
Arg Ala Ser Gln Asn Ile Tyr Asn Trp Leu Ala
1               5                   10
```

<210> SEQ ID NO 508
<211> LENGTH: 16
<212> TYPE: PRT
<213> ORGANISM: Homo sapiens

<400> SEQUENCE: 508

```
Arg Ser Ser Gln Ser Leu Val Asn Ser Asp Gly Asn Thr Tyr Leu Ser
1               5                   10                  15
```

<210> SEQ ID NO 509
<211> LENGTH: 11
<212> TYPE: PRT
<213> ORGANISM: Homo sapiens

<400> SEQUENCE: 509

```
Gln Ala Ser Gln Asp Val Ser Tyr Tyr Leu Asn
1               5                   10
```

<210> SEQ ID NO 510
<211> LENGTH: 12
<212> TYPE: PRT
<213> ORGANISM: Homo sapiens

<400> SEQUENCE: 510

```
Arg Ala Ser Gln Ser Val Ser Ser Asn Tyr Leu Ala
1               5                   10
```

<210> SEQ ID NO 511
<211> LENGTH: 11
<212> TYPE: PRT
<213> ORGANISM: Homo sapiens

<400> SEQUENCE: 511

```
Arg Ala Ser Gln Ala Ile Ser Asn Trp Leu Ala
1               5                   10
```

-continued

```
<210> SEQ ID NO 512
<211> LENGTH: 17
<212> TYPE: PRT
<213> ORGANISM: Homo sapiens

<400> SEQUENCE: 512

Arg Ser Ser Gln Ser Leu Leu Asp Ser Asn Asp Gly Asn Thr Tyr Leu
1               5                   10                  15
Asp

<210> SEQ ID NO 513
<211> LENGTH: 16
<212> TYPE: PRT
<213> ORGANISM: Homo sapiens

<400> SEQUENCE: 513

Arg Ser Ser Gln Ser Leu Leu His Arg Asn Glu Tyr Asn Tyr Leu Asp
1               5                   10                  15

<210> SEQ ID NO 514
<211> LENGTH: 11
<212> TYPE: PRT
<213> ORGANISM: Homo sapiens

<400> SEQUENCE: 514

Gln Ala Ser Gln Asp Ile Ser Asn Tyr Leu Asn
1               5                   10

<210> SEQ ID NO 515
<211> LENGTH: 11
<212> TYPE: PRT
<213> ORGANISM: Homo sapiens

<400> SEQUENCE: 515

Arg Ala Ser Gln Gly Ile Arg Asn Tyr Leu Ala
1               5                   10

<210> SEQ ID NO 516
<211> LENGTH: 11
<212> TYPE: PRT
<213> ORGANISM: Homo sapiens

<400> SEQUENCE: 516

Arg Ala Ser Gln Ile Ile Ala Ser Tyr Leu Asn
1               5                   10

<210> SEQ ID NO 517
<211> LENGTH: 11
<212> TYPE: PRT
<213> ORGANISM: Homo sapiens

<400> SEQUENCE: 517

Arg Thr Ser Gln Ser Val Ser Ser Tyr Leu Ala
1               5                   10

<210> SEQ ID NO 518
<211> LENGTH: 11
<212> TYPE: PRT
<213> ORGANISM: Homo sapiens

<400> SEQUENCE: 518

Arg Ala Ser Gln Gly Ile Ser Ile Tyr Leu Ala
1               5                   10
```

```
<210> SEQ ID NO 519
<211> LENGTH: 11
<212> TYPE: PRT
<213> ORGANISM: Homo sapiens

<400> SEQUENCE: 519

Gln Ala Ser Gln Asp Ile Asn Asn Tyr Leu Asn
1               5                   10

<210> SEQ ID NO 520
<211> LENGTH: 11
<212> TYPE: PRT
<213> ORGANISM: Homo sapiens

<400> SEQUENCE: 520

Arg Ala Ser Gln Ser Ile Lys Asn Asn Leu Ala
1               5                   10

<210> SEQ ID NO 521
<211> LENGTH: 12
<212> TYPE: PRT
<213> ORGANISM: Homo sapiens

<400> SEQUENCE: 521

Arg Ala Ser Gln Ser Leu Ser Asp Asn Tyr Leu Ala
1               5                   10

<210> SEQ ID NO 522
<211> LENGTH: 11
<212> TYPE: PRT
<213> ORGANISM: Homo sapiens

<400> SEQUENCE: 522

Arg Ala Ser Gln Arg Ile Ala Ser Tyr Leu Asn
1               5                   10

<210> SEQ ID NO 523
<211> LENGTH: 11
<212> TYPE: PRT
<213> ORGANISM: Homo sapiens

<400> SEQUENCE: 523

Gln Ala Ser Gln Gly Ile Ser Asn Tyr Leu Asn
1               5                   10

<210> SEQ ID NO 524
<211> LENGTH: 11
<212> TYPE: PRT
<213> ORGANISM: Homo sapiens

<400> SEQUENCE: 524

Arg Ala Ser Gln Gly Ile Arg Asn Phe Leu Ala
1               5                   10

<210> SEQ ID NO 525
<211> LENGTH: 11
<212> TYPE: PRT
<213> ORGANISM: Homo sapiens

<400> SEQUENCE: 525

Arg Ala Ser Gln Ser Val Thr Ser Asn Leu Ala
1               5                   10

<210> SEQ ID NO 526
```

```
<211> LENGTH: 11
<212> TYPE: PRT
<213> ORGANISM: Homo sapiens

<400> SEQUENCE: 526

Arg Ala Ser Gln Thr Ile Ala Ser Tyr Val Asn
1               5                   10

<210> SEQ ID NO 527
<211> LENGTH: 11
<212> TYPE: PRT
<213> ORGANISM: Homo sapiens

<400> SEQUENCE: 527

Arg Ala Ser Gln Thr Ile Ala Ser Tyr Val Asn
1               5                   10

<210> SEQ ID NO 528
<211> LENGTH: 11
<212> TYPE: PRT
<213> ORGANISM: Homo sapiens

<400> SEQUENCE: 528

Arg Ser Ser Gln Thr Ile Ser Val Phe Leu Asn
1               5                   10

<210> SEQ ID NO 529
<211> LENGTH: 11
<212> TYPE: PRT
<213> ORGANISM: Homo sapiens

<400> SEQUENCE: 529

Arg Ala Ser Gln Ser Val Thr Lys Tyr Leu Ala
1               5                   10

<210> SEQ ID NO 530
<211> LENGTH: 11
<212> TYPE: PRT
<213> ORGANISM: Homo sapiens

<400> SEQUENCE: 530

Arg Ala Ser Gln Ser Val Ser Ser Asn Leu Ala
1               5                   10

<210> SEQ ID NO 531
<211> LENGTH: 11
<212> TYPE: PRT
<213> ORGANISM: Homo sapiens

<400> SEQUENCE: 531

Arg Ala Ser Gln Thr Ile Ala Ser Tyr Val Asn
1               5                   10

<210> SEQ ID NO 532
<211> LENGTH: 16
<212> TYPE: PRT
<213> ORGANISM: Homo sapiens

<400> SEQUENCE: 532

Arg Ser Ser Gln Ser Leu Leu Arg Thr Asn Gly Tyr Asn Tyr Leu Asp
1               5                   10                  15

<210> SEQ ID NO 533
<211> LENGTH: 11
<212> TYPE: PRT
```

<213> ORGANISM: Homo sapiens

<400> SEQUENCE: 533

Arg Ala Ser Gln Ser Ile Ser Ser Trp Leu Ala
1               5                   10

<210> SEQ ID NO 534
<211> LENGTH: 11
<212> TYPE: PRT
<213> ORGANISM: Homo sapiens

<400> SEQUENCE: 534

Arg Ala Ser Gln Asn Ile Arg Thr Phe Ile Asn
1               5                   10

<210> SEQ ID NO 535
<211> LENGTH: 16
<212> TYPE: PRT
<213> ORGANISM: Homo sapiens

<400> SEQUENCE: 535

Arg Ser Ser Gln Ser Leu Leu His Arg Asn Gly Tyr Asn His Leu Asp
1               5                   10                  15

<210> SEQ ID NO 536
<211> LENGTH: 11
<212> TYPE: PRT
<213> ORGANISM: Homo sapiens

<400> SEQUENCE: 536

Arg Ala Gly Gln Gly Ile Arg Asn Asp Leu Gly
1               5                   10

<210> SEQ ID NO 537
<211> LENGTH: 16
<212> TYPE: PRT
<213> ORGANISM: Homo sapiens

<400> SEQUENCE: 537

Arg Ser Ser Arg Ser Leu Val His Ser Asp Gly Asn Thr Tyr Leu Ser
1               5                   10                  15

<210> SEQ ID NO 538
<211> LENGTH: 11
<212> TYPE: PRT
<213> ORGANISM: Homo sapiens

<400> SEQUENCE: 538

Arg Ala Ser Gln Ser Val Gly Asn Asn Leu Ala
1               5                   10

<210> SEQ ID NO 539
<211> LENGTH: 11
<212> TYPE: PRT
<213> ORGANISM: Homo sapiens

<400> SEQUENCE: 539

Arg Ala Ser Gln Ser Val Ser Ser His Leu Ala
1               5                   10

<210> SEQ ID NO 540
<211> LENGTH: 11
<212> TYPE: PRT
<213> ORGANISM: Homo sapiens

```
<400> SEQUENCE: 540

Arg Ala Ser Arg Ser Ile Thr Ser Trp Leu Ala
1               5                   10

<210> SEQ ID NO 541
<211> LENGTH: 7
<212> TYPE: PRT
<213> ORGANISM: Homo sapiens

<400> SEQUENCE: 541

Asn Thr Phe Asn Arg Val Thr
1               5

<210> SEQ ID NO 542
<211> LENGTH: 7
<212> TYPE: PRT
<213> ORGANISM: Homo sapiens

<400> SEQUENCE: 542

Gly Ala Ser Thr Leu Gln Ser
1               5

<210> SEQ ID NO 543
<211> LENGTH: 7
<212> TYPE: PRT
<213> ORGANISM: Homo sapiens

<400> SEQUENCE: 543

Leu Ala Ser Asn Arg Ala Ser
1               5

<210> SEQ ID NO 544
<211> LENGTH: 7
<212> TYPE: PRT
<213> ORGANISM: Homo sapiens

<400> SEQUENCE: 544

Gly Ala Ser Ser Arg Ala Thr
1               5

<210> SEQ ID NO 545
<211> LENGTH: 7
<212> TYPE: PRT
<213> ORGANISM: Homo sapiens

<400> SEQUENCE: 545

Ala Thr Ser Thr Leu Gln Ser
1               5

<210> SEQ ID NO 546
<211> LENGTH: 7
<212> TYPE: PRT
<213> ORGANISM: Homo sapiens

<400> SEQUENCE: 546

Ala Ala Ser Thr Leu Gln Ser
1               5

<210> SEQ ID NO 547
<211> LENGTH: 7
<212> TYPE: PRT
<213> ORGANISM: Homo sapiens

<400> SEQUENCE: 547
```

```
Gly Ala Ser Thr Gly Ala Thr
1               5

<210> SEQ ID NO 548
<211> LENGTH: 7
<212> TYPE: PRT
<213> ORGANISM: Homo sapiens

<400> SEQUENCE: 548

Glu Val Ser Ser Arg Phe Ser
1               5

<210> SEQ ID NO 549
<211> LENGTH: 7
<212> TYPE: PRT
<213> ORGANISM: Homo sapiens

<400> SEQUENCE: 549

Ala Ala Ser Thr Leu Gln Ser
1               5

<210> SEQ ID NO 550
<211> LENGTH: 7
<212> TYPE: PRT
<213> ORGANISM: Homo sapiens

<400> SEQUENCE: 550

Ala Ala Ser Ser Leu Gln Ser
1               5

<210> SEQ ID NO 551
<211> LENGTH: 7
<212> TYPE: PRT
<213> ORGANISM: Homo sapiens

<400> SEQUENCE: 551

Glu Ala Ser Asn Leu Glu Ser
1               5

<210> SEQ ID NO 552
<211> LENGTH: 7
<212> TYPE: PRT
<213> ORGANISM: Homo sapiens

<400> SEQUENCE: 552

Ala Ala Ser Arg Leu Glu Ser
1               5

<210> SEQ ID NO 553
<211> LENGTH: 7
<212> TYPE: PRT
<213> ORGANISM: Homo sapiens

<400> SEQUENCE: 553

Leu Gly Ser Asn Arg Ala Ser
1               5

<210> SEQ ID NO 554
<211> LENGTH: 7
<212> TYPE: PRT
<213> ORGANISM: Homo sapiens

<400> SEQUENCE: 554

Val Ala Ser Ile Leu Glu Ser
1               5
```

```
<210> SEQ ID NO 555
<211> LENGTH: 7
<212> TYPE: PRT
<213> ORGANISM: Homo sapiens

<400> SEQUENCE: 555

Gly Ala Ser Thr Arg Ala Thr
1               5

<210> SEQ ID NO 556
<211> LENGTH: 7
<212> TYPE: PRT
<213> ORGANISM: Homo sapiens

<400> SEQUENCE: 556

Gly Ala Ser Gly Arg Ala Thr
1               5

<210> SEQ ID NO 557
<211> LENGTH: 7
<212> TYPE: PRT
<213> ORGANISM: Homo sapiens

<400> SEQUENCE: 557

Ala Ala Ser Ser Leu Gln Ser
1               5

<210> SEQ ID NO 558
<211> LENGTH: 7
<212> TYPE: PRT
<213> ORGANISM: Homo sapiens

<400> SEQUENCE: 558

Gly Ala Ser His Arg Ala Thr
1               5

<210> SEQ ID NO 559
<211> LENGTH: 7
<212> TYPE: PRT
<213> ORGANISM: Homo sapiens

<400> SEQUENCE: 559

Thr Ala Ser Ser Leu Gln Ser
1               5

<210> SEQ ID NO 560
<211> LENGTH: 7
<212> TYPE: PRT
<213> ORGANISM: Homo sapiens

<400> SEQUENCE: 560

Gly Ala Ser Thr Arg Ala Thr
1               5

<210> SEQ ID NO 561
<211> LENGTH: 7
<212> TYPE: PRT
<213> ORGANISM: Homo sapiens

<400> SEQUENCE: 561

Ala Ala Ser Ser Leu Gln Ser
1               5
```

```
<210> SEQ ID NO 562
<211> LENGTH: 7
<212> TYPE: PRT
<213> ORGANISM: Homo sapiens

<400> SEQUENCE: 562

Trp Ala Ser Thr Arg Glu Ser
1               5

<210> SEQ ID NO 563
<211> LENGTH: 7
<212> TYPE: PRT
<213> ORGANISM: Homo sapiens

<400> SEQUENCE: 563

Ala Ala Ser Arg Arg Ala Thr
1               5

<210> SEQ ID NO 564
<211> LENGTH: 7
<212> TYPE: PRT
<213> ORGANISM: Homo sapiens

<400> SEQUENCE: 564

Lys Ser Ser Ile Leu Glu Ser
1               5

<210> SEQ ID NO 565
<211> LENGTH: 7
<212> TYPE: PRT
<213> ORGANISM: Homo sapiens

<400> SEQUENCE: 565

Asp Ala Ser Ser Leu Glu Ser
1               5

<210> SEQ ID NO 566
<211> LENGTH: 7
<212> TYPE: PRT
<213> ORGANISM: Homo sapiens

<400> SEQUENCE: 566

Leu Ala Ser Asn Arg Ala Ser
1               5

<210> SEQ ID NO 567
<211> LENGTH: 7
<212> TYPE: PRT
<213> ORGANISM: Homo sapiens

<400> SEQUENCE: 567

Gly Ala Ser Thr Arg Ala Thr
1               5

<210> SEQ ID NO 568
<211> LENGTH: 7
<212> TYPE: PRT
<213> ORGANISM: Homo sapiens

<400> SEQUENCE: 568

Ala Ala Ser Asn Leu Gln Ser
1               5

<210> SEQ ID NO 569
<211> LENGTH: 7
```

```
<212> TYPE: PRT
<213> ORGANISM: Homo sapiens

<400> SEQUENCE: 569

Asp Ala Ser Tyr Arg Val Thr
1               5

<210> SEQ ID NO 570
<211> LENGTH: 7
<212> TYPE: PRT
<213> ORGANISM: Homo sapiens

<400> SEQUENCE: 570

Asp Val Ser Asn Leu Glu Arg
1               5

<210> SEQ ID NO 571
<211> LENGTH: 7
<212> TYPE: PRT
<213> ORGANISM: Homo sapiens

<400> SEQUENCE: 571

Asp Ala Ser Asn Leu Glu Thr
1               5

<210> SEQ ID NO 572
<211> LENGTH: 7
<212> TYPE: PRT
<213> ORGANISM: Homo sapiens

<400> SEQUENCE: 572

Gly Ala Ser Thr Leu Asp Tyr
1               5

<210> SEQ ID NO 573
<211> LENGTH: 7
<212> TYPE: PRT
<213> ORGANISM: Homo sapiens

<400> SEQUENCE: 573

Leu Ala Ser Thr Arg Glu Tyr
1               5

<210> SEQ ID NO 574
<211> LENGTH: 7
<212> TYPE: PRT
<213> ORGANISM: Homo sapiens

<400> SEQUENCE: 574

Ala Ala Ser Thr Leu Gln Ser
1               5

<210> SEQ ID NO 575
<211> LENGTH: 7
<212> TYPE: PRT
<213> ORGANISM: Homo sapiens

<400> SEQUENCE: 575

Lys Glu Ser Asn Leu Glu Ser
1               5

<210> SEQ ID NO 576
<211> LENGTH: 7
<212> TYPE: PRT
<213> ORGANISM: Homo sapiens
```

```
<400> SEQUENCE: 576

Ala Ala Ser Ser Leu His Ser
1               5

<210> SEQ ID NO 577
<211> LENGTH: 7
<212> TYPE: PRT
<213> ORGANISM: Homo sapiens

<400> SEQUENCE: 577

Lys Ala Ser Ser Leu Glu Ser
1               5

<210> SEQ ID NO 578
<211> LENGTH: 7
<212> TYPE: PRT
<213> ORGANISM: Homo sapiens

<400> SEQUENCE: 578

Asp Ala Ser Thr Leu Glu Ser
1               5

<210> SEQ ID NO 579
<211> LENGTH: 7
<212> TYPE: PRT
<213> ORGANISM: Homo sapiens

<400> SEQUENCE: 579

Gly Ala Ser Lys Leu Gln Thr
1               5

<210> SEQ ID NO 580
<211> LENGTH: 7
<212> TYPE: PRT
<213> ORGANISM: Homo sapiens

<400> SEQUENCE: 580

Gly Ala Ser Ser Leu Gln His
1               5

<210> SEQ ID NO 581
<211> LENGTH: 7
<212> TYPE: PRT
<213> ORGANISM: Homo sapiens

<400> SEQUENCE: 581

Ala Ala Ser Thr Leu Gln Ser
1               5

<210> SEQ ID NO 582
<211> LENGTH: 7
<212> TYPE: PRT
<213> ORGANISM: Homo sapiens

<400> SEQUENCE: 582

Ala Ala Ser Arg Leu Gln Ser
1               5

<210> SEQ ID NO 583
<211> LENGTH: 7
<212> TYPE: PRT
<213> ORGANISM: Homo sapiens

<400> SEQUENCE: 583
```

Ala Ala Ser Thr Leu Gln Ser
1               5

<210> SEQ ID NO 584
<211> LENGTH: 7
<212> TYPE: PRT
<213> ORGANISM: Homo sapiens

<400> SEQUENCE: 584

Asp Ala Ser Asn Arg Ala Thr
1               5

<210> SEQ ID NO 585
<211> LENGTH: 7
<212> TYPE: PRT
<213> ORGANISM: Homo sapiens

<400> SEQUENCE: 585

Trp Ala Ser Thr Arg Ala Ser
1               5

<210> SEQ ID NO 586
<211> LENGTH: 7
<212> TYPE: PRT
<213> ORGANISM: Homo sapiens

<400> SEQUENCE: 586

Lys Ala Ser Thr Leu Glu Ser
1               5

<210> SEQ ID NO 587
<211> LENGTH: 7
<212> TYPE: PRT
<213> ORGANISM: Homo sapiens

<400> SEQUENCE: 587

Thr Thr Ser Thr Leu Arg Ser
1               5

<210> SEQ ID NO 588
<211> LENGTH: 7
<212> TYPE: PRT
<213> ORGANISM: Homo sapiens

<400> SEQUENCE: 588

Ala Ala Ser Thr Leu Gln Ser
1               5

<210> SEQ ID NO 589
<211> LENGTH: 7
<212> TYPE: PRT
<213> ORGANISM: Homo sapiens

<400> SEQUENCE: 589

Gly Ala Ser Ser Arg Ala Thr
1               5

<210> SEQ ID NO 590
<211> LENGTH: 7
<212> TYPE: PRT
<213> ORGANISM: Homo sapiens

<400> SEQUENCE: 590

Asp Ala Ser Thr Leu Ala Ser

-continued

```
1               5

<210> SEQ ID NO 591
<211> LENGTH: 7
<212> TYPE: PRT
<213> ORGANISM: Homo sapiens

<400> SEQUENCE: 591

Ala Ala Ser Ser Leu Gln Ser
1               5

<210> SEQ ID NO 592
<211> LENGTH: 7
<212> TYPE: PRT
<213> ORGANISM: Homo sapiens

<400> SEQUENCE: 592

Asp Ala Ser Ser Leu Glu Ser
1               5

<210> SEQ ID NO 593
<211> LENGTH: 7
<212> TYPE: PRT
<213> ORGANISM: Homo sapiens

<400> SEQUENCE: 593

Gln Ile Ser Lys Arg Phe Ser
1               5

<210> SEQ ID NO 594
<211> LENGTH: 7
<212> TYPE: PRT
<213> ORGANISM: Homo sapiens

<400> SEQUENCE: 594

Asp Thr Ser Asn Leu Val Thr
1               5

<210> SEQ ID NO 595
<211> LENGTH: 7
<212> TYPE: PRT
<213> ORGANISM: Homo sapiens

<400> SEQUENCE: 595

Gly Ala Ser Ser Arg Ala Ala
1               5

<210> SEQ ID NO 596
<211> LENGTH: 7
<212> TYPE: PRT
<213> ORGANISM: Homo sapiens

<400> SEQUENCE: 596

Ala Ala Ser Ser Leu Gln Ser
1               5

<210> SEQ ID NO 597
<211> LENGTH: 7
<212> TYPE: PRT
<213> ORGANISM: Homo sapiens

<400> SEQUENCE: 597

Thr Phe Ser Tyr Arg Ala Ser
1               5
```

```
<210> SEQ ID NO 598
<211> LENGTH: 7
<212> TYPE: PRT
<213> ORGANISM: Homo sapiens

<400> SEQUENCE: 598

Trp Gly Ser Asn Arg Ala Ser
1               5

<210> SEQ ID NO 599
<211> LENGTH: 7
<212> TYPE: PRT
<213> ORGANISM: Homo sapiens

<400> SEQUENCE: 599

Asp Ala Thr Lys Leu Glu Thr
1               5

<210> SEQ ID NO 600
<211> LENGTH: 7
<212> TYPE: PRT
<213> ORGANISM: Homo sapiens

<400> SEQUENCE: 600

Ala Ala Ser Thr Leu Gln Ser
1               5

<210> SEQ ID NO 601
<211> LENGTH: 7
<212> TYPE: PRT
<213> ORGANISM: Homo sapiens

<400> SEQUENCE: 601

Ala Ala Ser Ser Leu Gln Ser
1               5

<210> SEQ ID NO 602
<211> LENGTH: 7
<212> TYPE: PRT
<213> ORGANISM: Homo sapiens

<400> SEQUENCE: 602

Asp Ala Ser Asn Arg Ala Thr
1               5

<210> SEQ ID NO 603
<211> LENGTH: 7
<212> TYPE: PRT
<213> ORGANISM: Homo sapiens

<400> SEQUENCE: 603

Ala Ala Ser Thr Leu Gln Thr
1               5

<210> SEQ ID NO 604
<211> LENGTH: 7
<212> TYPE: PRT
<213> ORGANISM: Homo sapiens

<400> SEQUENCE: 604

Asp Ala Thr Asp Leu Glu Thr
1               5

<210> SEQ ID NO 605
```

```
<211> LENGTH: 7
<212> TYPE: PRT
<213> ORGANISM: Homo sapiens

<400> SEQUENCE: 605

Gly Ala Ser Ala Arg Ala Thr
1               5

<210> SEQ ID NO 606
<211> LENGTH: 7
<212> TYPE: PRT
<213> ORGANISM: Homo sapiens

<400> SEQUENCE: 606

Gly Ala Ser Ser Arg Pro Thr
1               5

<210> SEQ ID NO 607
<211> LENGTH: 7
<212> TYPE: PRT
<213> ORGANISM: Homo sapiens

<400> SEQUENCE: 607

Ala Ala Ser Ser Leu Gln Ser
1               5

<210> SEQ ID NO 608
<211> LENGTH: 7
<212> TYPE: PRT
<213> ORGANISM: Homo sapiens

<400> SEQUENCE: 608

Asp Ala Ser Asn Leu Glu Ser
1               5

<210> SEQ ID NO 609
<211> LENGTH: 7
<212> TYPE: PRT
<213> ORGANISM: Homo sapiens

<400> SEQUENCE: 609

Ala Ala Ser Thr Leu Gln Ser
1               5

<210> SEQ ID NO 610
<211> LENGTH: 7
<212> TYPE: PRT
<213> ORGANISM: Homo sapiens

<400> SEQUENCE: 610

Gly Ala Ser Thr Arg Ala Thr
1               5

<210> SEQ ID NO 611
<211> LENGTH: 7
<212> TYPE: PRT
<213> ORGANISM: Homo sapiens

<400> SEQUENCE: 611

Ala Ala Ser Ser Leu Gln Ser
1               5

<210> SEQ ID NO 612
<211> LENGTH: 7
<212> TYPE: PRT
```

<213> ORGANISM: Homo sapiens

<400> SEQUENCE: 612

Ala Ala Ser Asn Leu Gln Ser
1               5

<210> SEQ ID NO 613
<211> LENGTH: 7
<212> TYPE: PRT
<213> ORGANISM: Homo sapiens

<400> SEQUENCE: 613

Ala Ala Ser Ser Leu His Ser
1               5

<210> SEQ ID NO 614
<211> LENGTH: 7
<212> TYPE: PRT
<213> ORGANISM: Homo sapiens

<400> SEQUENCE: 614

Asp Ala Ser Asn Arg Ala Thr
1               5

<210> SEQ ID NO 615
<211> LENGTH: 7
<212> TYPE: PRT
<213> ORGANISM: Homo sapiens

<400> SEQUENCE: 615

Ser Ala Ser Thr Arg Ala Thr
1               5

<210> SEQ ID NO 616
<211> LENGTH: 7
<212> TYPE: PRT
<213> ORGANISM: Homo sapiens

<400> SEQUENCE: 616

Ala Ala Ser Arg Leu Gln Ser
1               5

<210> SEQ ID NO 617
<211> LENGTH: 7
<212> TYPE: PRT
<213> ORGANISM: Homo sapiens

<400> SEQUENCE: 617

Leu Gly Ser Ile Arg Ala Ser
1               5

<210> SEQ ID NO 618
<211> LENGTH: 7
<212> TYPE: PRT
<213> ORGANISM: Homo sapiens

<400> SEQUENCE: 618

Lys Ala Ser Ser Leu Glu Ser
1               5

<210> SEQ ID NO 619
<211> LENGTH: 7
<212> TYPE: PRT
<213> ORGANISM: Homo sapiens

```
<400> SEQUENCE: 619

Ala Ala Ser Lys Leu Glu Ser
1               5

<210> SEQ ID NO 620
<211> LENGTH: 7
<212> TYPE: PRT
<213> ORGANISM: Homo sapiens

<400> SEQUENCE: 620

Leu Gly Ser Asn Arg Ala Ser
1               5

<210> SEQ ID NO 621
<211> LENGTH: 7
<212> TYPE: PRT
<213> ORGANISM: Homo sapiens

<400> SEQUENCE: 621

Gly Ala Ser Thr Leu Gln Ser
1               5

<210> SEQ ID NO 622
<211> LENGTH: 7
<212> TYPE: PRT
<213> ORGANISM: Homo sapiens

<400> SEQUENCE: 622

Lys Ile Ser Asn Arg Phe Ser
1               5

<210> SEQ ID NO 623
<211> LENGTH: 7
<212> TYPE: PRT
<213> ORGANISM: Homo sapiens

<400> SEQUENCE: 623

Gly Ala Ser Thr Arg Ala Thr
1               5

<210> SEQ ID NO 624
<211> LENGTH: 7
<212> TYPE: PRT
<213> ORGANISM: Homo sapiens

<400> SEQUENCE: 624

Gly Ala Ser Thr Arg Ala Thr
1               5

<210> SEQ ID NO 625
<211> LENGTH: 7
<212> TYPE: PRT
<213> ORGANISM: Homo sapiens

<400> SEQUENCE: 625

Lys Ala Ser Ser Leu Gln Ser
1               5

<210> SEQ ID NO 626
<211> LENGTH: 13
<212> TYPE: PRT
<213> ORGANISM: Homo sapiens

<400> SEQUENCE: 626
```

-continued

Cys Gln Gln Arg Ser Asn Trp Pro Ala Leu Thr Phe
1               5                   10

<210> SEQ ID NO 627
<211> LENGTH: 12
<212> TYPE: PRT
<213> ORGANISM: Homo sapiens

<400> SEQUENCE: 627

Cys Gln Gln Ser Tyr Arg Thr Pro Pro Ile Asn Phe
1               5                   10

<210> SEQ ID NO 628
<211> LENGTH: 10
<212> TYPE: PRT
<213> ORGANISM: Homo sapiens

<400> SEQUENCE: 628

Cys Met Gln Ser Leu Gln Thr Pro Thr Phe
1               5                   10

<210> SEQ ID NO 629
<211> LENGTH: 13
<212> TYPE: PRT
<213> ORGANISM: Homo sapiens

<400> SEQUENCE: 629

Cys Gln Gln Tyr Asp Ser Ser Leu Ser Thr Trp Thr Phe
1               5                   10

<210> SEQ ID NO 630
<211> LENGTH: 10
<212> TYPE: PRT
<213> ORGANISM: Homo sapiens

<400> SEQUENCE: 630

Cys Gln Gln Ser Tyr Asn Thr Leu Thr Phe
1               5                   10

<210> SEQ ID NO 631
<211> LENGTH: 11
<212> TYPE: PRT
<213> ORGANISM: Homo sapiens

<400> SEQUENCE: 631

Cys Gln Gln Thr Asn Ser Phe Pro Tyr Thr Phe
1               5                   10

<210> SEQ ID NO 632
<211> LENGTH: 11
<212> TYPE: PRT
<213> ORGANISM: Homo sapiens

<400> SEQUENCE: 632

Cys Gln Gln Tyr Gly Arg Thr Pro Tyr Thr Phe
1               5                   10

<210> SEQ ID NO 633
<211> LENGTH: 11
<212> TYPE: PRT
<213> ORGANISM: Homo sapiens

<400> SEQUENCE: 633

Cys Met Gln Gly Leu Lys Ile Arg Arg Thr Phe
1               5                   10

```
<210> SEQ ID NO 634
<211> LENGTH: 11
<212> TYPE: PRT
<213> ORGANISM: Homo sapiens

<400> SEQUENCE: 634

Cys Gln Gln Val Asp Thr Tyr Pro Leu Thr Phe
1               5                   10

<210> SEQ ID NO 635
<211> LENGTH: 11
<212> TYPE: PRT
<213> ORGANISM: Homo sapiens

<400> SEQUENCE: 635

Cys Gln Gln Tyr Lys Ser Leu Pro Phe Thr Phe
1               5                   10

<210> SEQ ID NO 636
<211> LENGTH: 12
<212> TYPE: PRT
<213> ORGANISM: Homo sapiens

<400> SEQUENCE: 636

Cys Gln Gln Tyr His Ser Tyr Ser Gly Tyr Thr Phe
1               5                   10

<210> SEQ ID NO 637
<211> LENGTH: 11
<212> TYPE: PRT
<213> ORGANISM: Homo sapiens

<400> SEQUENCE: 637

Cys Gln Gln Tyr Ser Lys Ser Pro Ala Thr Phe
1               5                   10

<210> SEQ ID NO 638
<211> LENGTH: 11
<212> TYPE: PRT
<213> ORGANISM: Homo sapiens

<400> SEQUENCE: 638

Cys Met Gln Ala Leu Glu Thr Pro Leu Thr Phe
1               5                   10

<210> SEQ ID NO 639
<211> LENGTH: 11
<212> TYPE: PRT
<213> ORGANISM: Homo sapiens

<400> SEQUENCE: 639

Cys Gln Gln Ser Lys Ser Phe Pro Pro Thr Phe
1               5                   10

<210> SEQ ID NO 640
<211> LENGTH: 11
<212> TYPE: PRT
<213> ORGANISM: Homo sapiens

<400> SEQUENCE: 640

Cys Gln Gln Tyr Gly Gly Ser Gly Leu Thr Phe
1               5                   10
```

```
<210> SEQ ID NO 641
<211> LENGTH: 11
<212> TYPE: PRT
<213> ORGANISM: Homo sapiens

<400> SEQUENCE: 641

Cys Gln Gln Tyr Phe Gly Ser Pro Tyr Thr Phe
1               5                   10

<210> SEQ ID NO 642
<211> LENGTH: 11
<212> TYPE: PRT
<213> ORGANISM: Homo sapiens

<400> SEQUENCE: 642

Cys Gln Gln Ser Ala Asn Ser Pro His Thr Phe
1               5                   10

<210> SEQ ID NO 643
<211> LENGTH: 11
<212> TYPE: PRT
<213> ORGANISM: Homo sapiens

<400> SEQUENCE: 643

Cys Gln Gln Tyr Gly Ser Ser Leu Trp Thr Phe
1               5                   10

<210> SEQ ID NO 644
<211> LENGTH: 11
<212> TYPE: PRT
<213> ORGANISM: Homo sapiens

<400> SEQUENCE: 644

Cys Gln His Ser Tyr Asn Thr Pro Tyr Thr Phe
1               5                   10

<210> SEQ ID NO 645
<211> LENGTH: 12
<212> TYPE: PRT
<213> ORGANISM: Homo sapiens

<400> SEQUENCE: 645

Cys Gln Gln Tyr Asn Asn Trp Pro Pro Tyr Thr Phe
1               5                   10

<210> SEQ ID NO 646
<211> LENGTH: 11
<212> TYPE: PRT
<213> ORGANISM: Homo sapiens

<400> SEQUENCE: 646

Cys Leu Gln His Asn Ile Ser Pro Tyr Thr Phe
1               5                   10

<210> SEQ ID NO 647
<211> LENGTH: 11
<212> TYPE: PRT
<213> ORGANISM: Homo sapiens

<400> SEQUENCE: 647

Cys Gln Gln Phe Phe Arg Ser Pro Phe Thr Phe
1               5                   10

<210> SEQ ID NO 648
<211> LENGTH: 11
```

<212> TYPE: PRT
<213> ORGANISM: Homo sapiens

<400> SEQUENCE: 648

Cys Gln His Tyr Gly Asn Ser Leu Phe Thr Phe
1               5                   10

<210> SEQ ID NO 649
<211> LENGTH: 11
<212> TYPE: PRT
<213> ORGANISM: Homo sapiens

<400> SEQUENCE: 649

Cys Gln His Tyr Asn Ser Tyr Ser Gly Thr Phe
1               5                   10

<210> SEQ ID NO 650
<211> LENGTH: 12
<212> TYPE: PRT
<213> ORGANISM: Homo sapiens

<400> SEQUENCE: 650

Cys Gln Gln Tyr Asn Arg Asp Ser Pro Trp Thr Phe
1               5                   10

<210> SEQ ID NO 651
<211> LENGTH: 11
<212> TYPE: PRT
<213> ORGANISM: Homo sapiens

<400> SEQUENCE: 651

Cys Met Gln Gly Leu His Thr Pro Trp Thr Phe
1               5                   10

<210> SEQ ID NO 652
<211> LENGTH: 10
<212> TYPE: PRT
<213> ORGANISM: Homo sapiens

<400> SEQUENCE: 652

Cys Gln Gln Tyr Lys Asn Trp Tyr Thr Phe
1               5                   10

<210> SEQ ID NO 653
<211> LENGTH: 12
<212> TYPE: PRT
<213> ORGANISM: Homo sapiens

<400> SEQUENCE: 653

Cys Gln Gln Ser Tyr Ser Tyr Arg Ala Leu Thr Phe
1               5                   10

<210> SEQ ID NO 654
<211> LENGTH: 13
<212> TYPE: PRT
<213> ORGANISM: Homo sapiens

<400> SEQUENCE: 654

Cys Gln Gln Arg Ser Asn Trp Pro Pro Gly Leu Thr Phe
1               5                   10

<210> SEQ ID NO 655
<211> LENGTH: 11
<212> TYPE: PRT
<213> ORGANISM: Homo sapiens

<400> SEQUENCE: 655

Cys Gln Gln Tyr Asp Phe Leu Pro Tyr Thr Phe
1               5                   10

<210> SEQ ID NO 656
<211> LENGTH: 13
<212> TYPE: PRT
<213> ORGANISM: Homo sapiens

<400> SEQUENCE: 656

Cys Gln His Tyr Val Asn Leu Pro Pro Ser Phe Thr Phe
1               5                   10

<210> SEQ ID NO 657
<211> LENGTH: 11
<212> TYPE: PRT
<213> ORGANISM: Homo sapiens

<400> SEQUENCE: 657

Cys Gln Gln Phe Asn Thr Tyr Pro Phe Thr Phe
1               5                   10

<210> SEQ ID NO 658
<211> LENGTH: 11
<212> TYPE: PRT
<213> ORGANISM: Homo sapiens

<400> SEQUENCE: 658

Cys Gln Gln Tyr Tyr Gln Thr Pro Leu Thr Phe
1               5                   10

<210> SEQ ID NO 659
<211> LENGTH: 11
<212> TYPE: PRT
<213> ORGANISM: Homo sapiens

<400> SEQUENCE: 659

Cys Gln Gln Ser Tyr Thr Asn Pro Tyr Thr Phe
1               5                   10

<210> SEQ ID NO 660
<211> LENGTH: 10
<212> TYPE: PRT
<213> ORGANISM: Homo sapiens

<400> SEQUENCE: 660

Cys Gln Gln Tyr Lys Asn Asp Trp Thr Phe
1               5                   10

<210> SEQ ID NO 661
<211> LENGTH: 11
<212> TYPE: PRT
<213> ORGANISM: Homo sapiens

<400> SEQUENCE: 661

Cys Gln His Ser Tyr Ser Thr Arg Phe Thr Phe
1               5                   10

<210> SEQ ID NO 662
<211> LENGTH: 11
<212> TYPE: PRT
<213> ORGANISM: Homo sapiens

<400> SEQUENCE: 662

```
Cys Gln Gln Tyr Asn Ser Phe Pro Tyr Thr Phe
1               5                   10
```

<210> SEQ ID NO 663
<211> LENGTH: 11
<212> TYPE: PRT
<213> ORGANISM: Homo sapiens

<400> SEQUENCE: 663

```
Cys Gln Gln Tyr Asn Ser Leu Ser Pro Thr Phe
1               5                   10
```

<210> SEQ ID NO 664
<211> LENGTH: 11
<212> TYPE: PRT
<213> ORGANISM: Homo sapiens

<400> SEQUENCE: 664

```
Cys Gln Gln Ala Lys Ser Phe Pro Phe Thr Phe
1               5                   10
```

<210> SEQ ID NO 665
<211> LENGTH: 11
<212> TYPE: PRT
<213> ORGANISM: Homo sapiens

<400> SEQUENCE: 665

```
Cys Gln Gln Ala Asp Ser Phe Pro Phe Thr Phe
1               5                   10
```

<210> SEQ ID NO 666
<211> LENGTH: 11
<212> TYPE: PRT
<213> ORGANISM: Homo sapiens

<400> SEQUENCE: 666

```
Cys Gln Gln Leu Asn Ser Tyr Pro Arg Thr Phe
1               5                   10
```

<210> SEQ ID NO 667
<211> LENGTH: 11
<212> TYPE: PRT
<213> ORGANISM: Homo sapiens

<400> SEQUENCE: 667

```
Cys Gln Gln Ala Tyr Ser Phe Pro Arg Thr Phe
1               5                   10
```

<210> SEQ ID NO 668
<211> LENGTH: 11
<212> TYPE: PRT
<213> ORGANISM: Homo sapiens

<400> SEQUENCE: 668

```
Cys Gln Lys Tyr Asn Ser Ala Pro Gln Thr Phe
1               5                   10
```

<210> SEQ ID NO 669
<211> LENGTH: 11
<212> TYPE: PRT
<213> ORGANISM: Homo sapiens

<400> SEQUENCE: 669

```
Cys Gln Gln Tyr Gly Ser Pro Pro Trp Thr Phe
```

```
                1               5                   10
```

<210> SEQ ID NO 670
<211> LENGTH: 11
<212> TYPE: PRT
<213> ORGANISM: Homo sapiens

<400> SEQUENCE: 670

```
Cys Gln Gln Phe His Ser Thr Pro Arg Thr Phe
1               5                   10
```

<210> SEQ ID NO 671
<211> LENGTH: 11
<212> TYPE: PRT
<213> ORGANISM: Homo sapiens

<400> SEQUENCE: 671

```
Cys Gln Gln Tyr Asn Ser Phe Ser Phe Thr Phe
1               5                   10
```

<210> SEQ ID NO 672
<211> LENGTH: 11
<212> TYPE: PRT
<213> ORGANISM: Homo sapiens

<400> SEQUENCE: 672

```
Cys Gln Gln Tyr His Ser Phe Pro Tyr Thr Phe
1               5                   10
```

<210> SEQ ID NO 673
<211> LENGTH: 11
<212> TYPE: PRT
<213> ORGANISM: Homo sapiens

<400> SEQUENCE: 673

```
Cys Gln Gln Leu Asn Thr Tyr Pro Leu Thr Phe
1               5                   10
```

<210> SEQ ID NO 674
<211> LENGTH: 11
<212> TYPE: PRT
<213> ORGANISM: Homo sapiens

<400> SEQUENCE: 674

```
Cys Gln Gln Tyr Gly Ser Ser Pro Phe Thr Phe
1               5                   10
```

<210> SEQ ID NO 675
<211> LENGTH: 11
<212> TYPE: PRT
<213> ORGANISM: Homo sapiens

<400> SEQUENCE: 675

```
Cys Gln Gln Tyr Arg Ser Tyr Ser Tyr Thr Phe
1               5                   10
```

<210> SEQ ID NO 676
<211> LENGTH: 11
<212> TYPE: PRT
<213> ORGANISM: Homo sapiens

<400> SEQUENCE: 676

```
Cys Gln Gln Ser Tyr Ser Thr Pro Tyr Thr Phe
1               5                   10
```

<210> SEQ ID NO 677
<211> LENGTH: 11
<212> TYPE: PRT
<213> ORGANISM: Homo sapiens

<400> SEQUENCE: 677

Cys Gln Gln Tyr Asn Ile Tyr Ser Pro Thr Phe
1               5                   10

<210> SEQ ID NO 678
<211> LENGTH: 11
<212> TYPE: PRT
<213> ORGANISM: Homo sapiens

<400> SEQUENCE: 678

Cys Met Gln Ala Thr Gln Phe Pro Phe Thr Phe
1               5                   10

<210> SEQ ID NO 679
<211> LENGTH: 11
<212> TYPE: PRT
<213> ORGANISM: Homo sapiens

<400> SEQUENCE: 679

Cys Leu Gln Tyr His Tyr Leu Pro Tyr Thr Phe
1               5                   10

<210> SEQ ID NO 680
<211> LENGTH: 11
<212> TYPE: PRT
<213> ORGANISM: Homo sapiens

<400> SEQUENCE: 680

Cys Gln Gln Tyr Gly Asn Ser Pro Leu Thr Phe
1               5                   10

<210> SEQ ID NO 681
<211> LENGTH: 11
<212> TYPE: PRT
<213> ORGANISM: Homo sapiens

<400> SEQUENCE: 681

Cys Gln Gln Ala Asp Thr Phe Pro Phe Thr Phe
1               5                   10

<210> SEQ ID NO 682
<211> LENGTH: 11
<212> TYPE: PRT
<213> ORGANISM: Homo sapiens

<400> SEQUENCE: 682

Cys Met Gln Arg Ile Glu Phe Pro Tyr Thr Phe
1               5                   10

<210> SEQ ID NO 683
<211> LENGTH: 11
<212> TYPE: PRT
<213> ORGANISM: Homo sapiens

<400> SEQUENCE: 683

Cys Met Gln Thr Leu Gln Thr Pro Arg Thr Phe
1               5                   10

<210> SEQ ID NO 684

```
<211> LENGTH: 11
<212> TYPE: PRT
<213> ORGANISM: Homo sapiens

<400> SEQUENCE: 684

Cys Gln His Phe Ala Asn Leu Pro Tyr Thr Phe
 1               5                  10

<210> SEQ ID NO 685
<211> LENGTH: 11
<212> TYPE: PRT
<213> ORGANISM: Homo sapiens

<400> SEQUENCE: 685

Cys Gln Arg Tyr Asn Ser Ala Pro Leu Thr Phe
 1               5                  10

<210> SEQ ID NO 686
<211> LENGTH: 12
<212> TYPE: PRT
<213> ORGANISM: Homo sapiens

<400> SEQUENCE: 686

Cys Gln Gln Ser Tyr Ser Thr Pro Ile Phe Thr Phe
 1               5                  10

<210> SEQ ID NO 687
<211> LENGTH: 10
<212> TYPE: PRT
<213> ORGANISM: Homo sapiens

<400> SEQUENCE: 687

Cys Gln Gln Arg Ser Asp Trp Leu Thr Phe
 1               5                  10

<210> SEQ ID NO 688
<211> LENGTH: 11
<212> TYPE: PRT
<213> ORGANISM: Homo sapiens

<400> SEQUENCE: 688

Cys Gln Gln Leu Asn Ile Tyr Pro Leu Thr Phe
 1               5                  10

<210> SEQ ID NO 689
<211> LENGTH: 11
<212> TYPE: PRT
<213> ORGANISM: Homo sapiens

<400> SEQUENCE: 689

Cys Gln His Phe Ala Asn Leu Pro Tyr Thr Phe
 1               5                  10

<210> SEQ ID NO 690
<211> LENGTH: 12
<212> TYPE: PRT
<213> ORGANISM: Homo sapiens

<400> SEQUENCE: 690

Cys Gln Glu Tyr Asn Asn Trp Pro Leu Leu Thr Phe
 1               5                  10

<210> SEQ ID NO 691
<211> LENGTH: 11
<212> TYPE: PRT
```

<213> ORGANISM: Homo sapiens

<400> SEQUENCE: 691

Cys Gln Gln Tyr Gly Thr Thr Pro Ile Thr Phe
1               5                   10

<210> SEQ ID NO 692
<211> LENGTH: 12
<212> TYPE: PRT
<213> ORGANISM: Homo sapiens

<400> SEQUENCE: 692

Cys Gln Gln Ser Tyr Ser Thr Pro Ile Tyr Thr Phe
1               5                   10

<210> SEQ ID NO 693
<211> LENGTH: 11
<212> TYPE: PRT
<213> ORGANISM: Homo sapiens

<400> SEQUENCE: 693

Cys Gln Gln Tyr Asp Asn Phe Pro Tyr Thr Phe
1               5                   10

<210> SEQ ID NO 694
<211> LENGTH: 11
<212> TYPE: PRT
<213> ORGANISM: Homo sapiens

<400> SEQUENCE: 694

Cys Gln Lys Tyr Asn Ser Ala Pro Trp Thr Phe
1               5                   10

<210> SEQ ID NO 695
<211> LENGTH: 11
<212> TYPE: PRT
<213> ORGANISM: Homo sapiens

<400> SEQUENCE: 695

Cys Gln Gln Tyr Asn Asn Trp Pro Gln Thr Phe
1               5                   10

<210> SEQ ID NO 696
<211> LENGTH: 11
<212> TYPE: PRT
<213> ORGANISM: Homo sapiens

<400> SEQUENCE: 696

Cys Gln Gln Ser Tyr Ser Phe Pro Tyr Thr Phe
1               5                   10

<210> SEQ ID NO 697
<211> LENGTH: 12
<212> TYPE: PRT
<213> ORGANISM: Homo sapiens

<400> SEQUENCE: 697

Cys Gln Gln Ser Tyr Ser Val Pro Arg Leu Thr Phe
1               5                   10

<210> SEQ ID NO 698
<211> LENGTH: 10
<212> TYPE: PRT
<213> ORGANISM: Homo sapiens

```
<400> SEQUENCE: 698

Cys Gln Glu Ser Phe Ser Ser Ser Thr Phe
1               5                   10

<210> SEQ ID NO 699
<211> LENGTH: 10
<212> TYPE: PRT
<213> ORGANISM: Homo sapiens

<400> SEQUENCE: 699

Cys Gln His Arg Arg Ser Trp Pro Thr Phe
1               5                   10

<210> SEQ ID NO 700
<211> LENGTH: 12
<212> TYPE: PRT
<213> ORGANISM: Homo sapiens

<400> SEQUENCE: 700

Cys Gln Gln Tyr Asn Met Trp Pro Pro Trp Thr Phe
1               5                   10

<210> SEQ ID NO 701
<211> LENGTH: 11
<212> TYPE: PRT
<213> ORGANISM: Homo sapiens

<400> SEQUENCE: 701

Cys Gln Gln Ser Tyr Ser Ile Pro Trp Thr Phe
1               5                   10

<210> SEQ ID NO 702
<211> LENGTH: 11
<212> TYPE: PRT
<213> ORGANISM: Homo sapiens

<400> SEQUENCE: 702

Cys Met Gln Ser Leu Gln Thr Ser Ile Thr Phe
1               5                   10

<210> SEQ ID NO 703
<211> LENGTH: 11
<212> TYPE: PRT
<213> ORGANISM: Homo sapiens

<400> SEQUENCE: 703

Cys Gln Gln Tyr Asn Ser Tyr Pro Tyr Thr Phe
1               5                   10

<210> SEQ ID NO 704
<211> LENGTH: 11
<212> TYPE: PRT
<213> ORGANISM: Homo sapiens

<400> SEQUENCE: 704

Cys Gln Gln Gly His Ser Thr Pro Tyr Thr Phe
1               5                   10

<210> SEQ ID NO 705
<211> LENGTH: 11
<212> TYPE: PRT
<213> ORGANISM: Homo sapiens

<400> SEQUENCE: 705
```

-continued

Cys Met Gln Ala Leu Gln Thr Pro Arg Thr Phe
1               5                   10

<210> SEQ ID NO 706
<211> LENGTH: 11
<212> TYPE: PRT
<213> ORGANISM: Homo sapiens

<400> SEQUENCE: 706

Cys Leu Gln His Asn Ser Tyr Pro Trp Thr Phe
1               5                   10

<210> SEQ ID NO 707
<211> LENGTH: 10
<212> TYPE: PRT
<213> ORGANISM: Homo sapiens

<400> SEQUENCE: 707

Cys Leu Gln Ala Thr Gln Phe Leu Thr Phe
1               5                   10

<210> SEQ ID NO 708
<211> LENGTH: 11
<212> TYPE: PRT
<213> ORGANISM: Homo sapiens

<400> SEQUENCE: 708

Cys Gln Gln Tyr Asp Lys Trp Pro Glu Thr Phe
1               5                   10

<210> SEQ ID NO 709
<211> LENGTH: 11
<212> TYPE: PRT
<213> ORGANISM: Homo sapiens

<400> SEQUENCE: 709

Cys Gln Gln Tyr Asp Asn Trp Leu Pro Thr Phe
1               5                   10

<210> SEQ ID NO 710
<211> LENGTH: 11
<212> TYPE: PRT
<213> ORGANISM: Homo sapiens

<400> SEQUENCE: 710

Cys Gln Gln Tyr Asn Ser Tyr Pro Leu Thr Phe
1               5                   10

<210> SEQ ID NO 711
<211> LENGTH: 298
<212> TYPE: PRT
<213> ORGANISM: respiratory syncytial virus

<400> SEQUENCE: 711

Met Ser Lys Asn Lys Asp Gln Arg Thr Ala Lys Thr Leu Glu Lys Thr
1 5 10 15

Trp Asp Thr Leu Asn His Leu Leu Phe Ile Ser Ser Gly Leu Tyr Lys
20 25 30

Leu Asn Leu Lys Ser Ile Ala Gln Ile Thr Leu Ser Ile Leu Ala Met
35 40 45

Ile Ile Ser Thr Ser Leu Ile Ile Thr Ala Ile Ile Phe Ile Ala Ser
50 55 60

Ala Asn His Lys Val Thr Leu Thr Thr Ala Ile Ile Gln Asp Ala Thr

-continued

```
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp His Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295

<210> SEQ ID NO 712
<211> LENGTH: 292
<212> TYPE: PRT
<213> ORGANISM: respiratory syncytial virus

<400> SEQUENCE: 712

Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Ser Thr Tyr Leu Thr Gln Val Pro Pro
                85                  90                  95

Glu Arg Val Asn Ser Ser Lys Gln Pro Thr Thr Thr Ser Pro Ile His
            100                 105                 110

Thr Asn Ser Ala Thr Ile Ser Pro Asn Thr Lys Ser Glu Thr His His
        115                 120                 125

Thr Thr Ala Gln Thr Lys Gly Arg Ile Thr Thr Ser Thr Gln Thr Asn
    130                 135                 140
```

-continued

Lys Pro Ser Thr Lys Ser Arg Ser Lys Asn Pro Pro Lys Lys Pro Lys
145                 150                 155                 160

Asp Asp Tyr His Phe Glu Val Phe Asn Phe Val Pro Cys Ser Ile Cys
            165                 170                 175

Gly Asn Asn Gln Leu Cys Lys Ser Ile Cys Lys Thr Ile Pro Ser Asn
        180                 185                 190

Lys Pro Lys Lys Lys Pro Thr Ile Lys Pro Thr Asn Lys Pro Thr Thr
    195                 200                 205

Lys Thr Thr Asn Lys Arg Asp Pro Lys Thr Pro Ala Lys Met Pro Lys
210                 215                 220

Lys Glu Ile Ile Thr Asn Pro Ala Lys Lys Pro Thr Leu Lys Thr Thr
225                 230                 235                 240

Glu Arg Asp Thr Ser Ile Ser Gln Ser Thr Val Leu Asp Thr Ile Thr
                245                 250                 255

Pro Lys Tyr Thr Ile Gln Gln Gln Ser Leu His Ser Thr Thr Ser Glu
            260                 265                 270

Asn Thr Pro Ser Ser Thr Gln Ile Pro Thr Ala Ser Glu Pro Ser Thr
        275                 280                 285

Leu Asn Pro Asn
    290

<210> SEQ ID NO 713
<211> LENGTH: 77
<212> TYPE: PRT
<213> ORGANISM: respiratory syncytial virus

<400> SEQUENCE: 713

Gln Pro Thr Thr Val Lys Thr Lys Asn Thr Thr Thr Thr Gln Thr Gln
1               5                   10                  15

Pro Ser Lys Pro Thr Thr Lys Gln Arg Gln Asn Lys Pro Pro Asn Lys
            20                  25                  30

Pro Asn Asn Asp Phe His Phe Glu Val Phe Asn Phe Val Pro Cys Ser
        35                  40                  45

Ile Cys Ser Asn Asn Pro Thr Cys Trp Ala Ile Cys Lys Arg Ile Pro
    50                  55                  60

Asn Lys Lys Pro Gly Lys Lys Thr Thr Thr Lys Pro Thr
65                  70                  75

<210> SEQ ID NO 714
<211> LENGTH: 77
<212> TYPE: PRT
<213> ORGANISM: respiratory syncytial virus

<400> SEQUENCE: 714

His His Thr Thr Ala Gln Thr Lys Gly Arg Ile Thr Thr Ser Thr Gln
1               5                   10                  15

Thr Asn Lys Pro Ser Thr Lys Ser Arg Ser Lys Asn Pro Pro Lys Lys
            20                  25                  30

Pro Lys Asp Asp Tyr His Phe Glu Val Phe Asn Phe Val Pro Cys Ser
        35                  40                  45

Ile Cys Gly Asn Asn Gln Leu Cys Lys Ser Ile Cys Lys Thr Ile Pro
    50                  55                  60

Ser Asn Lys Pro Lys Lys Lys Pro Thr Ile Lys Pro Thr
65                  70                  75

<210> SEQ ID NO 715
<211> LENGTH: 24

```
-continued

<212> TYPE: DNA
<213> ORGANISM: Artificial Sequence
<220> FEATURE:
<223> OTHER INFORMATION: RSV-A forward

<400> SEQUENCE: 715
caacaaagat caacttctgt catc                                              24

<210> SEQ ID NO 716
<211> LENGTH: 25
<212> TYPE: DNA
<213> ORGANISM: Artificial Sequence
<220> FEATURE:
<223> OTHER INFORMATION: RSV-A reverse

<400> SEQUENCE: 716
gcacatcata attaggagta tcaat                                             25

<210> SEQ ID NO 717
<211> LENGTH: 25
<212> TYPE: DNA
<213> ORGANISM: Artificial Sequence
<220> FEATURE:
<223> OTHER INFORMATION: RSA probe

<400> SEQUENCE: 717
caccatccaa cggagcacag gagat                                             25
```

RECOMBINANT ANTIBODIES FOR TREATMENT OF RESPIRATORY SYNCYTIAL VIRUS INFECTIONS

CROSS-REFERENCE TO RELATED APPLICATIONS

This application claims the benefit of the filing date of U.S. Provisional Appl. No. 60/971,387, filed Sep. 11, 2007, Danish Appl. No. PA 2007 01291, filed Sep. 7, 2007, and International Appl. No. PCT/DK2007/000113, filed Mar. 6, 2007, each of which is incorporated by reference in its entirety.

REFERENCE TO SEQUENCE LISTING SUBMITTED ELECTRONICALLY

The content of the electronically submitted sequence listing Name: Seq.listing_ST25.txt; Size: 311,835 bytes; and Date of Creation: Aug. 11, 2010) is incorporated herein by reference in its entirety.

BACKGROUND OF THE INVENTION

Field of the Invention

The present invention relates to specific recombinant mono- and polyclonal antibody compositions for prevention, treatment or amelioration of one or more symptoms associated with respiratory syncytial virus infections. The invention also relates to polyclonal expression cell lines producing anti-RSV recombinant polyclonal antibody (anti-RSV rpAb). Further, the application describes diagnostic and pharmacological compositions comprising anti-RSV rpAb and use in prevention, treatment or amelioration of one or more symptoms associated with a RSV infection.

Respiratory syncytial virus (RSV) is a major cause for lower respiratory tract disease in infants and small children. Premature infants and children with an underlying health problem such as chronic lung disease or congenital heart disease are at the greatest risk for serious illness such as bronchiolitis and pneumonia following RSV infection. Recently, RSV was also recognized as an important pathogen in certain high-risk adults, such as immunocompromised adults, particularly bone marrow transplant recipients, elderly individuals and individuals with chronic pulmonary disease.

Human RSV is a member of the Pneumovirus subfamily of the family Paramyxoviridae, and exists as an A and B subtype. RSV is an enveloped, non-segmented, negative-sense RNA virus. The viral genome codes for at least 11 proteins of which three are the envelope associated proteins, F (fusion glycoprotein), G (receptor-binding glycoprotein), and SH (small hydrophobic protein). The envelope proteins are present on the viral surface, and to some extent also on the surface of infected cells. The F protein promotes fusion of the viral and cell membranes, thereby allowing penetration of the viral RNA into the cell cytoplasm. The F protein consists of two disulfide-linked subunits, $F_1$ and $F_2$, produced by proteolytical cleavage of an inactive, N-glycosylated precursor of 574 amino acids. The G protein is a type II trans-membrane glycoprotein of 289-299 amino acids (depending on the virus strain). The precursor form is 32 kDa, which matures to a protein of 80-90 kDa upon addition of both N- and O-linked oligosaccharides. The RSV G protein is responsible for the attachment of virions to the target cells. In addition to the membrane-bound form of the G protein, a truncated, soluble form is also produced. It has been suggested that the function of this is to redirect the immune response away from the virus and infected cells. Further it has been shown that the G protein is associated with a number of pro-inflammatory effects such as modification of chemokine and cytokine expression as well as leukocyte recruitment. The SH protein is a protein of 64-65 amino acids that is present in very low amounts on the surface of purified RSV particles, but is abundantly expressed on the surface of RSV-infected cells. The function of the SH protein has not been defined, but it is possible that it may aid virus protein transport through the Golgi complex (Rixon et al 2004, J. Gen. Virol. 85:1153-1165). Blocking the function of the G and F proteins is believed to be relevant in prevention of RSV infection.

The prevention and treatment of RSV infection has received considerable attention during the last decades, and include vaccine development, antiviral compounds (Ribavirin approved for treatment), antisense drugs, RNA interference (RNAi) technology and antibody products such as immunoglobulin and monoclonal antibodies (all reviewed in Maggon and Barik, 2004, Rev. med. Virol. 14:149-168). Of these approaches, the intravenous immunoglobulin, RSV-IVIG, and the monoclonal antibody, Palivizumab, have been approved for RSV prophylaxis in high-risk children.

Immunoglobulin products such as RSV-IVIG (RespiGam) are, however, known to have several drawbacks such as low specific activity resulting in need for injection of large volumes, which is difficult in children with limited venous access due to prior intensive therapy. Further, there is also the risk of transmission of viral diseases from serum-derived immunoglobulin products, as well as problems with batch-to-batch variations. Finally, it is difficult to obtain sufficient donors to meet the needs for hyperimmune RSV immunoglobulin production, since only approximately 8% of normal donors have RSV neutralizing antibody titers that are high enough.

Monoclonal antibodies against the F protein or the G protein have been shown to have neutralizing effect in vitro and prophylactic effects in vivo (e.g. Beeler and Coelingh 1989. J. Virol. 63:2941-50; Garcia-Barreno et al. 1989. J. Virol. 63:925-32; Taylor et al. 1984. Immunology 52: 137-142; Walsh et al. 1984, Infection and Immunity 43:756-758; U.S. Pat. Nos. 5,842,307 and 6,818,216). Today the monoclonal antibody Palivizumab has almost substituted the use of RSV-IVIG completely. Neutralization assays show that Palivizumab and RSV-IVIG perform equally well against RSV subtype B, whereas Palivizumab perform better against subtype A (Johnson et al. 1997. J. Infect. Dis. 176:1215-24.). However, despite the good neutralizing and prophylactic effects of monoclonal antibodies as illustrated by products like Palivizumab and Numax, these may also be associated with certain drawbacks due to the nature of the RSV virus.

RSV exists in two distinct antigenic groups or subtypes, A and B. Most of the RSV proteins are highly conserved between the two subgroups, with the F protein showing 91% amino acid similarity. However, the G protein displays extensive sequence variability, with only 53% amino acid similarity between the A and B subgroups (Sullender 2000. Clin. Microbiol. Rev. 13:1-15). Most of the proteins also show some limited intra subgroup variation, except for the G protein, which differs by up to 20% within subgroup A and 9% within subgroup B on amino acid level. The A and B virus subtypes co-circulate in most RSV epidemics, with the relative frequency varying between different years. Thus, a monoclonal antibody must be carefully selected such that it is capable of neutralizing both subtypes as well as intra subtype variations.

In addition to the issue of the two RSV subtypes and intra-subtype diversity, human RSV, like most RNA viruses, has the capacity of undergoing rapid mutations under selective pressure. The selection of RSV escape mutants in vitro using mAb is well documented (e.g. Garcia-Barreno et al. 1989. J. Virol. 63:925-32). Importantly, it was recently discovered that Palivizumab also selects for escape mutants, in vitro as well as in vivo, and that some of the isolated mutants are completely resistant to Palivizumab prophylaxis in cotton rats (Zhao and Sullender 2005. J. Virol. 79:3962-8 and Zhao et al. 2004. J. Infect. Dis. 190:1941-6.). Further, wild type RSV strains that are intrinsically resistant to Palivizumab may also exist, as demonstrated by the failure of the murine antibody, which Palivizumab originates from, to neutralize one clinical isolate (Beeler and Coelingh 1989. J. Virol. 63:2941-50). Furthermore, one apparently resistant virus has also been identified following Palivizumab prophylaxis in immunocompetent cotton rats (Johnson et al. 1997. J. Infect. Dis. 176:1215-24). Thus, under certain conditions, the use of a single, monospecific antibody may not be adequate or sufficient for the treatment of RSV disease, since escape mutants exist or may develop over time as a result of treatment.

A further consideration in relation to the utility of the RSV-IVIG and Palivizumab is the dose needed for efficient treatment. Serum concentrations of greater than 30 µg/ml have been shown to be necessary to reduce pulmonary RSV replication by 100 fold in the cotton rat model of RSV infection. For RSV-IVIG a monthly dose of 750 mg total protein/kg administrated intravenously was effective in reducing the incidence of RSV hospitalization in high-risk children, whereas for Palivizumab monthly intramuscular doses of 15 mg/kg proved effective. However, the administration of multiple intravenous or intramuscular large doses is inconvenient for the patient, and impedes the broad use of these products for the prophylaxis and treatment of the large group of adults at risk for RSV infection.

Thus, a need exists for an antibody product which is not dependent on the donor availability, and which binds immunospecifically to one or more RSV antigens covering subtypes A and B as well as any escape mutants arising due to virus mutations, is highly potent, have an improved pharmacokinetic profile, and thus have an overall improved therapeutic profile, and therefore requires less frequent administration and/or administration of a lower dose.

It is therefore the objective of the present invention to provide a highly potent alternative anti-RSV immunoglobulin product which is produced recombinantly and shows reactivity to subtypes A and B of the respiratory syncytial virus as well as to multiple epitopes on at least one of the major surface antigens to limit the possibility of escape mutations.

The invention also has as an objective to provide novel human anti-RSV antibody molecules as well as derivatives thereof, where the antibody molecules or derivatives exhibit improved characteristics over existing monoclonal anti-RSV antibodies and antibody derivatives.

DESCRIPTION OF THE INVENTION

The invention relates to antibodies capable of competing in binding with antibody 824 as defined herein or with its Fab fragment. Antibody 824 binds poorly to recombinant protein but with very high affinity to human cells infected with RSV, resulting in very potent neutralization of RSV. By providing antibody 824 the inventors have identified an epitope, which results in more efficient in vitro and in vivo neutralization than seen before for any single RSV epitope. By providing antibody 824, the inventors have also enabled the identification of further antibodies which bind to the same epitope.

These further antibodies may be of any origin and includes binding fragments as well as affinity matured antibodies. Antibodies capable of competing with antibody 824 may be identified in a cellular competition assay (determination of relative epitope specificities) as described in Example 1, section g-4.

In further aspects the invention relates to an anti-RSV antibody comprising a CDRH3 having the following formula: $CAX_1X_2X_3X_4X_5X_6PX_7X_8X_9X_{10}X_{11}W$ where $X_1$ to $X_{11}$ are selected individually from the groups of amino acids listed below $X_1$=R or K;
$X_2$=D, E, N or Q;
$X_3$=S, T, G or A;
$X_4$=S, T, G or A;
$X_5$=N, Q, D or E;
$X_6$=W, Y, F or H;
$X_7$=A, G, V, or S;
$X_8$=G, A, V, or S;
$X_9$=Y, F, W or H;
$X_{10}$=E or D; and
$X_{11}$=D, E, N or Q;
and a CDRL3 described by the following formula: $CX_1X_2X_3X_4X_5X_6PX_7TF$
where $X_1$ to $X_7$ are selected individually from the groups of amino acids listed below:
$X_1$=Q or H;
$X_2$=Q, E or H;
$X_3$=F, Y, W or H;
$X_4$=N, Q or H;
$X_5$=T, S, G or A;
$X_6$=Y, F, W or H; and
$X_7$=F, Y, W or H.

Antibodies comprising these CDR sequences based on antibody 824 are expected to result in very efficient virus neutralization both in vitro and in vivo as they are expected to bind the same epitope. In further aspects, the invention relates to nucleic acids encoding these CDR sequences, to nucleic acid encoding VL and VH sequences of antibody 824, to expression vectors encoding such antibodies and CDRs and to cells expressing these.

Preferably, the anti-RSV antibody comprises the CDR1, and CDR2 regions from the VH and VL pair of antibody 824 as set forth in SEQ ID NOs: 232, 317, 487, and 572, and a CDRH3 region having the formula $CAR_1D_2S_3S_4N_5W_6PA_7G_8Y_9E_{10}D_{11}W$ (SEQ ID NO 402), and a CDRL3 region having the formula $CQ_1Q_2F_3N_4T_5Y_6PF_7TF$ (SEQ ID NO 657).

In a further aspect the invention relates to an antibody composition comprising an antibody based on the CDR sequences above and one or more additional anti-RSV antibodies.

The invention also relates to an antibody composition comprising distinct members comprising heavy chain and light chain CDR1, CDR2 and CDR3 regions selected from the group of VH and VL pairs listed in Table 6, wherein the distinct members are the distinct members of one of antibody compositions 2 to 56 in Table 9 herein.

In further aspects the invention relates to a method of preventing, treating or ameliorating one or more symptoms associated with a RSV infection in a mammal, comprising administering an effective amount of an anti-RSV antibody according to the invention.

The use of a polyclonal antibody composition targeting multiple epitopes on RSV is expected to minimize the development of escape mutants and can also provide protection against diverse, naturally circulating viruses. In contrast to serum-derived RSV-IVIG, a polyclonal antibody of the present invention does not contain antibody molecules, which bind to non-RSV antigens.

The present invention provides a polyclonal anti-RSV antibody. Preferably, the polyclonal anti-RSV antibody is obtained from cells which do not naturally produce antibodies. Such an antibody is termed a recombinant polyclonal antibody (rpAb). An anti-RSV rpAb of the present invention is directed against multiple epitopes on the F or G protein. In particular an anti-RSV rpAb which is directed against multiple epitopes on both the G and F proteins is preferred. Preferably, G protein epitopes belonging to the conserved group and potentially also the subtype-specific group and the strain-specific group are covered by the anti-RSV rpAb. Further, antibodies with reactivity against the third envelope protein, small hydrophobic (SH) protein is a desired component of an anti-RSV rpAb of the present invention.

Further, the present invention provides pharmaceutical compositions where the active ingredient is an anti-RSV polyclonal antibody, as well as uses of such compositions for the prevention, amelioration or treatment of RSV infections.

The present invention further provides procedures for mirroring the humoral immune response raised upon infection with RSV, by isolating the original $V_H$ and $V_L$ gene pairs from such challenged individuals, and producing antibodies maintaining this original paring.

Definitions

The term "antibody" describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulin. The terms antibody or antibodies as used herein is used in the broadest sense and covers intact antibodies, chimeric, humanized, fully human and single chain antibodies, as well as binding fragments of antibodies, such as Fab, Fv fragments or scFv fragments, as well as multimeric forms such as dimeric IgA molecules or pentavalent IgM. In some instances, the present application uses the term "synthetic or semi-synthetic antibody analogue", which specifically refers to non-naturally occurring molecules which exhibit antibody characteristics (by exhibiting specific binding to RSV antigens) and includes CDRs from naturally occurring antibodies—such analogues are e.g. represented by scFv fragments, unibodies, diabodies etc, but could e.g. also be seemingly naturally occurring antibodies which are engineered to include the CDRs (e.g. by grafting techniques known in the art) from an anti-RSV antibody molecule disclosed herein—for instance, such an antibody analogue could comprise CDRs disclosed herein incorporated into an antibody molecule of another animal species or into a different antibody isotype or class from the same species.

The term "anti-RSV recombinant polyclonal antibody" or "anti-RSV rpAb" describes a composition of recombinantly produced diverse antibody molecules, where the individual members are capable of binding to at least one epitope on a respiratory syncytial virus, and where the polyclonal composition as a whole is capable of neutralizing RSV. Preferably, an anti-RSV rpAb composition neutralizes both RSV subtype A and B. Even more preferred the anti-RSV rpAb further comprise binding reactivity towards the G and F protein. Preferably, the composition is produced from a single polyclonal manufacturing cell line.

The term "cognate $V_H$ and $V_L$ coding pair" describes an original pair of $V_H$ and $V_L$ coding sequences contained within or derived from the same cell. Thus, a cognate $V_H$ and $V_L$ pair represents the $V_H$ and $V_L$ pairing originally present in the donor from which such a cell is derived. The term "an antibody expressed from a $V_H$ and $V_L$ coding pair" indicates that an antibody or an antibody fragment is produced from a vector, plasmid or similar containing the $V_H$ and $V_L$ coding sequence. When a cognate $V_H$ and $V_L$ coding pair is expressed, either as a complete antibody or as a stable fragment thereof, they preserve the binding affinity and specificity of the antibody originally expressed from the cell they are derived from. A library of cognate pairs is also termed a repertoire or collection of cognate pairs, and may be kept individually or pooled.

The terms "a distinct member of a recombinant polyclonal antibody" denotes an individual antibody molecule of the recombinant polyclonal antibody composition, comprising one or more stretches within the variable regions, which are characterized by differences in the amino acid sequence compared to the other individual members of the polyclonal protein. These stretches are in particular located in the CDR1, CDR2 and CDR 3 regions.

The term "epitope" is commonly used to describe a proportion of a larger molecule or a part of a larger molecule (e.g. antigen or antigenic site) having antigenic or immunogenic activity in an animal, preferably a mammal, and most preferably in a human. An epitope having immunogenic activity is a portion of a larger molecule that elicits an antibody response in an animal. An epitope having antigenic activity is a portion of a larger molecule to which an antibody immunospecifically binds as determined by any method well known in the art, for example, by the immunoassays described herein. Antigenic epitopes need not necessarily be immunogenic. An antigen is a substance to which an antibody or antibody fragment immunospecifically binds, e.g. toxin, virus, bacteria, proteins or DNA. An antigen or antigenic site often has more than one epitope, unless they are very small, and is often capable of stimulating an immune response. Antibodies binding to different epitopes on the same antigen can have varying effects on the activity of the antigen they bind depending on the location of the epitope. An antibody binding to an epitope in an active site of the antigen may block the function of the antigen completely, whereas another antibody binding at a different epitope may have no or little effect on the activity of the antigen alone. Such antibodies may however still activate complement and thereby result in the elimination of the antigen, and may result in synergistic effects when combined with one or more antibodies binding at different epitopes on the same antigen. In the present invention the larger molecule which the epitope is a proportion of is preferably a proportion of an RSV polypeptide. Antigens of the present invention are preferably RSV associated proteins, polypeptides or fragments thereof to which an antibody or antibody fragment immunospecifically binds. A RSV associated antigen may also be an analog or derivative of a RSV polypeptide or fragment thereof to which an antibody or antibody fragment immunospecifically binds.

The term "fully human" used for example in relation to DNA, RNA or protein sequences describes sequences which are between 98 to 100% human.

The term "immunoglobulin" commonly is used as a collective designation of the mixture of antibodies found in blood or serum, but may also be used to designate a mixture of antibodies derived from other sources.

The term "mirrors the humoral immune response" when used in relation to a polyclonal antibody refers to an antibody composition where the nucleic acid sequences encoding the individual antibody members are derived from a donor with an increased frequency of plasma cells producing anti-RSV specific antibodies. Such a donor may either be recovering from a RSV infection, has had close contact with an RSV infected individual, or has been subject to RSV vaccination (for examples of RSV vaccines see for example Maggon and Barik, 2004, Rev. med. Virol. 14:149-168). In order to mirror the affinity and specificity of antibodies raised in a donor upon infection or challenge, the sequences encoding the variable heavy chain ($V_H$) and the variable light chain ($V_L$) should be maintained in the gene pairs or combinations originally present in the donor (cognate pairs) when they are isolated. In order to mirror the diversity of a humoral immune response in a donor all the sequences encoding antibodies which bind to RSV are selected based on a screening procedure. The isolated sequences are analyzed with respect to diversity of the variable regions, in particular the CDR regions, but also with respect to the $V_H$ and $V_L$ family. Based on these analyses a population of cognate pairs representing the overall diversity of the RSV binding antibodies are selected. Such a polyclonal antibody typically have at least 5, 10, 20, 30, 40, 50, 100, 1000 or $10^4$ distinct members.

A composition is said to be "pharmacologically acceptable" if its administration can be tolerated by a recipient patient—the same of course applies to excipients, vehicles carriers and diluents being part of a composition.

The term "polyclonal antibody" describes a composition of different (diverse) antibody molecules which is capable of binding to or reacting with several different specific antigenic determinants/epitopes on the same or on different antigens, where each individual antibody in the composition is capable of reacting with a particular epitope. Usually, the variability of a polyclonal antibody is located in the so-called variable regions of the polyclonal antibody, in particular in the CDR1, CDR2 and CDR3 regions. In the present invention a polyclonal antibody may either be produced in one pot from a polyclonal cell line, or it may be a mixture of different polyclonal antibodies. A mixture of monoclonal antibodies is not as such considered a polyclonal antibody, since they are produced in individual batches and not necessarily from the same cell line which will result in e.g. post translational modification differences. However, if a mixture of monoclonal antibodies provide the same antigen/epitope coverage as a polyclonal antibody of the present invention it will be considered as an equivalent of the polyclonal antibody. When stating that a member of a polyclonal antibody specifically binds to or has specific reactivity against an antigen/antigenic site/epitope, it is herein meant that the binding constant is below 100 nM, preferably below 10 nM, even more preferred below 1 nM.

The term "recombinant antibody" is used to describe an antibody molecule or several molecules that is/are expressed from a cell or cell line transfected with an expression vector comprising the coding sequence of the antibody which is not naturally associated with the cell. If the antibody molecules in a recombinant antibody composition are diverse or different, the term "recombinant polyclonal antibody" or "rpAb" applies in accordance with the definition of a polyclonal antibody.

The term "recombinant polyclonal cell line" or "polyclonal cell line" refers to a mixture/population of protein expressing cells that are transfected with a repertoire of variant nucleic acid sequences (e.g. a repertoire of antibody encoding nucleic acid sequences), which are not naturally associated with the transfected cells. Preferably, the transfection is performed such that the individual cells, which together constitute the recombinant polyclonal cell line, each carry a transcriptionally active copy of a single distinct nucleic acid sequence of interest, which encodes one member of the recombinant polyclonal antibody of interest. Even more preferred, only a single copy of the distinct nucleic acid sequence is integrated at a specific site in the genome. The cells constituting the recombinant polyclonal cell line are selected for their ability to retain the integrated copy (copies) of the distinct nucleic acid sequence of interest, for example by antibiotic selection. Cells which can constitute such a polyclonal cell line can be for example bacteria, fungi, eukaryotic cells, such as yeast, insect cells, plant cells or mammalian cells, especially immortal mammalian cell lines such as CHO cells, COS cells, BHK cells, myeloma cells (e.g., Sp2/0 cells, NS0), NIH 3T3, YB2/0 and immortalized human cells, such as HeLa cells, HEK 293 cells, or PER.C6.

The terms "sequences encoding $V_H$ and $V_L$ pairs" or "$V_H$ and $V_L$ encoding sequence pairs" indicate nucleic acid molecules, where each molecule comprise a sequence that code for the expression of a variable heavy chain and a variable light chain, such that these can be expressed as a pair from the nucleic acid molecule if suitable promoter and/or IRES regions are present and operably linked to the sequences. The nucleic acid molecule may also code for part of the constant regions or the complete constant region of the heavy chain and/or the light chain, allowing for the expression of a Fab fragment, a full-length antibody or other antibody fragments if suitable promoter and/or IRES regions are present and operably linked to the sequences.

A recombinant polyclonal antibody is said to be administered in a "therapeutically effective amount" if the amount administered is physiologically significant, e.g. prevents or attenuates an RSV infection in an animal or human.

DESCRIPTION OF THE DRAWINGS

FIG. 2: Schematic outline of the multiplex overlap-extension RT-PCR (A) and the cloning steps (B). (A) Two sets of primers, CH+VH 1-8 and VK1-6+CK1, specific for $V_H$ and $V_L$ gene families, respectively, were used for the first PCR step. A homologous region between the $V_H$ or Vκ primers results in the generation of an overlap PCR product. In the second step this product is amplified in the nested PCR. The primers also include recognition sites for restriction enzymes that facilitate cloning. (B) The generated cognate linked $V_H$ and $V_L$ coding pairs are pooled and inserted into a mammalian IgG expression vector (e.g.

FIG. 3: Schematic presentation of a mammalian full-length antibody expression vector 00-VP-530. The vector comprises the following elements: Amp and Amp pro=ampicillin resistance gene and its promoter. pUC origin=pUC origin of replication. P1=mammalian promoter driving the expression of the light chain. P2=mammalian promoter driving the expression of the heavy chain. Leader IGHV=genomic human heavy chain leader. VH=heavy chain variable region encoding sequence. IgG1=Sequence encoding genomic immunoglobulin isotype G1 heavy chain constant region. Rabbit B-globin A=rabbit beta-globin polyA sequence. Kappa leader=sequence encoding for murine kappa leader. LC=Sequence of light chain encoding sequence. SV40 term=Simian virus 40 terminator sequence. FRT=A Flp recognition target site. Neo=neomycin resistance gene. SV40 poly A=Simian virus 40 poly A signal sequence

FIG. 5: Shows results from in vitro neutralization of RSV subtype A and B strains. Dilutions of anti-F antibody mixtures were tested for their ability to neutralize RSV Long (Panel A) and RSV B1 (Panel B) strains. Antibody mixture, anti-F(I), obtained from clones 810, 818, 819, 825 and 827 is shown as triangles (▲) and antibody mixture, anti-F(II), obtained from clones 735, 800, 810, 818, 819, 825, 827, 863, 880, 884 and 894 is shown as squares (■). Palivizumab is shown as diamonds (♦), and an isotype-matched negative control (anti-Rhesus D) antibody is shown as circles (●). The absorbance was measured at 490 nm and correlates with RSV replication.

DETAILED DESCRIPTION OF THE INVENTION

Target Antigens and Polyclonal Antibody Compositions

A polyclonal antibody of the present invention is composed of a number of distinct antibody molecules in the same composition. Each molecule is selected based on its ability to bind an RSV associated antigen. A polyclonal antibody of the present invention comprises binding reactivity corresponding to the compiled binding reactivity of the distinct antibody molecules constituting the polyclonal antibody composition.

Figure 1:
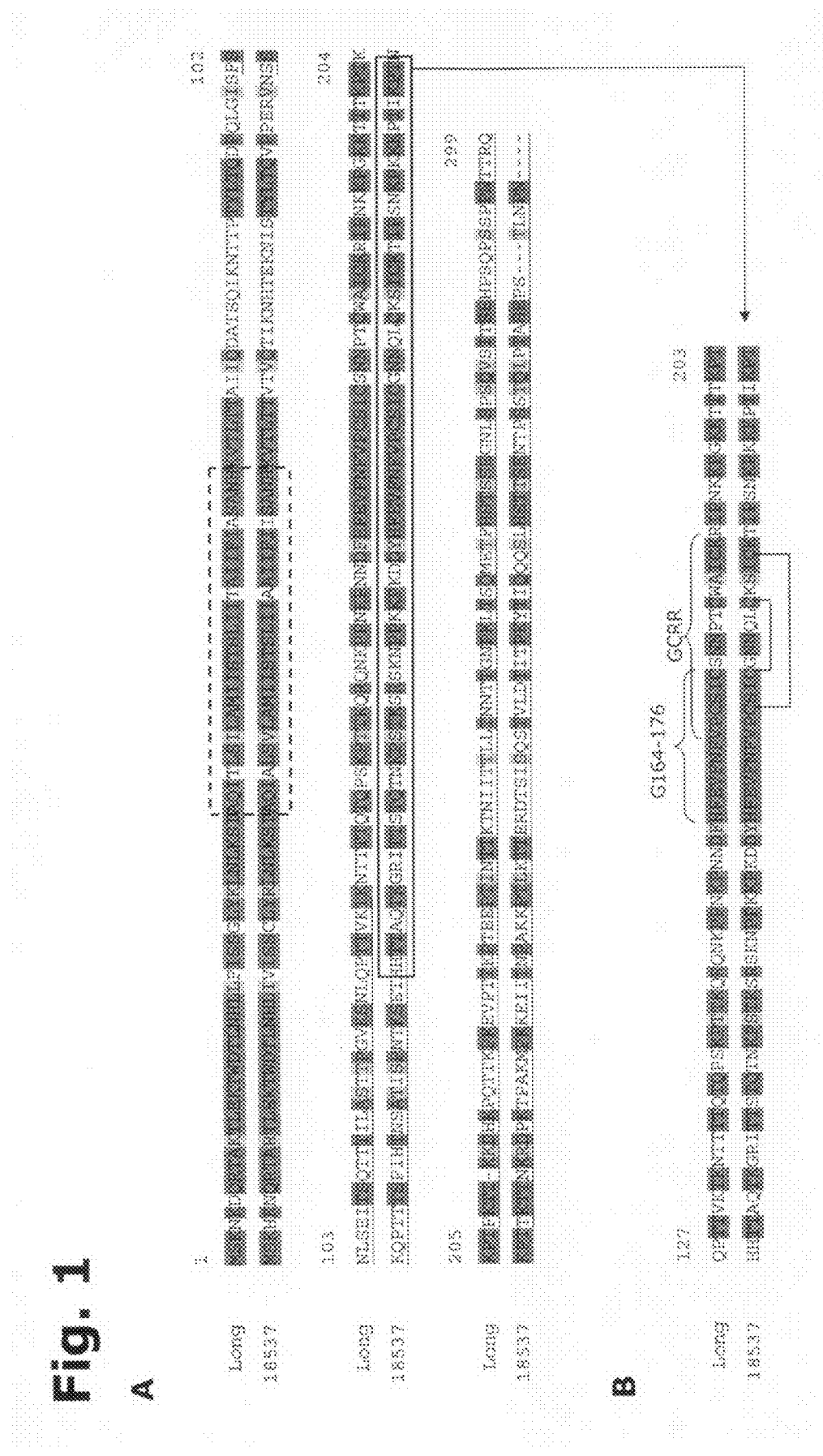
FIG. 1: (A) Alignment of the amino acid sequences of the whole G protein from the prototypic strains, Long (subtype A) and 18537 (subtype B). The signal/trans-membrane region is boxed with a dotted line. The two variable domains between amino acid 101-133 and 208-299 as identified by Cane et al. 1991 J. Gen. Virol. 72:2091-2096 are identified with an underline. The central fragment of the G protein has been expressed as a fusion protein in *E. coli* and is boxed in black. The 2 amino acid sequences are set forth in SEQ ID NOs: 711 (subtype A) and 712 (Subtype B). (B) Alignment of the central fragment, as indicated in (A). The location of the 13-aa conserved region (a.a. residue 164-176) and the G protein cysteine-rich region (GCRR) are indicated with brackets. The disulphide bridges in the GCRR (identical for both subtypes) are indicated with square brackets. The 2 amino acid sequences are set forth in SEQ ID NOs: 713 (Subtype A) and 714 (subtype B).

An anti-RSV polyclonal antibody of the present invention preferably comprise a compiled binding reactivity against both the G and F proteins and even more preferred against multiple epitopes to minimize the risk of development of escape mutants and achieve highest possible neutralizing capacity. At least five major antigenic sites that are recognized by neutralizing antibodies have been identified on the F protein (Lopez et al. 1998. J. Virol. 72:6922-8). All the antigenic sites have been mapped to the $F_1$ chain, and include site I, II, IV, V and VI, where site I and II also may be termed B and A, respectively. Site II is located in a protease-resistant region in the N-terminal segment, and sites IV, V and VI in the C-terminal end of the cysteine-rich region of the protein. Site I is located in the middle of this cysteine cluster. A further antigenic site on the F protein is site C in which the epitope F2 including amino acid positions 241 and 242 is located. Additionally, there are monoclonal antibodies binding to an antigenic site termed F1, comprising the epitopes termed F1a, F1b and F1c. Currently this antigenic site has not been mapped to a particular site on the F protein, but it seems to be overlapping with site I. The majority of these sites/epitopes give rise to broadly neutralizing antibodies, but some antibodies specific for antigenic site I have been shown to be subtype A-specific. Antibodies binding to site I also have a marginal effect in virus neutralization. The epitope recognized by Palivizumab is located in antigenic site II as judged by the localization of the selected escape mutations in amino acid position 272 (Zhao et al. 2004. J. Infect. Dis. 190:1941-6). Furthermore, three types of epitopes have been identified on the G protein: i) conserved epitopes that are present in all RSV strains, ii) group-specific epitopes that are present in all viruses belonging to the same subtype, and iii) strain-specific or variable epitopes that are present only in a subset of strains belong to the same subtype. The conserved and group-specific epitopes have been mapped to the central part of the G protein containing a cluster of four cysteines (amino acid residue 173, 176, 182 and 186) and a short amino acid segment (residues 164-176) of identical sequence among all human RSV isolates. The cysteine cluster is held by disulfide bonds between position 173-183 and 176-182 and constitutes the central part of the G protein cysteine-rich region (GCRR) ranging from amino acid residue 171-187, thereby the GCRR is overlapping with the 13 amino acid conserved region. The G glycoprotein appears to play a role in both induction of protective immunity and disease pathogenesis. For example, studies in mice have shown that the G glycoprotein primes for a Th2 CD4+ T cell response, characterized by production of IL-4, IL-5, IL-13 and pulmonary eosinophilia. Eosinophil recruitment and activation are promoted by several factors, such as IL-4 and IL-5. Further, expression of RSV G protein during acute infection in mice has been associated with a modified innate immune response characterized by decreased Th1 cytokine expression (e.g., IL-2 and gamma interferon), altered chemokine mRNA expression (e.g., MIP-1 alpha, MIP-1 beta, MIP-2, IP-10, MCP-1), and decreased NK cell trafficking to the infected lung. In particular the GCRR has been shown to play an important role in modulating the innate inflammatory response, thereby potentially delaying RSV clearance (Polack et al. 2005. PNAS 102:8996-9001). The GCRR comprise a CX3C motif at amino acid positions 182 to 186. Reduction in respiratory rates in RSV infected mice has been shown to be associated with the CX3C motif, since antibodies against this motif abolish the reduction in the respiratory rates (Tripp et al. 2003. J. Virol. 77:6580-6584 and US 2004/0009177 (application Ser. No. 10/420,387)). The strain-specific epitopes are preferentially localized in the variable C-terminal third of the G polypeptide, although a strain-specific epitope has been mapped to a variable region N-terminal to the cysteine cluster in the G protein ectodomain (Martinez et al. 1997. J. Gen. Virol. 78:2419-29). FIG. 1 shows an alignment of the G proteins from the Long strain (subtype A) and the 18537 strain (subtype B), indicating the various regions of the G protein. Generally, monoclonal anti-G protein antibodies have marginal effects on RSV neutralization. However, it has been reported that mixtures of monoclonal anti-G antibodies enhance neutralization of RSV in vitro as well as in vivo (Walsh et al. 1989. J. Gen. Virol. 70:2953-61 and Martinez and Melero 1998 J. Gen. Virol. 79:2215-20). The greatest effect of combining monoclonal anti-G antibodies is apparently achieved when the antibodies bind different epitopes, although a fraction of the virus still remained resistant to neutralization. Further, it has been shown that combinations of two different anti-F antibodies with different epitope specificities as well as combinations of one anti-F and one anti-G specific antibody showed an enhanced in vitro neutralizing effect on RSV (Anderson et al. 1988. J. Virol. 62: 4232-4238). Some of the advantages obtained by mixing monoclonal antibodies seem to be due to the individual properties of the monoclonal antibodies, such as an antagonistic effect, e.g. by blockage of the active site. Other effects seem to be synergistic for reasons that currently are not understood.

The mechanisms of RSV neutralization are complex and not completely understood. The large number of different epitopes, conserved, subtype specific as well as strain specific epitopes, identified on the F and G proteins alone, as well as the potential generation of escape mutants suggests that a wide spectrum of antibody specificities is needed to address all the neutralization mechanisms that may play a role in the prevention of RSV infection. Thus, it would be very difficult, in a rational way, to select the mixture of monoclonal antibodies that is capable of preventing RSV infection with RSV strain of both subtype A and B, as well as escape mutants and new strains arising from the RSV strains known today.

An aspect of the present invention is to provide a polyclonal anti-RSV antibody with a considerable diversity and broad anti-RSV specificity. The polyclonal anti-RSV antibody of the present invention is not dependent on the donor availability at the time of production and the batch to batch variation is considerably lower than observed for donor-derived anti-RSV immunoglobulin products (e.g. RSV IVIG). In a polyclonal anti-RSV antibody of the present in invention all the individual antibody members are capable of binding a RSV associated antigen and the polyclonal antibody is capable of neutralizing RSV subtype A and B. It is preferred that each distinct antibody of the polyclonal antibody binds an epitope which is not bound by any of the other members of the polyclonal antibody. A polyclonal anti-RSV antibody of the present invention will bind to RSV antigens in a multivalent manner, which usually results in synergistic neutralization, improved phagocytosis of infected cells by macrophages and improved antibody-dependent cellular cytotoxicity (ADCC) against infected cells as well as increased complement activation. Further, a polyclonal antibody of the present invention is not "diluted" by non-binding protein which is the case for RSV IVIG, where a dose of 750 mg total protein/kg is needed to be efficient. The percentage of RSV-specific antibodies within the 750 mg total protein is not known, but it is not likely to constitute more than maximally, 1%, and most likely less. Thus, when the in vitro potency of Palivizumab was estimated to be 25-30 times higher than that of RSV IVIG (Johnson et al. 1997. J. Infect. Dis. 176:1215-24), this is offset by a reduced specific activity of the RSV IVIG. Thus, if only 1% of the immunoglobulin molecules contained in the RSV-IVIG are specific for RSV, then the active dose of the RSV-IVIG polyclonal antibody is only 7.5 mg/kg which is lower than that of the monoclonal antibody Palivizumab.

For these reasons a recombinant polyclonal RSV-specific antibody of the present invention is expected to be significantly more potent than a monoclonal antibody, and it will therefore be possible to administer a smaller dose of a polyclonal antibody of the present invention, compared to the effective doses of Palivizumab and RSV IVIG. Thus, a polyclonal anti-RSV antibody of the present invention is also considered suitable for the prophylaxis and treatment of high-risk adults, in particular bone marrow transplant recipients, elderly individuals and individuals with chronic pulmonary disease. A further advantage of a polyclonal anti-RSV antibody of the present invention, is that the concentration of the individual antibody members is significantly lower than the concentration of a monoclonal antibody (even if the dose used is the same), hence the possibility that the individual antibody will be recognized as foreign by the immune system of the individual under treatment is decreased, and even if one individual antibody is eliminated by an immune response in the patient, this is not likely to affect the neutralizing capability or the clearance rate of the polyclonal anti-RSV antibody, since the remaining antibody members remain intact.

An embodiment of the present invention is a recombinant polyclonal anti-RSV antibody capable of neutralizing RSV subtype A and B, and where said polyclonal antibody comprises distinct antibody members which in union specifically binds at least three different epitopes on at least one RSV envelope protein. Preferably, the F protein is bound specifically by at least three distinct antibody members, and said epitopes are preferably located at different antigenic sites.

A further embodiment of the present invention is a recombinant polyclonal anti-RSV antibody capable of neutralizing RSV subtype A and B, and where said polyclonal antibody comprises distinct antibody members which in union provide specific reactivity against at least two RSV envelope proteins. The two envelope proteins can be selected from the RSV G protein, RSV F protein and RSV SH protein. Preferably, the polyclonal anti-RSV antibody of the present invention comprises anti-G and anti-F reactivity. The anti-G and anti-F reactivity of such a polyclonal antibody is preferably comprised of at least two distinct anti-G antibodies and at least one distinct anti-F antibody. Preferably, at least three distinct antibodies bind to different epitopes, thereby covering at least three different epitopes, and together the antibodies are capable of neutralizing RSV subtype A and subtype B strains equally well. Even more preferred the anti-G and anti-F reactivity of a polyclonal anti-RSV antibody of the present invention is comprised of any combination of the anti-G and anti-F reactivities described below. Most preferred a polyclonal anti-RSV antibody of the present invention is comprised of anti-G and anti-F reactivity against all the antigenic sites/epitopes mentioned below. To obtain the broadest specificity possible of a polyclonal anti-RSV antibody of the present invention, it is desired that one or more, preferably all the antigenic sites are covered by more than one distinct antibody. Consequently, it is preferred that several epitopes on the same antigen or antigenic site are bound by distinct members of a polyclonal antibody of the present invention.

With respect to the anti-G reactivity of a polyclonal anti-RSV antibody of the present invention, this reactivity is preferably directed against conserved epitopes. Even more preferred the anti-G reactivity is comprised of a first anti-G antibody capable of specifically binding a conserved epitope on the G-protein, and a second anti-G antibody capable of specifically binding the G protein cysteine-rich region (GCRR) The polyclonal anti-RSV antibody preferably comprise at least two distinct anti-G antibodies, where at least one first antibody is capable of specifically binding a conserved epitope on the G-protein, and at least one second antibody is capable of specifically binding a different conserved epitope or a group-specific epitope recognizing either with subtype A or subtype B. Preferably, the polyclonal antibody comprise at least three distinct anti-G antibodies where the first antibody is capable of specifically binding a conserved epitope on the G-protein, and the second antibody is capable of specifically binding a G protein of subtype A and the third antibody is capable of specifically binding a G protein of subtype B. The G protein cysteine-rich region (GCRR) partially overlaps with the upstream 13 amino acid region where the conserved epitopes are located and a region where the group specific epitopes are located. Thus, antibodies capable of specifically binding a conserved epitope as well as group specific antibodies may bind the GCRR if the epitope that they recognize is located in the GCRR. Preferably, at least one of the distinct antibodies characterized by their binding to a conserved epitope or a strain specific epitope also recognizes the GCRR. Antibodies binding to the CX3C motif of the GCRR are especially preferred from a virus neutralization point of view. However, antibodies binding to CX3C motifs may also bind a number of other unrelated human antigens, such as fractalkine and other human CX3C chemokines and thus produce undesired side-effects meaning that it will be a rational approach to test such antibodies for cross-reactivity (e.g. as demonstrated for certain antibodies in the examples) and later to test the same antibodies in suitable model systems. At any rate, it will always be necessary to test a given pharmaceutical, such as an antibody of the present invention, in a clinical trial before it can be established with a degree of certainty that side effects are absent, minor or at least acceptable. In addition to the conserved and group-specific anti-G reactivity additional anti-G reactivity directed against strain specific epitopes may also be comprised in the polyclonal anti-RSV antibody of the present invention. Strain-specific anti-G reactivity directed against the most abundant strain-specific epitopes present on virus strains which have resulted in RSV infection within the last five years is preferred. In the current invention strain-specific epitopes are understood as epitopes which only are present on a limited number of RSV strains. The addition of group-specific and/or strain specific anti-G antibodies can provide additional diversity to an anti-RSV antibody of the present invention, and may induce synergy when combined with antibodies with reactivity to the conserved region of the G protein. Preferably, the anti-G antibodies of the present invention neutralize RSV directly, block entry of the virus into the cell, prevent cell migration, inhibit inflammatory responses and/or prevent syncytia formation.

With respect to the anti-F reactivity of a polyclonal anti-RSV antibody of the present invention, this reactivity is preferably directed against at least one epitope on one or more of the antigenic sites I, II, IV, V, VI, C or F1. In further embodiments of the present invention at least two, three, four, five, six or all these antigenic sites/epitopes are covered by distinct antibodies in a polyclonal anti-RSV antibody of the present invention. Preferably, the anti-F antibodies of the present invention neutralize RSV directly and/or block entry of the virus into the cell and/or prevent syncytia formation.

In polyclonal anti-RSV antibody compositions of the present invention where the composition does not comprise binding reactivity directed against all the antigenic sites on the F protein, the presence of at least one distinct anti-F antibody which specifically binds an epitope of antigenic site II is preferred. Even more preferred the site II-specific anti-F antibody binds to the same epitope or antigenic site as the antibody Palivizumab. In addition to the site II-specific antibodies one or more distinct site IV-specific anti-F antibodies are desired, such an antibody preferably binds to the same epitope as RSVF2-5.

Subtype-specific anti-F antibodies are also known in the art. However, since the F protein shows 91% amino acid similarity between the two subgroups A and B, the subtype-specific anti-F antibodies are less abundant than for anti-G antibodies. Such strain-specific anti-F antibodies will, however, contribute to obtaining as broad specificity as possible, and are therefore also desired components of a polyclonal anti-RSV antibody of the present invention.

In addition to the RSV G and F protein antigens mentioned above, the RS virus expresses a third envelope protein, the small hydrophobic (SH) protein. Hyperimmune sera raised against peptides from the SH proteins have been shown to be unable to neutralize RSV in vitro (Akerlind-Stopner et al. 1993 J. Med. Virol. 40:112-120). However, since the protein is mainly expressed on infected cells, we believe that antibodies against the SH protein will have an effect on fusion inhibition and potentially be relevant for in vivo protection against RSV infections. This is supported by the fact that RSV strains lacking the SH gene replicate 10-fold less efficient in the upper respiratory tract (Bukreyev et al. 1997 J. Virol. 71:8973-82).

An additional embodiment of the present invention is a polyclonal anti-RSV antibody capable of neutralizing RSV subtype A and B and comprising anti-SH reactivity, and anti-G or anti-F reactivity. The C-terminus ranging from amino acid 41 to 64/65 (subtype A/B) of the SH protein is exposed on the cell surface. Hence, anti-SH reactivity against an epitope located in this area is desired. The C-terminus of the SH protein varies from subtype A and B, and it is therefore desired to include anti-SH reactivity against both subtype A and B in a polyclonal antibody of the present invention. This SH reactivity can be provided by at least two distinct anti-SH antibodies where the first antibody is capable of specifically binding SH subtype A and the second antibody is capable of specifically binding SH subtype B.

In one embodiment of the present invention a polyclonal anti-RSV antibody comprises specific reactivity against SH subtype A and/or B as well as specific reactivity against the G protein. The reactivity against the G protein can be composed of any of the reactivities mentioned above.

In an alternative embodiment the specific reactivity against SH subtype A and/or B can be combined with any of the anti-F reactivities described in the above to constitute a polyclonal anti-RSV antibody.

In a preferred embodiment of the present invention a polyclonal anti-RSV antibody comprises reactivity against all three of the envelope proteins, F, G and SH.

The reactivity comprised in a polyclonal anti-RSV antibody of the present invention may constitute any possible combination of distinct antibodies with specific binding reactivity against the antigens/antigenic sites and/or epitopes summarized in Table 1, as long as the combination is capable of neutralizing RSV subtype A and B. Preferably, the combination contains reactivity against at least two RSV envelope proteins.

Preferably, the individual distinct antibody members of a polyclonal antibody according to the present invention, have neutralizing and/or anti-inflammatory properties on their own. Antibodies without these particular properties may however also play a role in RSV clearance for example through complement activation.

TABLE 1

Summary of RSV associated antigens, antigenic sites and epitopes

| Antigen | Antigenic site/epitope |
| --- | --- |
| F Protein | Antigenic site I |
|  | Antigenic site II |
|  | Antigenic site IV |
|  | Antigenic site V |
|  | Antigenic site VI |
|  | Antigenic site C |
|  | F1 epitope |
| G Protein | Conserved region (a.a. 164-176) |
|  | Subtype A specific |
|  | Subtype B specific |
|  | GCRR (a.a. 171-187) |
|  | (conserved as well as strain specific) |
|  | CX3C motif (a.a. 182-186) |
|  | Strain specific |
| SH protein | Subtype A |
|  | Subtype B |

Preferably, a polyclonal antibody of the present invention is produced as a single batch or a few batches from a polyclonal cell line which is not naturally expressing antibody molecules (also termed recombinant polyclonal antibody expression). One of the advantages of producing a recombinant polyclonal antibody compared to mixing monoclonal antibodies, is the ability to produce an unlimited number of distinct antibody molecules at the same time (at a cost similar to that of producing a single monoclonal antibody). Thus, it is possible to include antibodies with reactivity towards a large number of RSV associated antigens, without increasing the cost of the end product significantly. In particular with a target as complex as the RSV, where the biology is not completely understood, individual antibodies which have not been shown to neutralize or protect against RSV alone, may when combined with other antibodies induce a synergistic effect. Thus, it can be an advantage to include distinct antibodies, in addition to those described above, in a polyclonal antibody composition, where the only criterion is that the individual antibody binds to an RSV associated antigen (e.g. assessed by binding to RSV infected cells). Preferably all the polyclonal anti-RSV antibody compositions described above are recombinant polyclonal anti-RSV antibody (anti-RSV rpAb) compositions.

One way to acquire potentially relevant antibodies that bind RSV target antigens which have not been verified as relevant antigens, but nonetheless may be so, is to generate a polyclonal antibody composition which is composed of individual antibodies raised by the immune response of a donor which has been infected with RSV (full immune response). In addition to obtaining antibodies representing a full immune response against RSV, a positive selection for antibodies binding to antigens that are likely to be of particular relevance in the protection, neutralization, and/or elimination of RSV infections, can be performed. Further, if antibodies to a particular antigen, antigenic site or epitope which is believed to be of relevance in the protection, neutralization and/or elimination of RSV are not identified in the full immune response of the donor, such antibodies may be raised by immunization/vaccination of a donor with that particular antigen (selected immune response). Generally, neutralization is assessed by in vitro neutralization assays such as plaque reduction, microneutralization or fusion-inhibition assays (e.g. Johnson et al. 1997. J. Infect. Dis. 176:1215-24). Hence, an antibody or antibody composition having a significant effect in one of these assays, when compared to a negative control are considered to be neutralizing. Protection is generally assessed by in vivo challenge experiments in e.g. the cotton rat model (e.g. Johnson et al. 1997. J. Infect. Dis. 176:1215-24) or the murine model (e.g. Taylor et al. 1984. Immunology 52, 137-142 and Mejias, et al. 2005. Antimicrob. Agents Chemother. 49: 4700-4707). The in vivo challenge experiments can either be performed in a prophylactic fashion, where the antibodies are administered prior to the viral challenge or as a treatment, where the antibodies are administered after viral challenge or as a combination of both.

A polyclonal antibody composition of the present invention can be composed of antibodies capable of binding a RSV antigen which is not necessarily known or not necessarily an envelope protein (the antibody binds to infected cells, but not to selected antigens or antigenic sites), but where the antibodies are acquired from a full immune response following a RSV infection, e.g. by obtaining nucleic acid sequences encoding the distinct antibodies from one or more donors with a RSV infection or recovering from a RSV infection. Secondly, antibodies from the same full immune response, which have been selected, based on their ability to bind a particular antigen, antigenic site and/or epitope, can be included in a polyclonal antibody of the present invention. Thirdly, distinct antibodies encoded from $V_H$ and $V_L$ pairs obtained from one or more donors which have been immunized/vaccinated with a particular RSV related antigen thereby raising a "selected" immune response in these donors, can be included in a polyclonal antibody composition of the present invention. Thus, antibodies derived by any of the mentioned techniques in the present invention may be combined into a single polyclonal antibody. Preferably the nucleic acids encoding the antibodies of the present invention are obtained from human donors and the antibodies produced are fully human antibodies.

The motivation behind the polyclonal antibody compositions of the present invention is: if a donor infected with RSV, raises a humoral immune response against an antigen, these antibodies are likely, at least to some extent, to contribute to viral clearance, and thereby qualify for inclusion in a polyclonal antibody product.

A further aspect of the present invention is to produce an anti-RSV rpAb wherein the composition of distinct antibody members mirrors the humoral immune response with respect to diversity, affinity and specificity against RSV envelope antigens. Preferably, the mirror of the humoral response is established by ensuring that one or more of the following are fulfilled i) the nucleic acid sequences coding for the $V_H$ and $V_L$ regions of the individual antibody members in such an anti-RSV rpAb are derived from a donor(s) who has raised a humoral immune response against RSV, for example following RSV infection; ii) the $V_H$ and $V_L$ coding sequences are isolated from the donor(s) such that the original pairing of the $V_H$ and $V_L$ coding sequences present in the donor(s) is maintained, iii) the $V_H$ and $V_L$ pairs, coding for the individual members of the rpAb, are selected such that the CDR regions are as diverse as possible; or iv) the specificity of the individual members of the anti-RSV rpAb are selected such that the antibody composition collectively binds antigens that elicit significant antibody responses in mammals. Preferably, the antibody composition collectively binds antigens, antigenic sites and/or epitopes which produce significant antibody titers in a serum sample from said donor(s). Such antigens, antigenic sites and/or epitopes are summarized in Table 1 above, but may also constitute unknown antigens, antigenic sites and/or epitopes as well as non-envelope antigens, as described above. Preferably, the donors are human, and the polyclonal antibody is a fully human antibody.

The present invention has identified a series of $V_H$ and $V_L$ pairs that can be expressed as full-length antibodies, Fab fragment or other antibody fragments that have binding specificity to a RSV associated antigen. The specific $V_H$ and $V_L$ pairs are identified by clone number in Table 6 in Example 2. An antibody containing a $V_H$ and $V_L$ pair as identified in Table 6 is preferably a fully human antibody. However, if desired, chimeric antibodies may also be produced.

A preferred anti-RSV recombinant polyclonal antibody of the present invention is composed of distinct members comprising heavy chain and light chain CDR1, CDR2 and CDR3 regions selected from the group of $V_H$ and $V_L$ pairs listed in Table 6. Preferably, the CDR regions are maintained in the pairing indicated in Table 6 and inserted into a desired framework. Alternatively, CDR regions from the heavy chain (CDRH) of a first clone are combined with the CDR regions from the light chain (CDRL) of a second clone (scrambling of $V_H$ and $V_L$ pairs). The CDR regions may also be scrambled within the light chain or heavy chain, for example by combining the CDRL1 region from a first clone with the CDRL2 and CDRL3 region from a second clone. Such scrambling is preferably performed among clones that bind the same antigen. The CDR regions of the present invention may also be subjected to affinity maturation, e.g. by point mutations.

Preferred Antibody Compositions

Particularly preferred antibody compositions comprising more than one distinct human antibody molecule have been identified by the present inventors. These include antibody compositions which are efficacious in virus neutralization assays (Table 9) and in vivo (Tables 10-11).

One particularly preferred antibody composition is an antibody composition comprising antibody 824 or an antibody derived therefrom as described herein and one or more additional anti-RSV antibodies. Antibody 824 on its own is a very potent antibody and when combined with other antibodies—in particular with antibodies directed against the G-protein—have a very high potency in vitro and in vivo.

The one or more additional anti-RSV antibodies may be selected from the group consisting of human antibodies, humanized antibodies, and chimeric human-mouse antibodies.

Preferably, the one or more additional anti-RSV antibodies are selected from the group consisting of the antibody molecules set forth in Table 6 herein, or a specifically binding fragment of said antibody molecule or a synthetic or semisynthetic antibody analogue, said binding fragment or analogue comprising at least the complementarity-determining regions (CDRs) of said isolated antibody molecule, except an antibody having the CDRs of clone 824.

A preferred antibody composition is composed of distinct members comprising heavy chain and light chain CDR1, CDR2 and CDR3 regions selected from the group of $V_H$ and $V_L$ pairs listed in Table 6, wherein the distinct members are the distinct members of one of antibody compositions 2 to 56 in Table 9 herein. Such antibody compositions have shown to be potent in neutralizing one or more RSV strains in vitro.

Preferably the antibody composition is capable of neutralizing RSV subtype A in a virus neutralization assay, more preferably the composition is also capable of neutralizing RSV subtype B in a virus neutralization assay. Suitable assays include the Plaque reduction and microneutralization assays described herein.

Particularly preferred compositions have demonstrated in vivo potency and comprise the distinct members selected from the distinct members of one of antibody compositions 2, 9, 13, 17, 18, 28, 33, and 56 of Table 9 herein.

In some embodiments the antibody composition does not contain anti-RSV antibodies in addition to antibodies with the CDRs of the distinct members described for each composition 2-56 in Table 9 herein.

Isolation and Selection of Variable Heavy Chain and Variable Light Chain Coding Pairs The process of generating an anti-RSV recombinant polyclonal antibody composition involves the isolation of sequences coding for variable heavy chains ($V_H$) and variable light chains ($V_L$) from a suitable source, thereby generating a repertoire of $V_H$ and $V_L$ coding pairs. Generally, a suitable source for obtaining $V_H$ and $V_L$ coding sequences are lymphocyte containing cell fractions such as blood, spleen or bone marrow samples from an animal or human which is infected with RSV or recovering from an RSV infection, or from an animal or human immunized/vaccinated with an RSV strain or proteins or DNA derived from such a strain. Preferably, lymphocyte containing fractions are collected from humans or transgenic animals with human immunoglobulin genes. The collected lymphocyte containing cell fraction may be enriched further to obtain a particular lymphocyte population, e.g. cells from the B lymphocyte linage. Preferably, the enrichment is performed using magnetic bead cell sorting (MACS) and/or fluorescence activated cell sorting (FACS), taking advantage of lineage-specific cell surface marker proteins for example for B cells, plasma blast and/or plasma cells. Preferably, the lymphocyte containing cell fraction is enriched with respect to B cells, plasma blasts and/or plasma cells. Even more preferred, cells with high CD38 expression and intermediate CD19 and/or CD45 expression are isolated from blood. These cells are sometimes termed circulating plasma cells, early plasma cells or plasma blasts. For ease, they are just termed plasma cells in the present invention, although the other terms may be used interchangeably.

The isolation of $V_H$ and $V_L$ coding sequences can either be performed in the classical way where the $V_H$ and $V_L$ coding sequences are combined randomly in a vector to generate a combinatorial library of $V_H$ and $V_L$ coding sequences pairs. However, in the present invention it is preferred to mirror the diversity, affinity and specificity of the antibodies produced in a humoral immune response upon RSV infection. This involves the maintenance of the $V_H$ and $V_L$ pairing originally present in the donor, thereby generating a repertoire of sequence pairs where each pair encodes a variable heavy chain ($V_H$) and a variable light chain ($V_L$) corresponding to a $V_H$ and $V_L$ pair originally present in an antibody produced by the donor from which the sequences are isolated. This is also termed a cognate pair of $V_H$ and $V_L$ encoding sequences and the antibody is termed a cognate antibody. Preferably, the $V_H$ and $V_L$ coding pairs of the present invention, combinatorial or cognate, are obtained from human donors, and therefore the sequences are completely human.

There are several different approaches for the generation of cognate pairs of $V_H$ and $V_L$ encoding sequences, one approach involves the amplification and isolation of $V_H$ and $V_L$ encoding sequences from single cells sorted out from a lymphocyte-containing cell fraction. The $V_H$ and $V_L$ encoding sequences may be amplified separately and paired in a second step or they may be paired during the amplification (Coronella et al. 2000. Nucleic Acids Res. 28: E85; Babcook et al 1996. PNAS 93: 7843-7848 and WO 2005/042774). A second approach involves in-cell amplification and pairing of the $V_H$ and $V_L$ encoding sequences (Embleton et al. 1992. Nucleic Acids Res. 20: 3831-3837; Chapal et al. 1997. Bio-Techniques 23: 518-524). A third approach is selected lymphocyte antibody method (SLAM) which combines a hemolytic plaque assay with cloning of $V_H$ and $V_L$ cDNA (Babcook et al. 1996. PNAS 93:7843-7848). In order to obtain a repertoire of $V_H$ and $V_L$ encoding sequence pairs which resemble the diversity of $V_H$ and $V_L$ sequence pairs in the donor, a high-throughput method with as little scrambling (random combination) of the $V_H$ and $V_L$ pairs as possible, is preferred, e.g. as described in WO 2005/042774 (hereby incorporated by reference).

In a preferred embodiment of the present invention a repertoire of $V_H$ and $V_L$ coding pairs, where the member pairs mirror the gene pairs responsible for the humoral immune response resulting from a RSV infection, is generated according to a method comprising the steps i) providing a lymphocyte-containing cell fraction from a donor infected with RSV or recovering from a RSV infection; ii) optionally enriching B cells or plasma cells from said cell fraction; iii) obtaining a population of isolated single cells, comprising distributing cells from said cell fraction individually into a plurality of vessels; iv) amplifying and effecting linkage of the $V_H$ and $V_L$ coding pairs, in a multiplex overlap extension RT-PCR procedure, using a template derived from said isolated single cells and v) optionally performing a nested PCR of the linked $V_H$ and $V_L$ coding pairs. Preferably, the isolated cognate $V_H$ and $V_L$ coding pairs are subjected to a screening procedure as described below.

Once the $V_H$ and $V_L$ sequence pairs have been generated, a screening procedure to identify sequences encoding $V_H$ and $V_L$ pairs with binding reactivity towards an RSV associated antigen is performed. Preferably, the RSV associated antigen is a RSV envelope protein, in particular RSV G protein, RSV F protein and RSV SH protein. If the $V_H$ and $V_L$ sequence pairs are combinatorial a phage display procedure can be applied to enrich for $V_H$ and $V_L$ pairs coding for antibody fragments binding to RSV prior to screening.

In order to mirror the diversity, affinity and specificity of the antibodies produced in a humoral immune response upon infection with RSV, the present invention has developed a screening procedure for the cognate pairs, in order to obtain the broadest diversity possible. For screening purposes the repertoire of cognate $V_H$ and $V_L$ coding pairs are expressed individually either as antibody fragments (e.g. scFv or Fab) or as full-length antibodies using either a bacterial or mammalian screening vector transfected into a suitable host cell. The repertoire of Fabs/antibodies is screened for reactivity to virus particles of one or more RSV strains. Preferably, at least two strains, one of subtype A and one of subtype B are used. Subtype A strains are for example Long (ATCC VR-26), A2 (ATCC VR-1540) or more recent Long-like subtype A isolates. Subtype B strains are for example 18537 (ATCC VR-1580), B1 (ATCC VR-1400), 9320 (ATCC VR-955) or more recent 18537-like isolates. In parallel, the repertoire of Fabs/antibodies is screened against selected antigens such as recombinant G protein, recombinant F protein and peptides derived from RSV antigens. The antigenic peptides can for example be selected from the conserved region of the G protein (amino acids 164-176) and the cysteine core region (amino acids 171-187 of subtype A as well as subtype B strains) of the G protein and, the extracellular region of the SH-protein (amino acids 42-64 of subtype A and 42-65 of subtype B). Preferably the peptides are biotinylated to facilitate immobilization onto beads or plates during screening. Alternative immobilization means may be used as well. The antigens are selected based on the knowledge of the RSV biology and the expected neutralizing and/or protective effect antibodies capable of binding to these antigens potentially can provide. This screening procedure can likewise be applied to a combinatorial phage display library. The recombinant G and/or F proteins used for screening can be expressed in bacteria, insect cells, mammalian cells or another suitable expression system. The G and/or F protein may either be expressed as a soluble protein (without the transmembrane region) or they may be fused to a third protein, to increase stability. If the G and/or F protein is expressed with a fusion tag, the fusion partner may be cleaved off prior to screening. Preferably, G and/or F proteins representative of both the subtype A and subtype B are expressed and used for screening. Additionally, strain-specific G proteins may be expressed and used for screening. In addition to the primary screening described above, a secondary screening may be performed, in order to ensure that none of the selected sequences encode false positives. In the second screening all the RSV/antigen binding $V_H$ and $V_L$ pairs identified in the first screening are screened again against both the virus strains and the selected antigens. Generally, immunological assays are suitable for the screening performed in the present invention. Such assays are well know in the art and constitute for example ELISPOTS, ELISA, FLISA, membrane assays (e.g. Western blots), arrays on filters, and FACS. The assays can either be performed without any prior enrichment steps, utilizing polypeptides produced from the sequences encoding the $V_H$ and $V_L$ pairs. In the event that the repertoire of $V_H$ and $V_L$ coding pairs are cognate pairs, no enrichment by e.g. phage display is needed prior to the screening. However, in the screening of combinatorial libraries, the immunoassays are preferably performed in combination with or following enrichment methods such as phage display, ribosome display, bacterial surface display, yeast display, eukaryotic virus display, RNA display or covalent display (reviewed in FitzGerald, K., 2000. Drug Discov. Today 5, 253-258).

The $V_H$ and $V_L$ pair encoding sequences selected in the screening are generally subjected to sequencing, and analyzed with respect to diversity of the variable regions. In particular the diversity in the CDR regions is of interest, but also the $V_H$ and $V_L$ family representation is of interest. Based on these analyses, sequences encoding $V_H$ and $V_L$ pairs representing the overall diversity of the RSV binding antibodies isolated from one or more donors are selected. Preferably, sequences with differences in all the CDR regions (CDRH1, CDRH2, CDRH3 and CDRL1, CDRL2 and CDRL3) are selected. If there are sequences with one or more identical or very similar CDR regions which belong to different $V_H$ or $V_L$ families, these are also selected. Preferably, at least the CDR3 region of the variable heavy chain (CDRH3) differs among the selected sequence pairs. Potentially, the selection of $V_H$ and $V_L$ sequence pairs can be based solemnly on the variability of the CDRH3 region. During the priming and amplification of the sequences, mutations may occur in the framework regions of the variable region, in particular in the first framework region. Preferably, the errors occurring in the first framework region are corrected in order to ensure that the sequences correspond completely or at least 98% to those of the donor, e.g. such that the sequences are fully human.

When it is ensured that the overall diversity of the collection of selected sequences encoding $V_H$ and $V_L$ pairs is highly representative of the diversity seen at the genetic level in a humoral response to a RSV infection, it is expected that the overall specificity of antibodies expressed from a collection of selected $V_H$ and $V_L$ coding pairs also are representative with respect to the specificity of the antibodies produced in the RSV infected donors. An indication of whether the specificity of the antibodies expressed from a collection of selected $V_H$ and $V_L$ coding pairs are representative of the specificity of the antibodies raised by infected donors can be obtained by comparing the antibody titers towards the virus strains as well as the selected antigens of the donor blood with the specificity of the antibodies expressed from a collection of selected $V_H$ and $V_L$ coding pairs. Additionally, the specificity of the antibodies expressed from a collection of selected $V_H$ and $V_L$ coding pairs can be analyzed further. The degree of specificity correlates with the number of different antigens towards which binding reactivity can be detected. In a further embodiment of the present invention the specificity of the individual antibodies expressed from a collection of selected $V_H$ and $V_L$ coding pairs is analyzed by epitope mapping.

Epitope mapping may be performed by a number of methodologies, which do not necessarily exclude each other. One way to map the epitope-specificity of an antibody clone is to assess the binding to peptides of varying lengths derived from the primary structure of the target antigen. Such peptides may be both linear and conformational and may be used in a number of assay formats, including ELISA, FLISA and surface plasmon resonance (SPR, Biacore). Furthermore, the peptides may be rationally selected using available sequence and structure data to represent e.g. extracellular regions or conserved regions of the target antigen, or the may be designed as a panel of overlapping peptides representing a selected part or all of the antigen (Meloen R H, Puijk W C, Schaaper W M M. Epitope mapping by PEPSCAN. In: Immunology Methods Manual. Ed Iwan Lefkovits 1997, Academic Press, pp 982-988). Specific reactivity of an antibody clone with one or more such peptides will generally be an indication of the epitope specificity. However, peptides are in many cases poor mimics of the epitopes recognized by antibodies raised against proteinaceous antigens, both due to a lack of conformation and due to the generally larger buried surface area of interaction between an antibody and a protein antigen as compared to an antibody and a peptide. A second method for epitope mapping, which allows for the definition of specificities directly on the protein antigen, is by selective epitope masking using existing, well defined antibodies. Reduced binding of a second, probing antibody to the antigen following blocking is generally indicative of shared or overlapping epitopes. Epitope mapping by selective masking may be performed by a number of immunoassays, including, but not restricted to, ELISA and Biacore, which are well known in the art (e.g. Ditzel et al. 1997. J. Mol. Biol. 267:684-695; Aldaz-Carroll et al. 2005. J. Virol. 79: 6260-6271). Yet another potential method for the determination of the epitope specificity of anti-virus antibodies is the selection of viral escape mutants in the presence of antibody. Sequencing of the gene(s) of interest from such escape mutants will generally reveal which amino acids in the antigen(s) that are important for the recognition by the antibody and thus constitute (part of) the epitope.

Preferably, individual members to be comprised in an anti-RSV rpAb of the present invention are selected such that the specificity of the antibody composition collectively covers both RSV subtype A and B, as well as the RSV associated antigens protein F and G, and preferably also SH.

Production of a Recombinant Polyclonal Antibody from Selected $V_H$ and $V_L$ Coding Pairs A polyclonal antibody of the present invention is produced from a polyclonal expression cell line in one or a few bioreactors or equivalents thereof. Following this approach the anti-RSV rpAb can be purified from the reactor as a single preparation without having to separate the individual members constituting the anti-RSV rpAb during the process. If the polyclonal antibody is produced in more than one bioreactor, the supernatants from each bioreactor can be pooled prior to the purification, or the purified anti-RSV rpAb can be obtained by pooling the antibodies obtained from individually purified supernatants from each bioreactor.

One way of producing a recombinant polyclonal antibody is described in WO 2004/061104 and WO 2006/007850 (PCT/DK2005/000501) (these references are hereby incorporated by reference). The method described therein, is based on site-specific integration of the antibody coding sequence into the genome of the individual host cells, ensuring that the $V_H$ and $V_L$ protein chains are maintained in their original pairing during production. Furthermore, the site-specific integration minimizes position effects and therefore the growth and expression properties of the individual cells in the polyclonal cell line are expected to be very similar. Generally, the method involves the following: i) a host cell with one or more recombinase recognition sites; ii) an expression vector with at least one recombinase recognition site compatible with that of the host cell; iii) generation of a collection of expression vectors by transferring the selected $V_H$ and $V_L$ coding pairs from the screening vector to an expression vector such that a full-length antibody or antibody fragment can be expressed from the vector (such a transfer may not be necessary if the screening vector is identical to the expression vector); iv) transfection of the host cell with the collection of expression vectors and a vector coding for a recombinase capable of combining the recombinase recognition sites in the genome of the host cell with that in the vector; v) obtaining/generating a polyclonal cell line from the transfected host cell and vi) expressing and collecting the polyclonal antibody from the polyclonal cell line.

Preferably mammalian cells such as CHO cells, COS cells, BHK cells, myeloma cells (e.g., Sp2/0 or NS0 cells), fibroblasts such as NIH 3T3, and immortalized human cells, such as HeLa cells, HEK 293 cells, or PER.C6, are used. However, non-mammalian eukaryotic or prokaryotic cells, such as plant cells, insect cells, yeast cells, fungi, E. coli etc., can also be employed. A suitable host cell comprises one or more suitable recombinase recognition sites in its genome. The host cell should also contain a mode of selection which is operably linked to the integration site, in order to be able to select for integrants, (i.e., cells having an integrated copy of an anti-RSV Ab expression vector or expression vector fragment in the integration site). The preparation of cells having an FRT site at a pre-determined location in the genome was described in e.g. U.S. Pat. No. 5,677,177. Preferably, a host cell only has a single integration site, which is located at a site allowing for high expression of the integrant (a so-called hot-spot).

Figure 3:
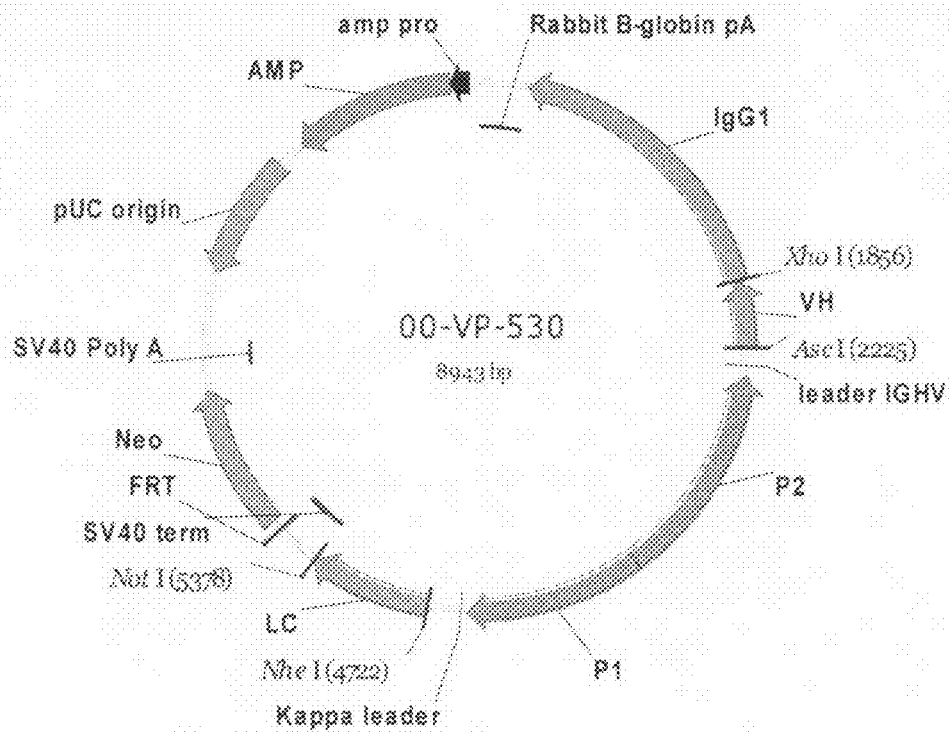
FIG. 3) by the use of the flanking XhoI and NotI restriction sites. Subsequently a bi-directional promoter is inserted into the AscI-NheI restriction site between the linked $V_H$ and $V_L$ coding sequences to facilitate expression of full length antibodies. PCR primers used are indicated by horizontal arrows. CH1: heavy chain constant domain 1, CL: constant domain, LC: light chain; Ab: antibody; P1-P2: bi-directional promoters.

A suitable expression vector comprises a recombination recognition site matching the recombinase recognition site(s) of the host cell. Preferably the recombinase recognition site is linked to a suitable selection gene different from the selection gene used for construction of the host cell. Selection genes are well known in the art, and include glutamine synthetase gene (GS), dihydrofolate reductase gene (DHFR), and neomycin, where GS or DHFR may be used for gene amplification of the inserted $V_H$ and $V_L$ sequence. The vector may also contain two different recombinase recognition sites to allow for recombinase-mediated cassette exchange (RMCE) of the antibody coding sequence instead of complete integration of the vector. RMCE is described in Langer et al 2002. Nucleic Acids Res. 30, 3067-3077; Schlake and Bode 1994. Biochemistry 33, 12746-12751 and Belteki et al 2003. Nat. biotech. 21, 321-324. Suitable recombinase recognition sites are well known in the art, and include FRT, 10× and attP/attB sites. Preferably the integrating vector is an isotype-encoding vector, where the constant regions (preferably including introns) are present in the vector prior to transfer of the $V_H$ and $V_L$ coding pair from the screening vector (or the constant regions are already present in the screening vector if screening is performed on full-length antibodies). The constant regions present in the vector can either be the entire heavy chain constant region ($CH_1$ to $CH_3$ or to $CH_4$) or the constant region encoding the Fc part of the antibody ($CH_2$ to $CH_3$ or to $CH_4$). The light chain Kappa or Lambda constant region may also be present prior to transfer. The choice of the number of constant regions present, if any, depends on the screening and transfer system used. The heavy chain constant regions can be selected from the isotypes IgG1, IgG2, IgG3, IgG4, IgA1, IgA2, IgM, IgD and IgE. Preferred isotypes are IgG1 and/or IgG3. Further, the expression vector for site-specific integration of the anti-RSV antibody-encoding nucleic acid contains suitable promoters or equivalent sequences directing high levels of expression of each of the $V_H$ and $V_L$ chains. FIG. 3 illustrates one possible way to design the expression vector, although numerous other designs are possible.

The transfer of the selected $V_H$ and $V_L$ coding pairs from the screening vector can be performed by conventional restriction enzyme cleavage and ligation, such that each expression vector molecule contain one $V_H$ and $V_L$ coding pair. Preferably, the $V_H$ and $V_L$ coding pairs are transferred individually, they may, however, also be transferred in-mass if desired. When all the selected $V_H$ and $V_L$ coding pairs are transferred to the expression vector a collection or a library of expression vectors is obtained. Alternative ways of transfer may also be used if desired. If the screening vector is identical to the expression vector, the library of expression vectors is constituted of the $V_H$ and $V_L$ sequence pairs selected during screening, which are situated in the screening/expression vector.

Methods for transfecting a nucleic acid sequence into a host cell are known in the art. To ensure site-specific integration, a suitable recombinase must be provided to the host cell as well. This is preferably accomplished by co-transfection of a plasmid encoding the recombinase. Suitable recombinases are for example Flp, Cre or phage ΦC31 integrase, used together with a host cell/vector system with the corresponding recombinase recognition sites. The host cell can either be transfected in bulk, meaning that the library of expression vectors is transfected into the cell line in one single reaction thereby obtaining a polyclonal cell line. Alternatively, the collection of expression vectors can be transfected individually into the host cell, thereby generating a collection of individual cell lines (each cell line produce an antibody with a particular specificity). The cell lines generated upon transfection (individual or polyclonal) are then selected for site specific integrants, and adapted to grow in suspension and serum free media, if they did not already have these properties prior to transfection. If the transfection was performed individually, the individual cell lines are analyzed further with respect to their grow properties and antibody production. Preferably, cell lines with similar proliferation rates and antibody expression levels are selected for the generation of the polyclonal cell line. The polyclonal cell line is then generated by mixing the individual cell lines in a predefined ratio. Generally, a polyclonal master cell bank (pMCB), a polyclonal research cell bank (pRCB) and/or a polyclonal working cell bank (pWCB) is laid down from the polyclonal cell line. The polyclonal cell line is generated by mixing the individual cell lines in a predefined ratio. The polyclonal cell line is distributed into ampoules thereby generating a polyclonal research cell bank (pRCB) or master cell bank (pMCB) from which a polyclonal working cell bank (pWCB) can be generated by expanding cells from the research or master cell bank. The research cell bank is primarily for proof of concept studies, in which the polyclonal cell line may not comprise as many individual antibodies as the polyclonal cell line in the master cell bank. Normally, the pMCB is expanded further to lay down a pWCB for production purposes. Once the pWCB is exhausted a new ampoule from the pMCB can be expanded to lay down a new pWCB.

One embodiment of the present invention is a polyclonal cell line capable of expressing a recombinant polyclonal anti-RSV antibody of the present invention.

A further embodiment of the present invention is a polyclonal cell line wherein each individual cell is capable of expressing a single $V_H$ and $V_L$ coding pair, and the polyclonal cell line as a whole is capable of expressing a collection of $V_H$ and $V_L$ encoding pairs, where each $V_H$ and $V_L$ pair encodes an anti-RSV antibody. Preferably the collection of $V_H$ and $V_L$ coding pairs are cognate pairs generated according to the methods of the present invention.

A recombinant polyclonal antibody of the present invention is expressed by culturing one ampoule from a pWCB in an appropriate medium for a period of time allowing for sufficient expression of antibody and where the polyclonal cell line remains stable (The window is approximately between 15 days and 50 days). Culturing methods such as fed batch or perfusion may be used. The recombinant polyclonal antibody is obtained from the culture medium and purified by conventional purification techniques. Affinity chromatography combined with subsequent purification steps such as ion-exchange chromatography, hydrophobic interactions and gel filtration has frequently been used for the purification of IgG. Following purification, the presence of all the individual members in the polyclonal antibody composition is assessed, for example by ion-exchange chromatography. The characterization of a polyclonal antibody composition is described in detail in WO 2006/007853 (PCT/DK2005/000504) (hereby incorporated by reference).

An alternatively method of expressing a mixture of antibodies in a recombinant host is described in WO 2004/009618. This method produces antibodies with different heavy chains associated with the same light chain from a single cell line. This approach may be applicable if the anti-RSV rpAb is produced from a combinatorial library.

Therapeutic Compositions

Another aspect of the invention is a pharmaceutical composition comprising as an active ingredient an anti-RSV rpAb or anti-RSV recombinant polyclonal Fab or another anti-RSV recombinant polyclonal antibody fragment. Preferably, the active ingredient of such a composition is an anti-RSV recombinant polyclonal antibody as described in the present invention. Such compositions are intended for prevention and/or treatment, of RSV infections. Preferably, the pharmaceutical composition is administered to a human, a domestic animal, or a pet.

The pharmaceutical composition further comprises a pharmaceutically acceptable excipient.

Anti-RSV rpAb or polyclonal fragments thereof may be administered within a pharmaceutically-acceptable diluent, carrier, or excipient, in unit dosage form. Conventional pharmaceutical practice may be employed to provide suitable formulations or compositions to administer to patients infected with RSV, or to patients who may be at high risk if infected with RSV. In a preferred embodiment the administration is prophylactic. In another preferred embodiment the administration is therapeutic, meaning that it is administered after the onset of symptoms relating to RSV infection. Any appropriate route of administration may be employed, for example, administration may be parenteral, intravenous, intra-arterial, subcutaneous, intramuscular, intraperitoneal, intranasal, aerosol, suppository, or oral administration. For example, pharmaceutical formulations may be in the form of, liquid solutions or suspensions; for oral administration, formulations may be in the form of tablets, capsules, chewing gum or pasta, and for intranasal formulations, in the form of powders, nasal drops, or aerosols.

The pharmaceutical compositions of the present invention are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (20th ed.), ed. A. R. Gennaro, 2000, Lippincott Williams & Wilkins, Philadelphia, Pa. and Encyclopedia of Pharmaceutical Technology, eds. J. Swarbrick and J. C. Boylan, 1988-1999, Marcel Dekker, New York, N.Y.).

Preferably solutions or suspensions of the active ingredient, and especially isotonic aqueous solutions or suspensions, are used to prepare pharmaceutical compositions of the present invention. In the case of lyophilized compositions that comprise the active ingredient alone or together with a carrier, for example mannitol, such solutions or suspensions may, if possible, be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

The injection compositions are prepared in customary manner under sterile conditions; the same applies also to introducing the compositions into ampoules or vials and sealing of the containers.

Pharmaceutical compositions for oral administration can be obtained by combining the active ingredient with solid carriers, if desired granulating the resulting mixture, and processing the mixture, if desired or necessary, after the addition of appropriate excipients, into tablets, pills, or capsules, which may be coated with shellac, sugar or both. It is also possible for them to be incorporated into plastics carriers that allow the active ingredients to diffuse or be released in measured amounts.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, tablets, pills, or capsules. The formulations can be administered to human individuals in therapeutically or prophylactically effective amounts (e.g., amounts which prevent, eliminate, or reduce a pathological condition) to provide therapy for a disease or condition. The preferred dosage of therapeutic agent to be administered is likely to depend on such variables as the severity of the RSV infection, the overall health status of the particular patient, the formulation of the compound excipients, and its route of administration.

Therapeutic Uses of the Compositions According to the Invention

The pharmaceutical compositions according to the present invention may be used for the treatment, amelioration or prophylaxis of a disease in a mammal. Conditions that can be treated or prevented with the present pharmaceutical compositions include prevention, and treatment of patients infected with RSV, or at risk of becoming infected with RSV, in particular patients who may be at high risk if infected with RSV. High-risk patients are for example infants and small children. In particular premature infants and children with an underlying problem such as chronic lung disease or congenital heart disease are at the greatest risk for serious illness such as bronchiolitis and pneumonia following RSV infection. Also high-risk adults, such as immunocompromised adults, particularly bone marrow transplant recipients, elderly individuals and individuals with chronic pulmonary disease, can preferably be subjected to prophylactic or therapeutic treatment with a pharmaceutical composition according to the present invention.

One embodiment of the present invention is a method of preventing, treating or ameliorating one or more symptoms associated with a RSV infection in a mammal, comprising administering an effective amount of an anti-RSV recombinant polyclonal antibody of the present invention to said mammal.

A further embodiment of the present invention is the use of an anti-RSV recombinant polyclonal antibody of the present invention for the preparation of a composition for the treatment, amelioration or prevention of one or more symptoms associated with a RSV infection in a mammal.

The effective amount may be at most 100 mg of the antibody per kg of body weight, such as at most 90, at most 80, at most 70, at most 60, at most 50, at most 40, at most 30, at most 20, at most 10, at most 9, at most 8, at most 7, at most 6, at most 5, at most 4, at most 3, at most 2, at most 1, at most 0.9, at most 0.8, at most 0.7, at most 0.6, at most 0.5, at most 0.4, at most 0.3, at most 0.2 and at most 0.1. mg per kg of body weight.

In other embodiments the effective amount is at least 0.01 mg of the antibody per kg of body weight, such as at least 0.05, 0.1, 0.2, 0.3, 0.4, 0.5, 0.6, 0.7, 0.8.

Preferably the effective amount is between 0.1-50 mg antibody per kg of body weight. More preferably the effective amount is between 1 and 20 mg antibody per kg of body weight.

The antibody may be administered at least 1 time per year, such as 1, 2, 3, 4, 5, 6, 7, 8, 9, 10, 11, 12, 13, 14, 15, 16, 17, 18, 19, and 20 times per year.

In particular, the antibody may be administered at regular intervals during the period of the year where there is an increased risk of attracting an RSV infection. The regular intervals may be weekly, bi-weekly, monthly, or bi-monthly.

Preferably, the mammal in the embodiments above is a human, domestic animal or a pet.

In a further embodiment the mammal, subject to the method of preventing treating or ameliorating one or more symptoms associated with a RSV infection, preferably has a body weight above 40 kg.

In embodiments where the subject is a human, it is preferably a premature infant, a child with chronic lung disease or congenital heart disease. In alternative embodiments the human is an immunocompromised adult, in particularly a bone marrow transplant recipient, an elderly individual or an individual with chronic pulmonary disease.

Diagnostic Use

Another embodiment of the invention is directed to diagnostic kits. Kits according to the present invention comprise an anti-RSV rpAb prepared according to the invention which protein may be labeled with a detectable label or non-labeled for non-label detection. The kit may be used to identify individuals infected with RSV.

An antibody-based diagnostic kit generally comprises the following: a) a capture antibody, b) a detector antibody, c) a positive control, and d) a negative control. Depending on the detection method, a single reagent may be used both as capture and detector antibody. A method based on surface plasmon resonance (SPR) is one example were a single antibody will suffice both for capture and specific detection of the antigen of interest. The anti-RSV rpAb of the invention may be used both as capture antibody and as detector antibody. As capture antibody, the non-labeled anti-RSV rpAb is adsorbed onto a solid support, e.g. the surface of the wells of an ELISA plate or microbeads, for subsequent capture of RSV particles or antigens in patient samples. Captured antigen is then detected using a different antibody (detector), which is either directly labeled or detected using a secondary conjugated antibody or reagent of sufficient specificity. As detector antibody, the anti-RSV rpAb of the invention may be used labeled or non-labeled and the amount of bound antibody detected directly (labeled rpAb) or using a secondary antibody or reagent (unlabeled rpAb).

The read-out of the diagnostic kit may e.g. be based on detection of fluorescence from an attached fluorogenic label or absorbance of an added chromogenic substrate catalyzed by an enzyme conjugated to the detector antibody or the secondary antibody (enzyme immunoassay). In a method based on SPR, the amount of bound antigen is detected in real-time by the changes in the local index of refraction as it binds to the adsorbed capture antibody. Independent of the read-out, by comparing the intensity of the signal to a standard curve generated using the positive control, the quantity of antigen present in the sample may be determined.

Antibody Molecules of the Present Invention and Aspects Related Thereto

It should be noted that the novel antibody molecules disclosed herein are believed to contribute to the state of the art in their own right. Hence, the present invention also relates to any one of the antibody molecules disclosed herein as well as to fragments and analogues of these antibodies, where said fragments or analogues at least incorporate the CDRs of the antibodies disclosed herein.

For instance it has been found by the present inventors that some of the fully human antibody molecules which have been isolated from human donors include binding sites that exhibit extremely high improved kinetic profiles over known prior art monoclonal antibodies when it comes to antigen binding. Thus, even though much focus is put on polyclonal antibody compositions in the present disclosure, all subject matter relating to utilization of polyclonal antibodies set forth herein is also relevant for any one of the single antibody molecules disclosed herein—i.e. all disclosures relating to formulation, dosage, administration etc. which relate to polyclonal antibody compositions of the present invention apply mutatis mutandis to the individual antibody molecules, antibody fragments and antibody analogues disclosed herein, preferably also the framework sequences.

Hence, the present invention also relates to an isolated human anti RSV-antibody molecule selected from the antibody molecules set forth in Table 6 herein, or a specifically binding fragment of said antibody molecule or a synthetic or semi-synthetic antibody analogue, said binding fragment or analogue comprising at least the complementarity-determining regions (CDRs) of said isolated antibody molecule. Often, framework regions from the variable regions of the native human antibody will be included too in the fragments or analogues, since the antigen specificity of antibodies are known to be dependent on the 3D organisation of CDRs and framework regions.

The expression "isolated antibody molecule" is intended to denote a collection of distinct antibodies which are isolated from natural contaminants, and which exhibit the same amino acid sequence (i.e. identical variable and constant regions).

Typically, the antibody molecule, fragment or analogue is derived from the antibodies listed in Table 6, or includes the heavy chain CDR amino acid sequences included in one of SEQ ID Nos: 1-44 and in the accompanying light chain CDR amino acid sequences having a SEQ ID NO which is 88 higher than the amino acid sequence selected from SEQ ID NOs. 144. This means that the antibody molecule, fragment or analogue will include the cognate pairs of variable regions found in the same out of the 44 clones discussed above.

As mentioned above, a number of the present antibody molecules exhibit very high affinities, so the invention also pertains to an isolated antibody molecule, an antibody fragment or a synthetic or semi-synthetic antibody analogue, which comprises CDRs identical to the CDRs in an Fab derived from a human antibody, said Fab having a dissociation constant, $K_D$, for the RSV G protein of at most 500 nM when measured performing surface plasmon resonance analysis on a Biacore 3000, using recombinant RSV G protein immobilized onto the sensor surface at very low density to avoid limitations in mass transport. The isolated antibody molecule, antibody fragment or synthetic or semi-synthetic antibody typically exhibit a lower $K_D$ of at most, 400 nM, such as at most 300 nM, at most 200 nM, at most 100 nM, at most 1 nM, at most 900 pM, at most 800 pM, at most 700, pM, at most 600 pM, at most 500 pM, at most 400 pM, at most 300 pM, at most 200 pM, at most 100 pM, at most 90 pM, and at most 80 pM. Details concerning the Biocore measurements are provided in the examples.

Another embodiment of the invention relates to an isolated antibody molecule, an antibody fragment or a synthetic or semi-synthetic antibody, which comprises an antigen binding site identical to the antigen binding site in an Fab derived from a human antibody, said Fab having a dissociation constant, $K_D$, for the RSV F protein of at most 500 nM when measured performing surface plasmon resonance analysis on a Biacore 3000, using recombinant RSV F protein immobilized onto the sensor surface at very low density to avoid limitations in mass transport. This isolated antibody, antibody fragment or synthetic or semi-synthetic antibody typically exhibits a KD of at most, 400 nM, such as at most 300 nM, at most 200 nM, at most 100 nM, at most 1 nM, at most 900 pM, at most 800 pM, at most 700, pM, at most 600 pM, at most 500 pM, at most 400 pM, at most 300 pM, at most 200 pM, at most 100 pM, at most 90 pM, at most 80 pM, at most 70 pM, at most 60 pM, at most 50 pM, at most 40 pM, at most 30 pM, at most 25 pM at most 20 pM, at most 15 pM, at most 10 pM, at most 9 pM, at most 8 pM, at most 7 pM, at most 6 pM, and at most 5 pM.

A specially useful antibody molecule or specifically binding fragment or synthetic or semi-synthetic antibody analogue comprises the CDRs of a human antibody produced in clone No. 810, 818, 819, 824, 825, 827, 858 or 894.

As mentioned above, these useful antibody molecules of the present invention may be formulated in the same way and for the same applications as the polyclonal formulations of the present invention. Hence, the present invention relates to an antibody composition comprising an antibody molecule, specifically binding fragment or synthetic or semi-synthetic antibody analogue discussed in this section in admixture with a pharmaceutically acceptable carrier, excipient, vehicle or diluent. The composition may comprise more than one binding specificity, and may e.g. include 2 distinct antibody molecules of the invention and/or specifically binding fragments and/or synthetic or semi-synthetic antibody analogues of the invention. The composition may even comprise at least 3 distinct antibody molecules and/or antibody fragments and/or synthetic or semisynthetic antibody analogues, specifically binding fragments or synthetic or semi-synthetic antibody analogues of the invention, and may therefore constitute a composition comprising at 4, 5, 6, 7, 9, 10, 11, 12, 13, 15, 16, 17, 18, 19, 20, 21, 22, 23, 24, 25, 26, 27, 28, 29 or 30 distinct antibody molecules and/or fragments and/or synthetic or semi-synthetic antibody analogues.

Especially interesting compositions include at least one antibody molecule, fragment or analogue of the invention which binds the RSV F protein and at least one antibody, fragment or analogue of the invention which binds the RSV G protein.

Also a part of the present invention is an isolated nucleic acid fragment which encodes the amino acid sequence of at least one CDR defined of an antibody molecule of the present invention, such as a nucleic acid fragment, which at least encodes the CDRs of an antibody produced by one of the clones listed in table 6. The nucleic acid fragment is typically DNA, but can also be RNA.

Another embodiment is an isolated nucleic acid fragment, which encodes the CDR sequences of a heavy chain amino acid sequence set forth in any one of SEQ ID NOs 1-44, or an isolated nucleic acid fragment, which encodes the CDR sequences of a light chain amino acid sequence set forth in any one of SEQ ID NOs 89-132. Preferred nucleic acid fragments of the invention encode the CDR sequences of a heavy chain amino acid sequence set forth in any one of SEQ ID NOs 1-44 and set forth in the accompanying light chain CDR amino acid sequences having a SEQ ID NO which is 88 higher than the amino acid sequence selected from SEQ ID NOs. 144. This of course means that the nucleic acid fragment will encode the cognate pairs of variable regions found in the same out of the 44 clones discussed above. The nucleic acid fragment may therefor include coding sequences comprised in SEQ ID NOs: 45-88 and/or 133-176.

Conveniently the nucleic acid fragments are introduced in a vector, which is also part of the present invention. Such a vector may be capable of autonomous replication, and is typically selected from the group consisting of a plasmid, a phage, a cosmid, a mini-chromosome, and a virus.

In the event the vector of the invention is an expression vector, it will preferably have the following outline (cf. also an exemplary vector in FIG. 3): (a) in the 5'→3' direction and in operable linkage at least one promoter for driving expression of a first nucleic acid fragment discussed above, which encodes at least one light chain CDR together with any necessary framework regions, optionally a nucleic acid sequence encoding a leader peptide, said first nucleic acid fragment, optionally a nucleic acid sequence encoding constant regions of an antibody, and optionally a nucleic acid sequence encoding a first terminator, and/or (b) in the 5'→3' direction and in operable linkage at least one promoter for driving expression of a second nucleic acid fragment of the invention, which encodes at least one heavy chain CDR together with any necessary framework regions, optionally a nucleic acid sequence encoding a leader peptide, said second nucleic acid fragment, optionally a nucleic acid sequence encoding constant regions, and optionally a nucleic acid sequence encoding a second terminator.

Such a vector is especially useful if it can be used to stably transform a host cell, which can subsequently be cultured in order to obtain the recombinant expression product. So, the preferred vector is one, which, when introduced into a host cell, is integrated in the host cell genome.

Hence, the invention also pertains to a transformed cell carrying the vector of the invention discussed in this section and also to a stable cell line which carries this vector and which expresses the nucleic acid fragment of the invention discussed in this section. Both the transformed cell and the cell line optionally secretes or carries its recombinant expression product (i.e. the inventive antibody molecule, antibody fragment or analogue) on its surface.

mAb 824 and Analogues

The present section relates to the monoclonal antibody 824 (mAb 824) and its analogues. The light chain of antibody 824 has the amino acid sequence set forth in SEQ ID NO 107. The variable region of the heavy chain has the amino acid sequence set forth in SEQ ID NO 19.

The invention relates to antibodies capable of competing in binding with antibody 824 as defined herein or with its Fab fragment. The antibody encoded by clone 824 as defined herein does not bind recombinant RSV antigen with particularly high affinity or potency. On the other hand, in virus neutralization assays (see Table 8) antibody 824 has a particularly low EC50 value against several different RSV isolates. When tested in an in vivo model of RSV infection (mouse challenge model, Example 1, k-1), mAb824 showed a significantly higher reduction in virus load than Synagis (Table 11b).

By providing antibody 824 the inventors have identified an epitope, which results in more efficient in vitro and in vivo neutralization than seen before for any single RSV epitope.

By providing antibody 824, the inventors have also enabled the identification of further antibodies which bind to the same epitope. These further antibodies may be of any origin and includes binding fragments as well as affinity matured antibodies. Antibodies capable of competing with antibody 824 may be identified in a cellular competition assay (determination of relative epitope specificities) as described in Example 1, section g-4.

A preferred antibody being capable of competing with antibody 824 is an anti-RSV antibody comprising a CDRH3 having the following formula: $CAX_1X_2X_3X_4X_5X_6PX_7X_8X_9X_{10}X_{11}W$ where $X_1$ to $X_{11}$ are selected individually from the groups of amino acids listed below
$X_1$=R or K (i.e. positively charged at physiological pH);
$X_2$=D, E, N or Q (i.e. fairly bulky, polar amino acids);
$X_3$=S, T, G or A (i.e. small, preferably polar amino acids);
$X_4$=S, T, G or A (i.e. small, preferably polar amino acids);
$X_5$=N, Q, D or E (i.e. fairly bulky, polar amino acids);
$X_6$=W, Y, F or H (i.e. bulky, aromatic amino acids);
$X_7$=A, G, V, or S (i.e. small amino acids);
$X_8$=G, A, V, or S (i.e. small amino acids);
$X_9$=Y, F, W or H (i.e. bulky, aromatic amino acids);
$X_{10}$=E or D (i.e. negatively charged at physiological pH); and
$X_{11}$=D, E, N or Q (i.e. fairly bulky, polar amino acids);
and a CDRL3 described by the following formula: $CX_1X_2X_3X_4X_5X_6PX_7TF$
where $X_1$ to $X_{11}$ are selected individually from the groups of amino acids listed below:
$X_1$=Q or H (i.e. bulky, polar amino acids);
$X_2$=Q, E or H (i.e. bulky, polar amino acids);
$X_3$=F, Y, W or H (i.e. bulky, aromatic amino acids);
$X_4$=N, Q or H (i.e. fairly bulky, polar amino acids);
$X_5$=T, S, G or A (i.e. small, preferably polar amino acids);
$X_6$=Y, F, W or H (i.e. bulky, aromatic amino acids); and
$X_7$=F, Y, W or H (i.e. bulky, aromatic amino acids).

The binding specificity of antibodies is determined primarily by the CDR3 region of the heavy and light chain. As is known in the art certain substitutions can be made in an amino acid sequence without altering the 3-D structure of the protein. It is thus expected that mutations as outlined above can be made to the CDR3 sequences of antibody 824 as defined herein while conserving the binding specificity and the potency of antibody 824.

The introduction of amino acid changes in a protein is known in the art. Antibodies with altered CDR3s compared to antibody 824 can be made and they can be tested in the virus neutralization assays as described in the examples. Conservation of the binding specificity can be verified in a competition assay with antibody 824.

Preferably, the anti-RSV antibody comprises the CDR1, and CDR2 regions from the VH and VL pair of antibody 824 as set forth in SEQ ID NOs: 232, 317, 487, and 572, and a CDRH3 region having the formula $CAR_1D_2S_3S_4N_5W_6PA_7G_8Y_9E_{10}D_{11}W$ (SEQ ID NO 402), and a CDRL3 region having the formula $CQ_1Q_2F_3N_4T_5Y_6PF_7TF$ (SEQ ID NO 657).

In preferred embodiments the CDRH3 has the amino acid sequence set forth in SEQ ID NO: 402 and/or the CDRL3 has the amino acid sequence set forth in SEQ ID NO: 657.

In one embodiment the antibody comprises the VH region (SEQ ID NO: 19) of antibody 824. The monoclonal antibody may also comprise the VL region (amino acids 1 to 107 of SEQ ID NO: 107) of antibody 824.

Preferably, the antibody comprises the light chain (SEQ ID NO: 107) of antibody 824.

The antibody may comprise the CH as defined in SEQ ID NO: 178. Other constant regions for the heavy chain may be used.

Preferably, the monoclonal antibody is capable of neutralizing subtypes A and B of RSV in a virus neutralization assay. The neutralization potency of the monoclonal antibody is preferably comparable to the potency of mAb824.

Preferably, the antibody is capable of providing a significant reduction of RSV virus load in the lungs of a mammal infected with RSV. Preferably this reduction is significant compared to the reduction provided by Synagis, and more preferably the reduction is comparable to the reduction provided by mAb824.

Antibody mAb824 and antibodies based on the CDR sequences of mAb824 may be combined with and one or more additional anti-RSV antibodies to provide a polyclonal antibody. Such polyclonal antibody or antibody mixture(s) may be less susceptible to escape mutants.

The one or more additional anti-RSV antibodies may be selected from the group consisting of human antibodies, humanized antibodies, and chimeric human-mouse antibodies. For example the additional antibody may be palivizumab (Synagis) or MEDI-524 (Numax).

Preferably, the one or more additional anti-RSV antibodies is selected from the group consisting of the antibody molecules set forth in Table 6 herein, or a specifically binding fragment of said antibody molecule or a synthetic or semi-synthetic antibody analogue, said binding fragment or analogue comprising at least the complementarity-determining regions (CDRs) of said isolated antibody molecule, except an antibody having the CDRs of clone 824.

Also provided are isolated nucleic acids comprising a sequence encodes an amino acid sequence of at least one CDR defined in this section.

The isolated nucleic acid fragment may encode the CDR sequences of a heavy chain amino acid sequence set forth in SEQ ID NO: 19. The isolated nucleic acid fragment may encode the CDR sequences of the light chain amino acid sequence set forth in SEQ ID NO: 107.

Preferably the isolated nucleic acid fragment encodes the CDR sequences of the heavy chain amino acid sequence set forth in SEQ ID NO: 19 and in the accompanying light chain CDR amino acid sequences having SEQ ID NO: 107. In another preferred embodiment the nucleic acid fragment includes coding sequences comprised in SEQ ID NO: 63 and/or 151.

The isolated nucleic acids and fragments may be inserted in to a vector.

The vector may be capable of autonomous replication and could be selected from the group consisting of a plasmid, a phage, a cosmid, a mini-chromosome, and a virus.

In another embodiment the vector comprises,
(a) in the 5'→3' direction and in operable linkage at least one promoter for driving expression of a first nucleic acid fragment as described in this section, which encodes at least one light chain CDR derived from clone 824 together with necessary framework regions, optionally a nucleic acid sequence encoding a leader peptide, said first nucleic acid fragment, optionally a nucleic acid sequence encoding constant regions, and optionally a nucleic acid sequence encoding a first terminator, and/or
(b) in the 5'→3' direction and in operable linkage at least one promoter for driving expression of a second nucleic acid fragment as described in this section, which encodes at least one heavy chain CDR derived from clone 824 together with necessary framework regions, optionally a nucleic acid sequence encoding a leader peptide, said second nucleic acid fragment, optionally a nucleic acid sequence encoding constant regions, and optionally a nucleic acid sequence encoding a second terminator.

The vector when introduced into a host cell, may be integrated in the host cell genome.

Also provided is as transformed cell carrying the vector as described in this section, and a stable cell line which carries the vector as described in this section and which expresses a nucleic acid fragment as described in this section, and which optionally secretes or carries its recombinant expression product on its surface.

EXAMPLE 1

This example is a collection of the methods applied to illustrate the present invention.

a. Sorting of Lambda-Negative Plasma Blasts from Donor Blood

The peripheral blood mononuclear cells (PBMC) were isolated from blood drawn from donors using Lymphoprep (Axis Shield) and gradient centrifugation according to the manufacturer's instructions. The isolated PBMC were either cryopreserved in FCS; 10% DMSO at −150° C. or used directly. The B cell fraction was labeled with anti-CD19 antibody and isolated from the PBMC fraction using magnetic cell sorting (MACS). The PBMC (1×10⁶ cells) were incubated with anti-CD19-FITC conjugated antibody (BD Pharmingen) for 20 min at 4° C. Cells were washed twice in, and re-suspended in MACS buffer (Miltenyi Biotec). Anti-FITC MicroBeads (Miltenyi Biotec) were mixed with the labeled cells and incubated for 15 min at 4° C. The washing procedure was repeated before the cell-bead suspension was applied to a LS MACS column (Miltenyi Biotec). The CD19 positive cell fraction was eluted from the column according to the manufactures instructions and either stored in FCS-10% DMSO, or single-cell sorted directly.

Plasma blasts were selected from the CD19⁺ B cell fraction by fluorescence activated cell sorting (FACS) based on the expression profile of CD19, CD38, and CD45 cell surface proteins. CD19 is a B-cell marker that is also expressed on plasma cell precursors, while CD38 is highly expressed on plasma blasts and plasma cells. The plasma blasts apparently have a somewhat lower expression of CD19 and CD45 than the rest of the CD19⁺ cells, which allows for the separation of a discrete population. The cells were washed in FACS buffer (PBS; 1% BSA) and stained for 20 min with anti-CD19-FITC, anti-CD38-APC, anti-Lambda-PE (BD Pharmingen). The Lambda-light chain staining was included in order to allow exclusion of cells that cannot serve as template for the PCR (see Section c). The stained cells were washed and re-suspended in FACS buffer.

The flow rate of the cells during the FACS was set at approximately 200 events/sec and the cell concentration was 5×10⁵/ml to obtain a high plasma cell rescue. The following set of gates was used. Each gate is a daughter of the former.

Gate 1: FSC/SSC gate. The lymphocyte population having the highest FSC was selected, thereby ensuring sorting of living cells.

Gate 2: SSCh/SSCw. This gate ensured sorting of single cells (doublet discrimination).

Gate 3: Events representing the plasma blasts were gated in the CD38/CD19 dot plot as CD38 High/CD19 intermediate.

Gate 4: Since the PCR procedure described in Section c only amplifies Kappa light chains, Lambda-negative events were gated in a Lambda/CD19 dot plot.

As an alternative or in addition to gate 3, the plasma blasts could also be identified as CD38high and CD45intermediate in a CD45/CD38 dot plot. This will require staining of the cells with anti-CD45-PerCP.

The resulting population that fulfilled these four criteria was single-cell sorted into 96-well PCR plates containing a sorting buffer (see Section c). The plates containing the cells were stored at −80° C.

b. ELISpot

ELISpot was used to estimate the percentage of plasma blasts expressing anti-RSV antibodies in obtained cell samples, i.e., PBMC, MACS-purified CD19⁺ cells, or a population of FACS sorted plasma blasts. 96-well plates with a nitrocellulose surface (Millipore) were coated with a solution of 25 µg/ml inactivated RSV Long particles (HyTest). The wells were blocked by incubation with RPMI, 2% milk powder and left at 4° C. for approximately 5 h followed by 1 h incubation at 37° C. Plates were washed and the cell samples were added in RPMI culture medium to each well followed by incubation at standard tissue culture conditions for 24 h. The secreted RSV-specific antibodies will bind to the immobilized virus particles surrounding the antibody producing cell. The cells were removed by washing three times in PBS; 0.01% Tween20 and three times in PBS. HRP-conjugated anti-human IgG (H+L) (CalTag) and HRP-conjugated anti-human IgA (Serotec) were added and allowed to react with the immobilized antibodies for 1 h at 37° C. The washing procedure was repeated and the chromogen substrate (3-amino-9-ethylcarbazole solubilized in N,N-DMF (di-methyl formamide)) was added. The color development was terminated after 4 min by addition of $H_2O$. Red spots were identified at the sites where antigen-specific antibody-secreting cells had been located.

c. Linkage of Cognate $V_H$ and $V_L$ Pairs

The linkage of $V_H$ and $V_L$ coding sequences was performed on the single cells obtained as described in Section a, facilitating cognate pairing of the $V_H$ and $V_L$ coding sequences. The procedure utilized a two step PCR procedure based on a one-step multiplex overlap-extension RT-PCR followed by a nested PCR. The primer mixes used in the present example only amplify Kappa light chains. Primers capable of amplifying Lambda light chains could, however, be added to the multiplex primer mix and nested PCR primer mix if desired. If Lambda primers are added, the sorting procedure in Section a should be adapted such that Lambda positive cells are not excluded. The principle for linkage of cognate $V_H$ and $V_L$ sequences is illustrated in FIG. 2.

The 96-well PCR plates produced in Section a, were thawed and the sorted cells served as template for the multiplex overlap-extension RT-PCR. The sorting buffer added to each well before the single-cell sorting contained reaction buffer (OneStep RT-PCR Buffer; Qiagen), primers for RT-PCR (see Table 2) and RNase inhibitor (RNasin, Promega). This was supplemented with OneStep RT-PCR Enzyme Mix (25× dilution; Qiagen) and dNTP mix (200 µM each) to obtain the given final concentration in a 20-µl reaction volume.

The plates were incubated for 30 min at 55° C. to allow for reverse transcription of the RNA from each cell. Following the RT, the plates were subjected to the following PCR cycle: 10 min at 94° C., 35×(40 sec at 94° C., 40 sec at 60° C., 5 min at 72° C.), 10 min at 72° C.

The PCR reactions were performed in H20BIT Thermal cycler with a Peel Seal Basket for 24 96-well plates (ABgene) to facilitate a high-throughput. The PCR plates were stored at −20° C. after cycling.

TABLE 2

RT-PCR multiplex overlap-extension primer mix

| Primer name | Final Conc. nM | Sequence | SEQ ID NO: |
|---|---|---|---|
| VH set | | | |
| CH-IgG | 0.2 | GACSGATGGGCCCTTGGTGG | 179 |
| CH-IgA | 0.2 | GAGTGGCTCCTGGGGAAGA | 180 |
| VH-1 | 0.04 | TATTCCCATGGCGCGCCCAGRTGCAGCTGGTGCART | 181 |
| VH-2 | 0.04 | TATTCCCATGGCGCGCCSAGGTCCAGCTGGTRCAGT | 182 |
| VH-3 | 0.04 | TATTCCCATGGCGCGCCCAGRTCACCTTGAAGGAGT | 183 |
| VH-4 | 0.04 | TATTCCCATGGCGCGCCSAGGTGCAGCTGGTGGAG | 184 |
| VH-5 | 0.04 | TATTCCCATGGCGCGCCCAGGTGCAGCTACAGCAGT | 185 |
| VH-6 | 0.04 | TATTCCCATGGCGCGCCCAGSTGCAGCTCAGGAGT | 186 |
| VH-7 | 0.04 | TATTCCCATGGCGCGCCGARGTGCAGCTGGTGCAGT | 187 |
| VH-8 | 0.04 | TATTCCCATGGCGCGCCCAGGTACAGCTGCAGCAGTC | 188 |
| LC set | | | |
| CK1 | 0.2 | ATATATATGCGGCCGCTTATTAACACTCTCCCCTGTTG | 189 |
| VL-1 | 0.04 | GGCGCGCCATGGGAATAGCTAGCCGACATCCAGWTGACCCAGTCT | 190 |
| VL-2 | 0.04 | GGCGCGCCATGGGAATAGCTAGCCGATGTTGTGATGACTCAGTCT | 191 |
| VL-3 | 0.04 | GGCGCGCCATGGGAATAGCTAGCCGAAATTGTGWTGACRCAGTCT | 192 |
| VL-4 | 0.04 | GGCGCGCCATGGGAATAGCTAGCCGATATTGTGATGACCCACACT | 193 |
| VL-5 | 0.04 | GGCGCGCCATGGGAATAGCTAGCCGAAACGACACTCACGCAGT | 194 |
| VL-6 | 0.04 | GGCGCGCCATGGGAATAGCTAGCCGAAATTGTGCTGACTCAGTCT | 195 |

W = A/T, R = A/G, S = G/C

For the nested PCR step, 96-well PCR plates were prepared with the following mixture in each well (20-μl reactions) to obtain the given final concentration: 1× FastStart buffer (Roche), dNTP mix (200 μM each), nested primer mix (see Table 3), Phusion DNA Polymerase (0.08 U; Finnzymes) and FastStart High Fidelity Enzyme Blend (0.8 U; Roche). As template for the nested PCR, 1 μl was transferred from the multiplex overlap-extension PCR reactions. The nested PCR plates were subjected to the following PCR cycle: 35×(30 sec at 95° C., 30 sec at 60° C., 90 sec at 72° C.), 10 min at 72° C.

Randomly selected reactions were analyzed on a 1% agarose gel to verify the presence of an overlap-extension fragment of approximately 1070 bp.

The plates were stored at −20° C. until further processing of the PCR fragments.

TABLE 3

Nested primer set

| Primer name | Final Conc. nM | Sequence | SEQ ID |
|---|---|---|---|
| CK2 | 0.2 | ACCGCCTCCACCGGCGGCCGCTTATTAACACTCTCCCCTGTTGAAGCTCTT | 196 |
| PJ 1-2 | 0.2 | GGAGGCGCTCGAGACGGTGACCAGGGTGCC | 197 |
| PJ 3 | 0.2 | GGAGGCGCTCGAGACGGTGACCATTGTCCC | 198 |
| PJ 4-5 | 0.2 | GGAGGCGCTCGAGACGGTGACCAGGGTTCG | 199 |
| PJ 6 | 0.2 | GGAGGCGCTCGAGACGGTGACCGTGGTCCC | 200 | d. Insertion of Cognate $V_H$ and $V_L$ Coding Pairs into a Screening Vector

In order to identify antibodies with binding specificity to RSV particles or antigens, the $V_H$ and $V_L$ coding sequences obtained as described in Section c were expressed as full-length antibodies. This involved insertion of the repertoire of $V_H$ and $V_L$ coding pairs into an expression vector and transformation into a host cell.

A two-step cloning procedure was employed for generation of a repertoire of expression vectors containing the linked $V_H$ and $V_L$ coding pairs. Statistically, if the repertoire of expression vectors contains ten times as many recombinant plasmids as the number of cognate paired $V_H$ and $V_L$ PCR products used for generation of the screening repertoire, there is 99% likelihood that all unique gene pairs are represented. Thus, if 400 overlap-extension V-gene fragments were obtained in Section c, a repertoire of at least 4000 clones was generated for screening.

Briefly, the repertoires of linked $V_H$ and $V_L$ coding pairs from the nested PCR in Section c were pooled (without mixing pairs from different donors). The PCR fragments were cleaved with XhoI and NotI DNA endonucleases at the recognition sites introduced into the termini of PCR products. The cleaved and purified fragments were ligated into an XhoI/NotI digested mammalian IgG expression vector (FIG. 3) by standard ligation procedures. The ligation mix was electroporated into E. coli and added to 2×YT plates containing the appropriated antibiotic and incubated at 37° C. over night. The amplified repertoire of vectors was purified from cells recovered from the plates using standard DNA purification methods (Qiagen). The plasmids were prepared for insertion of promoter-leader fragments by cleavage using AscI and NheI endonucleases. The restriction sites for these enzymes were located between the $V_H$ and $V_L$ coding gene pairs. Following purification of the vector, an AscI-NheI digested bi-directional mammalian promoter-leader fragment was inserted into the AscI and NheI restriction sites by standard ligation procedures. The ligated vector was amplified in E. coli and the plasmid was purified using standard methods. The generated repertoire of screening vectors was transformed into E. coli by conventional procedures. Colonies obtained were consolidated into 384-well master plates and stored. The number of arrayed colonies exceeded the number of input PCR products by at least 3-fold, thus giving 95% percent likelihood for presence of all unique V-gene pairs obtained in Section c.

e. Screening

The bacterial colonies arrayed in Section d were inoculated into culture medium in similar 384-well plates and grown overnight. DNA for transfection was prepared from each well in the cell culture plate. The day prior to transfection 384-well plates were seeded with CHO Flp-In cells (Invitrogen) at 3000 cells/well in 20 µl culture medium. The cells were transfected with the DNA using Fugene6 (Roche) according to the manufactures instructions. After 2-3 days incubation the full-length antibody-containing supernatants were harvested and stored for screening purposes.

Screening was performed using the Applied Biosystems 8200 FMAT™ System, a homogeneous bead-based soluble capture FLISA (fluorescent linked immunosorbent assay) (Swartzman et al. 1999, Anal. Biochem. 271:143-151). A number of antigens, including virus particles, recombinant G protein and biotinylated peptides derived from RSV antigens, were used for the screening. The peptides were derived from the conserved region (amino acids 164-176) and the cysteine core region (amino acids 171-187, strain Long and 18537) of the G protein and the extracellular region of the SH-protein (amino acids 42-64 of the A2 strain and 42-65 of the 18537 strain). Inactivated virus particles of RSV strain Long (HyTest) were immobilized on polystyrene beads by incubating 300 µl 5% w/v beads (6.79 µm diameter, Spherotech Inc.) with 300 µl virus stock (protein concentration: 200 µg/ml). Soluble recombinant G protein (amino acids 66-292 of the 18537 strain sequence) was similarly immobilized directly on polystyrene beads, whereas the biotinylated peptides were captured on precoated streptavidin polystyrene beads (6.0-8.0 µm diameter, Gerlinde Kisker) at saturating concentrations. The coating mixture was incubated overnight and washed twice in PBS. Beads were re-suspended in 50 ml PBS containing 1% bovine serum albumin (PBS/BSA) and 5 µl goat-anti-human IgG Alexa 647 conjugate (Molecular probes). Ten 1µl of re-suspended coating mixture was added to 20 µl antibody-containing supernatant in FMAT-compatible 384-well plates and incubated for approximately 12 h, after which the fluorescence at the bead surface in individual wells was measured. A fluorescence event was recognized as positive if its intensity was at least six standard deviations above the background baseline.

The clones resulting in primary hits were retrieved from the original master plates and collected in new plates. DNA was isolated from these clones and submitted for DNA sequencing of the V-genes. The sequences were aligned and all the unique clones were selected.

The selected clones were further validated. Briefly, $2 \times 10^6$ Freestyle 293 cells (Invitrogen) were transfected with 1.7 µg DNA from the selected clones and 0.3 µg pAdVAntage plasmid (Promega) in 2 ml Freestyle medium (Invitrogen) according to the manufacturers' instructions. After two days, supernatants were tested for IgG expression and reactivity with the different antigens used for the primary screening as well as recombinant purified F protein and an *E. coli* produced fragment of the G protein (amino acids 127-203 of the 18537 strain sequence) by FLISA and/or ELISA. Antibody supernatants were tested in serial dilutions allowing for a ranking of clones according to antigen reactivity.

f. Clone Repair

When using a multiplex PCR approach as described in Section c, a certain degree of intra- and inter-V-gene family cross-priming is expected due to the high degree of homology. The cross-priming introduces amino acids that are not naturally occurring in the immunoglobulin framework with several potential consequences, e.g. structural changes and increased immunogenicity, all resulting in a decreased therapeutic activity.

In order to eliminate these drawbacks and to ensure that selected clones mirror the natural humoral immune response, such cross-priming mutations were corrected in a process called clone repair.

In the first step of the clone repair procedure, the $V_H$ sequence was PCR amplified with a primer set containing the sequence corresponding to the $V_H$-gene the clone of interest originated from, thereby correcting any mutations introduced by cross-priming. The PCR fragment was digested with XhoI and AscI and ligated back into the XhoI/AscI digested mammalian expression vector (FIG. 3) using conventional ligation procedures. The ligated vector was amplified in *E. coli* and the plasmid was purified by standard methods. The $V_H$ sequence was sequenced to verify the correction and the vector was digested with NheI/NotI to prepare it for insertion of the light chain.

In the second step the complete light chain was PCR amplified with a primer set containing the sequence corresponding to the $V_L$-gene the clone of interest originated from, thereby correcting any mutations introduced by cross-priming. The PCR fragment was digested with NheI/NotI and ligated into the $V_H$ containing vector prepared above. The ligation product was amplified in *E. coli* and the plasmid was purified by standard methods. Subsequently, the light chain was sequenced to verify the correction.

In the case where the Kappa constant region of a selected clone contained mutations, introduced during the amplification of the genes as described in Section c, it was replaced by an unmutated constant region. This was done in an overlap PCR where the repaired $V_L$-gene (amplified without the constant region) was fused to a constant region with correct sequence (obtained in a separate PCR). The whole sequence was amplified and cloned into the $V_H$ containing vector as described above and the repaired light chain was sequenced to verify the correction.

g. Generation of a Polyclonal Cell Line

The generation of a polyclonal expression cell line producing a recombinant polyclonal antibody is a multi-step procedure involving the generation of individual expression cell lines which each express a unique antibody from a single $V_H$ and $V_L$ gene sequence. The polyclonal cell line is obtained by mixing the individual cell lines and distributing the mixture into ampoules thereby generating a polyclonal research cell bank (pRCB) or master cell bank (pMCB) from which a polyclonal working cell bank (pWCB) can be generated by expanding cells from the research or master cell bank. Generally, the polyclonal cell lines from the pRCB are used directly without generating a pWCB.

The individual steps in the process of generating a polyclonal cell line are described below.

g-1 Transfection and Selection of Mammalian Cell Lines

The Flp-In CHO cell line (Invitrogen) was used as starting cell line. In order to obtain a more homogenous cell line the parental Flp-In CHO cell line was sub-cloned by limited dilution and several clones were selected and expanded. Based on growth behavior one clone, CHO-Flp-In (019), was selected as starting cell line. The CHO-Flp-In (019) cells were cultured as adherent cells in HAM-F12 with 10% fetal calf serum (FCS).

The individual plasmid preparations each containing a selected and repaired $V_H$ and $V_L$ coding pair obtained in Section f, were co-transfected with Flp recombinase encoding plasmid into ~19×10⁶ CHO-Flp-In (019) cells (for further details, see WO 04/061104) in a T175 flask using Fugene6 (Roche). Cells were trypsinated after 24 h and transferred to a 2-layer (1260 cm²) cell factory (Nunc). Recombinant cell lines were selected by culturing in the presence of 500 μg/ml Geneticin, which was added 48 h after transfection. Approximately two weeks later clones appeared. Clones were counted and cells were trypsinated and hereafter cultured as pools of clones expressing one of the RSV-specific antibodies.

g-2 Adaptation to Serum Free Suspension Culture

The individual adherent anti-RSV antibody expressing cell cultures were trypsinated, centrifuged and transferred to separate shaker flasks (250 ml) with 1.15×10⁶ cells/ml in appropriate serum free medium (Excell302, JRH Biosciences; 500 μg/ml Geneticin, anti-clumping agent (1:250) and 4 mM L-glutamin). Growth and cell morphology were followed over several weeks. After 4-6 weeks the cell lines usually showed good and stable growth behavior with doubling times below 30 h and the adapted individual cell lines were then cryopreserved in multiple ampoules.

The individual antibodies expressed during adaptation were purified from the supernatants using the method described in Section i). The purified antibody was used for the characterization of antigen specificity and biochemical properties as described below.

g-3 Characterization of Cell Lines

All the individual cell lines were characterized with respect to antibody production and proliferation. This was performed with the following assays:

Production:

The production of recombinant antibodies of the individual expression cell lines were followed during the adaptation by Kappa specific ELISA. ELISA plates were coated overnight with goat-anti-human Fc purified antibody (Serotec) in carbonate buffer, pH 9.6. Plates were washed 6 times with washing buffer (PBS; 0.05% Tween 20) and blocked by incubation for 1 h in washing buffer containing 2% skim milk. Cell culture media supernatants were added and the incubated extended for 1 h. Plates were washed 6 times in washing buffer and secondary antibodies (goat-anti-human Kappa HRP, Serotec) were added and the incubation repeated. After vigorous washing the ELISA was developed with TMB substrate and reaction stopped by addition of $H_2SO_4$. Plates were read at 450 nm.

Further, intracellular staining was used to determine the general expression level as well as to determine the homogeneity of the cell population in relation to expression of recombinant antibody. 5×10⁵ cells were washed in cold FACS buffer (PBS; 2% FCS) before fixation by incubation in CellFix (BD-Biosciences) for 20 min. Cells were pelleted and permeabilized in ice cold methanol for 10 min and washed twice in FACS buffer. The suspension was fluorescently tagged antibody (Goat F(ab')₂ Fragment, Anti-human IgG(H+L)-PE, Beckman Coulter) was added. After 20 min on ice the cells were washed and re-suspended in FACS buffer followed by FACS analysis.

Proliferation:

Aliquots of the cell suspensions were taken two to three times a week and cell number, cell size and viability was determined by Vi-Cell XR (Cell viability analyzer, Beckman Coulter) analysis. The doubling time for the cell cultures was calculated using the cell numbers derived from Vi-Cell measurements.

g-4 Characterization of the Antigen Specificity of the Individual Antibodies

The antigen and epitope specificity of the individually expressed antibodies was assessed in order to allow for the generation of an anti-RSV rpAb with a well-characterized specificity. As already described in Section e, the antibodies identified during screening were validated by assessing their binding specificity to single RSV antigens (recombinant G protein, recombinant or purified F protein) or peptide fragments thereof (conserved region and cysteine-core motif of protein G, subtype A and B, known linear epitopes on protein F, and the extracellular domain of SH protein, subtype A and B) by FLISA, ELISA and surface plasmon resonance (SPR; Biacore). The epitope specificities were determined in ELISA by competition with well-characterized commercial antibodies, some of which are shown in Table 4. Not necessarily all the antibodies shown in Table 4 were used in the characterization of each individual antibody of the present invention, and potentially other antibodies or antibody fragments which have been characterized with respect to the antigen, antigenic site and/or epitope they bind may also be used. Briefly, the antibodies or antibody fragments used for epitope blocking were incubated with the immobilized antigen (RSV Long particles, HyTest) in large excess, i.e. concentrations 100 times the ones giving 75% maximum binding, as determined empirically(Ditzel et al., J. Mol. Biol. 1997, 267:684-695). Following washing, the individual antibody clones were incubated with the blocked antigen at various concentrations and any bound human IgG was detected using a Goat-anti-Human HRP conjugate (Serotec) according to standard ELISA protocols. Epitope specificities were further characterized by pair-wise competition between different antibody clones in Biacore using saturating concentrations (empirically determined) of both blocking and probing antibodies. Purified F or G protein immobilized by direct amine coupling (Biacore) was used as antigen. In both the ELISA- and Biacore-based epitope mapping, the reduced binding following epitope blocking was compared to the uncompeted binding.

TABLE 4

Monoclonal antibodies for epitope mapping of anti-F and anti-G antibodies

| MAb/Fab | Antigen | Antigenic Site | Epitope (aa) | Ref. |
|---|---|---|---|---|
| 131-2a | F | F1 | F1a | 1, 2 |
| 9C5 | F | F1 | F1a | 5 |
| 92-11c | F | F1 | F1b | 1, 2 |
| 102-10b | F | F1 | F1c | 1, 2 |
| 133-1h | F | C | F2 | 1, 2, 3 |
| 130-8f | F | C | F2 (241/421) | 1, 2, 3, 4 |
| 143-6c | F | A/II | F3 | 1, 2, 3 |
| Palivizumab | F | A/II | (272) | 8 |
| 1153 | F | A/II | (262) | 3, 4 |
| 1142 | F | A/II |  | 3 |
| 1200 | F | A/II | (272) | 2, 4 |
| 1214 | F | A/II | (276) | 3, 4 |
| 1237 | F | A/II | (276) | 3, 4 |
| 1129 | F | A/II | (275) | 3, 4 |
| 1121 | F | A/II |  | 3 |
| 1112 | F | B/I | (389) | 3, 6 |
| 1269 | F | B/I | (389) | 3, 6 |
| 1243 | F | C | (241/421) | 3, 6 |
| Fab 19 | F | A/II | (266) | 7 |
| RSVF2-5 | F | IV | (429) | 4 |
| Mab19 | F | IV | (429) | 12 |
| 7.936 | F | V | (432-447) | 13 |
| 9.432 | F | VI | (436) | 13 |
| 63-10f | G (A) | G11 | GCRR (A171-187) | 1, 2 |

TABLE 4-continued

Monoclonal antibodies for epitope mapping of anti-F and anti-G antibodies

| MAb/Fab | Antigen | Antigenic Site | Epitope (aa) | Ref. |
|---|---|---|---|---|
| 130-6d | G (A) | G12 | (A174-214) | 1, 2, 9 |
| 131-2g | G (A + B) | G13 | (150-173) | 1, 2, 9 |
| 143-5a | G (A + B) | G5a | | 2 |
| L9 | G (A + B) | A1/B1 | Conserved (164-176) | 14, 15 |
| 8C5 | G | ND | | 5 |
| 1C2 | G (A) | ND | GCRR (A172-188) | 10, 11 |
| 3F4 | G (A) | ND | | 10, 11 |
| 4G4 | G (A) | ND | GCRR (A172-188) | 10, 11 |

The column "Antigen" indicates the RSV associated antigen bound by the Mab/Fab, and if a subtype specificity is known this is indicated in ( ). The column "Epitope (aa)" indicates the name of the epitope recognized by the MAb/Fab, further in ( ) amino acid positions resulting in RSV escape mutants, or peptides/protein fragments towards which binding has been show, are indicated. The numbered references (Ref.) given in Table 4 correspond to:
1. Anderson et al., J. Clin. Microbiol. 1986, 23:475-480.
2. Anderson et al., J. Virol. 1988, 62:1232-4238.
3. Beeler & van Wyke Coelingh, J. Virol. 1989, 63:2941-2950.
4. Crowe et al., JID 1998, 177:1073-1076.
5. Sominina et al., Vestn Ross Akad Med Nauk 1995, 9:49-54.
6. Collins et al., Fields Virology, p. 1313-1351.
7. Crowe et al., Virology 1998, 252:373-375.
8. Zhao & Sullender, J. Virol. 2004, 79:3962-3968.
9. Sullender, Virology 1995, 209:70-79.
10. Morgan et al., J. Gen. Virol. 1987, 68:2781-2788.
11. McGill et al., J. Immunol. Methods 2005, 297:143-152.
12. Arbiza et al., J. Gen. Virol. 1992, 73:2225-2234.
13. Lopez et al. J. Virol. 1998, 72:6922-6928.
14. Walsh et al., J. Gen. Virol. 1989, 70:2953-2961.
15. Walsh et al., J. Gen. Virol. 1998, 79:479-487.

Furthermore, the antibody clones were also characterized in terms of binding to human laryngeal epithelial HEp-2 cells (ATCC CLL-23) infected with different RSV strains (Long, B1, or 18537) by FACS and/or ELISA. Binding to mock-infected HEp-2 cells was similarly analyzed.

Briefly, for the FACS assay, HEp-2 cells were infected with either the RSV Long (ATCC number VR-26) strain or the RSV B1 (ATCC number VR-1400) strain in serum-free medium at a ratio of 0.1 pfu/cell for 24 (Long strain) or 48 h (B1 strain). Following detachment and wash the cells were dispensed in 96-well plates and incubated with dilutions (4 pM-200 µM) of the individual anti-RSV antibodies for 1 h at 37° C. The cells were fixed in 1% formaldehyde and cell surface-bound antibody was detected by incubation with goat F(ab)$_2$ anti-human IgG-PE conjugate (Beckman Coulter) for 30 min at 4° C.

For the ELISA assay, HEp-2 cells were infected with either the RSV Long strain or the RSV 18537 strain (ATCC number VR-1580) in serum-free medium at a ratio of 0.01 pfu/cell. After two hours of incubation, medium with 10% fetal calf serum was added and the cells were incubated for additional 45 hours (Long strain) or 70 hours (18537 strain). Following wash, the cells were incubated with dilutions of the individual anti-RSV (0.1 µM-0.03 nM) antibodies for 1 hour at room temperature. The cell surface-bound antibody was detected by incubation with goat F(ab)$_2$ anti-human IgG-HRP conjugate (Jackson ImmunoResearch) for 1 hour at room temperature, followed by addition of TMB$^{PLUS}$ (Kem-En-Tec). After 10 min of incubation the reaction was terminated by H$_2$SO$_4$ and the absorbance measured. These cellular assays may also be used as a competition assay for determination of relative epitope specificities as described for the virus particle ELISA and SPR assay described above.

Selected clones identified as protein G-specific were also tested for cross-reactivity with recombinant human fractalkine (CX3CL1; R&D systems) by ELISA. Anti-human CX3CL1/Fractalkine monoclonal antibody (R&D systems) was used as a positive control.

g-5 Characterization of Binding Kinetics of the Individual Antibodies

Kinetic analysis of the antibodies of the invention was performed using surface plasmon resonance analysis on a Biacore 3000 (Biacore AB, Uppsala, Sweden), using recombinant antigens immobilized onto the sensor surface at very low density to avoid limitations in mass transport. The analysis was performed with Fab fragments prepared from individual antibody clones using the ImmunoPure Fab preparation Kit (Pierce). Briefly, a total of 200 resonance units (RU) recombinant protein F or a total of 50 RU recombinant protein G was conjugated to a CM5 chip surface using the Amine Coupling Kit (Biacore) according to the manufacturer's instructions. The Fab fragments were injected over the chip surface in serial dilutions, starting at an optimized concentration that did not result in RUmax values above 25 when tested on the chip with immobilized protein. The association rate constant (ka) and dissociation constant (kd) were evaluated globally using the predefined 1:1 (Langmuir) association and dissociation models in the BIAevaluation 4.1 software (BIAcore).

By performing the kinetic analyses on Fab fragments, it is ensured that the data obtained truly reflects the binding affinities towards RSV protein. If one used complete antibodies, the data would reflect binding avidities, which cannot readily be translated into a meaningful measure of the exact nature of the antibodies' binding characteristics vs. the antigen.

g-6 Characterization of the Biochemical Properties of Individual Antibodies

Heterogeneity is a common phenomenon in antibodies and recombinant proteins. Antibody modifications typically occur during expression, e.g. a post-translational modifications like N-glycosylation, proteolytic fragmentation, and N- and C-terminal heterogeneity resulting in size or charge heterogeneity. In addition, modifications like methionine oxidation and deamidation can occur during subsequent short or long term storage. Since these parameters need to be well-defined for therapeutic antibodies, they were analyzed prior to the generation of the polyclonal cell line.

The methods used for characterization of purified individual antibodies (see Section i) included SDS-PAGE (reducing and non-reducing conditions), weak cation exchange chromatography (IEX), size exclusion chromatography (SEC), and RP-HPLC (reducing and non-reducing conditions). The SDS-PAGE analysis under reducing and non-reducing conditions and SEC indicated that the purified antibodies were indeed intact with minute amounts of fragmented and aggregated forms. IEX profile analysis of the purified antibodies resulted in profiles with single peaks or chromatograms with multiple peaks, indicating charge heterogeneity in these particular antibodies. Antibody preparations resulting in multiple peaks in the IEX analysis and/or aberrant migration of either the light or heavy chain in SDS gels, or unusual RP-HPLC profiles were analyzed in detail for intact N-termini by N-terminal sequencing and for heterogeneity caused by differences in the oligosaccharide profiles. In addition, selected antibodies were analyzed for the presence of additional N-glycosylation sites in the variable chains using enzymatic treatment and subsequent SDS-PAGE analysis.

g-7 Establishment of a Polyclonal Cell Line for Anti-RSV Recombinant Polyclonal Antibody Production From the collection of established expression cell lines, a subset is selected to be mixed for the generation of a polyclonal cell line and the polyclonal research/master cell bank (pRCB/pMCB). The selection parameters can be defined according to the use of the polyclonal antibody to be produced from the polyclonal cell line and the performance of the individual cell lines. Generally the following parameters are considered:

Cell line characteristics; to optimize the stability of the polyclonal cell line, individual cell lines with doubling times between 21 and 30 hours and antibody productivity above 1 pg/cell/day are preferred.

Reactivity; the antigens/antigenic sites and epitopes which the anti-RSV rpAb shall exert reactivity against are carefully considered.

Protein chemistry; preferably antibodies with well-defined biochemical characteristics are included in the final anti-RSV rpAb.

The selected individual cell lines each expressing a recombinant anti-RSV antibody are thawed and expanded at 37° C. in serum free medium in shaker flasks to reach at least $4 \times 10^8$ cells of each clone having a population doubling time of 21-34 hours. The viabilities are preferably in the range of 93% to 96%. The polyclonal cell line is prepared by mixing $2 \times 10^6$ cells from each cell line. The polyclonal cell line is distributed into freeze ampoules containing $5.6 \times 10^7$ cells and cryopreserved. This collection of vials with a polyclonal cell line is termed the polyclonal research/master cell bank (pRCB/pMCB) from which the polyclonal working cell bank (pWCB) can be generated by expanding one ampoule from the pRCB/pMCB to reach a sufficient number of cells to lay down a polyclonal working cell bank (pWCB) of approximately 200 ampoules with the same cell density as the ampoules of the pRCB/pMCB. Samples from the cell banks are tested for mycoplasma and sterility.

h. Expression of a Recombinant Polyclonal Anti-RSV Antibody

Recombinant polyclonal anti-RSV antibody batches are produced in 5 liter bioreactors (B. Braun Biotech International, Melsungen, Germany). Briefly, vials from the pRCB or pWCB are thawed and expanded in shaker flasks (Corning). Cells in seed train are cultured in ExCell 302 medium with G418 and with anti-clumping agent at 37° C., 5% $CO_2$. The bioreactors are inoculated with $0.6 \times 10^6$ cells/ml suspended in 3 l ExCell 302 medium without G418 and without anti-clumping agent. The cell numbers/viable cells are monitored daily by CASY or ViCell counting. At 50 h, 2000 ml ExCell 302 medium is supplemented and after 92 h a temperature downshift from 37° C. to 32° C. is performed. The cell culture supernatant is harvested after 164 h and subjected to purification as described in Section i).

i. Purification of Individual Anti-RSV Antibodies and Polyclonal Anti-RSV Antibodies The antibodies expressed as described in Section g.g-2 and h, all of the IgG1 isotype, were affinity purified using a MabSelect SuRe column (Protein-A). The individual antibodies interacted with immobilized Protein A at pH 7.4, whereas contaminating proteins were washed from the column. The bound antibodies were subsequently eluted from the column by lowering of the pH to 2.7. The fractions containing antibodies, determined from absorbance measurements at 280 nm, were pooled and buffer changed using a G-25 column into 5 mM sodium acetate, 150 mM NaCl, pH 5 and stored at −20° C.

j. In Vitro Neutralization Assays j-1 Preparation of Live RSV for In Vitro Use

Human laryngeal epithelial HEp-2 cells (ATCC CLL-23) were seeded in 175 $cm^2$ flasks at $1 \times 10^7$ cells/flask. The cells were infected with either the RSV Long (ATCC number VR-26), the RSV A2 (Advanced Biotechnologies Inc., ATCC number VR-1540) the RSV B1 (ATCC number VR-1400) or the RSV B Wash/18537 (Advanced Biotechnologies Inc., ATCC number VR-1580) strain in 3 ml serum-free medium at a ratio of 0.1 pfu/cell. Cells were infected for 2 h at 37° C.; 5% $CO_2$ followed by addition of 37 ml of complete MEM medium. Cells were incubated until cytopathic effects were visible. The cells were detached by scraping and the media and cells were sonicated for 20 sec and aliquoted, snap frozen in liquid nitrogen and stored at −80° C.

j-2 Plaque Reduction Neutralization Test (PRNT)

HEp-2 cells were seeded in 96-well culture plates at $2 \times 10^4$ cells/well, and incubated overnight at 37° C.; 5% $CO_2$. The test substances were diluted in serum-free MEM and allowed to pre-incubate with RSV in the absence or presence of complement (Complement sera from rabbit, Sigma) for 30 min at 37° C. This mixture was applied to the monolayer of HEp-2 cells and incubated for 24-72 h at 37° C.; 5% $CO_2$. The cells were fixed with 80% acetone; 20% PBS for 20 min. After washing, biotinylated goat anti-RSV antibody (AbD Serotec) was added (1:200) in PBS with 1% BSA and incubated for 1 h at room temperature. After washing, HRP-avidin was added and allowed to incubate for 30 min. Plaques were developed by incubation with 3-amino-9-ethylcarbazole (AEC) substrate until plaques were visible by microscopy, e.g., for 25 min (RSV Long) or 45 min (RSV B1). Plaques were counted in a Bioreader (Bio-Sys GmbH). $EC_{50}$ values (effective concentrations required to induce a 50% reduction in the number of plaques) were calculated where applicable to allow for a comparison of the potencies.

j-3 Fusion Inhibition Assay

The fusion inhibition assay was essentially performed as the plaque reduction neutralization assay except that RSV was allowed to infect before addition of test substances. In practice, virus was added in serum-free medium to the monolayer of HEp-2 cells for 1.5 h. Supernatants were removed and test substances were added in complete MEM medium with or without complement (Complement sera from rabbit, Sigma). The plates were incubated overnight and processed as described above for the plaque reduction neutralization assay.

j-4 Microneutralization Assay

In addition to the PRNT and fusion inhibition assay described in Sections j-2 and j-3, a microneutralization assay based on the detection of RSV proteins was employed for the determination of RSV neutralization and fusion inhibition.

For the neutralization test, the test substances were diluted in serum-free MEM and allowed to pre-incubate with RSV in the absence or presence of complement (Complement sera from rabbit, Sigma) in 96-well culture plates for 30 min at room temperature. Trypsinated HEp-2 cells were added at $1.5 \times 10^4$ cells/well, and incubated for 2-3 days at 37° C.; 5% $CO_2$. The cells were washed and fixed with 80% acetone; 20% PBS for 15 minutes at 4° C. and dried. The plates were then blocked with PBS with 0.5% gelatin for 30 min at room temperature and stained with a pool of murine monoclonal antibodies against RSV proteins (NCL-RSV3, Novocastra), diluted 1:200 in PBS with 0.5% gelatin and 0.5% Tween-20, for 2 h at room temperature. After washing, Polyclonal Rabbit anti-mouse Immunoglobulin HRP-conjugate (P0260; Dako-Cytomation), diluted 1:1000 in PBS with 0.5% gelatin and 0.5% Tween-20 was added and allowed to incubate for 2 h at room temperature. The plates were washed and developed by addition of ortho-phenylendiamine. The reaction was stopped by addition of $H_2SO_4$ and the plates were read in an ELISA plate reader at 490 nm.

The fusion inhibition assay was essentially performed as the microneutralization test with the exception that virus was added to cells and incubated for 1.5 h at 37° C.; 5% $CO_2$ before the test substances, diluted in complete MEM, were added. The plates were incubated for 2-3 days at 37° C.; 5% $CO_2$ and developed as described above.

k. In Vivo Protection Assays k-1 Mouse Challenge Model 7-8-weeks old female BALB/c mice were inoculated intraperitoneally with 0.2 ml antibody preparation on day −1 of study. Placebo treated mice were similarly inoculated i.p. with 0.1 ml PBS buffer. On day 0 of study, the mice were anesthetized using inhaled isofluorane and inoculated intranasally with $10^{-6}$-$10^{-7}$ pfu of RSV strain A2 in 50 µl or with cell lysate (mock inoculum). Animals were allowed 30 seconds to aspirate the inoculum whilst held upright until fully recovered from the anaesthesia.

Five days after challenge, the mice were killed with an overdose of sodium pentobarbitone. At post-mortem, blood was obtained by exsanguination from the axillary vessels for preparation of sera. Lungs were removed and homogenized in 2.5 ml buffer with sterile sand. Lung homogenates were centrifuged to sediment sand and cell debris and supernatants were aliquoted and stored at −70° C.

In a long-term version of the challenge model, groups of animals were killed at different time points, i.e., 5, 27 and 69 days after challenge and lung homogenates and serum samples were prepared as described above. In addition, separate groups of animals that were killed at the same time points were used for bronchoalveolar lavage (BAL) and histopathology samples. Briefly, the airways were cannulated and lavaged with 1 ml of saline. The total number of cells present in the BAL was determined by light microscopy. Cytospin preparations of BAL cells were stained with hematoxylin and eosin and differential cell counts made using oil immersion microscopy. Following lavage, the lungs were fixated for histopathology. The fixed tissue samples were prepared by inflating the lungs with buffered formalin, and the fixed tissue was embedded in paraffin blocks for processing and hematoxylin and eosin staining by standard methods. The tissue samples were examined by light microscopy for signs of inflammation. Lung pathology scores were determined as the sum of the severity score multiplied by the prevalence score for each of 3 lung lobes (Table 5a). The maximal lung pathology score for one mouse is thus 36.

TABLE 5a

Lung histopathology scoring system used for the mouse challenge studies.

| Severity | Prevalence |
|---|---|
| 0 Normal | 0 Normal |
| 1 perivascular & peribronchial cell infiltration <3 cells thick | 1 <25% of sample |
| 2 perivascular & peribronchial cell infiltration 4 to 10 cells thick | 2 25 to 50% of sample |
| 3 perivascular & peribronchial cell infiltration >10 cells thick | 3 51-75% of sample |
| | 4 >75% of sample |

The virus load was initially determined by quantification of the number of RSV RNA copies in the lung samples using reverse transcriptase (RT-) PCR. RNA was extracted from the lung homogenate samples using the MagNA Pure LC Total Nucleic Acid kit (Roche Diagnostics) automated extraction system according to the manufacturer's instructions. Detection of RSV RNA was performed by single-tube real-time RT-PCR using the LightCycler instrument and reagents (Roche Diagnostics) with primers and fluorophore-labeled probes specific for the N gene of RSV subtype A as described by Whiley et al. (J. Clinical Microbiol. 2002, 40: 4418-22). Samples with known RSV RNA copy numbers were similarly analyzed to derive a standard curve.

Subsequently, the number of RSV RNA copies in the lung samples was determined using quantitative reverse transcriptase (RT-) PCR. RNA was extracted from the lung homogenate samples using the RNeasy mini kit (Qiagen) according to the manufacturer's instructions. Detection of RSV RNA was performed by using the SuperScript III Platinum One-Step Quantitative RT-PCR System (Invitrogen) with primers and fluorophore-labeled probes specific for the N gene of RSV subtype A as described in Table 5b below. Samples with known RSV RNA copy numbers were similarly analyzed to derive a standard curve.

TABLE 5b

RSV subtype A specific primers and probe for quantitative RT-PCR.

| Name | Sequence 5'-3' |
|---|---|
| RSV-A forward | CAA CAA AGA TCA ACT TCT GTC ATC (SEQ ID NO: 715) |
| RSV-A reverse | GCA CAT CAT AAT TAG GAG TAT CAA T (SEQ ID NO: 716) |
| RSA Probe | 6-FAM-CA CCA TCC AAC GGA GCA CAG GAG AT-TAMRA (SEQ ID NO: 717) |

The levels of different cytokines and chemokines in lung tissue samples were determined by a commercial multiplexed immunoassay at Rules-Based Medicine (Austin, Tex.) using their rodent multi-analyte profile (MAP).

k-2 Cotton Rat Challenge Model 6-8-weeks old female cotton rats (*Sigmodon hispidus*) are inoculated intraperitoneally with 0.5 ml antibody preparation or placebo (PBS) on day −1 of study. 24 hours later, the animals are lightly anaesthetised with isofluorane and given an intranasal challenge of $10^{-6}$-$10^{-7}$ pfu RSV strain A2 or control medium (mock inoculum). A total volume of 100 µl inoculum is administered and distributed evenly to both nares. After completion of the intranasal challenge each animal is held in the upright position for a minimum of 30 seconds to allow full inspiration of the inoculum. Five days after challenge, the animals are killed by lethal intraperitoneal injection of pentobarbitone and exsanguinated by cardiac puncture. Serum samples are obtained and frozen at −80° C. and each animal is dissected under aseptic conditions for removal of lungs and nasal tissue. The tissue samples are homogenized and the supernatants stored in aliquots at −80° C.

The virus load in the tissue samples is determined by quantification of the number of RSV RNA copies by a Taq-Man real-time assay based on the method of Van Elden et al. (J Clin Microbiol. 2003, 41(9):4378-4381). Briefly, RNA is extracted from the lung homogenate samples using the RNeasy (Qiagen) method according to the manufacturer's instructions. The extracted RNA is reverse transcribed into cDNA and subsequently amplified by PCR using the Superscript III Platinum One Step Quantitative RT-PCR System (Invitrogen) with primers and labelled probes specific for the N gene of RSV subtype A. Samples with known RSV concentrations are similarly analyzed to derive a standard curve.

k-3 Pharmacokinetics Study in Mice 7-8-weeks old female BALB/c mice were inoculated intraperitoneally with 0.2 ml antibody preparation on day O, Serum samples were taken from the orbital plexus at multiple time points (0 hours, 4 hours, 25 hours, days 3, 6, 9, 13, 16, 21, 24, and 29) after antibody treatment. Mice were sacrificed by cervical dislocation at days 1 (25 hours), 6 and 29 and lung tissues were removed and homogenized in 1.5 ml buffer using a tissuelyzer (Qiagen). The lung homogenates were afterwards centrifuged to sediment cell debris and supernatants were stored at −70° C. The levels of human antibody present in serum samples and lung homogenates were measured using a human IgG1 kappa ELISA.

EXAMPLE 2

In the present Example the isolation, screening, selection and banking of clones containing cognate $V_H$ and $V_L$ pairs expressed as full-length antibodies with anti-RSV specificity was illustrated.

Donors

A total of 89 donors were recruited among the employees and parents of the children who were hospitalized at the Department of Paediatrics at Hvidovre Hospital (Denmark) during the RSV season. A initial blood sample of 18 ml was drawn, CD19$^+$ B cells were purified (Example 1, Section a) and screened for the presence of anti-RSV antibodies using ELISpot (Example 1, Section b) and the frequency of plasma cells was determined by FACS analysis.

Eleven donors were found positive in the screening of the initial blood samples and a second blood sample of 450 ml was collected from ten of these. The plasma blasts were single-cell sorted according to Example 1, Section a. ELISpot was performed on a fraction of the CD19 positive B cells.

Four donors with ELISpot frequencies in the second blood donation between 0.2 and 0.6% RSV specific plasma cells (IgG$^+$ and IgA$^+$) of the total plasma cell population were identified. These frequencies were considered high enough to proceed to linkage of repertoires of cognate $V_H$ and $V_L$ pairs.

Isolation of Cognate $V_H$ and $V_L$ Coding Pairs

The nucleic acids encoding the antibody repertoires were isolated from the single cell-sorted plasma cells from the five donors, by multiplex overlap-extension RT-PCR (Example 1, section c). The multiplex overlap-extension RT-PCR creates a physical link between the heavy chain variable region gene fragment ($V_H$) and the full-length light chain (LC). The protocol was designed to amplify antibody genes of all $V_H$-gene families and the kappa light chain, by using two primer sets, one for $V_H$ amplification and one for the LC amplification.

Following the reverse transcription and multiplex overlap-extension PCR, the linked sequences were subjected to a second PCR amplification with a nested primer set.

Each donor was processed individually, and 1480 to 2450 overlap products were generated by the multiplex overlap-extension RT-PCR. The generated collection of cognate linked $V_H$ and $V_L$ coding pairs from each donor were pooled and inserted into a mammalian IgG expression vector (FIG. 3) as described in Example 1 section d). The generated repertoires were transformed into E. coli, and consolidated into twenty 384-well master plates and stored. The repertoires constituted between $1 \times 10^6$ and $3.6 \times 10^6$ clones per donor.

Screening

IgG antibody-containing supernatants were obtained from CHO cells transiently transfected with DNA prepared from bacterial clones from the master plates. The supernatants were screened as described in Example 1, section e. Approximately 600 primary hits were sequenced and aligned. The majority fell in clusters of two or more members, but there were also clones that only were isolated once, so-called singletons. Representative clones from each cluster and the singletons were subjected to validation studies as described in Example 1, section e). A number of the primary hits were excluded from further characterization due to unwanted sequence features such as unpaired cysteines, non-conservative mutations, which are potential PCR errors, insertions and/or deletion of multiple codons, and truncations.

A total of 85 unique clones passed the validation. These are summarized in Table 6. Each clone number specifies a particular $V_H$ and $V_L$ pair. The IGHV and IGKV gene family is indicated for each clone and specifies the frame work regions (FR) of the selected clones. The amino acid sequence of the complementarity determining regions (CDR) of an antibody expressed from each clone are shown, where CDRH1, CDRH2, CDRH3 indicate the CDR regions 1, 2 and 3 of the heavy chain and CDRL1, CDRL2 and CDRL3 indicate the CDR regions 1, 2 and 3 of the light chain.

The complete variable heavy and light chain sequence can be established from the information in Table 6.

Further details to the individual columns of Table 6 are given below.

The IGHV and IGKV gene family names, were assigned according to the official HUGO/IMGT nomenclature (IMGT; Lefranc & Lefranc, 2001, The Immunoglobulin FactsBook, Academic Press). Numbering and alignments are according to Chothia (Al-Lazikani et al. 1997 J. Mol. Biol. 273:927-48). Clone 809 has a 2 codon insertion 5' to CDRH1, which likely translates into an extended CDR loop. Clone 831 has a 1 codon deletion at position 31 in CDRH1.

The column "Ag" indicates the RSV associated antigen recognized by the antibody produced from the named clone, as determined by ELISA, FLISA and/or Biacore. "+" indicates that the clone binds to RSV particles and/or RSV-infected cells, but that the antigen has not been identified.

The column "Epitope" indicates the antigenic site or epitope recognized by the antibody produced from the named clone (see Table 4 and below). "U" indicates that the epitope is unknown. UCI and UCII refer to unknown cluster I and II. Antibodies belonging to these clusters have similar reactivity profiles but have currently not been assigned to a particular epitope. Some antibodies recognize complex epitopes, such as A&C. Epitopes indicated in ( ) have only been identified in ELISA.

TABLE 6

Summary of sequence and specificity of each unique validated clone.

| Clone | IGHV gene | CDRH1 | CDRH2 | CDRH3 | IGKV gene | CDRL1 | CDRL2 | CDRL3 | Ag | Epitope |
|---|---|---|---|---|---|---|---|---|---|---|
| 735 | 4-59 | D--YDWS | NIN----YRGNTNNPSLKS | CARDVGYGGGQYFAM--------DVW | 3-11 | RASQSVNS--------HLA | NTFNRVT | CQQRSNWPPALTF | F | UCI |
| 736 | 3-30 | T--YGMH | FIRY--DGSTQDYVDSVK | CAKDMDYYGSRSYSVTYYYGM--DVW | 1-39 | RASQRISN--------HLN | GASTLQS | CQQSYRTPP-INF | F | A/II |
| 743 | 1-69 | T--YALT | RITP--MFDITNYAQKFQG | CARRGAVALVPAAEDPYYYGM--DVW | 2-28 | RSSQSLLHS-NGNNYLD | LASNRAS | CMQLQT---PTF | G | Centr. dom |
| 744 | 1-2 | G--YYMH | WINT--SSGGTNYAQKFQG | CAREDGTMGTNSWYGWF-------DPW | 3-20 | RASQSVSSS-------YLA | GASSRAT | CQQYDSSLSTWTF | F | A/II |
| 793 | 3-11 | D--YYMS | YINR--GGTTIYYADSVKG | CARGLILALPTATVELGAF----DIW | 1-39 | RASQSITG--------YLN | ATSTLQS | CQQSYNT---LTF | G | Conserved |
| 794 | 1-18 | N--YGLN | WINA--YNDNTYYSPSLQG | CARSYRSQTDILTGRYKGPGDVFDNW | 1-12 | RASEGISS--------WLA | AASTLQS | CQQTNSFP--YTF | G | GCRRA |
| 795 | 4-30-4 | SGDYYWS | YIF---HSGTTYNPSLKS | CARDVDDFPVWGMNRYL------ALM | 3-20 | RASQSVSSS-------YLA | GASTGAT | CQQYGRTP--YTF | F | UCI |
| 796 | 3-30 | H--FGMH | IISY--DGNNVHYADSVKG | CAKDDVATDLAAYYYF-------DVW | 2-29 | RSSQSLLRS-DGKTFLY | EVSSRFS | CMQGLKIR--RTF | G | Conserved |
| 797 | 1-18 | R--FGIS | WISA--DNGNTYYAQNFQD | CVRGGVVTNRVYYYGM-------DVW | 1-9 | RASQGISS--------YLA | AASTLQS | CQQVDTYP--LTF | G | GCRRA |
| 798 | 7-4-1 | S--YVMN | WINT--NTGDPAYAQDFTG | CAWFGEFGLF-------------DFW | 1-16 | RASQDINN--------YLA | AASSLQS | CQQYKSLP--FTF | C | GCRRA |
| 799 | 3-30 | N--YGMH | VISY--DGRNKYFADSVKG | CARGSVQVWLHLGLF--------DNW | 1-5 | RASQSVSS--------WVA | EASNLES | CQQYHSYSG-YTF | F | U |
| 800 | 3-33 | D--YGMN | VIWH--DGSNKNYLDSVKG | CARITPYEFWSGYYF--------DFW | 1D-13 | RASQGITD--------SLA | AASRLES | CQQYSKSP--ATF | F | F1 |
| 801 | 3-33 | S--YAMH | VIYY--EGSNEYYADSVKG | CARKWLGM---------------DFW | 2-28 | RSSQSLLNS-NGFNVYD | LGSNRAS | CMQALETP--LTF | F | F1 |
| 802 | 3-48 | S--YEMN | YIGT--GGSDIYYGDSVKG | CARARPGYKV-------------DFW | 1-9 | RASQTVSSS-------YLA | VASILES | CQQSKSFP--PTF | F | U |
| 803 | 4-30-4 | SGDYFWS | YIY---SSGSTFYNASLKS | CARGTLYTTGGEM----------HIW | 3-20 | RASQTVSSS-------YLV | GASTRAT | CQQYGGSG--LTF | F | U |
| 804 | 3-64 | N--YAMH | ATST--DGSTYYADSLKG | CARRFWGFGNFF-----------DYW | 3-20 | RASQSVSSG-------YLA | GASGRAT | CQQYFGSP--YTF | F | F1 |
| 805 | 4-59 | G--DFWS | YIY---YRGSTYYNPSLKS | CAREGHHSSGSGDYSFF------DYW | 1-39 | RASQGINT--------YLN | AASSLQS | CQQSANSP--HTF | F | F1 |
| 806 | 5-51 | S--YWIG | IVYP--GDSDTTYSPSFQG | CVRRGGFCTATGCYAGHWF----DPW | 3-20 | RASQSISSG-------YLA | GASHRAT | CQQYGSSL--WTF | + | U |
| 808 | 2-70 | TTRMSVS | RID---WDDDKYYSTSLKT | CARIVFHTSGGYYNPYM------DVW | 1-39 | RASQTIAS--------YLS | TASSLQS | CQHSYNTP--YTF | F | (F1) |
| 809 | 5-51 | FVSTWIG | IINP--ADSDTRYSPSFQG | CARRAYDSGWHF-----------EHW | 3D-15 | RASQSVGS--------KLA | GASTRAT | CQQYNNWPP-YTF | F | (F1) |
| 810 | 1-69 | N--YAIN | RIIP--VFDTTNYAQKFQG | CLRGSTRGWDTDGF---------DIW | 1D-17 | RASQGISN--------YLV | AASSLQS | CLQHNISP--YTF | F | A/II |
| 811 | 1-46 | N--YYIH | VINP--NGGSTTSAQKFQD | CARQRSVTGGFDAWLLIPDAS--NTW | 4-1 | RSSETVLYTSKNQSYLA | WASTRES | CQQFFRSP--FTF | C | Conserved |
| 812 | 1-69 | S--YSIS | MILP--ISGTTNYAQTFQG | CARVFREFSTSTLDPYYF-----DYW | 3-20 | RASQSVSSS-------YIA | AASRRAT | CQHYGNSL--FTF | F | F1 |

TABLE 6-continued

Summary of sequence and specificity of each unique validated clone.

| Clone | IGHV gene | CDRH1 | CDRH2 | CDRH3 | IGKV gene | CDRL1 | CDRL2 | CDRL3 | Ag | Epitope |
|---|---|---|---|---|---|---|---|---|---|---|
| 813 | 5-51 | S--YWIG | IIYP--GDSDTRNSPSFQG | CVRQGGYDRNGYHEKYAF---DIW | 1-5 | RASQSISS-----WLA | KSSILES | CQHYNSYS--GTF | F | (F1) |
| 814 | 3-30-3 | D--YADMH | VISY--DGANEYYAESVKG | CARAGRSSMNEEVIMYF-----DNW | 1-5 | RASQSIGS-----RLA | DASSLES | CQQYNRDSP-WTF | G | Conserved |
| 816 | 3-23 | T--YAMT | VIRA--SGDSEIYADSVRG | CANIGQRRYCSGDHCYGHF---DYW | 2-28 | RSSQSLLHS-DGRYVVD | LASNRAS | CMQGLHTP--WTF | G | Conserved |
| 817 | 3-30 | T--HGMH | IISL--DGIKTHYADSVKG | CAKDHIGGINAYFEMTVPF---DGW | 3-15 | WASQTIGG-----NLA | GASTRAT | CQQYKNW---YTF | F | A/II |
| 818 | 2-70 | AGRVGVS | RID--WDDKAFRTSLKT | CARTQVFASGGYYLYL-----DHW | 1-39 | RASQTIAS-----YVN | AASNLQS | CQQSYSYRA-LTF | F | B/I/F1 |
| 819 | 4-30-4 | GADYYWS | FIY--DSGSTYNPSLRS | CARDLGYGGNSYSHSYYYGL--DVW | 3-11 | RASQSVSS-----SLA | DASYRVT | CQQRSNWPPGLTF | F | A/II |
| 822 | 5-51 | N--SWIG | IIYP--GDSTTYTPSFQG | CARQGRGF--------------GLW | 1D-33 | QASQDITY-----YLS | DVSNLER | CQQYDFLP--YTF | F | U |
| 823 | 4-b | SC-HFWG | SIF--HSGTTFHNPSLKS | CARVHGGGF-------------DHW | 1D-33 | QASQDIGD-----SLN | DASNLET | CQHYNLPPSFTF | F | U |
| 824 | 4-59 | N--YYWG | HIY--FGGNTNYNPSLQS | CARDSSNWPAGY----------EDW | 1D-13 | RPSQDISS-----ALA | GASTLDY | CQQFNTYP--FTF | F | A/II* (F1&C) |
| 825 | 1-18 | S--NGLS | WISA--SSGNKKYAPKFQG | CAKDGGTYVPYSDAP-------DFW | 4-1 | KSSQSVLYNSNNKNYLA | LASTREY | CQQYQTP--LTF | F | A/II* (UCI) |
| 827 | 1-24 | A--LSKH | FFDP--EDGDTGYAQKFQK | CATVAAAGNF------------DNW | 1-39 | RASQFISS-----YLH | AASTLQS | CQQSYTNP--YTF | F | (A&C/) IV* |
| 828 | 1-3 | T--NGLH | LINA--GNGDTRPSQKFQG | CARIAITMVRNPF---------DIW | 1-5 | RASQSIGS-----WLA | KESNLES | CQQYKND---WTF | + | A&C |
| 829 | 2-70 | RNRMSVS | RID--WDDKFYNTSLQT | CARTGIYDSSGYYLYF------DYW | 1-39 | RASQSIAS-----YLN | AASSLHS | CQHSYSTR--ETF | F | U (F1) |
| 830 | 1-18 | T--YGVS | WISA--YNGNTYYLQKLQG | CARDRVGGSSSEVLSRAKNYGL-DVW | 1-5 | RASQSVTS-----ELA | KASSLES | CQQYNSFP--YTF | G | GCRRA |
| 831 | 1-3 | ---YAMH | WINV--GNGQTKYSQRFQG | CARRASQYGEVYGNYF------DYW | 1-5 | RASQNIYN-----WLA | DASTLES | CQQYNSLS--PTF | F | A/II |
| 833 | 3-30 | Y--IGMH | AISY--DGSNKQYADSVKG | CAKDDFGNSNGVFMSRV-----AFW | 1-12 | RANQDIDN-----YLA | GASKLQT | CQQADSFP--FTF | G | Centr. dom |
| 834 | 1-18 | T--YGLN | WVSA--HNGNTYYAEKFHD | CVRGFNEQQLVPGLSFWF----DYW | 1-12 | RASQGISK-----RLA | GASSLQH | CQQLNSYP--RTF | G | GCRRA |
| 835 | 1-18 | S--YGFS | WSSV--YNGDTNYAQKFHG | CARDRNVLLPAAPFGGM-----DVW | 1-9 | RASQGISS-----YLA | AASTLQS | CQQAYSFP--RTF | G | GCRR |
| 836 | 4-b | SC-HYWG | SIY--DSGNTYTPSLKS | CARGSPGDAF------------DIW | 1-12 | RASQGIGT-----WLA | AASRLQS | CQQYSFP--RTF | F | (A/II) |
| 838 | 3-30 | T--FGMH | VISY--DGNKKYADSVKG | CAAQTPYFNESSGLV-------PDW | 1-27 | RASQGISN-----YLA | AASTLQS | CQKYNSAP--QTF | G | Conserved |
| 839 | 3-30 | S--YGLH | EISY--DGGSKFYTDSVKG | CARDLGDGYTAWGWF-------DPW | 3-20 | RASQSVGGR----SLA | DASNRAT | CQQYGSPP--WTF | G | GCRRA |

TABLE 6-continued

Summary of sequence and specificity of each unique validated clone.

| Clone | IGHV gene | CDRH1 3 3 1ab2345 | CDRH2 5 012abc3456789012345 | CDRH3 9 0 234567890abcdefghijklmn123 | IGKV gene | CDRL1 2 3 456789012abcdef234 | CDRL2 5 0123456 | CDRL3 8 9 9 89012345ab678 | Ag | Epitope |
|---|---|---|---|---|---|---|---|---|---|---|
| 841 | 1-18 | S--FGIS | WISA--YNQNTDYAQRLQD | CTRDESMLRGVTEGFPI----DYW | 4-1 | RSSQSVLYSSNNKNYLA | WASTRAS | CQQFHSTP--RTF | G | GCRRA |
| 842 | 1-18 | R--YGIS | WISA--YNGNTYYAQNLQG | CVISPDSTIAAAEYF------DYW | 1-5 | RASQTISN------SLA | KASTLES | CQQYNSFS--FTF | G | GCRRA |
| 843 | 1-18 | N--SGVS | WISA--YNGNTYYRQSLQD | CAREGHYSGSSSYQRDDAF--DIW | 1-16 | RASQGISN------YLA | TTSTLRS | CQQHSFP--YTF | G | GCRRA |
| 845 | 1-18 | S--YGIS | WIGT--DNGNTYYAQKFQC | CARGTIEATPEREYYYGM--DVW | 1-9 | RASQGISS------YLA | AASTLQS | CQQELNTYP--LTF | G | GCRRA |
| 846 | 4-30-2 | SGGYSWS | YIY---HSGSTYNPSLKS | CASRSFYGDY-----------VYW | 3-20 | RASQSVSSS-----YLA | GASSRAT | CQQYGSSP--FTF | F | U |
| 848 | 4-61 | SDKNYWS | RLY---PSGNTDYHPSLKS | CAKEGSGWYF-----------ESW | 1-5 | RASQGISA------WLA | DASTLAS | CQQYRSYS--YTF | F | U |
| 849 | 3-73 | G--STMH | RIRSKANSYATEYAASVKG | CTRHVGEMSTIWWYF------DLW | 1-39 | RASQSISS------YLN | AASSLQS | CQQSYSTP--YTF | F | U |
| 850 | 1-3 | T--YTLH | LINA--ANGHTKYSQRFQG | CAKSGSHYGEVYGAYF-----DYW | 1-5 | RASQNIYN------WLA | DASSLES | CQQYNIYS--PTF | F | (A/II) |
| 851 | 1-18 | S--LGFS | WTSA--HNGNTYYAEEFQD | CARDRGPGYSDSSPVVF----DYW | 2-24 | RSSQSLVNS-DGNTYLS | QISKRFS | CMQATQPP--FTF | G | GCRRA |
| 852 | 1-69 | G--YTIH | RLVP--SLNIPNYAQKFQG | CTRAPRGSTASHLLF------DYW | 1D-33 | QASQDVSY------YLN | DTSNLVT | CLQYHLP--YTF | F | U |
| 853 | 5-51 | N--YWIG | VIFP--ADSDARYSPSFQG | CARPKYYFDSSGQFSEMYYF--DFW | 3-20 | RASQSVSSN-----YLA | GASSRAA | CQQYGNSP--LTF | G | Centr. dom |
| 855 | 1-18 | N--YAFS | WISG--SNGNTYYAEKFQG | CARDLLRSTYF---------DYW | 1D-12 | RASQAISN------WLA | AASSLQS | CQQADTFP--FTF | G | GCRRA |
| 856 | 1-18 | N--YGFS | WISA--YNGNTYYAQNLQG | CARDGNTAGVDMWSRDFG---DIW | 2-40 | RSSQSLLDSNDGNTYLD | TFSYRAS | CMQRIEFP--YTF | G | GCRRA |
| 857 | 3-23 | S--YAMN | GISG--SGGSTYYGDSVKG | CAKEPWIDIVVASVISPYYYDGMDVW | 2-28 | RSSQSLLHR-NEYNYLD | WGSNRAS | CMQTLQTP--RTF | F | F1 |
| 858 | 1-69 | G--YTIS | RVVP--TLGFPNYAQKFQG | CARMNLGHSGRGF--------DMW | 1D-33 | QASQDISN------YLN | DATKLET | CQHFANLP--YTF | F | B/I/F1 |
| 859 | 3-33 | K--YGIH | VISY--DGSKKYPTDSVKG | CATGGVNTSWSDVEHSSSL--GYW | 1-27 | RASQGIRN------YLN | AASTLQS | CQRYNSAP--LTF | G | Conserved |
| 861 | 3-30 | S--YGMH | FIWN--DGSNKYADSVKG | CVKDEVYDSSGYYILYYF---DSW | 1-39 | RASQIIAS------YLN | AASSLQS | CQQSYSTPI--FTF | F | F1 |
| 863 | 3-23 | S--YTMS | SISA--STVLTYYADSVKG | CAKDYDFWSGYPGGQYWFF--DLW | 3-11 | RTSQSVSS------YLA | DASNRAT | CQQRSDW--LTF | F | A/II |
| 866 | 1-18 | T--YGIS | WISA--DNGNTYYAQKFQG | CVRGGTYSSDVEYYYGM----DVW | 1-9 | RASQGISI------YLA | AASTLQT | CQQLNTYP--LTF | G | GCRRA |
| 867 | 1-69 | R--YTIH | RVVP--SLGIPNYAPKFQG | CARLTLGSVTGRPGF------DSW | 1D-33 | QASQDINN------YLN | DATDLET | CQHFANLP--YTF | F | (F1) |

TABLE 6-continued

Summary of sequence and specificity of each unique validated clone.

| Clone | IGHV gene | CDRH1 | CDRH2 | CDRH3 | IGKV gene | CDRL1 | CDRL2 | CDRL3 | Ag | Epitope |
|---|---|---|---|---|---|---|---|---|---|---|
| 868 | 4-b | NA--YYWG | SIH---HSGSAYYNSSLKS | CARDTILTFGEPHWF-------DPW | 3-15 | RASQSIKN------NEA | GASARAT | CQEYNNWPL-LTF | G | Conserved |
| 869 | 3-30 | Y--YAMH | VISY--GETNKLYADSVKG | CARDLRYLTYYSCSGD-----DSW | 3-20 | RASQSLSDN------YEA | GASSRPT | CQQYGTTP--ITF | G | Conserved |
| 870 | 4-59 | N--YYWS | EIS--NTWSTNYNPSLKS | CARGLFYDSGGYYLFYF------QHW | 1-39 | RASQRIAS------YLN | AASSLQS | CQQSYSTPI-YTF | F | (F1) |
| 871 | 3-33 | N--YGMH | VIWY--DDSNKQYGDSVKG | CARASEYSISWRHRGVL-----DYW | 1D-33 | QASQGISN------YLN | DASNLES | CQQYDNFP--YTF | F | UCI |
| 874 | 3-30 | H--YGMH | VISH--DGNIKYSADSVKG | CHGEGYSTSWLGTAAL------DYW | 1-27 | RASQGIRN------FLA | AASTLQS | CQKYNSAP--WTF | G | Conserved |
| 879 | 3-23 | A--YAMS | AISG--GGGTTYYADSVKG | CAKTRGYSVTWGDAP-------DLW | 3-15 | RASQSVTS------NLA | GASTRAT | CQQYNNWP--QTF | F | U |
| 880 | 2-5 | TSKLGVG | LVD--WDDDRRYRPSLKS | CAHSAYYTSSGYYLQYF-----HNW | 1-39 | RASQTIAS------YVN | AASSLQS | CQQSYSFP--YTF | F | UCII |
| 881 | 3-48 | S--YEMT | HIGN--SGSMIYADSVKG | CARSDYDSSGYYLLYL-------DSW | 1-39 | RASQTIAS------YVN | AASNLQS | CQQSYSVPR-LTF | F | UCII |
| 884 | 1-3 | N--FAMH | YINA--VNGNTQYSQKFQG | CARNNGGSAIIF---------YYW | 1-39 | RASQTIAS------FLN | AASSLHS | CQESFSS---STF | F | U |
| 885 | 4-b | SN-YYWG | SMH--HSGSSYYKPSLKS | CARDLVVVTDISIKNYF------DPW | 3-11 | RSSQTISV------YLA | DASNRAT | CQHRRSW---PTF | F | U |
| 886 | 3-30 | S--YGMH | VISN--DGSNKYYADSVKG | CAKTTDQRLLVDWF--------DPW | 3-15 | RASQSVSS------NLA | SASTRAT | CQQYNMWPP-WTF | F | A/II |
| 887 | 2-70 | TSRMSVS | RID--WDDDKYSTSLKT | CARTIVYAPDSYYLYF-------DYW | 1-39 | RASQTIAS------YVN | AASRLQS | CQQSYSIP--WTF | F | U (F1) |
| 888 | 4-39 | SSNFYWG | SIF--YSGTTYNPSLKS | CARHGFRYCNNGVCSINLDAF--DIW | 2-28 | RSSQSLLRT-NGYNYLD | LGSIRAS | CMQSLQTS--ITF | G | GCRR |
| 889 | 1-18 | T--YGIS | WISA--YNGNTFYAQRLQG | CARDLRMLPGGLPTRRGM-----DVW | 1-5 | RASQSISS------WLA | KASSLES | CQQYNSYP--YTF | G | GCRRA |
| 890 | 1-46 | K--FYIH | IINP--SGGSTTVYAQTFQD | CARGIREGGVSVEDMMLVYSWF-DPW | 1-39 | RASQNIRT------FIN | AASKLES | CQQGHSTP--YTF | G | Conserved |
| 891 | 3-30 | S--YTMH | VVSY--DGNHNDYADSVKG | CVRAPGSMGL-----------DVW | 2-28 | RSSQSLLHR-NGYNHLD | LGSNRAS | CMQALQTP--RTF | G | Centr. dom |
| 892 | 3-15 | N--AWMS | LIKSHFEGGATDYAAPVKG | CAPLGGPTPP------------DYW | 1-17 | RAGQGIRN------DLG | GASTLQS | CLQHNSYP--WTF | + | U |
| 893 | 3-30 | I--YGMH | VISY--DGAKKFYANSVKG | CATASTYFYDSR----------DYW | 2-24 | RSSRSLVHS-DGNTYLS | KISNRFS | CLQATQF---LTF | G | Conserved |
| 894 | 3-33 | S--YTMH | VIWH--DGSNIRYADSVRG | CARVPFQIWSGLYF--------DHW | 3-15 | RASQSVGN------NLA | GASTRAT | CQQYDKWP--ETF | F | C* (UCI) |
| 924 | 4-b | SE-YYWG | SVH--HSGSTYNPSLKS | CARDRVALGVHYWYP-------DIW | 3-15 | RASQSVSS------HLA | GASTRAT | CQQYDNWL--PTF | G | Centr. dom |
| 955 | 1-46 | D--YCMH | ILNP--DGGTTFYAEKFQD | CAILIARAYCGLADGQEGDF--DTW | 1-5 | RASRSITS------WLA | KASSLQS | CQQYNSYP--LTF | SH | A2 aa42-64 |

* new binding experiments have confirmed binding to the epitope with asterisk

The amino acid sequences from top to bottom in the column termed CDRH1 are set forth in the same order in SEQ ID NOs: 201-285.

The amino acid sequences from top to bottom in the column termed CDRH2 are set forth in the same order in SEQ ID NOs. 286-370.

The amino acid sequences from top to bottom in the column termed CDRH3 are set forth in the same order in SEQ ID NOs: 371-455.

The amino acid sequences from top to bottom in the column termed CDRL1 are set forth in the same order in SEQ ID NOs. 456-540.

The amino acid sequences from top to bottom in the column termed CDRL2 are set forth in the same order in SEQ ID NOs: 541-625.

The amino acid sequences from top to bottom in the column termed CDRL3 are set forth in the same order in SEQ ID NOs. 626-710.

Characterization of Antigen Specificity

During validation the antigen specificity of the clones was determined to some degree by the binding to viral particles, soluble G and F protein as well as fragments of the G protein.

Figure 4:
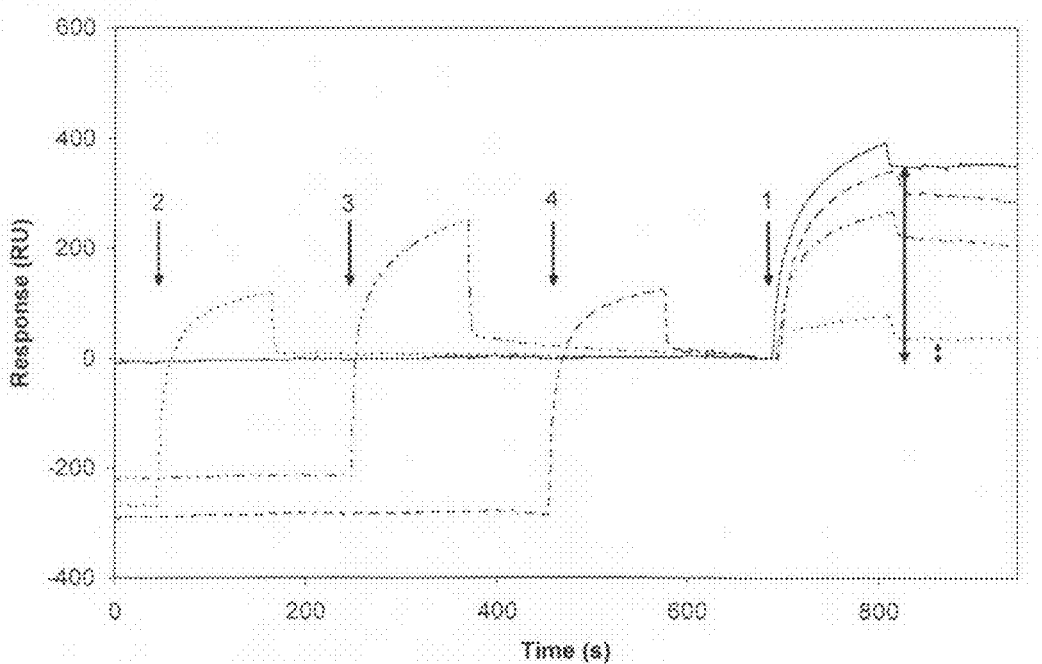
FIG. 4: Characterization of the epitope specificity of antibody obtained from clone 801 (Ab801) using Biacore analysis. Antibody 801 binding was tested in pair-wise competition for binding to protein F, using three antibodies, 9c5 (2), 133-h (3) and Palivizumab (4), which bind to antigenic site F1, C and II, respectively. The reference cell illustrates binding to protein F of uncompeted Ab801 (1). Injection times of the four antibodies are indicated by an arrow. The response is indicated in relative resonance units (RU). The long double headed arrow indicates the magnitude of the uncompeted response and the short double headed arrow indicates the magnitude of the 9c5 inhibited response.

For clones with anti-F reactivity the specificity of the individual antibodies expressed from the clones was assessed further in order to determine the antigenic site and, if possible, the epitope bound by the individual clones (see Example 1, Section g-4). FIG. 4, illustrates characterization of the epitope specificity of antibody obtained from clone 801 using Biacore analysis. The analysis show that when protein F is blocked by 133-1 h or Palivizumab (antigenic site C and II, respectively) prior to injection of antibody 801 into the Biacore cell, a high degree of antibody 801 binding can be detected. The binding of competed 801 antibody is reduced a little when compared to binding of uncompeted 801 antibody. The reduction is however so low that it is more likely to be due to steric hindrance than direct competition for the binding site. Blockage of protein F with the 9c5 antibody (antigenic site F1) prior to injection of antibody 801 into the Biacore cell shows an almost complete inhibition of antibody 801 binding to the F protein. It is therefore concluded that antibody 801 binds protein F at the F1 site, or very close to it.

For clones with anti-G reactivity the specificity of the individual antibodies expressed from the clones was assessed further to determine whether the individual antibody binds to the central domain of the G protein, to the conserved region, or to the GCRR, and also whether the epitope is conserved or subtype specific. This was done by ELISA and/or FLISA using the following G protein fragments:

G(B): residue 66-292 from RSV strain 18537 (expressed in DG44 CHO cells)

G(B) Fragment: Residue 127-203 from RSV strain 18537 (expressed in E. coli)

GCRR A: Residues 171-187 from RSV strain Long (synthesized with selectively formed cysteine bridges)

GCRR B: Residues 171-187 from RSV strain 18537 (synthesized with selectively formed cysteine bridges)

G conserved: Residues 164-176

Additional epitope analyses were also performed on the anti-G reactive clones by competition assays as described in Example 1, Section g-4.

Further, one of the clones identified in a screening procedure as described in Example 1, Section e, produces an SH specific antibody. Additionally, a number of clones bind one or more of the tested RSV strains, but the antigen has not been determined.

Data relating to antigen specificity for all the validated clones are summarized in Table 6. None of the validated clones bind to human laryngeal epithelial cells, nor does any of the tested G-specific clones (793, 816, 835, 841, 853, 855, 856, and 888) bind to human fractalkine (CX3CL1).

Characterization of Binding Kinetics

The binding affinity for recombinant RSV antigens was determined by surface plasmon resonance for a number antibody clones. The analysis was performed with Fab fragments prepared by enzymatic cleavage of the full-length antibodies. Data for a number of high-affinity antibody clones with $K_D$ values in the picomolar to nanomolar range is presented in Table 7. Fab fragments derived from commercially available Palivizumab (Synagis) were similarly analyzed for reference.

TABLE 7

Kinetic binding constants and affinities of selected clones.

| Fab clone (antigen) | $k_{on}$ ($10^5 M^{-1} s^{-1}$) | $k_{off}$ ($10^{-5}$ 1/s) | $t_{1/2}$ (min) | $K_D$ (pM) |
|---|---|---|---|---|
| 735 (F) | 4.07 | 9.18 | 130 | 226 |
| 810 (F) | 17.40 | 34.80 | 33 | 200 |
| 818 (F) | 1.92 | 2.20 | 530 | 115 |
| 817 (F) | 0.92 | 7.54 | 150 | 820 |
| 819 (F) | 3.56 | 4.99 | 230 | 140 |
| 825 (F) | 7.72 | 15.00 | 77 | 195 |
| 858 (F) | 4.97 | 0.34 | 3400 | 7 |
| 831 (F) | 3.72 | 42 | 28 | 1130 |
| 796 (G) | 8.33 | 40.3 | 28.67 | 480 |
| 811 (G) | 4.98 | 17.1 | 68 | 340 |
| 816 (G) | 20.20 | 17.80 | 65 | 90 |
| 838 (G) | 2.64 | 5.06 | 230 | 190 |
| 853 (G) | 17.7 | 140 | 8.25 | 790 |
| 859 (G) | 3.8 | 4.63 | 250 | 120 |
| Synagis (F) | 2.00 | 75.70 | 15 | 3780 |

Generation of a Cell Bank of Clones Expressing an Individual Antibody

A subset of 47 unique cognate $V_H$ and $V_L$ coding pairs corresponding to clone nr 735, 736, 744, 793, 795, 796, 799, 800, 801, 804, 810, 811, 812, 814, 816, 817, 818, 819, 824, 825, 827, 828, 829, 830, 831, 835, 838, 841, 853, 855, 856, 857, 858, 859, 861, 863, 868, 870, 871, 880, 881, 884, 885, 886, 888, 894 and 955 in Table 6 were selected for the generation of stable individual expression cell lines which each express a unique antibody from a single $V_H$ and $V_L$ gene sequence. The full sequences (DNA and deduced amino acid) of 44 selected clones (the above-identified except 828, 885, and 955) are shown in SEQ ID NOs 1-176.

The 44 clones are characterized by producing the following $V_H$ sequences, which are set forth in SEQ ID NOs. 1-44:

Clone No. 735:
QVQLQESGPGLVKPSETLSLTCTVSNGAIGDYDWSWIRQSPGKGLEWIGN

INYRGNTNYNPSLKSRVTMSLRTSTMQFSLKLSSATAADTAVYYCARDVG

YGGGQYFAMDVWSPGTTVTVSS

Clone No. 736:
QVQLVESGGGVVQPGGSLRLSCTASGFTFSTYGMHWVRQAPGKGLEWVAF

IRYDGSTQDYVDSVKGRFTISRDNSKNMVYVQMNSLRVEDTAVYYCAKDM

DYYGSRSYSVTYYYGMDVWGQGTTVTVSS

-continued

Clone No. 744:
QVQLVQSGAEVKKPGASVKVSCKASGYTFSGYYMHWVRQAPGQGLEWMGW
INTSSGGTNYAQKFQGRVTMTRDTSISTAHMELRRLRSDDTAVYYCARED
GTMGTNSWYGWFDPWGQGTLVTVSS Clone No. 793:
QVQLVESGGGLVKPGGSLRLSCAASGFPFGDYYMSWTRQAPGKGLEWVAY
INRGGTTWYADSVKGRFTISRDNAKNSLFLQMNSLRAGDTALYYCARGLI
LALPTATVELGAFDIWGQGTMVTVSS Clone No. 795:
QVQLQESGPGLVKPSQTLSLTCTVSGASISSGDYYWSWRQSPRKGLEWIG
YIFHSGTTYYNPSLKSRAVISLDTSKNQFSLRLTSVTAADTAVYYCARDV
DDFPVWGMNRYLALWGRGTLVTVSS Clone No. 796:
QVQLVESGGGVVQPGRSLRLSCAASGFSFSHFGMHWVRQVPGKGLEWVAI
ISYDGNNVHYADSVKGRFTISRDNSKNTLFLQMNSLRDDDTGVYYCAKDD
VATDLAAYYYFDVWGRGTLVTVSS Clone No. 799:
QVQLVESGGGVVQPGRSLKLSCEASGFNFNNYGMHWVRQAPGKGLEWVAV
ISYDGRNKYFADSVKGRFIISRDDSRNTVFLQMNSLRVEDTAVYYCARGS
VQVWLHLGLFDNWGQGTLVTVSS Clone No. 800:
QVQLVESGGAVVQPGRSLRLSCEVSGFSFSDYGMNWVRQGPGKGLEWVAV
IWHDGSNKNYLDSVKGRFTVSRDNSKNTLFLQMNSLRAEDTAVYYCARTP
YEFWSGYYFDFWGQGTLVTVSS Clone No. 801:
QVQLVESGGGVVQPGRSLRLSCAASGFPFNSYAMHWVRQAPGKGLEWVAV
IYYEGSNEYYADSVKGRFTISRDNSKNTLYLQMDSLRAEDTAVYYCARKW
LGMDFWGQGTLVTVSS Clone No. 804:
EVQLVESGGGLVRPGGSLRLSCSASGFTFSNYAMHWVRQAPGKRLEYVSA
TSTDGGSTYYADSLKGTFTISRDNSKNTLYLQMSSLSTEDTAIYYCARRF
WGFGNFFDYWGRGTLVTVSS Clone No. 810:
QVQLVQSGAEVKKSGSSVKVSCRASGGTFGNYAINWVRQAPGQGLEWVGR
IWVFDTTNYAQKFQGRVTITADRSTNTAIIMQLSSLRPQDTAMYYCLRGS
TRGWDTDGFDIWGQGTMVTVSS Clone No. 811:
QVQLVQSGAVVETPGASVKVSCKASGYIFGNYYIHWVRQAPGQGLEWMAV
INPNGGSTTSAQKFQDRITVTRDTSTTTVYLEVDNLRSEDTATYYCARQR
SVTGGFDAWLLWDASNTWGQGTMVTVSS Clone No. 812:
QVQLVQSGAEMKKPGSSVKVSCKASGGSFSSYSISWVRQAPGRGLEWVGM
ILPISGTTNYAQTFQGRVIISADTSTSTAYMELTSLTSEDTAVYFCARVF
REFSTSTLDPYYFDYWGQGTLVTVSS Clone No. 814:
QVQLVESGGGVVQPGKSVRLSCVGSGFRLMDYAMHWVRQAPGKGLDWVAV
ISYDGANEYYAESVKGRFTVSRDNSDNTLYLQMKSLRAEDTAVYFCARAG
RSSMNEEVIMYFDNWGLGTLVTVSS Clone No. 816:
EVQLLESGGGLVQPGGSLRLSCVASGFTFSTYAMTWVRQAPGKGLEWVSV
IRASGDSEWADSVRGRFTISRDNSKNTVFLQMDSLRVEDTAVYFCANIGQ
RRYCSGDHCYGHFDYWGQGTLVTVSS Clone No. 817:
QVQLVESGGGVVQPGRSLRLSCAASGFGFNTHGMHWVRQAPGKGLEWLSI
ISLDGIKTHYADSVKGRFTISRDNSKNTVFLQLSGLRPEDTAVYYCAKDH
IGGTNAYFEWTVPFDGWGQGTLVTVSS Clone No. 818:
QVTLRESGPAVVKPTETLTLTCAFSGFSLNAGRVGVSWIRQPPGQAPEWL
ARIDWDDDKAFRTSLKTRLSISKDSSKNQVVLTLSNMDPADTATYYCART
QVFASGGYYLYYLDHWGQGTLVTVSS Clone No. 819:
QVQLQESGPGLVKPSQTLSLTCTVSSGAISGADYYWSWIRQPPGKGLEWV
GFIYDSGSTYYNPSLRSRVTISIDTSKKQFSLKLTSVTAADTAVYYCARD
LGYGGNSYSHSYYYGLDVWGRGTTVTVSS Clone No. 824:
QVQLQESGPGLVKPSETLSLTCTVSGGSIGNYYWGWRQPPGKGLEWIGHI
YFGGNTNYNPSLQSRVTISVDTSRNQFSLKLNSVTAADTAVYYCARDSSN
WPAGYEDWGQGTLVTVSS Clone No. 825:
QVQLVQSGAEVKKPGASVKVSCKVSGYTFTSNGLSWVRQAPGQGFEWLGW
ISASSGNKKYAPKFQGRVTLTTDISTSTAYMELRSLRSDDTAVYYCAKDG
GTYVPYSDAFDFWGQGTMVTVSS Clone No. 827:
QVQLVQSGAEVKKPGASVKVSCRVSGHTFTALSKHWMRQGPGGGLEWMGF
FDPEDGDTGYAQKFQGRVTMTEDTATGTAYMELSSLTSDDTAVYYCATVA
AAGNFDNWGQGTLVTVSS Clone No. 829:
QVTLKESGPALVKATQTLTLTCTFSGFSLSRNRMSVSWIRQPPGKALEWL
ARIDWDDDKFYNTSLQTRLTISKDTSKNQVVLTMTNMDPVDTATYYCART
GIYDSSGYYLYYFDYWGQGTLVTVSS Clone No. 830:
QVQLVQSGAEVKVPGASVKVSCKASGYTFTTYGVSWVRQAPGQGLEWMGW
ISAYNGNTYYLQKLQGRVTMTTDTSTSTAYMELRGLRSDDTAMYYCARDR
VGGSSSEVLSRAKNYGLDVWGQGTTVTVSS Clone No. 831:
QVQLVQSGAEVKKPGASVKVSCKASANIFTYAMHWVRQAPGQRLEWMGWI
NVGNGQTKYSQRFQGRVTITRDTSATTAYMELSTLRSEDTAVYYCARRAS
QYGEVYGNYFDYWGQGTLVTVSS Clone No. 835:
QVQLVQSGAEVKRPGASVKVSCKASGYTFISYGFSWVRQAPGQGLEWMGW
SSVYNGDTNYAQKFHGRVNMTTDTSTNTAYMELRGLRSDDTAVYFCARDR
NVVLLPAAPFGGMDVWGQGTMVTVSS Clone No. 838:
QVQLVESGGGVVQPGTSLRLSCAASGFTFSTFGMHWVRQAPGKGLEWVAV
ISYDGNKKYYADSVKGRFTISRDNSKNTLYLQVNSLRVEDTAVYYCAAQT
PYFNESSGLVPDWGQGTLVTVSS Clone No. 841:
QVQLVQSGAEVKKPGASVKVSCKASGYTFISFGISWVRQAPGQGLEWMGWI
SAYNGNTDYAQRLQDRVTMTRDTATSTAYLELRSLKSDDTAVYYCTRDESM
LRGVTEGFGHDYWGQGTLVTVSS Clone No. 853:
EVQLVQSGAEVKKPGQSLKISCKTSGYIFTNYWIGWVRQRPGKGLEWMGV
IFPADSDARYSPSFQGQVTISADKSIGTAYLQWSSLKASDTAIYYCARIP
KYYFDSSGQFSEMYYFDFWGQGTLVTVSS Clone No. 855:
QVQLVQSGPEVKKPGASVKVSCKASGYVLTNYAFSWVRQAPGQGLEWLGW
ISGSNGNTYYAEKFQGRVTMTTDTSTSTAYMELRSLRSDDTAVYFCARDL
LRSTYFDYWGQGTLVTVSS Clone No. 856:
QVQLVQSGAEVKKPGASVKVSCKASGYTFSNYGFSWVRQAPGRGLEWMGW
ISAYNGNTYYAQNLQGRVTMTTDTSTTTAYMVLRSLRSDDTAMYYCARDG
NTAGVDMWSRDGFDIWGQGTMVTVSS Clone No. 857:
EVQLLESGGGLVQPGGPLRLSCVASGFSFSSYAMNWIRLAPGKGLEWVSG
ISGSGGSTYYGDSVKGRFTISRDNSKNTLYLQMNSLRAEDTAVYYCAKEP
WTDIVVASVISPYYYDGMDVWGQGTTVTVSS Clone No. 858:
QVQLVQSGAEVKKPGSSVKVSCKASGGSFDGYTISWLRQAPGQGLEWMGR
NLVVPTLGFPNYAQKIFQGRVTVTADRSTNTAYLELSRLTSEDTAVYYCA
RMGSHSGRPGFDMWGQGTLVTVSS Clone No. 859:
QVQLVESGGGVVQPGRSLRLSCAVSGSSFSKYGIHWVRQAPGKGLEWVAV
ISYDGSKKYFTDSVKGRFTIARDNSQNTVFLQMNSLRAEDTAVYYCATGG
GVNVTSWSDVEHSSSLGYWLGTLVTVSS Clone No. 861:
QVQLVESGGGVVQPGGSLRLSCAASGFTFSSYGMHWVRQAPGKGLEWVAF
IWNDGSNKYYADSVKGRFTISRDNSKNTLYLQMNSLRAEDTAVYYCVKDE
VYDSSGYYLYYFDSWGQGTLVTVSS Clone No. 863:
EVQLLESGGGLVQPGGSLRLSCAASGFTFSSYTMSWVRQAPGKGLEWVSS
ISASTVLTYYADSVKGRFTISRDNSKNTLYLQMSSLRAEDTAVYYCAKID
YDFWSGYPGGQYWFFDLWGRGTLVTVSS Clone No. 868:
QVQLQESGPGLVTPSETLSVTCTVSNYSIDNAYYWGWLRQPPGKGLEWIG
SIHHSGSAYYNSSLKSRATISDTSKNQFSLNLRSVTAADTAVYYCARDTI
LTFGEPHWFDPWGQGTLVTVSS Clone No. 870:
QVQLQESGPGLVKPSETLSLTCTVSGDSISNYYWSWRQPPGKGLEWIGEI
SNTWSTNYNPSLKSRVTISLDMPKNQLSLKLSSVTAADTAVYYCARGLFY
DSGGYYLFYFQHWGQGTLVTVSS Clone No. 871:
QVQLVESGGGVVQPGRSLRVSCAASGFTFSNYGMHWVRQAPGKGLEWVAV
IWYDDSNKQYGDSVKGRFTISRDNSKSTLYLQMDRLRVEDTAVYYCARAS
EYSISWRHRGVLDYWGQGTLVTVSS Clone No. 880:
QITLKESGPTLVRPTQTLTLTCTFSGFSLSTSKLGVGWIRQPPGKALEWL
ALVDWDDDRRYRPSLKSRLTVTKIDTSKNQVVLTMTNMDPVDTATYYCAH
SAYYTSSGYYLQYFHHWGPGTLVTVSS Clone No. 881:
EVQLVESGGGVVQPGGSLRLSCEVSGFTFNSYEMTWVRQAPGKGLEWVSH
IGNSGSMIYYADSVKGRFTISRDNAKNSLYLQMNSLRVEDTAVYYCARSD
YYDSSGYYLLYLDSWGHGTLVTVSS Clone No. 884:
QVQLVQSGAEVRKPGASVKVSCKASGHTFINFAMHWVRQAPGQGLEWMGY
INAVNGNTQYSQKFQGRVTFTRDTSANTAYMELSSLRSEDTAVYYCARNN
GGSAIIFYYWGQGTLVTVSS Clone No. 886:
QVQLVESGGGVVQPGRSLRLSCAASGFSFSSYGMHWVRQAPGKGLEWVAV
ISNDGSNKYYADSVKGRFTISRDNSKKTMYLQMNSLRAEDTAVYFCAKTT
DQRLLVDWFDPWGQGTLVTVSS Clone No. 888:
QLQLQESGPGLVKPSETLSLTCTASGGSINSSNFYWGWRQPPGKGLEWIG
SIFYSGTTYYNPSLKSRVTISVDTSKNQFSLKLSPVTAADTAVYHCARHG
FRYCNNGVCSINLDAFDIWGQGTMVTVSS Clone No. 894:
QVQLVESGGGVVQPGKSLRLSCAASGFRFSDYGMHWVRQAPSKGLEWVAV
IWHDGSNLRYADSVRGRFSISRDNSKNTLYLQMNSMRADDTAFYYCARVP
FQIWSGLYFDHWGQGTLVTVSS These V$_H$ amino acid sequences are in the clones encoded by the following nucleic acid sequences, which are also set forth as SEQ ID NOs. 45-88:

Clone No. 735:
caggtgcagctgcaggagtcgggcccaggactggtgaagccttcggagac
cctgtccctcacgtgcactgtgtctaatggcgccatcggcgactacgact
ggagctggattcgtcagtccccagggaagggactggagtggattgggaac
ataaattacagagggaacaccaactacaacccctccctcaagagtcgagt -continued caccatgtccctacgcacgtccacgatgcagttctccctgaagctgagct ctgcgaccgctgcggacacggccgtctattactgtgcgagagatgtaggc tacggtggcgggcagtatttcgcgatggacgtctggagcccagggaccac ggtcaccgtctcgagt Clone No. 736:
caggtgcagctggtggagtctgggggaggcgtggtccagcctgggggtc cctgagactctcctgtacagcgtctggattcaccttcagtacctatggca tgcactgggtccgccaggctcccggcaaggggctggaatgggtggcattt atacggtatgatggaagtactcaagactatgtagactccgtgaagggccg attcaccatctccagagacaattccaagaatatggtgtatgtgcagatga acagcctgagagttgaggacacggctgtctattactgtgcgaaagacatg gattactatggttcgcggagttattctgtcacctactactacggaatgga cgtctggggccaagggaccacggtcaccgtctcgagt Clone No. 744:
caggtgcagctggtgcagtctgggggctgaggtgaagaagcctggggcctc agtgaaggtctcctgcaaggcttctggatacaccttcagcggctattata tgcactgggtgcgacaggcccctggacaagggcttgagtggatgggatgg atcaacactagcagtggtggcacaaactatgcgcagaagtttcagggcag ggtcaccatgaccagggacacgtccatcagcacagcccacatggaactga ggaggctgagatctgacgacacggccgtgtattattgtgcgagagaggac ggcaccatgggtactaatagttggtatggctggttcgaccccctggggcca gggaaccctggtcaccgtctcgagt Clone No. 793:
caggtgcagctggtggagtctgggggaggcttggtcaagcctgggggtc cctgagactctcctgtgcggcctctggattccccttcggtgactactaca tgagctggatccgccaggctccagggaagggactggagtgggttgcatac attaatagaggtggcactaccatatactacgcagactctgtgaagggccg attcaccatctccagggacaacgccaagaactccctgtttctgcaaatga acagcctgagagccggggacacggccctctattactgtgcgagagggcta attctagcactaccgactgctacggttgagttaggagcttttgatatctg gggccaagggacaatggtcaccgtctcgagt Clone No. 795:
caggtgcagctgcaggagtcgggcccaggactggtgaagccttcacagac cctgtccctcacctgcactgtctctggtgcctccatcagcagtggtgatt attactggagttggatccgtcagtctccaaggaagggcctggagtggatt gggtacatcttccacagtgggaccacgtactacaacccgtccctcaagag tcgagctgtcatctcactggacacgtccaagaaccaattctccctgaggc tgacgtctgtgactgccgcagacacggccgtctattattgtgccagagat gtcgacgattttcccgtttgggtatgaatcgatatcttgccctctgggg ccggggaaccctggtcaccgtctcgagt Clone No. 796:
caggtgcagctggtggagtctgggggaggcgtggtccagcctgggaggtc cctgagactctcctgtgcagcctctggattcagcttcagtcactttggca tgcactgggtccgccaggttccaggcaagggctggagtgggtggcaatt atatcatatgatgggaataatgtacactatgccgactccgtaaagggccg attcaccatctccagagacaattccaagaacacgctgtttctgcaaatga acagcctgagagatgacgacacgggtgtgtattactgtgcgaaggacgac gtggcgacagatttggctgcctactactacttcgatgtctggggccgtgg caccctggtcaccgtctcgagt Clone No. 799:
caggtgcagctggtggagtctgggggcggcgtggtccagcctgggaggtc cctgaaactctcttgtgaagcctctggattcaacttcaataattatggca tgcactgggtccgccaggcaccaggcaaggggctggagtgggtggcagtt atttcatatgacggaagaaataagtattttgctgactccgtgaagggccg attcatcatctccagagacgattccaggaacacagtgtttctgcaaatga acagcctgcgagttgaagatacggccgtctattactgtgcgagaggcagc gtacaagtctggctacatttgggacttttttgacaactggggccagggaac cctggtcaccgtctcgagt Clone No. 800:
caggtgcagctggtggagtctgggggagccgtggtccagcctgggaggtc cctgagactctcctgtgaagtgtctggattcagtttcagtgactatggca tgaactgggtccgccaggtccaggcaaggggctggagtgggtggcagtt atatggcatgacggaagtaataaaaattatctagactccgtgaagggccg attcaccgtctccagagacaattccaagaacacattgtttctgcaaatga acagcctgagagccgaagacacggctgtatattactgtgcgaggacgcct tacgagttttggagtggctattactttgacttctggggccagggaaccct ggtcaccgtctcgagt Clone No. 801:
caggtgcagctggtggagtctgggggaggcgtggtccagcctgggaggtc cctgagactctcctgtgcagcgtctggattcccttcaatagctatgcca tgcactgggtccgccaggctccaggcaaggggctggagtgggtggcagtg atatattatgaagggagtaatgaatattatgcagactccgtgaagggccg attcaccatctccagagacaattccaagaacacactctgtatttgcaaatgg atagcctgagagccgaggacacggctgtctattactgtgcgaggaagtgg ctggggatggacttctggggccagggaaccctggtcaccgtctcgagt Clone No. 804:
gaggtgcagctggtggagtctgggggaggcttggtccggcctggggggtc cctgagactctcctgttcagcctctggattcaccttcagtaactatgcta tgcactgggtccgccaggctccagggaagagactggaatatgtttcagct actagtactgatgggggagcacatactacgcagactccctaaagggcac attcaccatctccagagacaattccaagaacacactgtatcttcaaatga gcagtctcagtactgaggacacggctatttattactgcgcccgccgattc tggggatttggaaacttttttgactactggggccggggaaccctggtcac cgtctcgagt -continued Clone No. 810:
caggtgcagctggtgcagtctggggctgaggtgaagaagtccgggtcctc
ggtgaaggtctcctgcagggcttctggaggcaccttcggcaattatgcta
tcaactgggtgcgacaggcccctggacaagggcttgagtgggtgggaagg
atcatccctgtctttgatacaacaaactacgcacagaagttccagggcag
agtcacgattaccgcggacagatccacaaacacagccatcatgcaactga
gcagtctgcgacctcaggacacggccatgtattattgtttgagaggttcc
acccgtggctgggatactgatggttttgatatctggggccaagggacaat
ggtcaccgtctcgagt Clone No. 811:
caggttcagctggtgcagtctggggctgtcgtggagacgcctggggcctc
agtgaaggtctcctgcaaggcatctggatacatcttcggcaactactata
tccactgggtgcggcaggcccctggacaagggcttgagtggatggcagtt
atcaatcccaatggtggtagcacaacttccgcacagaagttccaagacag
aatcaccgtgaccagggacacgtccacgaccactgtctatttggaggttg
acaacctgagatctgaggacacggccacatattattgtgcgagacagaga
tctgtaacaggggctttgacgcgtggcttttaatcccagatgcttctaa
tacctggggccaggggacaatggtcaccgtctcgagt Clone No. 812:
caggtgcagctggtgcagtctggggctgagatgaagaagcctgggtcctc
ggtgaaggtctcctgcaaggcttctggaggctccttcagcagctattcta
tcagctgggtgcgacaggcccctggacgagggcttgagtgggtgggaatg
atcctgcctatctctggtacaacaaactacgcacagacatttcagggcag
agtcatcattagcgcggacacatccacgagcacagcctacatggagctga
ccagcctcacatctgaagacacggccgtgtatttctgtgcgagagtctttt
agagaatttagcacctcgacccttgacccctactactttgactactgggg
ccagggaaccctggtcaccgtctcgagt Clone No. 814:
caggtgcagctggtggagtctgggggaggcgtggtccagcctgggaagtc
cgtgagactctcctgtgtaggctctggcttcaggctcatggactatgcta
tgcactgggtccgccaggctccaggcaaggggactggattgggtggcagtt
atttcatatgatggagccaatgaatactacgcagagtccgtgaagggccg
attcaccgtctccagagacaattcagacaacactctgtatctacaaatga
agagcctgagagctgaggacacggctgtgtatttctgtgcgagagcgggc
cgttcctctatgaatgaagaagttattatgtactttgacaactgggcct
gggaaccctggtcaccgtctcgagt Clone No. 816:
gaggtgcagctgttggagtctgggggaggcttggtccagcctggggggtc
cctgagactctcctgtgtagcctccggattcacctttagtacctacgcca
tgacctgggtccgccaggctccagggaaggggctggagtgggtctcagtc
attcgtgctagtggtgatagtgaaatctacgcagactccgtgaggggccg
gttcaccatctccagagacaattccaagaacacggtgtttctgcaaatgg acagcctgagagtcgaggacacggccgtatatttctgtgcgaatataggc
cagcgtcggtattgtagtggtgatcactgctacggacactttgactactg
gggccagggaaccctggtcaccgtctcgagt Clone No. 817:
caggtgcagctggtggagtctgggggaggcgtggtccaacctggggaggtc
cctgagactctcctgtgcagcctctggattcggcttcaacacccatggca
tgcactgggtccgccaggctccaggcaaggggctggagtggctgtcaatt
atctcacttgatgggattaagacccactatgcagactccgtgaagggccg
attcaccatctccagagacaattccaagaacacggtgtttctacaattga
gtggcctgagacctgaagacacggccgtgtatattactgtgcgaaagatcat
attgggggacgaacgcatattttgaatggacagtcccgtttgacggctg
gggccagggaaccctggtcaccgtctcgagt Clone No. 818:
caggtcaccttgagggagtctggtccagcggtggtgaagcccacagaaac
gctcactctgacctgcgcgccttctctgggttctcactcaacgccggtagag
tgggtgtgagttggatccgtcagcccccagggcaggcccggaatggctt
gcacgcattgattgggatgatgataaagcgttccgcacatctctgaagac
cagactcagcatctccaaggactcctccaaaaaccaggtggtccttacac
tgagcaacatggaccctgcggacacagccacatattactgtgcccggaca
caggtcttcgcaagtggaggctactacttgtactaccttgaccactgggg
ccagggaaccctggtcaccgtctcgagt Clone No. 819:
caggtgcagctgcaggagtcgggcccaggactggtgaagccttcacagac
cctgtccctcacctgcactgtctctagtggcgccatcagtggtgctgatt
actactggagttggatccgccagccccagggaagggcctggagtgggtt
gggttcatctatgacagtgggagcacctactacaacccgtccctcaggag
tcgagtgaccatatcaatagacacgtccaagaagcagttctccctgaagc
tgacctctgtgactgccgcagacacggccgtgtattactgtgccagagat
ctaggctacggtggtaactcttactcccactcctactactacggtttgga
cgtctggggccgagggaccacggtcaccgtctcgagt Clone No. 824:
caggtgcagctgcaggagtcgggcccaggactggtgaagccttcggagac
cctgtccctcacctgcactgtctctggtggctccatcggaaattactact
ggggctggatccggcagccccagggaagggacttgagtggattgggcat
atctacttcggtggcaacaccaactacaaccctccctccagagtcgagt
caccatttcagtcgacacgtccaggaaccagttctccctgaagttgaact
ctgtgaccgccgcggacacggccgtgtattactgtgcgagggatagcagc
aactggcccgcaggctatgaggactggggccagggaaccctggtcaccgt
ctcgagt Clone No. 825:
caggttcagctggtgcagtctggagctgaggtgaagaagcctggggcctc
agtgaaggtctcctgcaaggtttctggttacacccttaccagtaatggtc
tcagctgggtgcgacaggcccctggacaagggtttgagtggctgggatgg -continued atcagcgctagtagtggaaacaaaaagtatgccccgaaattccagggaag agtcaccttgaccacagacatttccacgagcacagcctacatggaactga ggagtctgagatctgacgatacggccgtatattactgtgcgaaagatggg ggcacctacgtgccctattctgatgcctttgatttctggggccaggggac aatggtcaccgtctcgagt Clone No. 827:
caggtccagctggtacagtctggggctgaggtgaagaagcctggggcctc agtgaaggtctcctgcagggtttccggacacactttcactgcattatcca aacactggatgcgacagggcctggaggagggcttgagtggatgggatttt tttgatcctgaagatggtgacacaggctacgcacagaagttccagggcag agtcaccatgaccgaggacacagccacaggcacagcctacatggagctga gcagcctgacatctgacgacacggccgtatattattgtgcaacagtagcg gcagctggaaactttgacaactggggccagggaaccctggtcaccgtctc gagt Clone No. 829:
caggtcaccttgaaggagtctggtcctgcgctggtgaaagccacacagac cctgacactgacctgcaccttctctgggttttcactcagtaggaatagaa tgagtgtgagctggatccgtcagcccccagggaaggccctggagtggctt gcacgcattgattgggatgatgataaattctacaacacatctctgcagac caggctcaccatctccaaggacacctccaaaaaccaggtggtccttacaa tgaccaacatggaccctgtggacacagccaccattactgcgcacggact gggatatatgatagtagtggttattacctctactactttgactactgggg ccagggaaccctggtcaccgtctcgagt Clone No. 830:
caggtgcagctggtgcagtctggagctgaggtgaaggtgcctggggcctc agtgaaggtctcctgcaaggcttctggttacacctttaccacttacggtg tcagctgggtgcggcaggcccctggacaagggcttgagtggatgggttgg atcagcgcttacaatggtaacacatactatctacagaagctccagggcag agtcaccatgaccacagacacatccacgagcacagcctacatggagctgc ggggcctgaggtctgacgacacggccatgtattactgtgcgagagatcgt gttgggggcagctcgtccgaggttctatcgcgggccaaaaactacggttt ggacgtctggggccaagggaccacggtcaccgtctcgagt Clone No. 831:
caggttcagctggtgcagtctggggctgaggtgaagaagcctggggcctc agttaaggtttcctgcaaggcttctgcaaacatcttcacttatgcaatgc attgggtgcgccaggcccccggacaaaggcttgagtggatgggatggatc aacgttggcaatggtcagacaaaatattcacagaggttccagggcagagt caccattaccagggacacgtccgcgactacagcctacatggagctgagca ccctgagatctgaggacacggccgtgtattactgtgcgaggcgtgcgagc caatatggggaggtctatggcaactactttgactactggggccaggggaac cctggtcaccgtctcgagt Clone No. 835:
caggtgcagctggtgcagtctggagctgaggtgaagaggcctggggcctc agtgaaggtctcctgcaaggcttcaggttacacctttatcagctatggtt tcagctgggtgcgacaggcccctggacaagggcttgagtggatgggatgg agcagcgtttacaatggtgacacaaactatgcacagaagttccacggcag agtcaacatgacgactgacacatcgacgaacacggcctacatggaactca ggggcctgagatctgacgacacggccgtgtatttctgtgcgagggatcgc aatgttgttctacttccagctgctccttttggaggtatggacgtctgggg ccaagggacaatggtcaccgtctcgagt Clone No. 838:
caggtgcagctggtggagtctgggggaggcgtggtccagccggggacttc cctgagactctcctgtgcagcctctggattcaccttcagtacgtttggca tgcactgggtccgccaggctccaggcaagggctggagtgggtggcagtt atatcatatgatggaaataagaaatactatgcagactccgtgaagggccg attcaccatctccagagacaattccaagaacacgctgtatctgcaagtga acagcctgagagtcgaggacacggctgtgtattactgtgcggcccaaact ccatatttcaatgagagcagtgggttagtgccggactggggccagggcac cctggtcaccgtctcgagt Clone No. 841:
caggtgcagctgggcagtctggagctgaggtgaagaagcctggggcctca gtgaaggtctcctgcaaggcttctggttacacctttatcagttttggcat cagctgggtgcgacaggccctgacaaggacttgagtggatgggatgga tcagcgcttacaatggtaacacagactatgcacagaggctccaggacaga gtcaccatgactagagacacagccacgagcacagcctacttggagctgag gagcctgaaatctgacgacacggccgtgtactattgcactagagacgagt cgatgcttcggggagttactgaaggattcggacccattgactactggggc cagggaaccctggtcaccgtctcgagt Clone No. 853:
gaagtgcagctggtgcagtctggagcagaggtgaaaaagccggggcagtc tctgaagatctcctgtaagacttctggatacatctttaccaactactgga tcggctgggtgcgccagaggcccgggaaaggcctggagtggatgggggtc atctttcctgctgactctgatgccagatacagcccgtcgttccaaggcca ggtcaccatctcagccgacaagtccatcggtactgcctacctgcagtgga gtagcctgaaggcctcggacaccgccatatattactgtgcgagaccgaaa tattactttgatagtagtgggcaattctccgagatgtactactttgactt ctggggccagggaaccctggtcaccgtctcgagt Clone No. 855:
caggttcagctggtgcagtctggacctgaggtgaagaagcctggggcctc agtgaaggtctcctgcaaggcttctggttatgtgttgaccaactatgcct tcagctgggtgcggcaggcccctggacaagggcttgagtggctgggatgg atcagcggctccaatggtaacacatactatgcagagaagttccagggccg agtcaccatgaccacagacacatccacgagcacagcctacatggagctga -continued ggagtctgagatctgacgacacggccgtttatttctgtgcgagagatctt ctgcggtccacttactttgactactggggccagggaaccctggtcaccgt ctcgagt Clone No. 856:
caggtgcagctggtgcagtctggagctgaggtgaagaagcctggggcctc agtgaaggtctcctgcaaggcttctggttacaccttttccaactacggtt tcagctgggtgcgacaggcccctggacgagggcttgagtggatgggatgg atcagcgcttacaatggtaacacatactatgcacagaacctccagggcag agtcaccatgaccacagacacatccacgaccacagcctacatggtactga ggagcctgagatctgacgacacggccatgtattactgtgcgagagatgga aatacagcaggggttgatatgtggtcgcgtgatggttttgatatctgggg ccaggggacaatggtcaccgtctcgagt Clone No. 857:
gaggtgcagctgttggagtctgggggaggcttggtacagcctggggggcc cctgaggctctcctgtgtagcctctggattcagctttagcagctatgcca tgaactggatccgcctggctccagggaaggggctggagtgggtctcaggt attagtggtagcggtggtagcacttactacgagactccgtgaagggccg gttcaccatctccagagacaattccaagaacacgctgtatctgcaaatga acagcctgagagccgaggacacggccgtatattactgtgcgaaagagccg tggatcgatatagtagtggcatctgttatatcccctactactacgacgg aatggacgtctggggccaagggaccacggtcaccgtctcgagt Clone No. 858:
caggttcagctggtgcagtctggggctgaggtgaagaagcctgggtcctc ggtgaaggtctcctgcaaggcctctgaggatccttcgacggctacacta tcagctggctgcgacaggcccctggacaggggcttgagtggatgggaagg gtcgtccctacacttggttttccaaactacgcacagaagttccaaggcag agtcaccgttaccgcggacagatccaccaacacagcctacttggaattga gcagactgacatctgaagacacggccgtatattactgtgcgaggatgaat ctcggatcgcatagcgggcgcccgggttcgacatgtggggccaaggaac cctggtcaccgtctcgagt Clone No. 859:
caggtgcagctggtggagtctgggggaggcgtggtccagcctggggaggtc cttgagactctcctgtgcagtgtctggatccagcttcagtaaatatggca tacactgggtccgccaggctccaggcaaggggctggagtgggtggcagtt atatcgtatgatggaagtaaaaagtatttcacagactccgtgaagggccg attcaccatcgccagagacaattcccagaacacggttttctgcaaatga acagcctgagagccgaggacacggctgtctattactgtgcgacaggaggg ggtgttaatgtcacctcgtggtccgacgtagagcactcgtcgtccttagg ctactggggcctgggaaccctggtcaccgtctcgagt Clone No. 861:
caggtgcagctggtggagtctgggggaggcgtggtccagcctgggggtc cctgagactctcctgtgcagcgtctggattcaccttcagtagctatggca tgcactgggtccgccaggctccaggcaaggggctggagtgggtggcattt -continued atatggaatgatggaagtaataaatactatgcagactccgtgaagggccg attcaccatctccagagacaattccaagaacacgctgtatctgcaaatga acagcctgagagctgaggacacggctgtgtattactgtgtgaaagatgag gtctatgatagtagtggttattacctgtactactttgactcttggggcca gggaaccctggtcaccgtctcgagt Clone No. 863:
gaggtgcagctgttggagtctgggggaggcttggtacagcctgggggtc cctgagactctcctgtgcagcctctggattcacgtttagctcctatacca tgagctgggtccgccaggctccagggaaggggctggagtgggtctcaagt attagtgctagtactgttctcacatactacgcagactccgtgaagggccg cttcaccatctccagagacaattccaagaacacgctgtatctgcaaatga gtagcctgagagccgaggacacggccgtatattactgtgcgaaagattac gatttttggagtggctatcccgggggacagtactggttcttcgatctctg gggccgtggcaccctggtcaccgtctcgagt Clone No. 868:
caggtgcagctgcaggagtcgggcccaggactggtgacgccttcggagac cctgtccgtcacttgcactgtctctaattattccatcgacaatgcttact actggggctggatccggcagcccccagggaagggtctggagtggataggc agtatccatcatagtgggagcgcctactacaattcgtccctcaagagtcg agccaccatatctatagacacgtccaagaaccaattctcgttgaacctga ggtctgtgaccgccgcagacacggccgtatattactgtgcgcgcgatacc atcctcacgttcggggagccccactggttcgaccctggggccagggaac cctggtcaccgtctcgagt Clone No. 870:
caggtgcagctgcaggagtcgggcccaggactggtgaagccttcggagac cttgtccctcacctgcactgtctcaggtgactccatcagtaattactact ggagttggatccggcagccccagggaagggactggagtggattggagaa atatctaacacttggagcaccaattacaaccctccctcaagagtcgagt caccatatctctagacatgcccaagaaccagttgtccctgaagctgagct ctgtgaccgctgcggacacggccgtatattactgtgcgagagggcttttc tatgacagtggtggttactactttgttttacttccaacactggggccaggg caccctggtcaccgtctcgagt Clone No. 871:
cagggcagctggtggagtctgggggaggcgtggtccagcctggaggtcc ctgagagtctcctgtgcagcgtctggattcaccttcagtaactatggcat gcactgggtccgccaggctccaggcaaggggctggagtgggtggcagtta tatggtatgatgacagtaataaacagtatggagactccgtgaagggccga ttcaccatctccagagacaattccaagagtacgctgtatctgcaaatgga cagactgagagtcgaggacacggctgtgtattattgtgcgagagcctccg agtatagtatcagctggcgacacaggggggtccttgactactggggccag ggaaccctggtcaccgtctcgagt -continued Clone No. 880:
cagatcaccttgaaggagtctggtcctacgctggtgagacccacacagac cctcacactgacctgcaccttctctgggttctcactcagcactagtaaac tgggtgtgggctggatccgtcagcccccaggaaaggccctggagtggctt gcactcgttgattgggatgatgataggcgctacaggccatctttgaagag caggctcaccgtcaccaaggacacctccaaaaaccaggtggtccttacaa tgaccaacatggaccctgtggacacagccacatattactgtgcacacagt gcctactatactagtagtggttattaccttcaatacttccatcactgggg cccgggcaccctggtcaccgtctcgagt Clone No. 881:
gaggtgcagctggtggagtctgggggaggcgtggtacagcctggaggctc cctgagactctcctgtgaagtctccggattcaccttcaatagttatgaaa tgacctgggtccgccaggcccagggaaggggctggagtgggtttcacac attggtaatagtggttctatgatatactacgctgactctgtgaagggccg attcaccatctccagagacaacgccaagaactcactatatctgcaaatga acagcctgagagtcgaggacacggctgtttattactgtgcgaggtcagat tactatgatagtagtggttattatctcctctacttagactcctggggcca tggaaccctggtcaccgtctcgagt Clone No. 884:
caggtgcagctggtgcagtctggggctgaggtgaggaagcctggggcctc agtgaaggtttcctgcaaggcttctggacatactttcattaactttgcta tgcattgggtgcgccaggccccgggacaggggcttgagtggatgggatac atcaacgctgtcaatggtaacacacagtattcacagaagttccaggcag agtcaccttacgagggacacatccgcgaacacagcctacatggagctga gcagcctgagatctgaagacacggctgtgtattactgtgcgagaaacaat gggggctctgctatcatttttactactggggccagggaaccctggtcac cgtctcgagt Clone No. 886:
caggtgcagctggtggagtctgggggaggcgtggtccagcctggaggtc cctgagactctcctgtgcagcctctggattcagcttcagtagctatggca tgcactgggtccgccaggctccaggcaaggggctggagtgggtggcagtt atatcaaatgatggaagtaataaatactatgcagactccgtgaagggccg attcaccatctccagagacaattccaagaaaacgatgtatctgcaaatga acagcctgagagctgaggacacggctgtgtatttctgtgcgaagacaaca gaccagcggctattagtggactggttcgaccctggggccagggaaccct ggtcaccgtctcgagt Clone No. 888:
cagctgcagctgcaggagtcgggcccaggactggtgaagccatcggagac cctgtccctcacctgcactgcctctggtggctccatcaacagtagtaatt tctactggggctggatccgccagccccagggaaggggctggagtggatt gggagtatctttatagtgggaccacctactacaacccgtccctcaagag tcgagtcaccatatccgtagacacgtccaagaaccagttctccctgaagc -continued tgagccctgtgaccgccgcagacacggctgtctatcactgtgcgagacat ggcttccggtattgtaataatggtgtatgctctataaatctcgatgctt tgatatctggggccaagggacaatggtcaccgtctcgagt Clone No. 894:
caggtgcagctggtggagtctgggggaggcgtcgtccagcctggaaagtc cctgagactctcctgtgcagcgtctggattcagattcagtgactacggca tgcactgggtccggcaggctccaagcaaggggctggagtgggtggcagtt atctggcatgacggaagtaatataaggtatgcagactccgtgaggggccg attttccatctccagagacaattccaagaacacgctgtatttgcaaatga acagcatgagagccgacgacacggcttttttattattgtgcgagagtcccg ttccagatttggagtggtctttattttgaccactggggccagggaaccct ggtcaccgtctcgagt In the same clones, the complete amino acid sequences of the light chains (i.e. light chains including constant and variable regions) have the following amino acid sequences, which are also set forth as SEQ ID NOs: 89-132:

Clone No. 735:
EIVLTQSPATLSLSPGERATLSCRASQSVNSHLAWYQQKLPGQAPRLLIY

NTFNRVTGIPARFSGSGSGTDFTLTISSLATEDFGVYYCQQRSNWPPALT

FGGGTKVEIKRTVAAPSVFIFPPSDEQLKSGTASVVCLLNNYPREAKVQW

KVDNALQSGNSQESVTEQDSKDSTYSLSSTLTLSKADYEKHKVYACEVTH

QGLSSPVTKSFNRGEC

Clone No. 736:
DIQMTQSPSSLSASVGDRVTFTCRASQRISNHLNWYQQKPGKAPKLLIFG

ASTLQSGAPSRFSGSGSGTDFTLTITNVQPDDFATYYCQQSYRTPPINFG

QGTRLDIKRTVAAPSVFIIPPSDEQLKSGTASVVCLLNNFYPREAKVQWK

VDNALQSGNSQESVTEQDSKDSTYSLSSTLTLSKADYEKIHKVYACEVTH

QGLSSPVTKSFNRGEC

Clone No. 744:
EIVLTQSPGTLSLSPGERATLSCRASQSVSSSYLAWYQQKPGQAPRLLIY

GASSRATGWDRFSGSGSGTDFTLTISRLEPEDFAVYYCQQYDSSLSTWTF

GQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTH

QGLSSPVTKSFNRGEC

Clone No. 793:
DIQMTQSPSSLSASVGDRVTITCRASQSITGYLNWYQQKPGKAPKLLIYA

TSTLQSEVPSRFSGSGSGTDFTLTISSLQPEDFATYYCQQSYNTLTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

Clone No. 795:
EIVLTQSPGTLSLSPGERATLSCRASQSVSSSYLAWYQQKPGQAPRLLIH

GASTGATGTPDRFSGSGSGTDFTLTISTLEPEDFAVYYCQQYGRTPYTFG

-continued

QGTKLENKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC

Clone No. 796:
DIVMTQTPLSLSVTPGQPASISCRSSQSLLRSDGKTFLYWYLQKPGQSPQ
PLMYEVSSRFSGVPDRFSGSGSGADFTLNISRVETEDVGIYYCMQGLKIR
RTFGPGTKVEIKRTVAAPSVHFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC Clone No. 799:
DIQMTQSPSTLSASVGDRVTFSCRASQSVSSWVAWYQQKPGKAPKLLISE
ASNLESGVPSRFSGSGSGTEFTLTISSLQPEDFATYYCQQYHSYSGYTFG
QGTKIEIKRTVAAPSVFIIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC Clone No. 800:
AIQLTQSPSSLSASVGDRVTLTCRASQGITDSLAWYQQKPGKAPKVLLYA
ASRLESGVPSRFSGRGSGTDFTLTISSLQPEDFATYYCQQYSKSPATFGP
GTKVEIRRTVAAPSVFWPPSDEQLKSGTASVVCLLNINFYPREAKVQWKV
DNALQSGNSQESVTEQDSKDSTYSLSSTLTLSKADYEKHKVYACEVTHQG
LSSPVTKSFNRGEC Clone No. 801:
DIVMTQSPLSLPVTPGEPASISCRSSQSLLNSNGFNYVDWYLQKPGQSPQ
LLIYLGSNRASGVPDRFSGSGSGTDFTLKISRVEAEDVGVYYCMQALETP
LTFGGGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC Clone No. 804:
EIVLTQSPGTLSLSPGGRATLSCRASQSVSSGYLAWYQQKPGQAPRLLIY
GASGRATGIPDRFSGSGSGTDFTLTISRLEPEDFAVYYCQQYFGSPYTFG
QGTKLELKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Clone No. 810:
NIQMTQSPSAMSASVGDRVTITCRASQGISNYLVWFQQKPGKVPKRLIYA
ASSLQSGVPSRFSGSGSGTEFTLTISSLQPEDFATYYCLQHNISPYTFGQ
GTKLETKRTVAAPSVFWPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Clone No. 811:
DIVMTQSPDSLAVSLGERATTNCRSSETVLYTSKNQSYLAWYQQKARQPP
KLLLYWASTRESGVPARFSGSGSGTDFTLAISSLQAEDVAVYYCQQFFRS
PPFTFGPGTRLEIKRTVAAPSVFIFPPSDEQLKSGTASVVCLLNNFYPREA

KVQWKVDNALQSGNSQESVTEQDSKDSTYSLSSTLTLSKADYEKHKVYAC
EVTHQGLSSPVTKSFNRGEC

Clone No. 812:
EIVLTQSPGTLSLSPGERVTLSCRASQSVSSSYIAWYQQKPGQAPRLVIY
AASRRATGVPDRFSGSGSATDFTLTISRLEPEDLAVYYCQHYGNSLFTFG
PGTKVDVKRTVAAPSVFWPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Clone No. 814:
DIQMTQSPSTLSASVGDRVTITCRASQSIGSRLAWYQQQPGKAPKFLIYD
ASSLESGVPSRFSGSGSGTEFTLTISSLQPEDLATYYCQQYNRDSPWTFG
QGTKVEIKRTVAAPSVFWPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Clone No. 816:
DIVMTQSPLSLPVTPGEPASISCRSSQSLLHSDGRYYVDWYLQKLPGQSP
HLLIYLASNRASGVPDRFTGSGSGTDFTLKISRVEAEDVGVYYCMQGLHT
PWTFGQGTKVDIKRTVAAPSVFWPPSDEQLKSGTASVVCLLNMYPREAKV
QWKVDNALQSGNSQESVTEQDSKDSTYSLSSTLTLSKADYEKHKVYACEV
THQGLSSPVTKSFNRGEC Clone No. 817:
EIVMTQSPATLSASPGERATLSCWASQTIGGNLAWYQQKPGQAPRLLIYG
ASTRATGVPARFSGSGSGTEFTLAISSLQSEDFAVYYCQQYKNWYTFGQG
TKLELKRTVAAPSVFWPPSDEQLKSGTASVVCLLNNFYPREAKVQWKVDN
ALQSGNSQESVTEQDSKDSTYSLSSTLTLSKADYEKHKVYACEVTHQGLS
SPVTKSFNRGEC Clone No. 818:
DIQMTQSPSSLSASVGDRVTITCRASQTIASYVNWYQQKPGRAPSLLIYA
ASNLQSGVPPRFSGSGSGTDFTLTISGLQPDDFATYYCQQSYSYRALTFG
GGTKVEIKRTVAAPSVFWPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Clone No. 819:
EIVLTQSPATLSLSPGERATLSCRASQSVSSSLAWYQQTPGQAPRLLIYD
ASYRVTGWARFSGSGSGIDFTLTISSLEPEDFAVYYCQQRSNWPPGLTFG
GGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Clone No. 824:
AIQLTQSPSSLSASVGDTVTVTCRPSQDISSALAWYQQKPGKPPKLLIYG
ASTLDYGVPLRFSGTASGTHFTLTISSLQPEDFATYYCQQFNTYPFTFGP
GTKVDIKRTVAAPSVFWPPSDEQLKSGTASVVCLLNNFYPREAKVQWKVD -continued

NALQSGNSQESVTEQDSKDSTYSLSSTLTLSKADYEKHKVYACEVTHQGL
SSPVTKSFNRGEC

Clone No. 825:
DIVMTQSPDSLAVSLGERATINCKSSQSVLYNSNNKNYLAWYQQKPGQPP
KLLIHLASTREYGVPDRFSGSGSGTDFALIISSLQAEDVAVYYCQQYYQT
PLTFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC Clone No. 827:
DIQMTQSPSSLAASVGDRVTITCRASQFISSYLHWYQQRPGKAPKLLMYA
ASTLQSGVPSRFSGSGSGTDFTLTISSLQPEDFATYYCQQSYTNPYTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKLHKVYACEVTHQ
GLSSPVTKSFNRGEC Clone No. 829:
DIQMTQSPSSLSASVGDRVTITCRASQSIASYLNWYQQKPGKALPKLLIY
AASSLHSGVPSRFSGSGSGTDFTLTISSLQPEDFATYYCQHSYSTRFTFG
PGTKVDVKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Clone No. 830:
DIQMTQSPSTLSASVGDRVTITCRASQSVTSELAWYQQKPGKAPNFLIYK
ASSLESGVPSRFSGSGSGTEFTLTISSLQPDDFATYYCQQYNSFPYTFGQ
GTKLEIKRTVAAPSVFWPPSDEQLKSGTASVVCLLNNIYPREAKVQWKVD
NALQSGNSQESVTEQDSKDSTYSLSSTLTLSKADYEKHKVYACEVTHQGL
SSPVTKSFNRGEC Clone No. 831:
DIQMTQSPSTLSASVGDRLTITCRASQNIYNWLAWYQQKPGKAPKLLIYD
ASTLESGVPSRFSGSGSGTEFTLTISSLQPDDFATYYCQQYNSLSPTFGQ
GTKVEIKRTVAAPSVFWPPSDEQLKSGTASVVCLLNMYPREAKVQWKVDN
ALQSGNSQESVTEQDSKDSTYSLSSTLTLSKADYEKHKVYACEVTHQGLS
SPVTKSFNRGEC Clone No. 835:
DIQLTQSPSFLSASLEDRVTITCRASQGISSYLAWYQQKPGKAPKLLLDA
ASTLQSGVPSRFSGSGSGTEFTLTISSLQPEDFATYYCQQLNSYPRTFGQ
GTKVDIKRTVAAPSVFWPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Clone No. 838:
DIQMTQSPSSLSASVGDRVSITCRASQGISNYLAWYQQKPGKVPKLLIYA
ASTLQSGVPSRFSGSGSGTDFTLTISSLQPEDVATYYCQKYNSAPQTFGQ
GTKVEIKRTVAAPSVFIEPPSDEQLKSGTASVVCLLNNFYPREAKVQWKV

DNALQSGNSQESVTEQDSKDSTYSLSSTLTLSKADYEKHKVYACEVTHQG
LSSPVTKSFNRGEC

Clone No. 841:
DIVMTQSPDSLAVSLGERATLNCRSSQSVLYSSNNKNYLAWYQQKPGQPP
KLLVYWASTRASGVPDRFSGSGSGTDFTLTLSSLQAEDVAVYYCQQFHST
PRTFGQGTKVEIKRTVAAPSVFIFPPSDEQLKSGTASVVCLLNNFYPREA
KVQWKVDNALQSGNSQESVTEQDSKDSTYSLSSTLTLSKADYEKLHKVYA
CEVTHQGLSSPVTKSFNRGEC Clone No. 853:
EIVLTQSPGTLSLSPGERATLSCRASQSVSSNYLAWYQQKPGQAPRLLIY
GASSRAAGMPDRFSGSGSGTDFTLTISRLEPEDFAVYYCQQYGNSPLTFG
GGTEVEIIKRTVAAPSVFTFPPSDEQLKSGTASVVCLLNNFYPREAKVQW
KVDNALQSGNSQESVTEQDSKDSTYSLSSTLTLSKADYEKIHKVYACEVT
HQGLSSPVTKSFNRGEC Clone No. 855:
DIQMTQSPSSVSASVGDRVTITCRASQAISNWLAWYQQKPGKAPKLLIYA
ASSLQSGVPSRFSGSGSGTDFTLTISGLQPEDFATYYCQQADTFPFTFGP
GTKVDIIKRTVAAPSVFWPPSDEQLKSGTASVVCLLNNFYPREAKVQWKV
DNALQSGNSQESVTEQDSKDSTYSLSSTLTLSKADYEKIHKVYACEVTHQ
GLSSPVTKSFNRGEC Clone No. 856:
DIVMTQTPLSLPVTPGEPASISCRSSQSLLDSNDGNTYLDWYLQKPGQSP
QLLIYTFSYRASGVPDRFSGSGSGTDFTLKISRVEAEDVGVYYCMQRIEF
PYTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC Clone No. 857:
DIVMTQSPLSLPVTPGEPASISCRSSQSLLHRNEYNYLDWYLQKPGQSPQ
LLIYWGSNRASGVPDRFSGSGSGTDFTLKISRVEAEDVGVYYCMQTLQTP
RTFGQGTKVETKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTTKSFNRGEC Clone No. 858:
DIQMTQSPSSVSASVGDRVTITCQASQDISNYLNWYQQKPGKAPKLLWDA
TKLETGVPTRFIGSGSGTDFTVTITSLQPEDVATYYCQHFANLPYTFGQG
TKLEIKRTVAAPSVFWPPSDEQLKSGTASVVCLLNNFYPREAKVQWKVDN
ALQSGNSQESVTEQDSKDSTYSLSSTLTLSKADYEKHKVYACEVTHQGLS
SPVTKSFNRGEC Clone No. 859:
DIQMTQSPSSLSASVGDRVTITCRASQGIIRNYLAWYQQKPGKVPKLLVF
AASTLQSGVPSRFSGSGSGTDFTLTISSLQPEDVATYYCQRYNSAPLTFG
GGTKVEIKRTVAAPSVFIFPPSDEQLKSGTASVVCLLNNFYPREAKVQWK -continued

```
VDNALQSGNSQESVTEQDSKDSTYSLSSTLTLSKADYEKHKVYACEVTHQ
GLSSPVTKSFNRGEC

Clone No. 861:
DIQMTQSPSSLSASVGDRVTITCRASQHASYLNWYQQKPGRAPKLLIYAA
SSLQSGVPSRFSGSGSGTDFTLTISSLQPEDFATYYCQQSYSTPIFTFGP
GTKVNIIKRTVAAPSVFWPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Clone No. 863:
EIVLTQSPATLSLSPGERATLSCRTSQSVSSYLAWYQQKPGQAPRLLIYD
ASNRATGIPARFSGSGSGTDFTLTISSLEPEDFAVYYCQQRSDWLTFGGG
TKVEIKRTVAAPSVFWPPSDEQLKSGTASVVCLLNNFYPREAKVQWKVDN
ALQSGNSQESVTEQDSKDSTYSLSSTLTLSKADYEKHKVYACEVTHQGLS
SPVTKSFNRGEC Clone No. 868:
EIVMTQSPATLSVSPGERATLSCRASQSIKNNLAWYQVKPGQAPRLLTSG
ASARATGIPGRFSGSGSGTDFTLTISSLQSEDIAVYYCQEYNNWPLLTFG
GGTKVEIQRTVAAPSVFWPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Clone No. 870:
DIQMTQSPPSLSASVGDRVTITCRASQRIASYLNWYQQKPGRAPKILLWA
ASSLQSGVPSRFSGSGSGTDFTLTISSLQPEDYATYYCQQSYSTPTYTFG
QGTKLEIIKRTVAAPSVFWPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC
Clone No. 871:
DIQMTQSPSSLSASVGDRVTITCQASQGISNYLNWYQQKPGKAPKLLWDA
SNLESEVPSRFSGRGSGTDFTFSISSLQPEDLATYFCQQYDNFPYTFGQG
TKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Clone No. 880:
DIQMTQSPSSLAASVGDRVTITCRASQTIASYVNWYQQKPGKAPNLLIYA
ASSLQSGVPSRFSGSGSGTDFTLTISSLQPEDFASYFCQQSYSFPYTFGQ
GTKLDIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Clone No. 881:
DIQMTQSPSSLSASVGDRVTITCRASQTIASYVNWYQQKPGKAPKLLIYA
ASNLQSGVPSRFSGSGSGTDFTLTISSLQPEDFATYYCQQSYSVPRLTFG
GGTKVDITRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Clone No. 884:
DIQMTQSPSSLSASVGDRVTITCRSSQTISVFLNWYQQKPGKAPKLLIYA
ASSLHSAVPSRFSGSGSGTDFTLTISSLQPEDSATYYCQESFSSSTFGGG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC Clone No. 886:
EIVMTQSPATLSVSPGETATLSCRASQSVSSNLAWYQHKPGQAPRLLIHS
ASTRATGIIPARFSGSGSGTEFTLTISSLQSEDFAVYYCQQYNMWPPWTF
GQGTKVEIIKRTVAAPSVFIFPPSDEQLKSGTASVVCLLNNFYPREAKVQ
WKVDNALQSGNSQESVTEQDSKDSTYSLSSTLTLSKADYEKHIKVYACEV
THQGLSSPVTKSFNRGEC Clone No. 888:
DIVMTQSPLSLPVTPGAPASISCRSSQSLLRTNGYNYLDWYLQKPGQSPQ
LLIYLGSIRASGVPDRFSGSGSGTDFTLKISRVEAEDVGVYYCMQSLQTS
ITFGQGTRLEIIQRTVAAPSVFWPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC Clone No. 894:
EIVMTQSPATLSVSPGERATLSCRASQSVGNNLAWYQQRPGQAPRLLIYG
ASTRATGWARFSGSGSGTEFTLTISSLQSEDFAVYYCQQYDKWPETFGQG
TKVDIKRTVAAPSVFIIPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC
```

The light chain encoding nucleic acid fragments in these clones have the following nucleic acid sequences, which are also provided as SEQ ID NOs: 133-176:

```
Clone No 735:
gaaattgtgttgacacagtctccagccaccctgtccttgtctccaggaga
aagagccacctctcctgcagggccagtcagagtgttaacagccacttag
cctggtaccaacagaaacctggccaggctcccaggctcctcatctataat
acattcaatagggtcactggcatcccagccaggttcagtggcagtgggtc
tgggacagacttcactctcaccatcagcagccttgcgactgaagattttg
gcgtttattactgtcagcagcgtagcaactggcctcccgccctcactttc
ggcggagggaccaaagtggagatcaaacgaactgtggctgcaccatctgt
cttcatcttcccgccatctgatgagcagttgaaatctggaactgcctctg
ttgtgtgcctgctgaataacttctatcccagagaggccaaagtacagtgg
aaggtggataacgcccccaatcgggtaactcccaggagagtgtcacaga
gcaggacagcaaggacagcacctacagcctcagcagcaccctgacgctga
gcaaagcagactacgagaaacacaaagtctacgcctgcgaagtcacccat
cagggcctgagctcgcccgtcacaaagagcttcaacaggggagagtgt
```

Clone No 736:
gacatccagatgacccagtctccatcctccctgtctgcatctgtgggaga
cagagtcaccttcacttgccgggccagtcagaggattagcaaccatttaa
attggtatcaacaaaagccagggaaagcccctaaactcctgatctttggt
gcatccactcttcaaagtggggcccatcaaggttcagtggcagtggatc
tgggacagatttcactctcaccatcactaatgtacaacctgacgattttg
caacttactactgtcaacagagttacagaactcccccgatcaacttcggc
caagggacacgcctggacattaagcgaactgtggctgcaccatctgtctt
catcttcccgccatctgatgagcagttgaaatctggaactgcctctgttg
tgtgcctgctgaataacttctatcccagagaggccaaagtacagtggaag
gtggataacgcccfccaatcgggtaactcccaggagagtgtcacagagca
ggacagcaaggacagcacctacagcctcagcagcaccctgacgctgagca
aagcagactacgagaaacacaaagtctacgcctgcgaagtcacccatcag
ggcctgagctcgcccgtcacaaagagcttcaacaggggagagtgt Clone No 744:
gaaattgtgttgacgcagtctccaggcaccctgtctttgtctccagggga
aagagccaccctctcctgcagggccagtcagagtgttagcagcagctact
tagcctggtatcagcagaaacctggccaggctcccaggctcctcatctat
ggtgcatccagcagggccactggcatcccagacaggttcagtggcagtgg
gtctgggacagacttcactctcaccatcagcagactggagcctgaagatt
ttgcagtgtattactgtcagcagtatgatagctcactttctacgtggacg
ttcggccaagggaccaaggtggaaatcaaacgaactgtggctgcaccatc
tgtcttcatcttcccgccatctgatgagcagttgaaatctggaactgcct
ctgttgtgtgcctgctgaataacttctatcccagagaggccaaagtacag
tggaaggtggataacgcccfccaatcgggtaactcccaggagagtgtcac
agagcaggacagcaaggacagcacctacagcctcagcagcaccctgacgc
tgagcaaagcagactacgagaaacacaaagtctacgcctgcgaagtcacc
catcagggcctgagctcgcccgtcacaaagagcttcaacaggggagagtg
t Clone No 793:
gacatccagatgacccagtctccatcctccctgtctgcatctgtaggaga
cagagtcaccatcacttgccgggcaagtcagagcattaccggctatttaa
attggtatcagcagaaaccagggaaagcccctaaactcctgatctatgct
acatccactttgcaaagtgaggtcccatcaaggttcagtggcagtggatc
tgggacagatttcactctcaccatcagcagtcttcaacctgaagattttg
caacttactactgtcaacagagttataataccctcactttcggcggaggg
accaaggtggagatcaaacgaactgtggctgcaccatctgtcttcatctt
cccgccatctgatgagcagttgaaatctggaactgcctctgttgtgtgcc
tgctgaataacttctatcccagagaggccaaagtacagtggaaggtggat
aacgcccfccaatcgggtaactcccaggagagtgtcacagagcaggacag
caaggacagcacctacagcctcagcagcaccctgacgctgagcaaagcag actacgagaaacacaaagtctacgcctgcgaagtcacccatcagggcctg
agctcgcccgtcacaaagagcttcaacaggggagagtgt Clone No 795:
gaaattgtgttgacgcagtctccaggcaccctgtctttgtctccagggga
aagagccaccctctcctgcagggccagtcagagtgttagcagcagctact
tagcctggtatcagcagaaacctggccaggctcccaggctcctcatacat
ggcgcatccaccggggccactggcaccccagacaggttcagtggcagtgg
gtctgggacagacttcactctcaccatcagtacactggagcctgaagatt
ttgcagtgtattactgtcagcaatatggtaggacaccgtacacttttggc
caggggaccaagctggagaacaaacgaactgtggctgcaccatctgtctt
catcttcccgccatctgatgagcagttgaaatctggaactgcctctgttg
tgtgcctgctgaataacttctatcccagagaggccaaagtacagtggaag
gtggataacgcccfccaatcgggtaaetcccaggagagtgtcacagagca
ggacagcaaggacagcacctacagcctcagcagcaccctgacgctgagca
aagcagactacgagaaacacaaagtctacgcctgcgaagtcacccatcag
ggcctgagctcgcccgtcacaaagagcttcaacaggggagagtgt Clone No 796:
gatattgtgatgacccagactccactctctctgtccgtcacccctggaca
gccggcctccatctcctgcaggtctagtcagagcctcctgcgaagtgatg
gaaagacgtttttgtattggtatctgcagaagccaggccagtctccccaa
cccctaatgtatgaggtgtccagccggttctctggagtgccagataggtt
cagtggcagcgggtcaggggcagatttcacactgaacatcagccgggtgg
agactgaggatgttggggatctattactgcatgcaaggttttgaaaattcgt
cggacgtttggcccagggaccaaggtcgaaatcaagcgaactgtggctgc
accatctgtcttcatcttcccgccatctgatgagcagttgaaatctggaa
ctgcctctgttgtgtgcctgctgaataacttctatcccagagaggccaaa
gtacagtggaaggtggataacgcccfccaatcgggtaactcccaggagag
tgtcacagagcaggacagcaaggacagcacctacagcctcagcagcaccc
tgacgctgagcaaagcagactacgagaaacacaaagtctacgcctgcgaa
gtcacccatcagggcctgagctcgcccgtcacaaagagcttcaacagggg
agagtgt Clone No 799:
gacatccagatgacccagtctccttccaccctgtctgcatctgtaggaga
cagagtcaccttctcttgccgggccagtcagagtgttagtagttgggtgg
cctggtatcagcagaaaccaggaaaagcccctaagctcctgatctctgag
gcctccaatttggaaagtggggtcccatcccggttcagcggcagtggatc
cgggacagaattcactctcaccatcagcagcctgcagcctgaagattttg
caacttattactgccaacagtatcatagttactctgggtacacttttggc
caggggaccaagttggaaatcaagcgaactgtggctgcaccatctgtctt
catcttcccgccatctgatgagcagttgaaatctggaactgcctctgttg
tgtgcctgctgaataacttctatcccagagaggccaaagtacagtggaag
gtggataacgcccfccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacaggggagagtgt Clone No 800:
gccatccagttgacccagtctccatcgtccctgtctgcatctgtaggcga cagagtcaccctcacttgccgggcgagtcagggcattaccgattctttag cctggtatcagcagaaaccagggaaagcccctaaggtcctgctctatgct gcttccagattggaaagtggggtcccatccaggttcagtggccgtggatc tgggacggatttcactctcaccatcagcagcctgcagcctgaagactttg caacttattactgtcaacagtattctaagtcccctgcgacgttcggccca gggaccaaggtggaaatcagacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 801:
gatattgtgatgacccagtctccactctccctgcccgtcacccctggaga gccggcctccatctcctgcaggtctagtcagagcctcctaaatagtaatg gattcaactatgtggattggtacctgcagaagccagggcagtctccacaa ctcctgatctatttgggttctaatcgggcctccggggtccctgacaggtt cagtggcagtggatcaggcacagattttacactgaaaatcagcagagtgg aggctgaggatgttggggtttattactgcatgcaagctctagaaaactccg ctcactttcggcggagggaccaaggtggagatcaaacgaactgtggctgc accatctgtcttcatcttcccgccatctgatgagcagttgaaatctggaa ctgcctctgttgtgtgcctgctgaataacttctatcccagagaggccaaa gtacagtggaaggtggataacgccctccaatcgggtaactcccaggagag tgtcacagagcaggacagcaaggacagcacctacagcctcagcagcaccc tgacgctgagcaaagcagactacgagaaacacaaagtctacgcctgcgaa gtcacccatcagggcctgagctcgcccgtcacaaagagcttcaacagggg agagtgt Clone No 804:
gaaattgtgttgacgcagtctccaggcaccctgtctttgtctccaggggg aagagccaccctctcctgcagggccagtcagagtgttagcagcggctact tagcctggtaccagcagaaacctggccaggctcccaggctcctcatctat ggtgcatccggcagggccactggcatcccagacaggttcagtggcagtgg gtctgggacagacttcactctcaccatcagcagactggagcctgaagatt ttgcaggtattactgtcagcagtattttggctcaccgtacacttttggcc aggggaccaagctggagctcaaacgaactgtggctgcaccatctgtcttc atcttcccgccatctgatgagcagttgaaatctggaactgcctctgttgt gtgcctgctgaataacttctatcccagagaggccaaagtacagtggaagg tggataacgccctccaatcgggtaactcccaggagagtgtcacagagcag gacagcaaggacagcacctacagcctcagcagcaccctgacgctgagcaa agcagactacgagaaacacaaagtctacgcctgcgaagtcacccatcagg gcctgagctcgcccgtcacaaagagcttcaacaggggagagtgt Clone No 810:
aacatccagatgacccagtctccatctgccatgtctgcatctgtaggaga cagagtcaccatcacttgtcgggcgagtcagggcattagtaattatttag tctggtttcagcagaaaccagggaaagtccctaagcgcctgatctatgct gcatccagtttgcaaagtggggtcccatcaaggttcagcggcagtggatc tgggacagaattcactctcacaatcagcagcctgcagcctgaagattttg caacttattactgtctacagcataatatttccccttacacttttggccag gggaccaagctggagaccaaacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 811:
gacatcgtgatgacccagtctccagactcctggctgtgtctctgggcga gagggccaccatcaactgcaggtccagtgagactgttttatacacctcta aaaatcagagctacttagcttggtaccagcagaaaagcacgacagcctcct aaactactcctttactgggcatctacccgggaatccggggtccctgcccg attcagtggcagcggatctgggacagatttcactctcgccatcagcagcc tgcaggctgaagatgtggcagtttattactgtcagcaatttttttaggagt cctttcactttcggccccgggaccagactggagattaaacgaactgtggc tgcaccatctgtcttcatcttcccgccatctgatgagcagttgaaatctg gaactgcctctgttgtgtgcctgctgaataacttctatcccagagaggcc aaagtacagtggaaggtggataacgccctccaatcgggtaactcccagga gagtgtcacagagcaggacagcaaggacagcacctacagcctcagcagca ccctgacgctgagcaaagcagactacgagaaacacaaagtctacgcctgc gaagtcacccatcagggcctgagctcgcccgtcacaaagagcttcaacag gggagagtgt Clone No 812:
gaaattgtgttgacgcagtctccaggcaccctgtctttgtctccagggga aagagttaccctctcttgcagggccagtcagagtgttagcagcagttaca tagcctggtaccagcagaagcctggccaggctcccaggctcgtcatctat gctgcatcccgcagggccactggcgtcccagacaggttcagtggcagtgg gtctgcgacagacttcactctcaccatcagtagactggagcctgaagatc ttgcagtgtattactgtcagcactatggtaactcactattcactttcggc -continued cctgggaccaaggtggatgtcaaacgaactgtggctgcaccatctgtctt
catcttcccgccatctgatgagcagttgaaatctggaactgcctctgttg
tgtgcctgctgaataacttctatcccagagaggccaaagtacagtggaag
gtggataacgccctccaatcgggtaactcccaggagagtgtcacagagca
ggacagcaaggacagcacctacagcctcagcagcaccctgacgctgagca
aagcagactacgagaaacacaaagtctacgcctgcgaagtcacccatcag
ggcctgagctcgcccgtcacaaagagcttcaacaggggagagtgt Clone No 814:
gacatccagatgacccagtctccctccaccctgtctgcatctgtcggaga
cagagtcaccatcacttgccgggccagtcagagtattggtagccggttgg
cctggtatcagcagcaaccagggaaagcccctaaattcctgatctatgat
gcctccagtttggaaagtggggtcccatcaaggttcagcggcagtggatc
agggacagaattcactctcaccatcagcagcctgcagccggaggatcttg
caacttattactgccaacagtacaatagagattctccgtggacgttcggc
caagggaccaaggtggaaatcaagcgaactgtggctgcaccatctgtctt
catcttcccgccatctgatgagcagttgaaatctggaactgcctctgttg
tgtgcctgctgaataacttctatcccagagaggccaaagtacagtggaag
gtggataacgccctccaatcgggtaactcccaggagagtgtcacagagca
ggacagcaaggacagcacctacagcctcagcagcaccctgacgctgagca
aagcagactacgagaaacacaaagtctacgcctgcgaagtcacccatcag
ggcctgagctcgcccgtcacaaagagcttcaacaggggagagtgt Clone No 816:
gatattgtgatgacccagtctccactctcctgcccgtcaccccaggaga
gccggcctccatctcctgcaggtctagtcagagcctcctgcatagtgatg
gacgctactatgtggattggtacctgcagaagccagggcagtctccacac
ctcctgatctatttggcttctaatcgggcctccggggtccctgacaggtt
cactggcagtggatcaggcacagattttacactgaaaatcagcagagtgg
aggctgaggatgttggcgtttattactgcatgcaaggtctacacactcct
tggacgttcggccaggggaccaaggtggacatcaagcgaactgtggctgc
accatctgtcttcatcttcccgccatctgatgagcagttgaaatctggaa
ctgcctctgttgtgtgcctgctgaataacttctatcccagagaggccaaa
gtacagtggaaggtggataacgccctccaatcgggtaactcccaggagag
tgtcacagagcaggacagcaaggacagcacctacagcctcagcagcaccc
tgacgctgagcaaagcagactacgagaaacacaaagtctacgcctgcgaa
gtcacccatcagggcctgagctcgcccgtcacaaagagcttcaacagggg
agagtgt Clone No 817:
gaaattgtaatgacacagtctccagccaccctgtctgcgtcccaggggga
aagagccaccctctcctgttgggcagtcagactattggaggcaacttag
cctggtaccagcagaaacctggccaggctcccaggctcctcatctatggt
gcatccaccagggccactggtgtcccagccaggttcagtggcagtgggtc
tgggacagagttcactctcgccatcagcagcctgcagtctgaagattttg -continued cagtttattactgtcagcagtataaaaactggtacacttttggccagggg
accaagctggagctcaaacgaactgtggctgcaccatctgtcttcatctt
cccgccatctgatgagcagttgaaatctggaactgcctctgttgtgtgcc
tgctgaataacttctatcccagagaggccaaagtacagtggaaggtggat
aacgccctccaatcgggtaactcccaggagagtgtcacagagcaggacag
caaggacagcacctacagcctcagcagcaccctgacgctgagcaaagcag
actacgagaaacacaaagtctacgcctgcgaagtcacccatcagggcctg
agctcgcccgtcacaaagagcttcaacaggggagagtgt Clone No 818:
gacatccagatgacccagtctccatcctccctgtctgcatctgtaggaga
cagagtcaccatcacttgccgggcaagtcagaccattgccagttacgtaa
attggtaccaacaaaaaccagggagagcccctagtctcctgatctatgct
gcatctaacttgcagagtggggtcccaccaaggttcagtggcagtggatc
tgggacagacttcactctcaccatcagcggtctgcaacctgacgattttg
caacttattactgtcaacagagttacagttatcgagcgctcactttcggc
ggagggaccaaggtggagatcaaacgaactgtggctgcaccatctgtctt
catcttcccgccatctgatgagcagttgaaatctggaactgcctctgttg
tgtgcctgctgaataacttctatcccagagaggccaaagtacagtggaag
gtggataacgccctccaatcgggtaactcccaggagagtgtcacagagca
ggacagcaaggacagcacctacagcctcagcagcaccctgacgctgagca
aagcagactacgagaaacacaaagtctacgcctgcgaagtcacccatcag
ggcctgagctcgcccgtcacaaagagcttcaacaggggagagtgt Clone No 819:
gaaattgtgttgacacagtctccagccaccctgtcgttgtcccagggga
aagagccaccctctcctgcagggccagtcagagtgttagcagctccttag
cctggtaccaacagacacctggccaggctcccaggcttctcatctatgat
gcgtcctacagggtcactggcatcccagccaggttcagtggcagtgggtc
tgggatagacttcactctcaccatcagcagcctagagcctgaagattttg
cagtttactattgtcagcagcgtagcaactggcctcggggctcactttc
ggcggggggaccaaggtggagatcaaacgaactgtggctgcaccatctgt
cttcatcttcccgccatctgatgagcagttgaaatctggaactgcctctg
ttgtgtgcctgctgaataacttctatcccagagaggccaaagtacagtgg
aaggtggataacgccctccaatcgggtaactcccaggagagtgtcacaga
gcaggacagcaaggacagcacctacagcctcagcagcaccctgacgctga
gcaaagcagactacgagaaacacaaagtctacgcctgcgaagtcacccat
cagggcctgagctcgcccgtcacaaagagcttcaacaggggagagtgt Clone No 824:
gccatccagttgacccagtctccatcctccctgtctgcatctgttggaga
cacagtcaccgtcacttgccggccaagtcaggacattagcagtgctttag
cctggtatcagcagaaaccagggaaacctcctaagctcctgatctatggt
gcctccactttggattatggggtcccattaaggttcagcggcactgcatc -continued tgggacacatttcactctcaccatcagcagcctgcaacctgaagattttg caacttattactgtcaacagtttaatacttacccattcactttcggccct gggaccaaagtggatatcaaacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 825:
gacatcgtgatgacccagtctccagactccctggctgtgtctctgggcga gagggccaccatcaactgcaagtccagccagagtgttttatacaactcca acaataagaactacttagcctggtatcagcagaaaccaggacagcctcct aagctcctcattcacttggcatctacccgggaatacggggtccctgaccg attcagtggcagcgggtctgggacagatttcgctctcatcatcagcagcc tgcaggctgaagatgtggcagtttactactgtcaacaatattatcaaact cctctaacttttggccaggggaccaaggtggagatcaaacgaactgtggc tgcaccatctgtcttcatcttcccgccatctgatgagcagttgaaatctg gaactgcctctgttgtgtgcctgctgaataacttctatcccagagaggcc aaagtacagtggaaggtggataacgccctccaatcgggtaactcccagga gagtgtcacagagcaggacagcaaggacagcacctacagcctcagcagca ccctgacgctgagcaaagcagactacgagaaacacaaagtctacgcctgc gaagtcacccatcagggcctgagctcgcccgtcacaaagagcttcaacag gggagagtgt Clone No 827:
gacatccagatgacccagtctccatcctccctggctgcatctgtaggaga cagagtcaccatcacttgccgggcaagtcagttcattagcagctatttac attggtatcagcaaagaccaggcaaggcccctaaactcctgatgtatgct gcctccactttgcaaagtggggtcccatcaaggttcagtggcagtggatc tgggacagatttcactctcaccatcagcagtctgcaacctgaagattttg caacttactactgtcaacagagttacactaacccatacttttggccag gggaccaagctggagatcaaacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 829:
gacatccagatgacccagtctccatcctccctatctgcatctgtaggaga cagagtcaccatcacttgccgggcaagtcagagcattgccagctatttaa attggtatcagcagaaaccagggaaagccccaaaactcctgatctatgct -continued gcatccagtttgcatagtggggtcccatcaagattcagtggcagtggatc tgggacagatttcactctcaccatcagcagtctgcaacctgaagattttg caacttactactgtcaacacagttacagtactcgattcactttcggccct gggaccaaagtggatgtcaaacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 830:
gacatccagatgacccagtctccttcgaccctgtctgcatctgtaggaga cagagtcaccatcacttgccgggccagtcagagtgttactagtgagttgg cctggtatcagcagaaaccagggaaagccctaacttcctgatctataag gcgtctagtttagaaagtggggtcccatcaaggttcagcggcagtggatc tgggacagaattcactctcaccatcagcagcctgcagcctgatgattttg caacttattactgccaacagtataatagttttccgtacacttttggccag gggaccaagctggagatcaaacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 831:
gacatccagatgacccagtctccttccaccctgtctgcatctgtaggcga cagactcaccatcacttgccgggccagtcagaatatttataactggttgg cctggtatcagcagaaaccagggaaagcccctaaactcctgatctatgac gcctccactttggaaagtggggtcccatcaaggttcagcggcagtggatc tgggacagagttcactctcaccatcagcagcctgcagcctgatgattttg cgacttattactgccaacaatataatagtttgtctccgacgttcggccaa gggaccaaggtggaaatcaagcgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 835:
gacatccagttgacccagtctccatccttcctgtctgcatctttagaaga cagagtcactatcacttgccgggccagtcagggcattagcagttatttag -continued cctggtatcagcaaaaaccagggaaagcccctaagctcctgctcgatgct
gcatccactttgcaaagtggggtcccatcaaggttcagcggcagtggatc
tgggacagagttcactctcacaatcagcagcctgcagcctgaagattttg
caacttattactgtcaacagcttaatagttaccctcggacgttcggccaa
gggaccaaggtggacatcaaacgaactgtggctgcaccatctgtcttcat
cttcccgccatctgatgagcagttgaaatctggaactgcctctgttgtgt
gcctgctgataacttctatcccagagaggccaaagtacagtggaaggtg
gataacgccctccaatcgggtaactcccaggagagtgtcacagagcagga
cagcaaggacagcacctacagcctcagcagcaccctgacgctgagcaaag
cagactacgagaaacacaaagtctacgcctgcgaagtcacccatcagggc
ctgagctcgcccgtcacaaagagcttcaacaggggagagtgt Clone No 838:
gacatccagatgacccagtctccatcctccctgtctgcatctgtaggaga
cagagtcagcatcacttgccgggcgagtcagggcattagcaattatttag
cctggtatcagcagaaaccagggaaggttcctaagctcctgatctatgct
gcatccactttgcaatcaggggtcccatctcggttcagtggcagtggatc
tgggacagatttcactctcaccatcagcagcctgcagcctgaggatgttg
caacttattactgtcaaaagtataacagtgcccctcaaacgttcggccaa
gggaccaaggtggaaatcaaacgaactgtggctgcaccatctgtcttcat
cttcccgccatctgatgagcagttgaaatctggaactgcctctgttgtgt
gcctgctgataacttctatcccagagaggccaaagtacagtggaaggtg
gataacgccctccaatcgggtaactcccaggagagtgtcacagagcagga
cagcaaggacagcacctacagcctcagcagcaccctgacgctgagcaaag
cagactacgagaaacacaaagtctacgcctgcgaagtcacccatcagggc
ctgagctcgcccgtcacaaagagcttcaacaggggagagtgt Clone No 841:
gacatcgtgatgacccagtctccagactccctggctgtgtctctgggcga
gagggccaccatcaactgcaggtccagccagagtgttttatacagctcca
acaataagaactacttagcttggtaccagcagaaaccaggacagcctcct
aagctgctcgtttactgggcatcaacccgggcatccggggtccctgaccg
attcagtggcagcgggtctgggacagatttcactctcaccctcagcagcc
tgcaggctgaagatgtggcagtttattactgtcagcagtttcatagtact
cctcggacgttcggccaagggaccaaggtggagatcaaacgaactgtggc
tgcaccatctgtcttcatcttcccgccatctgatgagcagttgaaatctg
gaactgcctctgttgtgtgcctgctgataacttctatcccagagaggcc
aaagtacagtggaaggtggataacgccctccaatcgggtaactcccagga
gagtgtcacagagcaggacagcaaggacagcacctacagcctcagcagca
ccctgacgctgagcaaagcagactacgagaaacacaaagtctacgcctgc
gaagtcacccatcagggcctgagctcgcccgtcacaaagagcttcaacag
gggagagtgt Clone No 853:
gaaattgtgttgacgcagtctccaggcaccctgtctttgtctccagggga
aagagccaccctctcctgcagggccagtcagagtgttagcagcaactact
tagcctggtaccagcagaaacctggccaggctcccaggctcctcatctat
ggtgcatccagcagggccgctggcatgccagacaggttcagtggcagtgg
gtctgggacagacttcactctcaccatcagcagactggagcctgaagatt
ttgcagtgtattactgtcagcagtatggtaactcaccgctcactttcggc
ggagggaccgaggtggagatcaaacgaactgtggctgcaccatctgtctt
catcttcccgccatctgatgagcagttgaaatctggaactgcctctgttg
tgtgcctgctgataacttctatcccagagaggccaaagtacagtggaag
gtggataacgccctccaatcgggtaactcccaggagagtgtcacagagca
ggacagcaaggacagcacctacagcctcagcagcaccctgacgctgagca
aagcagactacgagaaacacaaagtctacgcctgcgaagtcacccatcag
ggcctgagctcgcccgtcacaaagagcttcaacaggggagagtgt Clone No 855:
gacatccagatgacccagtctccatcttctgtgtctgcatctgtaggaga
cagagtcaccatcacttgtcgggcgagtcaggctattagtaactggttag
cctggtatcagcagaaaccaggaaaagcccctaagctcctgatctatgct
gcatccagtttgcaaagtggggtcccatcaagattcagcggcagtggatc
tgggacagatttcactctcactatcagcggcctgcagcctgaggattttg
caacttactattgtcaacaggctgacactttccctttcactttcggccct
gggaccaaagtggatatcaaacgaactgtggctgcaccatctgtcttcat
cttcccgccatctgatgagcagttgaaatctggaactgcctctgttgtgt
gcctgctgataacttctatcccagagaggccaaagtacagtggaaggtg
gataacgccctccaatcgggtaactcccaggagagtgtcacagagcagga
cagcaaggacagcacctacagcctcagcagcaccctgacgctgagcaaag
cagactacgagaaacacaaagtctacgcctgcgaagtcacccatcagggc
ctgagctcgcccgtcacaaagagcttcaacaggggagagtgt Clone No 856:
gatattgtgatgacccagactccactctccctgcccgtcacccctggaga
gccggcctccatctcctgcaggtctagtcagagcctcttggatagtaatg
atggaaacacctatttggactggtacctgcagaagccagggcagtctcca
cagctcctgatttatacattttcctatcgggcctctggagtcccagacag
gttcagtggcagtgggtctggcactgatttcacactgaaaatcagcaggg
tggaggccgaggatgttggagtttattactgcatgcaacgtatcgagttt
ccgtacacttttggccaggggaccaagctggagatcaaacgaactgtggc
tgcaccatctgtcttcatcttcccgccatctgatgagcagttgaaatctg
gaactgcctctgttgtgtgcctgctgataacttctatcccagagaggcc
aaagtacagtggaaggtggataacgccctccaatcgggtaactcccagga
gagtgtcacagagcaggacagcaaggacagcacctacagcctcagcagca
ccctgacgctgagcaaagcagactacgagaaacacaaagtctacgcctgc -continued gaagtcacccatcagggcctgagctcgcccgtcacaaagagcttcaacag gggagagtgt Clone No 857:
gatattgtgatgacccagtctccactctccctgcccgtcaccctggaga gccggcctccatctcctgcaggtctagtcagagcctcctgcatagaaatg agtacaactatttggattggtacttgcagaagccagggcagtctccacag ctcctgatctattgggggttctaatcgggcctccggggtccctgacaggtt cagtggcagtggatcaggcacagattttacactgaaaatcagcagagtgg aggctgaggatgttgggtttattactgcatgcaaactctacaaactcct cggacgttcggccaagggaccaaggtggaaatcaaacgaactgtggctgc accatctgtcttcatcttcccgccatctgatgagcagttgaaatctggaa ctgcctctgttgtgtgcctgctgaataacttctatcccagagaggccaaa gtacagtggaaggtggataacgccctccaatcgggtaactcccaggagag tgtcacagagcaggacagcaaggacagcacctacagcctcagcagcaccc tgacgctgagcaaagcagactacgagaaacacaaagtctacgcctgcgaa gtcacccatcagggcctgagctcgcccgtcacaaagagcttcaacagggg agagtgt Clone No 858:
gacatccagatgacccagtctccatcctccgtgtctgcatctgtgggaga cagagtcaccatcacttgccaggcgagtcaagacattagcaactatttaa attggtatcagcagaaaccagggaaagcccctaagctcctgatcttcgat gcaaccaaattggagacaggggtcccaacaaggttcattggaagtggatc tgggacagattttactgtcaccatcaccagcctgcagcctgaagatgttg caacatattactgtcaaacactttgctaatctcccatacacttttggccag gggaccaagctggagatcaagcgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 859:
gacatccagatgacccagtctccatcttccctgtctgcatctgtaggaga cagagtcaccatcacttgccgggcgagtcagggcattaggaattatttag cctggtatcagcagaaaccagggaaagttcctaagctcctggtctttgct gcatccactttgcaatcaggggtcccatctcggttcagtggcagtggatc tgggacagatttcactctcaccatcagcagcctgcagcctgaggatgttg caacttattactgtcaaaggtataacagtgccccgctcacttttggcgga gggacgaaggtggagatcaaacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga -continued cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 861:
gacatccagatgacccagtctccatcctccctgtctgcatctgtaggaga cagagtcaccatcacttgccgggcaagtcagatcattgccagctatttaa attggtatcagcagaaaccaggcagagccctaagctcctgatctatgct gcatccagtttgcaaagtggggtcccatcaaggttcagtggcagtggatc tgggacagatttcactctcaccatcagcagtctgcaacctgaagattttg caacttactactgtcaacagagttacagtaccccatattcactttcggc cctgggaccaaggtgaatatcaaacgaactgtggctgcaccatctgtctt catcttcccgccatctgatgagcagttgaaatctggaactgcctctgttg tgtgcctgctgaataacttctatcccagagaggccaaagtacagtggaag gtggataacgccctccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacaggggagagtgt Clone No 863:
gaaattgtgttgacacagtctccagccaccctgtctttgtctccagggga aagagccaccctctcctgcaggaccagtcagagtgttagcagctacttag cctggtaccaacagaaacctggccaggctcccaggctcctcatctatgat gcttccaatagggccactggcatcccagccaggttcagtggcagtgggtc tgggacagacttcactctcaccatcagcagcctagagcctgaagattttg cagtttattactgtcagcagcgtagtgactggctcacttttcggcggaggg accaaggtggagatcaaacgaactgtggctgcaccatctgtcttcatctt cccgccatctgatgagcagttgaaatctggaactgcctctgttgtgtgcc tgctgaataacttctatcccagagaggccaaagtacagtggaaggtggat aacgccctccaatcgggtaactcccaggagagtgtcacagagcaggacag caaggacagcacctacagcctcagcagcaccctgacgctgagcaaagcag actacgagaaacacaaagtctacgcctgcgaagtcacccatcagggcctg agctcgcccgtcacaaagagcttcaacaggggagagtgt Clone No 868:
gaaattgtaatgacacagtctccagccaccctgtctgtgtctccagggga aagagccaccctctcctgcagggccagtcagagtattaaaaacaacttgg cctggtaccaggtgaaacctggccaggctcccaggctcctcacctctggt gcatccgccagggccactggaattccaggcaggttcagtggcagtgggtc tgggactgacttcactctcaccatcagcagcctccagtctgaagatattg cagtttattactgtcaggagtataataattggcccctgctcacttttcggc ggagggaccaaggtggagatccaacgaactgtggctgcaccatctgtctt catcttcccgccatctgatgagcagttgaaatctggaactgcctctgttg tgtgcctgctgaataacttctatcccagagaggccaaagtacagtggaag -continued gtggataacgccctccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacaggggagagtgt Clone No 870:
gacatccagatgacccagtctcctccctccctgtctgcatctgtgggaga cagagtcaccatcacttgccgggcaagtcagaggattgccagctatttaa attggtatcagcagaaaccagggagagcccctaagctcctgatctttgct gcatccagtttacaaagtggggtcccatcaaggttcagtggcagtggatc tgggacagacttcactctcaccatcagtagtctgcaacctgaagattatg cgacttactactgtcaacagagttacagtactcccatctacacttttggc caggggaccaagctggagatcaaacgaactgtggctgcaccatctgtctt catcttcccgccatctgatgagcagttgaaatctggaactgcctctgttg tgtgcctgctgaataacttctatcccagagaggccaaagtacagtggaag gtggataacgccctccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacaggggagagtgt Clone No 871:
gacatccagatgacccagtctccatcctccctgtctgcatctgtaggaga cagagtcaccatcacttgccaggcgagtcagggcattagcaactatttaa attggtatcaacagaaaccagggaaagcccctaagctcctgatcttcgat gcatccaatttggaatcagaggtcccatcaaggttcagtggacgtggatc tgggacagattttactttctccatcagcagcctgcagcctgaagatattg caacatatttctgtcaacagtatgataatttcccgtacacttttggccag gggaccaagctggagatcaaacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 880:
gacatccagatgacccagtctccatcctccctggctgcatctgtaggaga cagagtcaccatcacctgccgggcaagtcagacgattgccagttatgtaa attggtatcaacagaaaccagggaaagcccctaatctcctgatctatgct gcatccagtttgcaaagtggggtcccatcaaggttcagtggcagtggatc tgggacagatttcactctcaccatcagcagtctgcaacctgaagattttg catcttactctgtcaacagagttacagtttcccgtacacttttggccag gggaccaagctggatatcaaacgaactgtggctgcaccatctgtcttcat cttcccgccatctgatgagcagttgaaatctggaactgcctctgttgtgt gcctgctgaataacttctatcccagagaggccaaagtacagtggaaggtg -continued gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt Clone No 881:
gacatccagatgacccagtctccatcctccctgtctgcatctgtaggaga cagagtcaccatcacttgccgggcaagtcagaccattgccagctatgtaa attggtatcagcagaaaccagggaaagcccctaagctcctgatctatgct gcatccaatttgcaaagtggggtcccttcaaggttcagtggcagtggatc tgggacagatttcactctcaccatcagcagtctgcaacctgaagattttg caacttactactgtcaacagagttacagtgtccctcggctcactttcggc ggagggaccaaggtggacatcacacgaactgtggctgcaccatctgtctt catcttcccgccatctgatgagcagttgaaatctggaactgcctctgttg tgtgcctgctgaataacttctatcccagagaggccaaagtacagtggaag gtggataacgccctccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacaggggagagtgt Clone No 884:
gacatccagatgacccagtctccatcctccctgtctgcatctgtaggaga cagagtcaccatcacttgccggtcaagtcagaccattagcgtcttttaa attggtatcagcagaaaccagggaaagcccctaagctcctgatctatgcc gcatccagtttgcacagtgcggtcccatcaaggttcagtggcagtggatc tgggacagatttcactctcaccatcagcagtctgcaacctgaagattctg caacttactactgtcaagagagtttcagtagctcaacttcggcggaggg accaaggtggagatcaaacgaactgtggctgcaccatctgtcttcatctt cccgccatctgatgagcagttgaaatctggaactgcctctgttgtgtgcc tgctgaataacttctatcccagagaggccaaagtacagtggaaggtggat aacgccctccaatcgggtaactcccaggagagtgtcacagagcaggacag caaggacagcacctacagcctcagcagcaccctgacgctgagcaaagcag actacgagaaacacaaagtctacgcctgcgaagtcacccatcagggcctg agctcgcccgtcacaaagagcttcaacaggggagagtgt Clone No 886:
gaaattgtaatgacacagtctccagccaccctgtctgtgtctccagggga aacagccaccctctcctgcagggccagtcagagtgttagcagcaacttag cctggtaccaacataaacctggccaggctcccaggctcctcatccatagt gcatccaccagggccactgggatcccagccaggttcagtggcagtgggtc tgggacagagttcactctcaccataagcagcctgcagtctgaagattttg cagtttattactgtcagcagtataatatgtggcctcctggacgttcggc caagggaccaaggtggaaatcaaacgaactgtggctgcaccatctgtctt catcttcccgccatctgatgagcagttgaaatctggaactgcctctgttg -continued
```
tgtgcctgctgaataacttctatcccagagaggccaaagtacagtggaag gtggataacgccctccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacaggggagagtgt Clone No 888:
gatattgtgatgacccagtctccactctcctgcccgtcacccctggagc gccgcctccatctcctgcaggtctagtcagagcctcctgcgtactaatg gatacaactatttggattggtacctgcagaagccagggcagtctccacag ctcctgatctatttgggttctattcgggcctccgggtccctgacaggtt cagtggcagtggctcaggcacagattttacactgaaaatcagcagagtgg aggctgaggatgttggggtttattactgcatgcaatctctacaaacttcg atccacttcggccaagggacacgactggagattaaacgaactgtggctgc accatctgtcttcatcttcccgccatctgatgagcagttgaaatctggaa ctgcctctgttgtgtgcctgctgaataacttctatcccagagaggccaaa gtacagtggaaggtggataacgccctccaatcgggtaactcccaggagag tgtcacagagcaggacagcaaggacagcacctacagcctcagcagcaccc tgacgctgagcaaagcagactacgagaaacacaaagtctacgcctgcgaa gtcacccatcagggcctgagctcgcccgtcacaaagagcttcaacagggg agagtgt Clone No 894:
gaaattgtaatgacacagtctccagccaccctgtctgtgtctccggggga aagagccaccctctcctgcagggctagtcagagtgttggcaacaacttag cctggtaccagcagagacctggccaggctcccagactcctcatctatggt gcgtccaccagggccactggtatcccagcaggttcagtggcagtgggtc tgggacagagttcactctcaccatcagcagcctgcagtctgaggattttg cagtttattactgtcagcagtatgataagtggcctgagacgttcggccag gggaccaaggtggacatcaagcgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt
```

In all of the above-discussed 44 clones, the encoded antibodies include the same constant IgG heavy chain, which has the following amino acid sequence (SEQ ID NO: 178):

SASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRVE

PKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

-continued
KEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSR

WQQGNVFSCSVMHEALHNHYTQKSLSLSPGK

The genomic sequence encoding this heavy chain has the following nucleic acid sequence (SEQ ID NO: 177):

```
agtgcctccaccaagggcccatcggtcttccccctggcaccctcctccaa gagcacctctgggggcacagcggccctgggctgcctggtcaaggactact tccccgaaccggtgacggtgtcgtggaactcaggcgccctgaccagcggc gtgcacaccttcccggctgtcctacagtcctcaggactctactccctcag cagcgtggtgaccgtgccctccagcagcttgggcacccagacctacatct gcaacgtgaatcacaagcccagcaacaccaaggtggacaagagagttggtg agaggccagcacagggagggagggtgtctgctggaagccaggctcagcgc tcctgcctggacgcatcccggctatgcagtcccagtccagggcagcaagg caggcccgtctgcctcttcacccggaggcctctgcccgccccactcatg ctcaggagagggtcttctggcttttcccaggctctgggcaggcacag gctaggtgcccctaacccaggcctgcacacaaaggggcaggtgctgggc tcagacctgccaagagccatatccggaggaccctgcccctgacctaagc ccaccccaaaggccaaactctccactccctcagctcggacaccttctctc ctcccagattccagtaactcccaatcttctctctgcagagcccaaatctt gtgacaaaactcacacatgcccaccgtgcccaggtaagccagcccaggcc tcgcccctccagctcaaggcgggacaggtgccctagagtagcctgcatcca gggacaggccccagccgggtgctgacacgtccacctccatctcttcctca gcacctgaactcctgggggaccgtcagcttcctcttccccccaaaaccc aaggacacccctcatgatctcccggacccctgaggtcacatgcgtggtggt ggacgtgagccacgaagaccctgaggtcaagttcaactggtacgtggacgg cgtggaggtgcataatgccaagacaaagccgcgggaggagcagtacaaca gcacgtaccgtgtggtcagcgtcctcaccgtcctgcaccaggactggctg aatggcaaggagtacaagtgcaaggtctccaacaaagccctcccagcccc catcgagaaaaccatctccaaagccaaaggtgggacccgtggggtgcgag ggccacatggacagaggccggctcggcccaccctctgccctgagagtgac cgctgtaccaacctctgtccctacagggcagccccgagaaccacaggtgt acaccctgcccccatcccgggaggagatgaccaagaaccaggtcagcctg acctgcctggtcaaaggcttctatcccagcgacatcgccgtggagtggga gagcaatgggcagccggagaacaactacaagaccacgcctcccgtgctgg actccgacggctccttcttcctctatagcaagctcaccgtggacaagagc aggtggcagcaggggaacgtcttctcatgctccgtgatgcatgaggctct gcacaaccactacacgcagaagagcctctccctgtccccgggtaaatga
```

In this sequence exons are indicated by double underlining. Further, the initial Ser-encoding nucleotides agt (bold underline) are created as a consequence of the introduction into the XhoI digested expression vector of an XhoI digested PCR product encoding the variable heavy chain site in the IgG expression vector.

The above-discussed $V_H$ and $V_L$ coding pairs were selected according to the binding specificity to various antigens and peptides in ELISA and/or FLISA, epitope mapping, antigen diversity, and sequence diversity. The selected cognate V-gene pairs were subjected to clone repair (Example 1, Section f) if errors were identified. The individual expression constructs were co-transfected with a Flp-recombinase expressing plasmid into the CHO-FlpIn recipient cell line (Invitrogen), followed by antibiotic selection of integrants. The transfections, selection, and adaptation to serum free culture was performed as described in Example 1, section g-1 and g-2.

The stably transfected, serum free suspension culture adapted individual expression cell lines were cryopreserved in multiple ampoules, to generate a cell bank of individual antibody producing cell lines.

EXAMPLE 3

In vitro neutralization experiments have been performed both with single antibody clones and with combinations of purified antibodies. All the antibody mixtures described below are constituted of a number of individual anti-RSV antibodies of the present invention, which were combined into a mixture using equal amounts of the different antibodies.

Testing of Single Antibodies

Initially, the neutralizing activity of each antibody was determined in the PRNT in the presence of complement against RSV subtype A and B strains as described above in Example 1, section j-2. The $EC_{50}$ values of a number of the purified antibodies are shown in Table 8. Interestingly, while most anti-F antibodies individually exhibited virus neutralizing activity, no $EC_{50}$ values could be determined for the majority of the anti-RSV protein G antibodies. This could be interpreted as indicating that these antibodies are not capable of neutralizing the vireo individually. However, subsequent refinement of the assay yielded $EC_{50}$ values for clones with G-reactivity as well. Blank fields indicate that the analysis has not been performed yet. ND indicates that an $EC_{50}$ value could not be determined in the PRNT due to a very low or lacking neutralizing activity.

TABLE 8

$EC_{50}$ values of purified anti-RSV protein F and protein G antibodies against RSV subtype A and B.

| Clone | Antigen-specificity | $EC_{50}$ value (µg/ml) | | | |
|---|---|---|---|---|---|
| | | Long | A2 | 18537 | B1 |
| 793 | G | 2.52 | | 0.09 | |
| 800 | F | 0.15 | | | 0.16 |
| 810 | F | 0.04-0.06 | 0.02 | 0.02-0.14 | 0.29 |
| 816 | G | ND | | ND | |
| 818 | F | (1.86) 0.15* | | 0.21 | |
| 819 | F | 0.18 | | 0.09 | |
| 824 | F | 0.03 | 0.007 | 0.02 | 0.07 |
| 825 | F | 0.12 | | 0.04 | |
| 827 | F | 0.16 | | 0.10 | |
| 831 | F | 0.08 | | 0.72 | 1.66 |
| 853 | G | (1.49) 0.13* | | 0.14 | |
| 855 | G | 6.35 | | ND | |
| 856 | G | ND | | ND | |

TABLE 8-continued $EC_{50}$ values of purified anti-RSV protein F and protein G antibodies against RSV subtype A and B.

| Clone | Antigen-specificity | $EC_{50}$ value (µg/ml) | | | |
|---|---|---|---|---|---|
| | | Long | A2 | 18537 | B1 |
| 858 | F | ND | | 0.13 | |
| 868 | G | ND | | | |
| 880 | F | 0.38 | | 0.95 | 0.40 |
| 888 | G | 0.14 | | | |
| 894 | F | 0.08 | | 0.07 | |
| Synagis | F | 0.14 | 0.15 | 0.20 | |

*value from new determination

Mixtures of Anti-F Antibodies

The ability of mixtures of anti-RSV protein F antibodies to neutralize RSV strains of subtype A and B was compared with the neutralizing effect obtained using Palivizumab (also an anti-F antibody). The neutralization capability was assessed using the microneutralization test or the PRNT as described in Example 1, Section j. In an initial experiment two antibody mixtures, anti-F(I) and anti-F(II), containing five and eleven distinct anti-F antibodies, respectively were compared against Palivizumab using the microneutralizating test. Anti-F(I) is composed of antibodies obtained from clones 810, 818, 819, 825 and 827. Antibodies 810 and 819 bind to antigenic site A/II, antibody 818 to site B/I or F1, antibody 825 binds to a complex epitope overlapping with sites A and C and antibody 827 binds to another complex epitope overlapping with site IV (see Table 6). Anti-F(II) is composed of antibodies obtained from clones 735, 800, 810, 818, 819, 825, 827, 863, 880, 884 and 894. Anti-F(II) contains multiple binders to some of the defined antigenic sites: antibodies 810, 819 and 863 binds A/II, antibodies 800 and 818 binds F1 (or B/I), antibodies 827 and 825 to the complex epitopes described above, antibodies 735 and 894 belong to unknown cluster (UC)I, antibody 880 to UCII, and 884 binds to another currently unknown epitope (see Table 6). As shown in FIG. 5, both composition Anti-F(I) and F(II) were more potent than Palivizumab with respect to neutralization of RSV strains of both subtypes.

FIG. 5 also shows that the combination of five antibodies (anti-F(I)) appeared to be more potent than the combination of eleven antibodies (Anti-F(II)). The anti-F(I) mixture contains some of the most potent individually neutralizing antibodies of the different epitope specificities that have been defined so far. The anti-F(II) mixture contains the same five highly potent antibodies, but it also contains additional binders to some of the defined epitopes and the included antibodies also display a wider range of neutralizing activity on their own. It is thus possible that the activity of the highly potent antibodies becomes diluted in the anti-F(II) combination due to competition for binding to the neutralizing epitopes on the F protein. However, since there potentially are other effects than the neutralizing effect associated with each individual antibody, e.g. increased phagocytosis, increased antibody-dependent cellular cytotoxicity (ADCC), anti-inflammatory effects, complement activation, and a decreased likelihood of generating escape mutants, when considered in vivo, this result should not be taken as an indication that a mixture of five is better than a mixture of eleven antibodies when used in vivo.

Both the in vitro assays and the combinations of clones have been refined since this initial experiment and a number of combinations of F-specific antibody clones that are highly potent in the presence of complement have been identified. The neutralizing potencies, expressed as $EC_{50}$ values (effective concentrations required to induce a 50% reduction in the number of plaques), of additional anti-F antibody compositions are listed in Table 9. Irrespective of the exact number of clones in the compositions, the majority of the tested combinations of F-specific antibodies are more potent than Palivizumab with respect to neutralization of RSV strain subtype A.

Mixtures of Anti-G Antibodies

Figure 7:
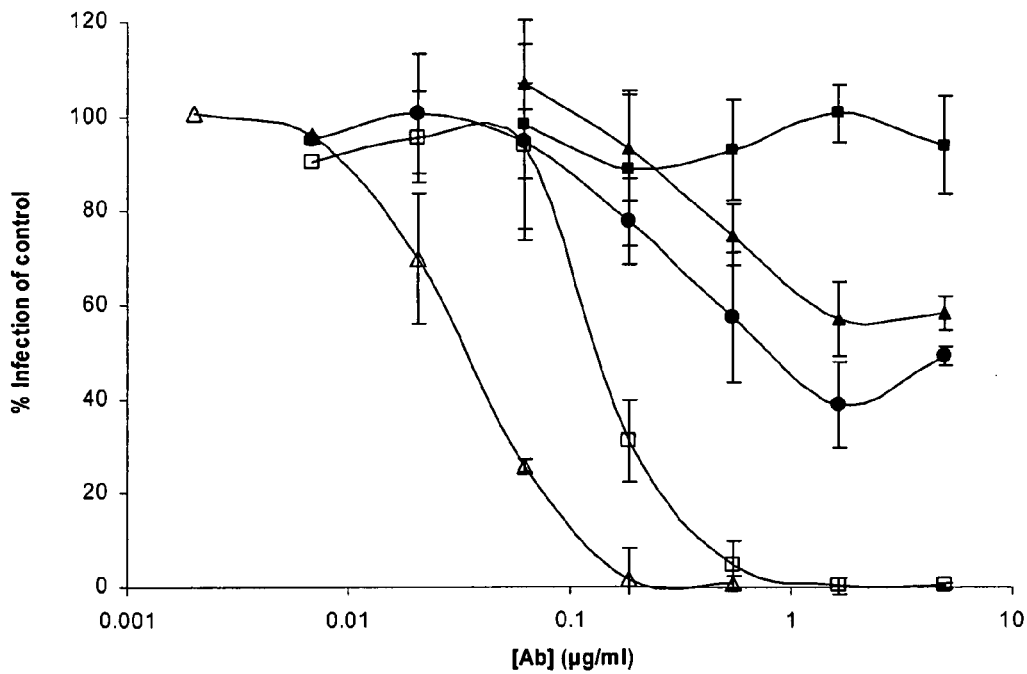
FIG. 7: Shows results from an in vitro neutralization of RSV by combinations of anti-G antibody clones as measured by the PRNT in the presence of active complement. Dilutions of individual antibody compositions (described in Table 9) were incubated with RSV strain Long in the presence of rabbit complement and afterwards allowed to infect HEp-2 cells. After 24 hours of incubation, the degree of infection was detected using immunodetection of RSV-specific plaques. Anti-RSV rpAb 13 is shown as open triangles (Δ), anti-RSV rpAb 35 as triangles (▲), anti-RSV rpAb 36 as squares (■), anti-RSV rpAb 41 as circles (●) and anti-RSV rpAb 45 as open squares (□). Data are presented as % infection compared to control ±SD.

The ability of mixtures of anti-G antibodies to neutralize RSV strains of subtype A was tested using the PRNT as described in Example 1, section j-2. The $EC_{50}$ values from the tested anti-G antibody compositions are listed in Table 9. Most of the compositions of two anti-G antibodies did not exhibit a markedly increased ability to neutralize virus compared to the individual anti-G antibodies. Some combinations of two or three anti-G antibodies never reached 100% neutralization of the virus, irrespective of the concentration. However, when additional anti-G antibodies were added to the composition the potency increased, possibly indicating a synergistic neutralizing effect between the anti-G antibodies. FIG. 7 shows an example of the increase in potency when combining multiple G-specific clones.

Mixtures of Anti-F and Anti-G Antibodies

The ability of mixtures of anti-RSV protein F and protein G antibodies to neutralize RSV subtype B strain was compared with the neutralizing effect obtained using Palivizumab. The neutralization capability was assessed using either the microneutralization fusion inhibition assay as described in Example 1, Section j-4 or the plaque reduction neutralization assay (Example 1, section j-2).

Figure 6:
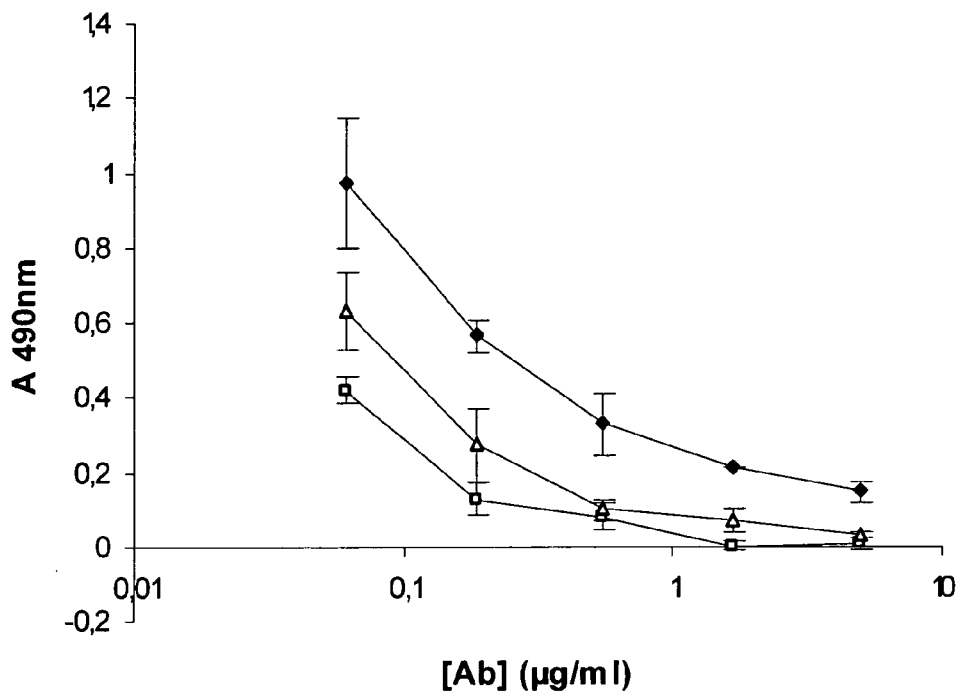
FIG. 6: Shows results from an in vitro RSV fusion inhibition assay. Dilutions of antibody mixtures were tested for their ability to neutralize RSV B1 strain. Antibody mixture, anti-F(I)G, obtained from clones 810, 818, 819, 825, 827, 793, 796, 838, 841, 856 and 888 is shown as open squares (□) and antibody mixture, anti-F(II)G, obtained from clones 735, 800, 810, 818, 819, 825, 827, 863, 880, 884, 894, 793, 796, 838, 841, 856 and 888 is shown as open triangles (Δ). Palivizumab is shown as diamonds (♦). The absorbance was measured at 490 nm and correlates with RSV replication.

Initially, the neutralizing activity of two antibody mixtures, anti-F(I)G and anti-F(II)G, was measured in the microneutralization fusion inhibition assay. Each of these mixtures contains the anti-F antibodies of composition anti-F(I) and anti-F(II) described above as well as anti-G antibodies obtained from clones 793, 796, 838, 841, 856 and 888, where antibodies 793, 796, 838 bind to the conserved region of the G protein, 841, 856 binds to the GCRR of RSV subtype A and 888 binds to the GCRR of both subtypes (see Table 6). As shown in FIG. 6, both composition Anti-F(I)G and F(II)G were more potent than Palivizumab with respect to neutralization of the RSV B1 strain. Further, the neutralizing activity of the two mixtures was more or less equal. Thus, it seems that when the anti-F antibodies are combined with a number of protein G-specific clones, the potency difference previously observed between the two anti-F antibody mixtures is diminished. This may indicate a general increase in the neutralizing activity when antibodies that recognize a wide range of antigens and epitopes on RSV are combined.

A large number of different combinations of both anti-F and anti-G antibodies have since then been tested in the PRNT in the presence or absence of complement. $EC_{50}$ values obtained by this assay in the presence of active complement are presented in Table 9. All of the tested compositions including both anti-F and anti-G antibodies do neutralize RSV subtype A and the majority of these are more potent than Palivizumab.

The results and results shown in Tables 7 and 8 also show that antibodies with naturally high affinities could repeatedly be obtained from human donors using the antibody cloning technique of the present invention.

TABLE 9

$EC_{50}$ values of combinations of anti-RSV antibodies against RSV subtype A and B. Blank fields indicate that the analysis has not been performed yet. ND indicates that an $EC_{50}$ value could not be determined in the PRNT due to a very low or lacking neutralizing activity.

| Composition | | EC50 value (µg/ml) | | | |
|---|---|---|---|---|---|
| Number | Antibodies in composition | Long | A2 | 18537 | B1 |
| 1 | 810, 818, 819, 825, 827 | 0.19 | | | 0.38 |
| 2 | 810, 818, 819, 825, 827, 831, 858, 863, 884, 894, 793, 796, 816, 838, 853, 856, 859, 888 | 0.34 | | | |
| 3 | 810, 818, 825, 827, 884, 886, 793, 853, 868, 888 | 0.30 | | | |
| 4 | 810, 818, 825, 827, 831, 858, 884, 886, 793, 796, 816, 853, 856, 868, 888 | 0.19 | | | |
| 5 | 810, 818, 825, 827, 831, 858, 884, 886, 793, 853, 868, 888 | 0.21 | | | |
| 6 | 810, 819, 825, 827, 831, 793, 853, 856, 858, 868 | 0.20 | | | |
| 7 | 810, 811, 817, 819, 825, 827, 831, 838, 853, 856, 858, 859, 863, 868 | 0.18 | | | |
| 8 | 800, 801, 811, 838, 853, 855, 859, 861, 880, 894, 736, 795, 796, 799 | (ND) 0.92* | | | |
| 9 | 810, 818, 825 | 0.14 | | 0.03 | 0.29 |
| 10 | 810, 818, 819, 825, 827, 884 | 0.21 | | | 0.42 |
| 11 | 810, 818, 819, 825, 827, 884, 886 | 0.15 | | | 0.29 |
| 12 | 793, 816, 853, 856 | 0.06 | | | |
| 13 | 793, 816, 853, 855, 856 | 0.03 | 0.03 | 0.86 | |
| 14 | 793, 868, 888, 853, 856 | 0.34 | | | |
| 15 | 793, 796, 818, 816, 838, 853, 855, 856, 859, 868, 888 | 0.11 | | | |
| 16 | 810, 818, 827 | 0.11 | | | 0.21 |
| 17 | 810, 818, 825, 827, 858, 886 | 0.10 | | 0.05 | 0.16 |

TABLE 9-continued

EC$_{50}$ values of combinations of anti-RSV antibodies against RSV subtype A and B. Blank fields indicate that the analysis has not been performed yet. ND indicates that an EC$_{50}$ value could not be determined in the PRNT due to a very low or lacking neutralizing activity.

| Composition Number | Antibodies in composition | EC50 value (µg/ml) | | | |
|---|---|---|---|---|---|
| | | Long | A2 | 18537 | B1 |
| 18 | 810, 818, 825, 827, 858, 886, 793, 816, 853, 855, 856 | 0.04 | | 0.06 | 0.15 |
| 19 | 818, 825, 827, 858, 886, 793, 816, 853, 855, 856 | 0.06 | | | |
| 20 | 810, 818, 819, 825, 827, 858, 793, 816, 853, 855, 856 | 0.10 | | 0.06 | |
| 21 | 810, 793, 816, 853, 855, 856 | 0.04 | | | |
| 22 | 818, 825, 827, 831, 858, 886, 793, 816, 853, 855, 856 | 0.06 | | | |
| 23 | 818, 825, 827, 831, 858, 819, 793, 816, 853, 855, 856 | 0.06 | | 0.03 | |
| 24 | 818, 827, 831, 858, 819, 793, 816, 853, 855, 856 | 0.06 | | 0.04 | |
| 25 | 810, 818, 819, 824, 825, 827, 858, 793, 816, 853, 855, 856 | 0.07 | | | |
| 26 | 831, 818, 819, 824, 825, 827, 858, 793, 816, 853, 855, 856 | 0.08 | | | |
| 27 | 831, 818, 819, 824, 827, 858, 793, 816, 853, 855, 856 | 0.05 | | | |
| 28 | 810, 818, 824 | 0.03-0.06 | 0.04 | 0.04 | 0.04 |
| 29 | 810, 824 | 0.05 | | | |
| 30 | 818, 824 | 0.04 | | | |
| 31 | 810, 818 | 0.08-0.11 | | | |
| 32 | 824, 793, 816, 853, 855, 856 | 0.05 | | | |
| 33 | 810, 818, 819, 824, 825, 827, 858, 894, 793, 816, 853, 855, 856 | 0.03-0.07 | 0.06 | 0.03 | 0.06 |
| 34 | 810, 818, 819, 824, 825, 827, 894, 793, 816, 853, 855, 856 | 0.07 | | | |
| 35 | 793, 816 | 5.94 | | | |
| 36 | 855, 856 | ND | | | |
| 37 | 793, 856 | ND | | | |
| 38 | 793, 853 | 2.35 | | | |
| 39 | 853, 856 | 0.21 | | | |
| 40 | 793, 853, 856 | 2.84 | | | |
| 41 | 793, 816, 853 | 1.97 | | | |
| 42 | 853, 855, 856 | 0.25 | | | |
| 43 | 793, 816, 853, 856 | 0.45 | | | |
| 44 | 793, 853, 855 | 0.26 | | | |
| 45 | 793, 853, 855, 856 | 0.16 | | | |
| 46 | 816, 853, 855, 856 | 0.07 | | | |
| 47 | 816, 856 | 0.06 | | | |
| 48 | 816, 853 | 0.75 | | | |
| 49 | 816, 853, 856 | 0.07 | | | |
| 50 | 810, 818, 824, 816 | 0.09 | | | |
| 51 | 810, 818, 824, 853 | 0.11 | | | |
| 52 | 810, 818, 824, 856 | 0.10 | | | |
| 53 | 810, 818, 824, 816, 853 | 0.09 | | | |
| 54 | 810, 818, 824, 816, 856 | 0.05 | | | |
| 55 | 810, 818, 824, 853, 856 | 0.08 | | | |
| 56 | 810, 818, 824, 816, 853, 856 | 0.05 | 0.03-0.05 | 0.03 | 0.06 |
| | Palivizumab (Synagis) | 0.14 | 0.15 | 0.20 | |

*value from new determination

EXAMPLE 4

Reduction of Viral Loads in the Lungs of RSV-Infected Mice

The in vivo protective capacity of combinations of purified antibodies of the invention against RSV infection has been demonstrated in the BALB/c mouse model (Taylor et al. 1984. Immunology 52, 137-142; Mejias, et al. 2005. Antimicrob. Agents Chemother. 49: 4700-4707) as described in Example 1, Section k-1. In Table 10, data from an experiment with three different anti-RSV rpAb consisting of equal amounts of different antibody clones of the invention (described in table 9) are presented in comparison with data from uninfected control animals and placebo (PBS) treated animals of the same experiment. Each treatment group contained 5 mice and the samples were obtained on day five post-infection, which is approximately at the peak of virus replication in this model. As shown in Table 10, the rpAb combinations effectively reduce the virus load by at least an order of magnitude when given prophylactically. Copy numbers are presented as means ±standard deviations. The copy number was at or below the limit of detection of this assay, i.e., 3.8 log 10 RNA copies/ml, for two of the treatment groups.

TABLE 10

Virus loads in the lungs of mice following prophylaxis and RSV challenge.

| Treatment group | Virus load by RT-PCR (log10 RNA copies/ml) | New data |
|---|---|---|
| Uninfected | Negative | |
| PBS | 5.14 ± 0.09 | 4.25 |
| Anti-RSV rpAb 18 (50 mg/kg) | ND | |
| Anti-RSV rpAb 18 (5 mg/kg) | 4.61 ± 0.22 | 3.64 |
| Anti-RSV rpAb 9 (50 mg/kg) Small F Hi | ND | |
| Anti-RSV rpAb 9 (5 mg/kg) Small F Lo | 4.74 ± 0.38 | 3.82 |
| Anti-RSV rpAb 17 (50 mg/kg) Large F Hi | 4.41 ± 0.14 | 3.04 |
| Anti-RSV rpAb 17 (5 mg/kg) Large F Lo | 4.69 ± 0.05 | 3.90 |

Samples have subsequently been analyzed using a different quantitative RT-PCR set-up (described in Section k-1). In table 11a, data from an experiment with four different anti-RSV rpAb consisting of equal amounts of different antibody clones of the invention (described in table 9) and clone 810 alone are presented in comparison with data from uninfected control animals and placebo (PBS) treated animals of the same experiment. Each treatment group contained 5 mice and the samples were obtained on day five post-infection, which is approximately at the peak of virus replication in this model. As shown in Table 11a, the rpAb combinations effectively reduce the virus load by at least an order of magnitude when given prophylactically at 25 mg/kg of body weight. Copy numbers are presented as means ±standard deviations.

TABLE 11a

Virus loads in the lungs of mice following prophylaxis and RSV challenge.

| Treatment group (dose) | Virus load by RT-PCR (log10 RSV RNA copies/ng total RNA) |
|---|---|
| Uninfected | Negative |
| PBS | 4.11 ± 0.12 |
| Anti-RSV rpAb 18 (25 mg/kg) | 2.74 ± 0.16 |
| Anti-RSV rpAb 18 (5 mg/kg) | 3.40 ± 0.09 |
| Anti-RSV rpAb 9 (25 mg/kg) | 2.95 ± 0.19 |
| Anti-RSV rpAb 9 (5 mg/kg) | 3.56 ± 0.31 |
| Anti-RSV rpAb 17 (25 mg/kg) | 2.81 ± 0.29 |
| Anti-RSV rpAb 17 (5 mg/kg) | 3.39 ± 0.12 |
| Anti-RSV rpAb 13 (25 mg/kg) | 3.02 ± 0.33 |
| Anti-RSV rpAb 13 (5 mg/kg) | 3.34 ± 0.26 |
| Clone 810 (25 mg/kg) | 3.03 ± 0.16 |
| Clone 810 (5 mg/kg) | 3.37 ± 0.22 |

In table 11b, data from a second study with three different anti-RSV rpAb consisting of equal amounts of different antibody clones of the invention (described in table 9) and clone 824 alone are presented in comparison with data from uninfected control animals, placebo (PBS) treated animals and Palivizumab (Synagis) treated animals of the same experiment. Each treatment group contained 5 mice and the samples were obtained on day five post-infection. Copy numbers are presented as means ±standard deviations.

In table 11c, data from a third study with anti-RSV rpAb 33 consisting of equal amounts of different antibody clones of the invention (described in table 9) are presented in comparison with data from uninfected control animals, placebo (PBS) treated animals and Palivizumab (Synagis) treated animals of the same experiment. Each treatment group except the last three contained 5 mice and the samples were obtained on day five post-infection. One mouse was removed from each of the groups treated with anti-RSV rpAb 33 at 15, 5 and 1.5 mg/kg body weight since it was discovered that they were never injected with antibody. Copy numbers are presented as means ±standard deviations.

In all three studies, there is a statistically significant reduction of the RSV RNA copy number in the antibody-treated groups as compared to the Placebo-treated control (p<0.05; homoscedastic t-test). In the second study, the virus load in the groups treated with the antibodies of the invention are significantly lower than in the Synagis-treated groups at the corresponding doses (Table 11b). In the third study, the virus load is significantly lower in the groups treated with the anti-RSV rpAb 33 than in the Synagis-treated groups at all tested doses (Table 11c).

TABLE 11b

Virus loads in the lungs of mice following prophylaxis and RSV challenge.

| Treatment group (dose) | Virus load by RT-PCR (log10 RSV RNA copies/ng total RNA) |
|---|---|
| Uninfected | Negative |
| PBS | 4.22 ± 0.20 |
| Synagis (15 mg/kg) | 3.68 ± 0.25 |
| Synagis (3 mg/kg) | 3.83 ± 0.12 |
| Anti-RSV rpAb 28 (15 mg/kg) | 2.96 ± 0.19 |
| Anti-RSV rpAb 28 (3 mg/kg) | 3.32 ± 0.23 |
| Anti-RSV rpAb 33 (15 mg/kg) | 2.95 ± 0.30 |
| Anti-RSV rpAb 33 (3 mg/kg) | 3.66 ± 0.07 |
| Anti-RSV rpAb 56 (15 mg/kg) | 2.66 ± 0.18 |
| Anti-RSV rpAb 56 (3 mg/kg) | 3.25 ± 0.38 |
| Clone 824 (15 mg/kg) | 2.51 ± 0.28 |
| Clone 824 (3 mg/kg) | 3.09 ± 0.18 |

TABLE 11c

Virus loads in the lungs of mice following prophylaxis and RSV challenge. The asterisk indicates that the group only contained four animals.

| Treatment group (dose) | Virus load by RT-PCR (log10 RSV RNA copies/ng total RNA) |
|---|---|
| Uninfected | Negative |
| PBS | 4.13 ± 0.17 |
| Synagis (45 mg/kg) | 3.56 ± 0.22 |
| Synagis (15 mg/kg) | 3.60 ± 0.27 |
| Synagis (5 mg/kg) | 3.77 ± 0.14 |
| Synagis (1.5 mg/kg) | 3.86 ± 0.12 |
| Anti-RSV rpAb 33 (45 mg/kg) | 2.38 ± 0.18 |
| Anti-RSV rpAb 33 (15 mg/kg)* | 2.70 ± 0.18 |
| Anti-RSV rpAb 33 (5 mg/kg)* | 3.15 ± 0.24 |
| Anti-RSV rpAb 33 (1.5 mg/kg)* | 3.53 ± 0.12 |

Finally, in Table 11d, data from a long-term study with anti-RSV rpAb 33 consisting of equal amounts of different antibody clones constituting rpAB 33 (described in table 9) are presented in comparison with data from uninfected control animals and placebo (PBS) treated animals of the same experiment. Each treatment group contained 5 mice and the samples were obtained on day 5, 27 and 69 post-infection. Copy numbers are presented as means ±standard deviations. Due to the very low copy numbers on day 69 post-infection, copy numbers were calculated per ml of lung tissue. The limit of detection of this assay is approximately 2 log 10 RNA copies/ml lung tissue homogenate.

At all three time points, there is a statistically significant reduction of the RSV RNA copy number in the antibody-treated group as compared to the Placebo-treated control (p<0.01; homoscedastic t-test) (Table 11d).

TABLE 11d

Virus loads in the lungs of mice following prophylaxis and RSV challenge. Each treatment group contained 5 animals per time point.

| Treatment group (dose) | Virus load by RT-PCR (log10 RSV RNA copies/ml lung homogenate) | | |
|---|---|---|---|
| | Day 5 | Day 27 | Day 69 |
| Uninfected | Negative | Negative | Negative |
| PBS | 9.36 ± 0.15 | 4.52 ± 0.22 | 4.05 ± 0.18 |
| Anti-RSV rpAb 33 (45 mg/kg) | 7.51 ± 0.22 | 3.22 ± 0.22 | 2.68 ± 0.41 |

Cytokine and Chemokine Levels in Lung Samples from RSV Infected Mice

Lung samples from a pilot mouse prophylaxis study were analyzed by a commercial multiplexed immunoassay to determine the levels of different cytokines and chemokines following RSV infection and antibody prophylaxis with rpAb 18 (Table 9) as described in Example 1, Section k-1. Samples from uninfected and untreated animals were also analyzed to obtain normative data for the BALB/c mouse. All samples were obtained on day five post-infection. Data are presented as means ±standard deviations.

The analysis showed (Table 12) that the levels of a number of cytokines and chemokines that have been indicated as important markers of RSV infection and the subsequent inflammatory response, both in humans and mice, including interferon (IFN)-γ, interleukin (IL)-1β, IL-4, IL-6, IL-8 (KC/GROα), IL-10, macrophage inflammatory protein (MIP)-1α, Regulated upon activation of normal T cell expressed and secreted (RANTES, CCL5) and tumor necrosis factor (TNF)-α were increased in the lungs of the placebo-treated animals, whereas the lungs of the animals treated with approx. 50 mg/kg of rpAb had levels more or less on par with the uninfected control animals. Similar results were also obtained with other anti-RSV rpAb combinations. It should be noted that mice do not have a clear-cut homologue for IL-8, but they have a functional homologue for human GROα (similar function to IL-8) named KC.

The kinetics of the inflammatory response and the dose-response effects of antibody prophylaxis remain to be investigated.

TABLE 12

Levels of cytokines and chemokines in lung tissue from RSV infected mice

| Level in tissue sample (pg/ml) | Uninfected control mice | Placebo treated mice | anti-RSV rpAb treated mice |
|---|---|---|---|
| IL-1β | 270 ± 71 | 570 ± 100 | 310 ± 140 |
| IL-4 | 7.7 ± 4.7 | 26 ± 4.6 | 14 ± 8.5 |
| IL-6 | 6.4 ± 2.6 | 22 ± 12 | 8.2 ± 3.8 |
| IL-10 | 120 ± 17 | 320 ± 58 | 170 ± 41 |
| IFN-γ | 20 ± 7.6 | 420 ± 88 | 81 ± 72 |
| KC/GROα (IL-8) | 51 ± 38 | 290 ± 83 | 94 ± 99 |
| MIP-1α (CCL3) | 39 ± 16 | 940 ± 170 | 160 ± 110 |
| RANTES (CCL5) | 60 ± 28 | 380 ± 32 | 140 ± 66 |
| TNF-α | 18 ± 6.1 | 95 ± 10 | 38 ± 25 |

Effect of Antibody Prophylaxis on Pulmonary Pathology and Infiltrating Cells in RSV Infected Mice The lung tissue histopathology samples from the long-term study were examined for signs of inflammation and scored according to the system described in Example 1, Section k-1. Each treatment group contained 5 mice and the samples were obtained on day 5, 27 and 69 post-infection. One mouse was removed from the group treated with anti-RSV rpAb 33 and killed on day 5 post-infection since it was discovered that it had not been injected with antibody. Data are presented as means ±standard deviations. Five days after RSV infection, there was a significant increase in pulmonary pathology in the placebo-treated mice when compared with the uninfected control mice ($p<0.005$; heteroscedastic t-test; Table 13). The signs of inflammation decreased over time, but were still significant compared to the uninfected control mice at day 69 post-infection ($p<0.0001$). The pulmonary pathology was characterized by peribronchiolar and perivascular accumulations of lymphocytes and alveolitis at day 5 post-infection and by small perivascular and peribronchiolar accumulations of lymphocytes at days 27 and 69 post-infection. In contrast, there was little or no lymphoid accumulation in the lungs of antibody-treated mice and the lungs were similar to those of uninfected control mice. Pulmonary pathology in the placebo-treated mice was also significantly greater than in the antibody-treated mice ($p<0.02$ at day 5, $<0.03$ at day 27 and $<0.0001$ at day 69).

TABLE 13

Mouse lung pathology scores following prophylaxis and RSV challenge. The asterisk indicates that the group only contained four animals.

| Treatment group (dose) | Lung pathology score (Severity × Prevalence) | | |
|---|---|---|---|
| | Day 5 | Day 27 | Day 69 |
| Uninfected | 0 | 0.4 ± 0.5 | 0 |
| PBS | 10.8 ± 4.3 | 2.8 ± 1.1 | 2.6 ± 0.5 |
| Anti-RSV rpAb 33 (45 mg/kg) | 3 ± 0.8* | 0.6 ± 0.9 | 0.2 ± 0.4 |

The perivascular and peribronchiolar lymphoid accumulations in the lungs of RSV-infected mice, 28 and 70 days after infection correlated with increased numbers of lymphocytes in the BAL. As shown in Table 14, there was a significant increase in the number of inflammatory cells in BAL from placebo-treated mice compared with control uninfected mice at days 5, 27 and 69 post-infection ($p<0.002$; $p<0.03$; $p<0.03$ respectively). The pulmonary inflammatory response in mice treated with anti-RSV rpAb 33 was significantly less than that in placebo-treated mice at all time points and ($p<0.003$ at day 5; $p<0.03$ at day 27; $p<0.02$ at day 69 respectively). The groups are the same as for the lung pathology described above and data are presented as means ±standard deviations.

TABLE 14

Leukocyte counts in BAL following prophylaxis and RSV challenge. The asterisk indicates that the group only contained four animals.

| Treatment group (dose) | BAL cell counts (×$10^5$) | | |
|---|---|---|---|
| | Day 5 | Day 27 | Day 69 |
| Uninfected | 1.1 ± 0.2 | 1.4 ± 0.3 | 1.0 ± 0.1 |
| PBS | 7.2 ± 2.0 | 3.0 ± 1.0 | 1.8 ± 0.5 |
| Anti-RSV rpAb 33 (45 mg/kg) | 1.8 ± 0.5* | 1.5 ± 0.3 | 0.9 ± 0.1 |

Pharmacokinetics of Human rpAb in Mice

The pharmacokinetic profile of combinations of purified antibodies of the invention was determined in BALB/c mice as described in Example 1, section 1. Two different anti-RSV rpAb 33 and anti-RSV rpAb 56 (see Table 9), consisting of equal amounts of different antibody clones of the invention were investigated. Each treatment group consisted of 15 mice. The measured human IgG levels in serum samples and lung homogenates corresponds to the level of anti-RSV rpAb present at the specific time points.

Figure 8:
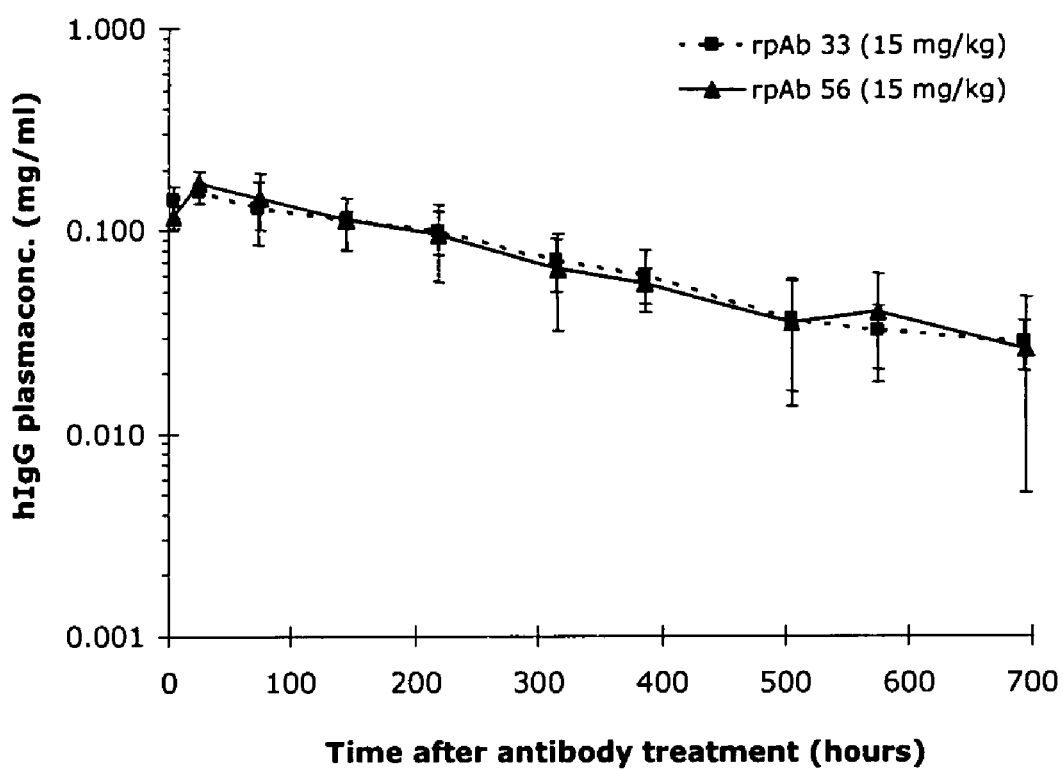
FIG. 8. The pharmacokinetics profile of anti-RSV rpAb 33 and rpAb 56 in mice. BALB/c mice were treated with the anti-RSV rpAb 33 and anti-RSV rpAb 56 (antibody compositions of Table 9) at a dose of 15 mg/kg. Serum samples were taken at a number of time points ranging from day 0 (before inoculation) until day 29. Each point represents the mean human IgG1 level in serum at sampling time±standard deviation.

FIG. 8 shows the serum pharmacokinetic profiles of anti-RSV rpAb 33 and anti-RSV rpAb 56 at an antibody dose of 15 mg/kg. Using these data, a number of parameters were determined, which are summarized in Table 15. The two different Anti-RSV rpAb compositions have similar pharmacokinetic profiles with a half-life ($T_{1/2}$) of 11 days. These findings have been verified using a dose of 37.5 mg/kg.

TABLE 15

Serum pharmacokinetic data obtained in mice

|  | $C_{max}$ (mg/ml) | $T_{max}$ (hours) | AUC (0-694)* | $T_{1/2}$ (days) |
|---|---|---|---|---|
| Anti-RSV rpAb 33 | 15.4 | 25 | 51 | 11.1 |
| Anti-RSV rpAb 56 | 17.2 | 25 | 52 | 11.0 |

*Area Under Curve between time = 0 hours and time = 694 hours.

Since the primary target of RSV during infection is the lung tissue, the presence of anti-RSV rpAb in this tissue is vital for efficacy. To determine the distribution of anti-RSV rpAb 33 and anti-RSV rpAb 56 (according to Table 9) to lung tissue, the IgG1 levels was measured in lung homogenates at days 1 (25 hours), 6, and 29 after antibody treatment. At all measured time points, the levels of anti-RSV rpAb 33 and anti-RSV rpAb 56 in lung tissue was found to be almost identical with a maximal average IgG1 concentration around 0.006 mg/ml at day 1 after antibody treatment. At days 6 and 29 the levels had decreased. However, IgG1 could still be measured in lung tissue at day 29 after antibody treatment. These findings show that not only is anti-RSV rpAb composition 33 and anti-RSV rpAb composition 56 present in lung tissue shortly after treatment but antibodies can be found in detectable levels up to at least 29 days after treatment.

---

What is claimed is:

1. An anti-RSV (respiratory syncytial virus) antibody, or antigen binding fragment thereof, comprising:
    (i) a $V_H$ CDR1 region comprising the amino acid sequence of SEQ ID NO:232;
    (ii) a $V_H$ CDR2 region comprising the amino acid sequence of SEQ ID NO:317;
    (iii) a $V_H$ CDR3 region comprising the amino acid sequence of SEQ ID NO:402;
    (iv) a $V_L$ CDR1 region comprising the amino acid sequence of SEQ ID NO:487;
    (v) a $V_L$ CDR2 region comprising the amino acid sequence of SEQ ID NO:572; and
    (vi) a $V_L$ CDR3 region comprising the amino acid sequence of SEQ ID NO:657.

2. The antibody or antigen binding fragment of claim 1, comprising a $V_H$ region as defined in SEQ ID NO: 19.

3. The antibody or antigen binding fragment of claim 1, comprising a $V_L$ region as defined by amino acids 1 to 107 of SEQ ID NO: 107.

4. The antibody or antigen binding fragment of claim 1, comprising a light chain as defined in SEQ ID NO: 107.

5. The antibody or antigen binding fragment of claim 1, comprising a $C_H$ as defined in SEQ ID NO: 178.

6. A composition comprising the anti-RSV antibody or antigen binding fragment of claim 1, and one or more additional anti-RSV antibodies.

7. The composition of claim 6, wherein the one or more additional anti-RSV antibodies are selected from the group consisting of human antibodies, humanized antibodies, and chimeric human-mouse antibodies.

8. The antibody composition of claim 6, wherein the one or more additional anti-RSV antibodies comprises:
    (i) a CDRH1 selected from the group consisting of SEQ ID NOs: 201-285;
    (ii) a CDRH2 selected from the group consisting of SEQ ID NOs: 286-370;
    (iii) a CDRH3 selected from the group consisting of SEQ ID NOs: 371-455;
    (iv) a CDRL1 selected from the group consisting of SEQ ID NOs: 456-540;
    (v) a CDRL2 selected from the group consisting of SEQ ID NOs: 541-625; and
    (vi) a CDRL3 selected from the group consisting of SEQ ID NOs: 626-710.

9. A composition comprising the anti-RSV antibody or antigen binding fragment of claim 1.

10. A method of preventing, treating or ameliorating one or more symptoms associated with a RSV infection in a mammal, comprising administering an effective amount of the anti-RSV antibody or antigen binding fragment of claim 1.

11. The method according to claim 10, wherein the effective amount is between 0.1-50 mg antibody per kg of body weight.

12. The method according to claim 10, wherein the anti-RSV antibody or antigen binding fragment is administered at least 1 time per year.

13. The method according to claim 12, wherein the anti-RSV antibody or antigen binding fragment is administered at regular intervals during a period of the year where there is an increased risk of attracting an RSV infection.

14. The method according to claim 13, wherein the regular intervals are weekly, bi-weekly, monthly, or bi-monthly.

* * * * *

UNITED STATES PATENT AND TRADEMARK OFFICE
CERTIFICATE OF CORRECTION

| | | |
|---|---|---|
| PATENT NO. | : 7,879,329 B2 | Page 1 of 1 |
| APPLICATION NO. | : 12/073538 | |
| DATED | : February 1, 2011 | |
| INVENTOR(S) | : Lantto et al. | |

It is certified that error appears in the above-identified patent and that said Letters Patent is hereby corrected as shown below:

On the Title page of the patent, please insert therein section (63), Related U.S. Application Data, --Continuation of application No. PCT/DK2007/000113, filed on Mar. 6, 2007.--

Signed and Sealed this
Third Day of May, 2011

David J. Kappos
*Director of the United States Patent and Trademark Office*